United States Patent
Johnson et al.

(10) Patent No.: US 11,807,873 B2
(45) Date of Patent: Nov. 7, 2023

(54) CONVERSION OF S-LIGNIN COMPOUNDS TO USEFUL INTERMEDIATES

(71) Applicant: Alliance for Sustainable Energy, LLC, Golden, CO (US)

(72) Inventors: Christopher W. Johnson, Denver, CO (US); Allison Jean Zimont Werner, Denver, CO (US); Gregg Tyler Beckham, Golden, CO (US); Sandra Fabienne Notonier, Marseilles (FR)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/504,901

(22) Filed: Oct. 19, 2021

(65) Prior Publication Data

US 2022/0119849 A1 Apr. 21, 2022

Related U.S. Application Data

(60) Provisional application No. 63/093,636, filed on Oct. 19, 2020.

(51) Int. Cl.
| | |
|---|---|
| *C12N 9/02* | (2006.01) |
| *C12P 7/44* | (2006.01) |
| *C12R 1/39* | (2006.01) |
| *C12R 1/40* | (2006.01) |
| *C12N 1/20* | (2006.01) |

(52) U.S. Cl.
CPC ......... *C12N 9/0071* (2013.01); *C12N 9/0069* (2013.01); *C12N 9/0073* (2013.01); *C12P 7/44* (2013.01); *C12N 1/205* (2021.05); *C12R 2001/39* (2021.05); *C12R 2001/40* (2021.05); *C12Y 114/13082* (2013.01)

(58) Field of Classification Search
CPC .. C12N 9/0071; C12N 9/0069; C12N 9/0073; C12P 7/44
See application file for complete search history.

(56) References Cited

U.S. PATENT DOCUMENTS

| | | | |
|---|---|---|---|
| 4,952,501 A | 8/1990 | Jasin et al. | |
| 2020/0071731 A1 | 3/2020 | Beckham et al. | |

FOREIGN PATENT DOCUMENTS

| | | | |
|---|---|---|---|
| JP | 2005-278549 | * | 10/2005 |
| JP | 2011-229426 | * | 11/2011 |

OTHER PUBLICATIONS

Studer. Residue mutations and their impact on protein structure and function: detecting beneficial and pathogenic changes. Biochem. J. (2013) 449, 581-594.*
English Translation of JP 2005-278549. 2022.*
English Translation of JP 2011-229426. 2022.*

(Continued)

*Primary Examiner* — Yong D Pak
(74) *Attorney, Agent, or Firm* — Michael A. McIntyre; Sam J. Barkley

(57) ABSTRACT

The present disclosure relates to a genetically modified microbial cell that includes a first genetic modification resulting in the expression of an exogenous vanillate demethylase, such that the microbial cell is capable of metabolizing an S-lignin decomposition product and producing 2-pyrone-4,6-dicarboxylate (PDC).

16 Claims, 58 Drawing Sheets

Specification includes a Sequence Listing.

(56) References Cited

OTHER PUBLICATIONS

Abe et al., "A tetrahydrofolate-dependent O-demethylase, LigM, is crucial for catabolism of vanillate and syringate in Sphingomonas paucimobilis SYK-6", Journal of Bacteriology, 2005, vol. 187, No. 6, pp. 2030-2037.
Barry et al., "Characterizing the promiscuity of LigAB, a lignin catabolite degrading extradiol dioxygenase from Sphingomonas paucimobilis SYK-6", Biochemistry, 2013, vol. 52, No. 38, pp. 6724-6736.
Beckham et al., "Opportunities and challenges in biological ligninvalorization", Current Opinion in Biotechnology, Dec. 2016, vol. 42, pp. 40-53.
Brunel et al., "Cloning and sequencing of Pseudomonas genes encoding vanillate demethylase", Journal of Bacteriology, 1988, vol. 170, No. 10, pp. 4924-4930.
Capyk et al., "Characterization of 3-Ketosteroid 9α-Hydroxylase, a Rieske Oxygenase in the Cholesterol Degradation Pathway of *Mycobacterium tuberculosis*", Journal of Biological Chemistry, 2009, vol. 284, No. 15, pp. 9937-9946.
Chen et al., "The iron-sulfur centers and the function of hydrogenase from Clostridium pasteurianum", Advances in Experimental Medicine and Biology, 1976, vol. 74, pp. 68-82.
Ge et al., "Reactivity of toluate dioxygenase with substituted benzoates and dioxygen",Journal of Bacteriology, 2002, vol. 184, No. 15, pp. 4096-4103.
Graf et al., "Genetic engineering of Pseudomonas putida KT2440 for rapid and high-yield production of vanillin from ferulic acid", Applied Microbiology and Biotechnology, 2014, vol. 98, No. 1, pp. 137-149.
Elmore et al., "Development of a high efficiency integration system and promoter library for rapid modification of Pseudomonas putida KT2440", Metabolic Engineering Communications, 2017, vol. 5, pp. 1-8.
Hara et al., "Characterization of the 4-carboxy-4-hydroxy-2-oxoadipate aldolase gene and operon structure of the protocatechuate 4,5-cleavage pathway genes in Sphingomonas paucimobilis SYK-6", Journal of Bateriology, 2003, vol. 185, No. 1, pp. 41-50.
Hibi et al., "Functional coupling between vanillate-O-demethylase and formaldehyde detoxification pathway. FEMS Microbiology Letters, 2005, vol. 253, No. 2, pp. 237-242.
Hogancamp et al., "Functional Annotation of LigU as a 1,3-Allylic Isomerase during the Degradation of Lignin in the Protocatechuate 4,5-Cleavage Pathway from the Soil *Bacterium sphingobium* sp. SYK-6", Biochemistry, 2018, vol. 57, No. 19, pp. 2837-2845.
Johnson et al., "Aromatic catabolic pathway selection for optimal production of pyruvate and lactate from lignin", Metabolic Engineering, 2015, vol. 28, pp. 240-247.
Johnson et al., "Enhancing muconic acid production from glucose and lignin-derived aromatic compounds via increased protocatechuate decarboxylase activity", Metabolic Engineering Communications, 2016, vol. 3, pp. 111-119.
Johnson et al., "Eliminating a global regulator of carbon catabolite repression enhances the conversion of aromatic lignin monomers to muconate in Pseudomonas putida KT2440", Metabolic Engineering Communications, 2017, vol. 5, pp. 19-25.
Johnson et al., "Innovative Chemicals and Materials from Bacterial Aromatic Catabolic Pathways", Joule, 2019, vol. 3, No. 6, pp. 1523-1537.
Kamimura et al., "A bacterial aromatic aldehyde dehydrogenase critical for the efficient catabolism of syringaldehyde", Scientific Reports, 2017, vol. 7, No. 44422, pp. 1-12.
Kasai et al., "Characterization of the 3-O-methylgallate dioxygenase gene and evidence of multiple 3-O-methylgallate catabolic pathways in Sphingomonas paucimobilis SYK-6", Journal of Bacteriology, 2004, vol. 186, No. 15, pp. 4951-4959.
Kasai et al., "Characterization of the gallate dioxygenase gene: three distinct ring cleavage dioxygenases are involved in syringate degradation by Sphingomonas paucimobilis SYK-6", Journal of Bacteriology, 2005, vol. 187, No. 15,pp. 5067-5074.
Kersten et al., "2-pyrone-4,6-dicarboxylic acid, a catabolite of gallic acids in *Pseudomonas* species", Journal of Bacteriology, 1982, vol. 152, No. 3, pp. 1154-1162.
Lanfranchi et al., "Exploring the selective demethylation of aryl methyl ethers with a Pseudomonas rieske monooxygenase", ChemBioChem, 2019, vol. 20, pp. 118-125.
Linger et al., "Lignin valorization through integrated biological funneling and chemical catalysis", PNAS, 2014, vol. 111, No. 33, pp. 12013-12018.
Lynch et al., "Broad host range vectors for stable genomic library construction", Biotechnology and Bioengineering, 2006, vol. 94, pp. 151-158.
Masai et al., "Characterization of Sphingomonas paucimobilis SYK-6 genes involved in degradation of lignin-related compounds", Journal of Industrial Microbiology and Biotechnology, 1999, vol. 23, Nos. 4-5, pp. 364-373.
Masai et al., "A novel tetrahydrofolate-dependent O-demethylase gene is essential for growth of Sphingomonaspaucimobilis SYK-6 with syringate", Journal of Bacteriology, 2004, vol. 186, No. 9, pp. 2757-2765.
Michinobu et al., "Polyesters of 2-Pyrone 4,6-Dicarboxylic Acid (PDC) Obtained from a Metabolic Intermediate of Lignin", Polymer Journal, 2008, vol. 40, pp. 68-75.
Morawski et al., "Substrate range and genetic analysis of Acinetobacter vanillate demethylase", Journal of Bacteriology, 2000, vol. 182, No. 5, pp. 1383-1389.
Nishimura et al., "Expression and substrate range of Streptomyces vanillate demethylase", Biological and Pharmaceutical Bulletin, 2014, vol. 37, No. 9, pp. 1564-1568.
Nogales et al., "Molecular characterization of the gallate dioxygenase from Pseudomonas putida KT2440. The prototype of a new subgroup of extradiol dioxygenases", Journal of Biological Chemistry, 2005, vol. 280, vol. 42, pp. 35382-35390.
Nogales et al., "Unravelling the gallic acid degradation pathway in bacteria: the gal cluster from Pseudomonas putida", Molecular Microbiology, 2011, vol. 79, No. 2, pp. 359-374.
Perez et al., "Funneling aromatic products of chemically depolymerized lignin into 2-pyrone-4-6-dicarboxylic acid with Novosphingobium aromaticivorans", Green Chemistry, 2019, vol. 9, pp. 1340-1350.
Rahimi et al., "Formic-acid-induced depolymerization of oxidized lignin to aromatics", Nature, 2014, vol. 515, No. 7526, pp. 249-252.
Salvachúa et al., "Towards lignin consolidated bioprocessing simultaneous lignin depolymerization and product generation by bacteria", Green Chemistry, 2015, vol. 17, No. 11, pp. 4951-4967.
Salvachúa et al., "Lignin depolymerization by fungal secretomes and a microbial sink", 2016, Green Chemistry, vol. 18, No. 22, pp. 6046-6062.
Salvachúa et al., "Bioprocess development for muconic acid production from aromatic compounds and lignin", Green Chemistry, 2018, vol. 20, pp. 5007-5019.
Salvachúa et al., "Outer membrane vesicles catabolize lignin-derived aromatic compounds in Pseudomonas putida KT2440", PNAS, 2020, vol. 117, No. 17, pp. 9302-9310.
Salvachúa et al., "Metabolic engineering of Pseudomonas putida for increased polyhydroxyalkanoate production from lignin", Microbial Biotechnology, 2020, vol. 13, No. 1, pp. 290-298.
Senavirathne et al., "Expression and purification of nuclease-free protocatechuate 3,4-dioxygenase for prolonged single-molecule fluorescence imaging", Analytical Biochemistry, 2018, vol. 556, pp. 78-84.
Simon et al., "Comprehensive proteome analysis of the response of Pseudomonas putida KT2440 to the flavor compound vanillin", Journal of Proteomics, 2014, vol. 109, pp. 212-227.
Sonoki et al., "Glucose-Free cis, cis-Muconic Acid Production via New Metabolic Designs Corresponding to the Heterogeneity of Lignin", ACS Sustainable Chemistry & Engineering, 2018, vol. 6, No. 1, pp. 1256-1264.
Sze et al., "Degradation of substituted mandelic acids by meta fission reactions", Journal of Bacteriology, 1987, vol. 169, No. 8, pp. 3833-3835.

(56) References Cited

OTHER PUBLICATIONS

Vardon et al., "Adipic acid production from lignin", Energy & Environmental Science, 2015, vol. 8, No. 2, pp. 617-628.

* cited by examiner

SEQUENCE LISTING

```
<160> NUMBER OF SEQ ID NOS: 64

<210> SEQ ID NO 1
<211> LENGTH: 720
<212> TYPE: DNA
<213> ORGANISM: Pseudomonas putida

<400> SEQUENCE: 1
atgcccgccc aggacaacag ccgcttcgtg atccgtgatc gcaactggca ccctaaagcc      60
cttacgcctg actacaagac ctccgttgcc cgctcgccgc gccaggcact ggtcagcatt     120
ccgcagtcga tcagcgaaac cactggtccg gactttccc atctgggctt cggcgcccac     180
gaccatgacc tgctgctgaa cttcaataac ggtggcctgc ccattggcga gcgcatcatc     240
gtcgccggcc gtgtcgtcga ccagtacggc aagcctgtgc cgaacacttt ggtggagatg     300
tggcaagcca acgccggcgg ccgctatcgc cacaagaacg atcgctacct ggcgcccctg     360
gacccgaact tcggtggtgt tgggcggtgt ctgaccgacc gtgacggcta ttacagcttc     420
cgcaccatca agccgggccc gtacccatgg cgcaacggcc cgaacgactg gcgcccggcg     480
catatccact tcgccatcag cggcccatcg atcgccacca agctgatcac ccagttgtac     540
ttcgaaggtg acccgctgat cccgatgtgc ccgatcgtca agtcgatcgc caacccgcaa     600
```

```
gccgtgcagc agttgatcgc caagctcgac atgagcaacg ccaacccgat ggactgcctg      660
gcctaccgct ttgacatcgt gctgcgcggc cagcgcaaga cccacttcga aaactgctga      720
```

<210> SEQ ID NO 2
<211> LENGTH: 239
<212> TYPE: PRT
<213> ORGANISM: Pseudomonas putida

<400> SEQUENCE: 2

```
Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser Val Ala Arg Ser
            20                  25                  30

Pro Arg Gln Ala Leu Val Ser Ile Pro Gln Ser Ile Ser Glu Thr Thr
        35                  40                  45

Gly Pro Asp Phe Ser His Leu Gly Phe Gly Ala His Asp His Asp Leu
    50                  55                  60

Leu Leu Asn Phe Asn Asn Gly Gly Leu Pro Ile Gly Glu Arg Ile Ile
65                  70                  75                  80

Val Ala Gly Arg Val Val Asp Gln Tyr Gly Lys Pro Val Pro Asn Thr
                85                  90                  95

Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
        115                 120                 125

Arg Cys Leu Thr Asp Arg Asp Gly Tyr Tyr Ser Phe Arg Thr Ile Lys
    130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Gln Leu Ile Ala Lys
        195                 200                 205

Leu Asp Met Ser Asn Ala Asn Pro Met Asp Cys Leu Ala Tyr Arg Phe
    210                 215                 220

Asp Ile Val Leu Arg Gly Gln Arg Lys Thr His Phe Glu Asn Cys
225                 230                 235
```

<210> SEQ ID NO 3
<211> LENGTH: 606
<212> TYPE: DNA
<213> ORGANISM: Pseudomonas putida

<400> SEQUENCE: 3

```
atgccaatcg aactgctgcc ggaaacccct tcgcagactg ccggccccta cgtgcacatc       60
ggcctggccc tggaagccgc cggcaaccCG accgcgacc aggaaatctg gaactgcctg      120
gccaagccag cgccccggg cgagcacatt ctgctgatcg ccacgtata tgacggaaac      180 ggccacctgg tgcgcgactc gttcctggaa gtgtggcagg ccgacgccaa cggtgagtac      240
caggatgcct acaacctgga aaacgccttc aacagctttg ccgcacggc taccaccttc      300 gatgccggtg agtggacgct gcaaacggtc aagccgggtg tggtgaacaa cgctgctggc      360
gtgccgatgg cgccgcacat caacatcagc ctgtttgccc gtggcatcaa catccacctg      420
```

-continued

```
cacacgcgcc tgtatttcga tgatgaggcc caggccaatg ccaagtgccc ggtgctcaac    480
ctgatcgagc agccgcagcg gcgtgaaacc ttgattgcca agcgttgcga agtggatggg    540
aagacggcgt accgctttga tatccgcatt caggggggaag gggagaccgt cttcttcgac   600
ttctga                                                               606
```

<210> SEQ ID NO 4
<211> LENGTH: 201
<212> TYPE: PRT
<213> ORGANISM: Pseudomonas putida

<400> SEQUENCE: 4

```
Met Pro Ile Glu Leu Leu Pro Glu Thr Pro Ser Gln Thr Ala Gly Pro
1               5                   10                  15

Tyr Val His Ile Gly Leu Ala Leu Glu Ala Ala Gly Asn Pro Thr Arg
            20                  25                  30

Asp Gln Glu Ile Trp Asn Cys Leu Ala Lys Pro Asp Ala Pro Gly Glu
        35                  40                  45

His Ile Leu Leu Ile Gly His Val Tyr Asp Gly Asn Gly His Leu Val
    50                  55                  60

Arg Asp Ser Phe Leu Glu Val Trp Gln Ala Asp Ala Asn Gly Glu Tyr
65                  70                  75                  80

Gln Asp Ala Tyr Asn Leu Glu Asn Ala Phe Asn Ser Phe Gly Arg Thr
                85                  90                  95

Ala Thr Thr Phe Asp Ala Gly Glu Trp Thr Leu Gln Thr Val Lys Pro
            100                 105                 110

Gly Val Val Asn Asn Ala Ala Gly Val Pro Met Ala Pro His Ile Asn
        115                 120                 125

Ile Ser Leu Phe Ala Arg Gly Ile Asn Ile His Leu His Thr Arg Leu
    130                 135                 140

Tyr Phe Asp Asp Glu Ala Gln Ala Asn Ala Lys Cys Pro Val Leu Asn
145                 150                 155                 160

Leu Ile Glu Gln Pro Gln Arg Arg Glu Thr Leu Ile Ala Lys Arg Cys
                165                 170                 175

Glu Val Asp Gly Lys Thr Ala Tyr Arg Phe Asp Ile Arg Ile Gln Gly
            180                 185                 190

Glu Gly Glu Thr Val Phe Phe Asp Phe
        195                 200
```

<210> SEQ ID NO 5
<211> LENGTH: 420
<212> TYPE: DNA
<213> ORGANISM: Pseudomonas putida

<400> SEQUENCE: 5

```
atgaccgaga agaaagaacg catcgacgtg cacgcctacc tggccgagtt cgacgacatc    60
ccaggcaccc gtgtgttcac cgcccagcgt gcccgtaagg gctacaacct gaaccagttc   120
gccatgagcc tgatgaaggc cgagaaccgc gagcgcttca aggccgacga gagcgcctac   180
ctggacgaat ggaacctgac cccagccgcc aaagccgccg tgctggcccg tgactacaac   240
gccatgatcg acgagggtgg caacgtgtac ttcctgagca agctgttcag caccgacggc   300
aagagcttcc agttcgccgc cggtagcatg accggcatga cccaagagga atacgcccag   360
atgatgatcg atggcggtcg cagcccagcc ggtgtgcgca gcatcaaggg tggctactga   420
```

<210> SEQ ID NO 6

```
<211> LENGTH: 139
<212> TYPE: PRT
<213> ORGANISM: Pseudomonas putida

<400> SEQUENCE: 6

Met Thr Glu Lys Lys Glu Arg Ile Asp Val His Ala Tyr Leu Ala Glu
1               5                   10                  15

Phe Asp Asp Ile Pro Gly Thr Arg Val Phe Thr Ala Gln Arg Ala Arg
            20                  25                  30

Lys Gly Tyr Asn Leu Asn Gln Phe Ala Met Ser Leu Met Lys Ala Glu
        35                  40                  45

Asn Arg Glu Arg Phe Lys Ala Asp Glu Ser Ala Tyr Leu Asp Glu Trp
    50                  55                  60

Asn Leu Thr Pro Ala Ala Lys Ala Ala Val Leu Ala Arg Asp Tyr Asn
65                  70                  75                  80

Ala Met Ile Asp Glu Gly Gly Asn Val Tyr Phe Leu Ser Lys Leu Phe
                85                  90                  95

Ser Thr Asp Gly Lys Ser Phe Gln Phe Ala Ala Gly Ser Met Thr Gly
            100                 105                 110

Met Thr Gln Glu Glu Tyr Ala Gln Met Met Ile Asp Gly Gly Arg Ser
        115                 120                 125

Pro Ala Gly Val Arg Ser Ile Lys Gly Gly Tyr
    130                 135

<210> SEQ ID NO 7
<211> LENGTH: 909
<212> TYPE: DNA
<213> ORGANISM: Pseudomonas putida

<400> SEQUENCE: 7
atggcccgtg tgaccaccgg catcaccagc agccacatcc agccctgggt gccgccatc      60 caaaccggca ccagcgacaa cgactactgg ggtccggtgt tcaagggcta ccagccgatc    120
cgcgactgga tcaagcagcc aggcaacatg ccggacgtgt tgatcctggt gtacaacgac    180
cacgccagcg ccttcgacat gaacatcatc ccgaccttcg ccatcggctg cgccgaaacc    240
ttcaagccag ccgacgaggg ctggggtccg cgtccagtgc cggatgtgaa gggccatccg    300
gacctggcct ggcatatcgc ccagagcctg atcctggacg aattcgatat gaccatcatg    360
aaccagatgg acgtggacca cggctgcacc gtgccgctga gcatgatctt cggcgagccg    420
gaagagtggc cgtgcaaggt gatcccgttc ccggtgaacg tggtgaccta tcgccaccg    480 agcggcaagc gctgcttcgc cctgggcgac agcatccgtg ccgccgtgga agcttccc      540 gaggacctga acgtgcacgt gtggggcacc ggtggcatgt cgcaccagct gcaaggtccg    600
cgtgccggtc tgatcaacaa agagttcgac ctgaacttca tcgacaagct gatcagcgac    660
ccggaagaac tgagcaagat gccgcacatc cagtacctgc gcgagagcgg cagcgagggc    720
gtggaactgg tgatgtggct gatcatgcgt ggtgccctgc ggaaaaggt gcgcgacctg     780 tacaccttct accatatccc agccagcaac accgcgctgg gtgccatgat cctgcagccg    840
gaagaaaccg ccggcacccc actggaaccg cgtaaggtga tgagcggtca cagcctggcc    900
caggcctga                                                            909

<210> SEQ ID NO 8
<211> LENGTH: 302
<212> TYPE: PRT
<213> ORGANISM: Pseudomonas putida
```

<400> SEQUENCE: 8

Met Ala Arg Val Thr Thr Gly Ile Thr Ser Ser His Ile Pro Ala Leu
1               5                   10                  15

Gly Ala Ala Ile Gln Thr Gly Thr Ser Asp Asn Asp Tyr Trp Gly Pro
            20                  25                  30

Val Phe Lys Gly Tyr Gln Pro Ile Arg Asp Trp Ile Lys Gln Pro Gly
        35                  40                  45

Asn Met Pro Asp Val Val Ile Leu Val Tyr Asn Asp His Ala Ser Ala
    50                  55                  60

Phe Asp Met Asn Ile Ile Pro Thr Phe Ala Ile Gly Cys Ala Glu Thr
65                  70                  75                  80

Phe Lys Pro Ala Asp Glu Gly Trp Gly Pro Arg Pro Val Pro Asp Val
                85                  90                  95

Lys Gly His Pro Asp Leu Ala Trp His Ile Ala Gln Ser Leu Ile Leu
            100                 105                 110

Asp Glu Phe Asp Met Thr Ile Met Asn Gln Met Asp Val Asp His Gly
        115                 120                 125

Cys Thr Val Pro Leu Ser Met Ile Phe Gly Glu Pro Glu Glu Trp Pro
130                 135                 140

Cys Lys Val Ile Pro Phe Pro Val Asn Val Val Thr Tyr Pro Pro Pro
145                 150                 155                 160

Ser Gly Lys Arg Cys Phe Ala Leu Gly Asp Ser Ile Arg Ala Ala Val
                165                 170                 175

Glu Ser Phe Pro Glu Asp Leu Asn Val His Val Trp Gly Thr Gly Gly
            180                 185                 190

Met Ser His Gln Leu Gln Gly Pro Arg Ala Gly Leu Ile Asn Lys Glu
        195                 200                 205

Phe Asp Leu Asn Phe Ile Asp Lys Leu Ile Ser Asp Pro Glu Glu Leu
210                 215                 220

Ser Lys Met Pro His Ile Gln Tyr Leu Arg Glu Ser Gly Ser Glu Gly
225                 230                 235                 240

Val Glu Leu Val Met Trp Leu Ile Met Arg Gly Ala Leu Pro Glu Lys
                245                 250                 255

Val Arg Asp Leu Tyr Thr Phe Tyr His Ile Pro Ala Ser Asn Thr Ala
            260                 265                 270

Leu Gly Ala Met Ile Leu Gln Pro Glu Glu Thr Ala Gly Thr Pro Leu
        275                 280                 285

Glu Pro Arg Lys Val Met Ser Gly His Ser Leu Ala Gln Ala
290                 295                 300

<210> SEQ ID NO 9
<211> LENGTH: 948
<212> TYPE: DNA
<213> ORGANISM: Pseudomonas putida

<400> SEQUENCE: 9
atgcgtatcg ccctggccgg tgccggtgcc ttcggcgaaa agcatctgga cggcctgaag    60
aacatcgacg gcgtggaaat cgtgagcatc atcagccgca aggccgagca agccgccgag   120
gtggccgcca agtacggtgc caaacacagc ggcaccgacc tgagcgaagc cctggccgt    180 gatgacgtgg acgccgtgat cctgtgcacc ccgacccaga tgcacgccga gcaagcgatc   240
gcctgcatga cgccggtaa gcacgtgcag gtcgagatcc cgctggccga cagctgggcc   300
gacgccgagg ccgtgatgaa gaagtcgcaa gaaaccggtc tggtgtgcat ggtgggccac   360

```
acccgtcgct tcaacccgag ccaccagtac atccacaaca agatcgtggc cggtgagctg      420
gccatccagc agatggacgt ccagacctac ttcttccgtc gcaagaacat gaacgccaag      480
ggcgaaccgc gtagctggac cgaccatctg ctgtggcacc atgccgccca caccgtggac      540
ctgttcgcct accaagccgg taagatcgtc caggccaacg ccgtgcaggg tccgatccac      600
ccggaactgg gtatcgccat ggacatgagc atccagctga agtcggaaac cggtgccatc      660
tgcaccctga gcctgagctt caacaacgac ggtccgctgg gcaccttctt ccgctacatc      720
tgcgacaacg gcacctggat cgcccgttac gacgacctgg tgaccggcaa agaggaaccg      780
gtcgacgtca gcaaggtgga cgtgagcatg aacggcatcg agctgcagga ccgcgagttc      840
atcgccgcca tccgcgaagg ccgtgagccg aacagcagcg tggcccgtgt gctggactgc      900
taccgcgtgc tgggcgagct ggaagtgcag ctggaaaagc agggctga                  948
```

<210> SEQ ID NO 10
<211> LENGTH: 315
<212> TYPE: PRT
<213> ORGANISM: Pseudomonas putida

<400> SEQUENCE: 10

```
Met Arg Ile Ala Leu Ala Gly Ala Gly Ala Phe Gly Glu Lys His Leu
1               5                   10                  15

Asp Gly Leu Lys Asn Ile Asp Gly Val Glu Ile Val Ser Ile Ile Ser
            20                  25                  30

Arg Lys Ala Glu Gln Ala Ala Glu Val Ala Ala Lys Tyr Gly Ala Lys
        35                  40                  45

His Ser Gly Thr Asp Leu Ser Glu Ala Leu Ala Arg Asp Asp Val Asp
    50                  55                  60

Ala Val Ile Leu Cys Thr Pro Thr Gln Met His Ala Glu Gln Ala Ile
65                  70                  75                  80

Ala Cys Met Asn Ala Gly Lys His Val Gln Val Glu Ile Pro Leu Ala
                85                  90                  95

Asp Ser Trp Ala Asp Ala Glu Ala Val Met Lys Lys Ser Gln Glu Thr
            100                 105                 110

Gly Leu Val Cys Met Val Gly His Thr Arg Arg Phe Asn Pro Ser His
        115                 120                 125

Gln Tyr Ile His Asn Lys Ile Val Ala Gly Glu Leu Ala Ile Gln Gln
    130                 135                 140

Met Asp Val Gln Thr Tyr Phe Phe Arg Arg Lys Asn Met Asn Ala Lys
145                 150                 155                 160

Gly Glu Pro Arg Ser Trp Thr Asp His Leu Leu Trp His His Ala Ala
                165                 170                 175

His Thr Val Asp Leu Phe Ala Tyr Gln Ala Gly Lys Ile Val Gln Ala
            180                 185                 190

Asn Ala Val Gln Gly Pro Ile His Pro Glu Leu Gly Ile Ala Met Asp
        195                 200                 205

Met Ser Ile Gln Leu Lys Ser Glu Thr Gly Ala Ile Cys Thr Leu Ser
    210                 215                 220

Leu Ser Phe Asn Asn Asp Gly Pro Leu Gly Thr Phe Phe Arg Tyr Ile
225                 230                 235                 240

Cys Asp Asn Gly Thr Trp Ile Ala Arg Tyr Asp Asp Leu Val Thr Gly
                245                 250                 255

Lys Glu Glu Pro Val Asp Val Ser Lys Val Asp Val Ser Met Asn Gly
            260                 265                 270
```

```
Ile Glu Leu Gln Asp Arg Glu Phe Ile Ala Ala Ile Arg Glu Gly Arg
            275                 280                 285

Glu Pro Asn Ser Ser Val Ala Arg Val Leu Asp Cys Tyr Arg Val Leu
        290                 295                 300

Gly Glu Leu Glu Val Gln Leu Glu Lys Gln Gly
305                 310                 315

<210> SEQ ID NO 11
<211> LENGTH: 1065
<212> TYPE: DNA
<213> ORGANISM: Pseudomonas putida

<400> SEQUENCE: 11
atgtttccga aaacgcatg gtatgtggcg tgtacgccgg atgaaatcgc agataaaccg      60
ctgggccgcc aaatctgcaa cgaaaaaatc gtgttttatc gcgggcccga gggtcgtgtg     120
gccgctgtcg aggactttg tccacaccgt gggcccac tctcgctggg tttcgtccgg       180
gatggcaagc tcatctgcgg ttatcacggt ttggagatgg ggtgcgaggg taaaaccctc    240
gctatgccgg ccagcgcgt gcagggtttt ccttgtatta agtcgtacgc tgtcgaggag    300
cggtatgggt ttatctgggt ctggcctggt gatcgtgaac tggccgaccc tgctttgatt   360
caccatttgg agtgggcaga caacccggag tgggcttacg gcgggggctt gtatcatatt    420
gcatgcgact accggctgat gattgacaac ctgatggact tgaccacga gacctatgtg    480
cacgcatcct ccatcggtca gaagagatt gatgaggccc cggtgagcac ccgcgtcgaa    540
ggggacacgg tgattacctc ccggtacatg gacaacgtca tggccccgcc gttctggcgc   600
gctgccttgc gtggcaatgg gctcgccgat gatgtcccag tggatcgctg caaatctgt    660
cgtttcgcgc caccatcgca tgtcctcatc gaagtgggcg tggcacatgc tggcaaaggg   720
ggttatgatg cccctgccga atacaaagcc ggctcgatcg tcgtcgattt tattacgcca    780
gagtcggaca cgagcatttg gtacttttgg ggcatggctc gcaattttcg tccccaaggt   840
acggagttga cggagaccat tcgtgtcggg caaggcaaga tctttgcgga agacctggac    900
atgctggagc agcagcagcg gaacttgctg gcctatcctg agcggcaact cctgaaactc    960
aatatcgatg ctgggggcgt gcaatcgcgt cgggtgatcg atcgcattct ggcggctgaa   1020
caagaagctg cggatgcggc cctgatcgct cgttcggcga gctga                   1065

<210> SEQ ID NO 12
<211> LENGTH: 354
<212> TYPE: PRT
<213> ORGANISM: Pseudomonas putida

<400> SEQUENCE: 12

Met Phe Pro Lys Asn Ala Trp Tyr Val Ala Cys Thr Pro Asp Glu Ile
1               5                   10                  15

Ala Asp Lys Pro Leu Gly Arg Gln Ile Cys Asn Glu Lys Ile Val Phe
            20                  25                  30

Tyr Arg Gly Pro Glu Gly Arg Val Ala Ala Val Glu Asp Phe Cys Pro
        35                  40                  45

His Arg Gly Ala Pro Leu Ser Leu Gly Phe Val Arg Asp Gly Lys Leu
    50                  55                  60

Ile Cys Gly Tyr His Gly Leu Glu Met Gly Cys Glu Gly Lys Thr Leu
65                  70                  75                  80

Ala Met Pro Gly Gln Arg Val Gln Gly Phe Pro Cys Ile Lys Ser Tyr
                85                  90                  95
```

Ala Val Glu Glu Arg Tyr Gly Phe Ile Trp Val Trp Pro Gly Asp Arg
            100                 105                 110

Glu Leu Ala Asp Pro Ala Leu Ile His His Leu Glu Trp Ala Asp Asn
        115                 120                 125

Pro Glu Trp Ala Tyr Gly Gly Leu Tyr His Ile Ala Cys Asp Tyr
    130                 135                 140

Arg Leu Met Ile Asp Asn Leu Met Asp Leu Thr His Glu Thr Tyr Val
145                 150                 155                 160

His Ala Ser Ser Ile Gly Gln Lys Glu Ile Asp Glu Ala Pro Val Ser
                165                 170                 175

Thr Arg Val Glu Gly Asp Thr Val Ile Thr Ser Arg Tyr Met Asp Asn
            180                 185                 190

Val Met Ala Pro Pro Phe Trp Arg Ala Ala Leu Arg Gly Asn Gly Leu
        195                 200                 205

Ala Asp Asp Val Pro Val Asp Arg Trp Gln Ile Cys Arg Phe Ala Pro
    210                 215                 220

Pro Ser His Val Leu Ile Glu Val Gly Val Ala His Ala Gly Lys Gly
225                 230                 235                 240

Gly Tyr Asp Ala Pro Ala Glu Tyr Lys Ala Gly Ser Ile Val Val Asp
                245                 250                 255

Phe Ile Thr Pro Glu Ser Asp Thr Ser Ile Trp Tyr Phe Trp Gly Met
            260                 265                 270

Ala Arg Asn Phe Arg Pro Gln Gly Thr Glu Leu Thr Glu Thr Ile Arg
        275                 280                 285

Val Gly Gln Gly Lys Ile Phe Ala Glu Asp Leu Asp Met Leu Glu Gln
    290                 295                 300

Gln Gln Arg Asn Leu Leu Ala Tyr Pro Glu Arg Gln Leu Leu Lys Leu
305                 310                 315                 320

Asn Ile Asp Ala Gly Gly Val Gln Ser Arg Arg Val Ile Asp Arg Ile
                325                 330                 335

Leu Ala Ala Glu Gln Glu Ala Ala Asp Ala Ala Leu Ile Ala Arg Ser
            340                 345                 350

Ala Ser

<210> SEQ ID NO 13
<211> LENGTH: 954
<212> TYPE: DNA
<213> ORGANISM: Pseudomonas putida

<400> SEQUENCE: 13
atgattgagg tgattatttc ggcgatgcgc ctggtcgccc aagatattat ctcgctcgaa      60
ttcgtccgcg ctgatggcgg tttgctcccc cccgtgaaag ctggcgctca tgtcgatgtg     120
catttgcctg gcggtctcat ccgccaatac tcgctgtgga atcaacctgg ggcccaatcc     180
cactactgta ttggtgtgct gaaggatcct gcctcgcggg gtgggtcgaa agctgtgcat     240
gaaaacctcc gtgtcggtat gcgggtgcag atctcggagc tcgcaatcct ctttccattg     300
gaggaaggcg tcgagcgcag cttgctgttc gccggggga ttgggattac ccctatcctg     360
tgtatggctc aagaattggc agcccgtgaa caagatttcg aattgcatta ctgtgcgcgg     420
tcgacggatc gcgccgcctt tgtggagtgg ctcaaagtct gcgattttgc cgatcacgtc     480
cgtttccatt tcgataacgg gcccgaccaa caaaagttga acgctgctgc tctcttggca     540
gcagaggctg agggcacgca cctctatgtc tgtggtcctg ggggtttcat gggtcatgtg     600
ctggacaccg cgaaagaaca gggttgggct gataaccgct tgcatcgtga gtactttgct     660

-continued

```
gctgccccaa atgtctccgc ggatgatggt tccttcgagg tgcgtatcca ttcgacgggt    720
caggtcctgc aagtcccagc ggaccaaacc gtgtcccaag tcctggacgc tgcaggtatt    780
atcgtcccag tgagctgtga gcaaggcatt tgcggtacgt gcattacccg cgtcgtcgac    840
ggtgagcctg atcaccgcga tttcttcctg acggacgccg aaaaggcaaa aatgatcaa     900 tttacgccgt gctgttcgcg ggcgaagagc gcctgcctcg tgctggactt gtaa          954
```

<210> SEQ ID NO 14
<211> LENGTH: 317
<212> TYPE: PRT
<213> ORGANISM: Pseudomonas putida

<400> SEQUENCE: 14

```
Met Ile Glu Val Ile Ile Ser Ala Met Arg Leu Val Ala Gln Asp Ile
1               5                   10                  15

Ile Ser Leu Glu Phe Val Arg Ala Asp Gly Gly Leu Leu Pro Pro Val
                20                  25                  30

Glu Ala Gly Ala His Val Asp Val His Leu Pro Gly Gly Leu Ile Arg
            35                  40                  45

Gln Tyr Ser Leu Trp Asn Gln Pro Gly Ala Gln Ser His Tyr Cys Ile
        50                  55                  60

Gly Val Leu Lys Asp Pro Ala Ser Arg Gly Gly Ser Lys Ala Val His
65                  70                  75                  80

Glu Asn Leu Arg Val Gly Met Arg Val Gln Ile Ser Glu Pro Arg Asn
                85                  90                  95

Leu Phe Pro Leu Glu Glu Gly Val Glu Arg Ser Leu Leu Phe Ala Gly
            100                 105                 110

Gly Ile Gly Ile Thr Pro Ile Leu Cys Met Ala Gln Glu Leu Ala Ala
        115                 120                 125

Arg Glu Gln Asp Phe Glu Leu His Tyr Cys Ala Arg Ser Thr Asp Arg
130                 135                 140

Ala Ala Phe Val Glu Trp Leu Lys Val Cys Asp Phe Ala Asp His Val
145                 150                 155                 160

Arg Phe His Phe Asp Asn Gly Pro Asp Gln Gln Lys Leu Asn Ala Ala
                165                 170                 175

Ala Leu Leu Ala Ala Glu Ala Glu Gly Thr His Leu Tyr Val Cys Gly
            180                 185                 190

Pro Gly Gly Phe Met Gly His Val Leu Asp Thr Ala Lys Glu Gln Gly
        195                 200                 205

Trp Ala Asp Asn Arg Leu His Arg Glu Tyr Phe Ala Ala Pro Asn
        210                 215                 220

Val Ser Ala Asp Gly Ser Phe Glu Val Arg Ile His Ser Thr Gly
225                 230                 235                 240

Gln Val Leu Gln Val Pro Ala Asp Gln Thr Val Ser Gln Val Leu Asp
                245                 250                 255

Ala Ala Gly Ile Ile Val Pro Val Ser Cys Glu Gln Gly Ile Cys Gly
            260                 265                 270

Thr Cys Ile Thr Arg Val Val Asp Gly Glu Pro Asp His Arg Asp Phe
        275                 280                 285

Phe Leu Thr Asp Ala Glu Lys Ala Lys Asn Asp Gln Phe Thr Pro Cys
        290                 295                 300

Cys Ser Arg Ala Lys Ser Ala Cys Leu Val Leu Asp Leu
305                 310                 315
```

```
<210> SEQ ID NO 15
<211> LENGTH: 19
<212> TYPE: DNA
<213> ORGANISM: Artificial Sequence
<220> FEATURE:
<223> OTHER INFORMATION: Primer oAM204

<400> SEQUENCE: 15
aacgagaagg tcaacgtgc                                                    19

<210> SEQ ID NO 16
<211> LENGTH: 19
<212> TYPE: DNA
<213> ORGANISM: Artificial Sequence
<220> FEATURE:
<223> OTHER INFORMATION: Primer oAM205

<400> SEQUENCE: 16
ttgagcaaca cctgcttgc                                                    19

<210> SEQ ID NO 17
<211> LENGTH: 21
<212> TYPE: DNA
<213> ORGANISM: Artificial Sequence
<220> FEATURE:
<223> OTHER INFORMATION: Primer oCJ054

<400> SEQUENCE: 17
atcggctcgt ataatgtgtg g                                                 21

<210> SEQ ID NO 18
<211> LENGTH: 18
<212> TYPE: DNA
<213> ORGANISM: Artificial Sequence
<220> FEATURE:
<223> OTHER INFORMATION: Primer oCJ135

<400> SEQUENCE: 18
aggctgatgt tgatgtgc                                                     18

<210> SEQ ID NO 19
<211> LENGTH: 18
<212> TYPE: DNA
<213> ORGANISM: Artificial Sequence
<220> FEATURE:
<223> OTHER INFORMATION: Primer oCJ163

<400> SEQUENCE: 19
ttgtccagca gggttgtc                                                     18

<210> SEQ ID NO 20
<211> LENGTH: 19
<212> TYPE: DNA
<213> ORGANISM: Artificial Sequence
<220> FEATURE:
<223> OTHER INFORMATION: Primer oCJ290

<400> SEQUENCE: 20
aatacgcaaa ccgcctctc                                                    19

<210> SEQ ID NO 21
<211> LENGTH: 18
<212> TYPE: DNA
<213> ORGANISM: Artificial Sequence
<220> FEATURE:
<223> OTHER INFORMATION: Primer oCJ291
```

<400> SEQUENCE: 21
gtagctgaca ttcatccg                                            18

<210> SEQ ID NO 22
<211> LENGTH: 18
<212> TYPE: DNA
<213> ORGANISM: Artificial Sequence
<220> FEATURE:
<223> OTHER INFORMATION: Primer oCJ534

<400> SEQUENCE: 22
cctcggtgag ttttctcc                                            18

<210> SEQ ID NO 23
<211> LENGTH: 51
<212> TYPE: DNA
<213> ORGANISM: Artificial Sequence
<220> FEATURE:
<223> OTHER INFORMATION: Primer oSN099

<400> SEQUENCE: 23
agtgagcgca acgcaattaa tgtgagttag gaattcatgg cgccgccagt g        51

<210> SEQ ID NO 24
<211> LENGTH: 18
<212> TYPE: DNA
<213> ORGANISM: Artificial Sequence
<220> FEATURE:
<223> OTHER INFORMATION: Primer oSN103

<400> SEQUENCE: 24
ccactgcgcc agcgacgc                                            18

<210> SEQ ID NO 25
<211> LENGTH: 54
<212> TYPE: DNA
<213> ORGANISM: Artificial Sequence
<220> FEATURE:
<223> OTHER INFORMATION: Primer oSN223

<400> SEQUENCE: 25
gaaagtcatc ctgccctcgt cgtaagacgg ggcggccgcg ggaggctctc cggg    54

<210> SEQ ID NO 26
<211> LENGTH: 57
<212> TYPE: DNA
<213> ORGANISM: Artificial Sequence
<220> FEATURE:
<223> OTHER INFORMATION: Primer oSN224

<400> SEQUENCE: 26
taaataaaaa caaaacccgg agagcctccc gcggccgccc cgtcttacga cgagggc    57

<210> SEQ ID NO 27
<211> LENGTH: 59
<212> TYPE: DNA
<213> ORGANISM: Artificial Sequence
<220> FEATURE:
<223> OTHER INFORMATION: Primer oSN225

<400> SEQUENCE: 27
cctgagtgct tgcggcagcg tgaagctagg gatccgaggt gaactacacc ttccagagc    59

<210> SEQ ID NO 28

<211> LENGTH: 18
<212> TYPE: DNA
<213> ORGANISM: Artificial Sequence
<220> FEATURE:
<223> OTHER INFORMATION: Primer oSN226

<400> SEQUENCE: 28
gcttcaggcg agttggcg                                                18

<210> SEQ ID NO 29
<211> LENGTH: 20
<212> TYPE: DNA
<213> ORGANISM: Artificial Sequence
<220> FEATURE:
<223> OTHER INFORMATION: Primer oSN238

<400> SEQUENCE: 29
tgacctactt catgggcctg                                              20

<210> SEQ ID NO 30
<211> LENGTH: 20
<212> TYPE: DNA
<213> ORGANISM: Artificial Sequence
<220> FEATURE:
<223> OTHER INFORMATION: Primer oSN239

<400> SEQUENCE: 30
gaagttgaaa cggtccgagg                                              20

<210> SEQ ID NO 31
<211> LENGTH: 50
<212> TYPE: DNA
<213> ORGANISM: Artificial Sequence
<220> FEATURE:
<223> OTHER INFORMATION: Primer oSN234

<400> SEQUENCE: 31
agtgagcgca acgcaattaa tgtgagttag gaattcatcg gcggcgcagt             50

<210> SEQ ID NO 32
<211> LENGTH: 59
<212> TYPE: DNA
<213> ORGANISM: Artificial Sequence
<220> FEATURE:
<223> OTHER INFORMATION: Primer oSN235

<400> SEQUENCE: 32
ccgtcacacg atcaagcggg ttgcatcggg cggccgcgcc atattgctcg tctacgccc   59

<210> SEQ ID NO 33
<211> LENGTH: 58
<212> TYPE: DNA
<213> ORGANISM: Artificial Sequence
<220> FEATURE:
<223> OTHER INFORMATION: Primer oSN236

<400> SEQUENCE: 33
ttcaccctgg gcgtagacga gcaatatggc gcggccgccc gatgcaaccc gcttgatc    58

<210> SEQ ID NO 34
<211> LENGTH: 57
<212> TYPE: DNA
<213> ORGANISM: Artificial Sequence
<220> FEATURE:
<223> OTHER INFORMATION: Primer oSN237

<400> SEQUENCE: 34
ccctgagtgc ttgcggcagc gtgaagctag ggatccaggc tcatgtcctg catgctg    57

<210> SEQ ID NO 35
<211> LENGTH: 59
<212> TYPE: DNA
<213> ORGANISM: Artificial Sequence
<220> FEATURE:
<223> OTHER INFORMATION: Primer oSN267

<400> SEQUENCE: 35
ggaattgtga gcggataaca atttcacact ctagagaaca gaggactttc gcatggctc    59

<210> SEQ ID NO 36
<211> LENGTH: 54
<212> TYPE: DNA
<213> ORGANISM: Artificial Sequence
<220> FEATURE:
<223> OTHER INFORMATION: Primer oSN268

<400> SEQUENCE: 36
ttacgctgga gtctgaggct cgtcctgaat gatatctcag ttgggcgctt tgcc    54

<210> SEQ ID NO 37
<211> LENGTH: 19
<212> TYPE: DNA
<213> ORGANISM: Artificial Sequence
<220> FEATURE:
<223> OTHER INFORMATION: Primer oSN269

<400> SEQUENCE: 37
ccgcgacaag ccgctggac    19

<210> SEQ ID NO 38
<211> LENGTH: 32
<212> TYPE: DNA
<213> ORGANISM: Artificial Sequence
<220> FEATURE:
<223> OTHER INFORMATION: Primer vanA-F

<400> SEQUENCE: 38
accccatatg tatccaaaga atacctggta tg    32

<210> SEQ ID NO 39
<211> LENGTH: 25
<212> TYPE: DNA
<213> ORGANISM: Artificial Sequence
<220> FEATURE:
<223> OTHER INFORMATION: Primer vanA-R

<400> SEQUENCE: 39
tgggaagctt tcacgccgga ttcgc    25

<210> SEQ ID NO 40
<211> LENGTH: 27
<212> TYPE: DNA
<213> ORGANISM: Artificial Sequence
<220> FEATURE:
<223> OTHER INFORMATION: Primer vanB-F

<400> SEQUENCE: 40
accccatatg attgacgcag tggtcgt    27

<210> SEQ ID NO 41
<211> LENGTH: 30
<212> TYPE: DNA

<213> ORGANISM: Artificial Sequence
<220> FEATURE:
<223> OTHER INFORMATION: Primer vanB-R

<400> SEQUENCE: 41
tgggaagctt tcagatatcc agcacgagca            30

<210> SEQ ID NO 42
<211> LENGTH: 34
<212> TYPE: DNA
<213> ORGANISM: Artificial Sequence
<220> FEATURE:
<223> OTHER INFORMATION: Primer galA-F

<400> SEQUENCE: 42
tctagatcat atggctcgta tcattggtgg cctg            34

<210> SEQ ID NO 43
<211> LENGTH: 52
<212> TYPE: DNA
<213> ORGANISM: Artificial Sequence
<220> FEATURE:
<223> OTHER INFORMATION: Primer galA-R

<400> SEQUENCE: 43
tgtctcgaga ttggattgga agtacaggtt ctcgttgggc gctttgccag cc            52

<210> SEQ ID NO 44
<211> LENGTH: 24
<212> TYPE: DNA
<213> ORGANISM: Artificial Sequence
<220> FEATURE:
<223> OTHER INFORMATION: Primer pcaH-F

<400> SEQUENCE: 44
ttccaatcca atatgcccgc ccag            24

<210> SEQ ID NO 45
<211> LENGTH: 27
<212> TYPE: DNA
<213> ORGANISM: Artificial Sequence
<220> FEATURE:
<223> OTHER INFORMATION: Primer pcaH-R

<400> SEQUENCE: 45
caccatgcga tcgcagagaa cctgtac            27

<210> SEQ ID NO 46
<211> LENGTH: 22
<212> TYPE: DNA
<213> ORGANISM: Artificial Sequence
<220> FEATURE:
<223> OTHER INFORMATION: Primer Ht-pcaH_fw

<400> SEQUENCE: 46
aggcgtatca cgaggcccttt tc            22

<210> SEQ ID NO 47
<211> LENGTH: 20
<212> TYPE: DNA
<213> ORGANISM: Artificial Sequence
<220> FEATURE:
<223> OTHER INFORMATION: Primer pcaH-i_fw

<400> SEQUENCE: 47
gcacaagaac gaccgttacc            20

<210> SEQ ID NO 48
<211> LENGTH: 20
<212> TYPE: DNA
<213> ORGANISM: Artificial Sequence
<220> FEATURE:
<223> OTHER INFORMATION: Primer PcaG-i_rv

<400> SEQUENCE: 48
tgggcttcat catcgaagta                                          20

<210> SEQ ID NO 49
<211> LENGTH: 21
<212> TYPE: DNA
<213> ORGANISM: Artificial Sequence
<220> FEATURE:
<223> OTHER INFORMATION: Primer oAW093

<400> SEQUENCE: 49
gcattgacct accacgccga c                                        21

<210> SEQ ID NO 50
<211> LENGTH: 21
<212> TYPE: DNA
<213> ORGANISM: Artificial Sequence
<220> FEATURE:
<223> OTHER INFORMATION: Primer oAW094

<400> SEQUENCE: 50
cccaaccgct gaactgttcg g                                        21

<210> SEQ ID NO 51
<211> LENGTH: 23
<212> TYPE: DNA
<213> ORGANISM: Artificial Sequence
<220> FEATURE:
<223> OTHER INFORMATION: Primer oAW099

<400> SEQUENCE: 51
gcacataggt ctcgtgggtc aag                                      23

<210> SEQ ID NO 52
<211> LENGTH: 26
<212> TYPE: DNA
<213> ORGANISM: Artificial Sequence
<220> FEATURE:
<223> OTHER INFORMATION: Primer oAW100

<400> SEQUENCE: 52
gaccaacaaa agttgaacgc tgctgc                                   26

<210> SEQ ID NO 53
<211> LENGTH: 21
<212> TYPE: DNA
<213> ORGANISM: Artificial Sequence
<220> FEATURE:
<223> OTHER INFORMATION: Primer oAW101

<400> SEQUENCE: 53
ggatcgctgg caaatctgtc g                                        21

<210> SEQ ID NO 54
<211> LENGTH: 24
<212> TYPE: DNA
<213> ORGANISM: Artificial Sequence
<220> FEATURE:

```
<223> OTHER INFORMATION: Primer oAW102

<400> SEQUENCE: 54
tgtatggctc aagaattggc agcc                                              24

<210> SEQ ID NO 55
<211> LENGTH: 20
<212> TYPE: DNA
<213> ORGANISM: Artificial Sequence
<220> FEATURE:
<223> OTHER INFORMATION: Primer T7_fw

<400> SEQUENCE: 55
taatacgact cactataggg                                                   20

<210> SEQ ID NO 56
<211> LENGTH: 19
<212> TYPE: DNA
<213> ORGANISM: Artificial Sequence
<220> FEATURE:
<223> OTHER INFORMATION: Primer T7_rv

<400> SEQUENCE: 56
gctagttatt gctcagcgg                                                    19

<210> SEQ ID NO 57
<211> LENGTH: 1089
<212> TYPE: DNA
<213> ORGANISM: Pseudomonas putida

<400> SEQUENCE: 57
atgtatccaa agaatacctg gtatgttgcg tgtacgccag atgaaattgc tactaagccg       60
ctgggccgtc aaatctgtgg cgagaaaatc gttttctacc gtgcacgtga gaatcaagtc      120
gcggccgttg aagatttctg cccgcatcgc ggtgcgccgc tgagcctggg ttacgtggaa      180
gatggcaacc tggtttgcgg ttaccacggc tggtcatgg gctgcgatgg taagaccgtg       240
agcatgccgg gtcaacgtgt ccgcggtttt ccgtgcaata aaaccttcgc agccgtggaa      300
cgttacggtt ttatctgggt ctggccgggt gaccaagcgc aggcagaccc ggctctgatc      360
ccgcacctgg agtgggcagt gtccgatgag tgggcgtacg gtggcggcct gttccatatt      420
ggttgcgact accgcttgat gatcgacaac ctgatggact tgacccacga acgtatgtt       480
cacgccagca gcattggtca gaaagaaatc gacgaagcgc cgccggttac gacggtcacc      540
ggcgacgaag ttgtgactgc ccgtcacatg gaaaacatta tggcgcctcc gttctggcgt      600
atggcactgc gcggtaatgg tctggcggac gacgtgccgg tggaccgttg gcagatttgt      660
cgctttaccc ctccgtcgca cgttttgatt gaggtcggcg tcgcccatgc tggtaagggt      720
ggctatcacg ctgaggcaca acataaagcg agctccatcg ttgtggattt catcaccccg      780
gagagcgaca cctctatttg gtacttttgg ggcatggcgc gcaactttgc agcacacgat      840
cagaccctga cggataatat tcgcgagggt cagggtaaga tcttcagcga agatctggaa      900
atgctggagc gtcagcaaca aaacctgtta gcgcatccgg agcgtaacct cctgaaactg      960
aacattgatg ccggtggcgt gcagagccgt aaggtactgg agcgcatcat tgcccaagag     1020
cgtgcgccgc agccgcagct gattgcgacg agcgcgaatc cggcgggtca tcaccaccac     1080
caccattga                                                             1089

<210> SEQ ID NO 58
<211> LENGTH: 972
```

```
<212> TYPE: DNA
<213> ORGANISM: Pseudomonas putida

<400> SEQUENCE: 58
atgattgacg cagtggtcgt gtcccgcaat gatgaagcac aaggaatctg ttcgttcgag    60
ctcgcggcgg ccgacggcag cctgctgccc gcgttcagcg ccggggccca tatcgacgtg   120
catctgcccg atggcttggt ccgacagtat agcctctgca accaccctga ggaacgccac   180
agatacctga tcgtgtcct caacgaccct gcgagccggg gcggatcccg gtcactgcat    240
gaacaagtgc aggccggtgc caggctccgg atctccgccc gcggaacttt gtttcctctg   300
gccgagggcg cccagaggtc cctgctgttc gcgggcggaa tcggcatcac tccaatcctg   360
tgcatggccg aacagctgtc cgactccgga caggcctttg agctccacta ctgtgcccgc   420
tcatccgaga gagcagcctt cgtggaacgg attagatccg ctcctttcgc ggaccgcctg   480
tttgtgcact cgacgagca gcccgagact gccctggata ttgcgcaagt gctgggaaac   540
ccgcaggacg atgtgcacct ctacgtgtgc ggccccgggg gcttcatgca acacgtgctg   600
gattccgcca agggactggg gtggcaggaa gccaaccttc accgggaata cttcgccgcc   660
gcaccggtgg acgcctccaa tgatggatcg ttcgctgtgc aagtcgggtc aaccggacaa   720
gtgttcgaag tgccggccga ccgcaccgtg gtccaagtgc ttgaagagaa cggaatcgaa   780
atcgctatgt cgtgcgaaca gggaatttgc ggtacctgtc tgactcgggt gctgcagggt   840 accccccgacc accgggacct tttcctgacc gaagaggaac aggctctgaa cgaccagttc   900
accccatgct gctcgaggtc taagaccccg ctgctcgtgc tggatatcgg tcatcaccac   960
caccaccatt ga                                                       972

<210> SEQ ID NO 59
<211> LENGTH: 1085
<212> TYPE: DNA
<213> ORGANISM: Pseudomonas putida

<400> SEQUENCE: 59
accccatatg tatccaaaga atacctggta tgttgcgtgt acgccagatg aaattgctac    60
taagccgctg ggccgtcaaa tctgtggcga gaaaatcgtt ttctaccgtg cacgtgagaa   120
tcaagtcgcg gccgttgaag atttctgccc gcatcgcggt gcgccgctga gcctgggtta   180
cgtggaagat ggcaacctgg tttgcggtta ccacggcctg gtcatgggct gcgatggtaa   240
gaccgtgagc atgccgggtc aacgtgtccg cggttttccg tgcaataaaa ccttcgcagc   300
cgtggaacgt tacggtttta tctgggtctg gccgggtgac caagcgcagg cagacccggc   360
tctgatcccg cacctggagt gggcagtgtc cgatgagtgg gcgtacggtg gcggcctgtt   420
ccatattggt tgcgactacc gcttgatgat cgacaacctg atggacttga cccacgaaac   480
gtatgttcac gccagcagca ttggtcagaa agaaatcgac gaagcgccgc cggttacgac   540
ggtcaccggc gacgaagttg tgactgcccg tcacatggaa acattatggg cgcctccgtt   600
ctggcgtatg gcactgcgcg gtaatggtct ggcggacgac gtgccggtgg accgttggca   660
gatttgtcgc tttaccccctc cgtcgcacgt tttgattgag gtcggcgtcg cccatgctgg   720 taaggggtggc tatcacgctg aggcacaaca taaagcgagc tccatcgttg tggatttcat   780
caccccggag agcgacacct ctatttggta cttttgggggc atggcgcgca actttgcagc   840
acacgatcag accctgacgg ataatattcg cgagggtcag ggtaagatct tcagcgaaga   900
tctggaaatg ctggagcgtc agcaacaaaa cctgttagcg catccggagc gtaacctcct   960
```

-continued

| | |
|---|---:|
| gaaactgaac attgatgccg gtggcgtgca gagccgtaag gtactggagc gcatcattgc | 1020 |
| ccaagagcgt gcgccgcagc cgcagctgat tgcgacgagc gcgaatccgg cgggtaagct | 1080 |
| tccca | 1085 |

<210> SEQ ID NO 60
<211> LENGTH: 989
<212> TYPE: DNA
<213> ORGANISM: Pseudomonas putida

<400> SEQUENCE: 60

| | |
|---|---:|
| accccatatg attgacgcag tggtcgtgtc ccgcaatgat gaagcacaag gaatctgttc | 60 |
| gttcgagctc gcggcggccg acggcagcct gctgcccgcg ttcagcgccg gggcccatat | 120 |
| cgacgtgcat ctgcccgatg gcttggtccg acagtatagc ctctgcaacc accctgagga | 180 |
| acgccacaga tacctgatcg gtgtcctcaa cgaccctgcg agccggggcg atcccggtc | 240 |
| actgcatgaa caagtgcagg ccggtgccag gctccggatc tccgccccgc ggaacttgtt | 300 |
| tcctctggcc gagggcgccc agaggtccct gctgttcgcg gcggaatcg gcatcactcc | 360 |
| aatcctgtgc atggccgaac agctgtccga ctccggacag gcctttgagc tccactactg | 420 |
| tgcccgctca tccgagagag cagccttcgt ggaacggatt agatccgctc ctttcgcgga | 480 |
| ccgcctgttt gtgcacttcg acgagcagcc cgagactgcc ctggatattg cgcaagtgct | 540 |
| gggaaacccg caggacgatg tgcacctcta cgtgtgcggc cccgggggct tcatgcaaca | 600 |
| cgtgctggat ccgccaagg gactggggtg gcaggaagcc aaccttcacc gggaatactt | 660 |
| cgccgccgca ccgtggacg cctccaatga tggatcgttc gctgtgcaag tcgggtcaac | 720 |
| cggacaagtg ttcgaagtgc cggccgaccg caccgtggtc caagtgcttg aagagaacgg | 780 |
| aatcgaaatc gctatgtcgt gcgaacaggg aatttgcggt acctgtctga ctcgggtgct | 840 |
| gcagggtacc cccgaccacc gggaccttt cctgaccgaa gaggaacagg ctctgaacga | 900 |
| ccagttcacc ccatgctgct cgaggtctaa gaccccgctg ctcgtgctgg atatcggtca | 960 |
| tcaccaccac caccattgaa agcttccca | 989 |

<210> SEQ ID NO 61
<211> LENGTH: 1396
<212> TYPE: DNA
<213> ORGANISM: Pseudomonas putida

<400> SEQUENCE: 61

| | |
|---|---:|
| atgcatcacc atcatcacca tcaccatgcg atcgcagaga acctgtactt ccaatccaat | 60 |
| atgcccgccc aggacaacag ccgcttcgtg atccgtgatc gcaactggca ccccaaagcc | 120 |
| cttacgcctg actacaaaac gtccattgcc cgctcgccgc gccaggcact ggtcagcatt | 180 |
| ccacagtcga tcagcgaaac cactggtccg aactttttccc acctgggctt cggcgcccac | 240 |
| gaccatgacc tgctgctgaa cttcaacaac ggtggcctgc caatcggcga gcgcatcatc | 300 |
| gtggccggcc gcgtcgtcga ccagtacggc aagcctgtgc cgaacaccct ggtggagatg | 360 |
| tggcaagcca acgccggtgg ccgctaccgg cacaagaacg accgttacct ggcaccgctg | 420 |
| gacccgaact tggtggtgt cggccgttgc ctgaccgaca cgacggcta ctacagcttc | 480 |
| cgcaccatca agccgggccc gtaccctgg cgcaacggcc cgaacgactg gcgcccggcg | 540 |
| cacatccact tcggcatcag cggcccgtcg attgcgacca agctgatcac ccagttgtat | 600 |
| ttcgagggtg acccgctgat cccgatgtgc ccgatcgtca gtcgatcgc caaccctgaa | 660 |
| gctgtacagc agttgatcgc caagctcgac atgaacaacg ccaacccgat ggactgcctg | 720 |

| | |
|---|---|
| gcctaccgct tgacatcgt gctgcgcggc cagcgcaaga cccacttcga aaactgctga | 780 |
| ggaacccgcc atgccaatcg aactgctgcc ggaaacccct tcgcagaccg ccggcccta | 840 |
| cgtgcacatc ggcctggccc tggaagcggc cggcaacccg accgcgatc aggaaatctg | 900 |
| gaaccgcctg gccaagccgg acgcgccagg cgagcacatt ctgctactcg gccaggtgta | 960 |
| tgacggtaac ggccacctgg tgcgcgactc gttcctggaa gtgtggcagg ccgacgccaa | 1020 |
| tggcgagtat caggatgcct acaacctgga gaacgcttc aacagcttcg ccgcaccgc | 1080 |
| caccaccttc gatgctggcg agtggacgct gcacacggtc aagccgggtg tggtgaacaa | 1140 |
| tgctgctggc gtgccgatgg cgccgcacat caacatcagc ctgtttgccc gtggcatcaa | 1200 |
| catccacctg cacacgcgcc tgtacttcga tgatgaagcc caagccaacg ccaagtgccc | 1260 |
| ggtgctcaac ctgattgagc agccgcagcg gcgtgaaacc ttgattgcca agcgttgcga | 1320 |
| agtggatggg aaaacggcgt atcgtttcga tatccgtatt caggggaag gcgagaccgt | 1380 |
| cttcttcgac ttctga | 1396 |

<210> SEQ ID NO 62
<211> LENGTH: 1272
<212> TYPE: DNA
<213> ORGANISM: Pseudomonas putida

<400> SEQUENCE: 62

| | |
|---|---|
| catatggctc gtatcattgg tggcctggcc gtctcccaca ccccaaccat cggcttcgca | 60 |
| gtcgaccacg acaaacagga agaagccgcc tgggcgccga tcttcgaaag cttcgagccg | 120 |
| atccgcacgt ggctgcagca gcgccagccg gacgtactct tctatatctt caacgaccac | 180 |
| atcacctcgt tcttctttga ccattacagc gccttcaccc tgggcgtaga cgagcaatat | 240 |
| ggcgtggccg atgaaggggg caacccgcgg gacctgccgc cagtgggcgg ccacgcagcg | 300 |
| ctgtcgcgac acatcggcca gagcctgatg gccgatgagt tcgacatgag cttttttccgc | 360 |
| gacaagccgc tggaccacgg cttcttctcg cccatgtcgg cgctgctgcc ctgcgatgaa | 420 |
| agctggcccg tacagatcgt gccgctgcag gtcggcgtac tgcagctgcc gatacccacg | 480 |
| gcgcggcgct gctacaaact gggccaggca ttgcgccgcg ccatcgagag ctaccccgaa | 540 |
| gacctcaagg tggcgatcgt cgccaccggc ggggtgtcac accaggtgca cggcgagcgt | 600 |
| tgcggcttca acaacccaga gtgggacgcg cagttccttg acctgctggt gaacgacccg | 660 |
| cagcgcctta ccgagatgac actggccgag tacgccacgc tcggcggcat ggaaggtgcc | 720 |
| gaggtgatta cctggctgat catgcgtggc acgttgtctg ccaacgttga gcgcaagcac | 780 |
| caaagctact acctgccgtc gatgaccggc atcgccaccc tgctgctgga aaaccgtgac | 840 |
| caggcactgc cggcgccggt caacgaacgt caccgccagc acatgcagca tcagctggca | 900 |
| ggggctgagc agcttgaagg cacctacccc tacaccctgg agcgcagtgc caagggctac | 960 |
| cgcctgaaca agttcttgca tcgcatgatt gagccgcagt ggcgccagcg tttcctgagc | 1020 |
| gaacccgaag cgctgtaccg cgaggcgggc ctgagcgaag aggaaagcga cctgctgcgc | 1080 |
| cgccgcgact ggcgtgggct gatccactat ggggtgatct tctttgtact ggagaagcta | 1140 |
| ggcgccgtac tgggtgtgtc caacctgac atttacgccg ccatgcgcgg gcagagcatc | 1200 |
| gaggacttca tgaagacccg taaccagcag gttcgctact cggtggctgg caaagcgccc | 1260 |
| aactgactcg ag | 1272 |

<210> SEQ ID NO 63

<211> LENGTH: 1290
<212> TYPE: DNA
<213> ORGANISM: Pseudomonas sp. HR199

<400> SEQUENCE: 63

```
cgcagcctta atggatccat taaataaaaa caaaacccgg agagcctccc gcggccgcga      60
gctgttgaca attaatcatc ggctcgtata atgtgtggaa ttgtgagcgg ataacaattt     120
cacactctgg ctgagaggca tcaaaataag gtaggtcgtt tatgtttccg aaaaacgcat     180
ggtatgtggc gtgtacgccg gatgaaatcg cagataaacc gctgggccgc caaatctgca     240
acgaaaaaat cgtgttttat cgcgggcccg agggtcgtgt ggccgctgtc gaggactttt     300
gtccacaccg tggggcccca ctctcgctgg gtttcgtccg ggatggcaag ctcatctgcg     360
gttatcacgg tttggagatg gggtgcgagg gtaaaaccct cgctatgccg ggccagcgcg     420
tgcagggttt tccttgtatt aagtcgtacg ctgtcgagga gcggtatggg tttatctggg     480
tctggcctgg tgatcgtgaa ctggccgacc ctgctttgat tcaccatttg gagtgggcag     540
acaacccgga gtgggcttac ggcggggggct tgtatcatat tgcatgcgac taccggctga     600
tgattgacaa cctgatggac ttgacccacg agacctatgt gcacgcatcc tccatcggtc     660
agaaagagat tgatgaggcc ccggtgagca cccgcgtcga aggggacacg gtgattacct     720
cccggtacat ggacaacgtc atggccccgc cgttctggcg cgctgccttg cgtggcaatg     780
ggctcgccga tgatgtccca gtggatcgct ggcaaatctg tcgtttcgcg ccaccatcgc     840
atgtcctcat cgaagtgggc gtggcacatg ctggcaaagg gggttatgat gcccctgccg     900
aatacaaagc cggctcgatc gtcgtcgatt ttattacgcc agagtcggac acgagcattt     960
ggtactttg gggcatggct cgcaattttc gtccccaagg tacggagttg acggagacca    1020
ttcgtgtcgg gcaaggcaag atctttgcgg aagacctgga catgctggag cagcagcagc    1080
ggaacttgct ggcctatcct gagcggcaac tcctgaaact caatatcgat gctggggggcg    1140
tgcaatcgcg tcgggtgatc gatcgcattc tggcggctga acaagaagct gcggatgcgg    1200
ccctgatcgc tcgttcggcg agctgatcta gactacaaag cgacacggca acgtataagg    1260
aggtttttta tgattgaggt gattatttcg                                     1290
```

<210> SEQ ID NO 64
<211> LENGTH: 1103
<212> TYPE: DNA
<213> ORGANISM: Pseudomonas sp. HR199

<400> SEQUENCE: 64

```
cggccctgat cgctcgttcg gcgagctgat ctagactaca aagcgacacg gcaacgtata      60
aggaggtttt ttatgattga ggtgattatt tcggcgatgc gcctggtcgc ccaagatatt     120
atctcgctcg aattcgtccg cgctgatggc ggtttgctcc ccccgtgga agctggcgct     180
catgtcgatg tgcatttgcc tggcggtctc atccgccaat actcgctgtg gaatcaacct     240
ggggcccaat cccactactg tattggtgtg ctgaaggatc ctgcctcgcg gggtgggtcg     300
aaagctgtgc atgaaaaacct ccgtgtcggt atgcgggtgc agatctcgga gcctcgcaat     360
ctctttccat tggaggaagg cgtcgagcgc agcttgctgt tcgccggggg gattgggatt     420
accctatcc tgtgtatggc tcaagaattg gcagcccgtg aacaagattt cgaattgcat     480
tactgtgcgc ggtcgacgga tcgcgccgcc tttgtggagt ggctcaaagt ctgcgatttt     540
gccgatcact ccgtttccaa tttcgataac gggcccgacc aacaaaagtt gaacgctgct     600
gctctcttgg cagcagaggc tgagggcacg cacctctatg tctgtggtcc tgggggtttc     660
```

```
atgggtcatg tgctggacac cgcgaaagaa cagggttggg ctgataaccg cttgcatcgt    720
gagtactttg ctgctgcccc aaatgtctcc gcggatgatg gttccttcga ggtgcgtatc    780
cattcgacgg gtcaggtcct gcaagtccca gcggaccaaa ccgtgtccca agtcctggac    840
gctgcaggta ttatcgtccc agtgagctgt gagcaaggca tttgcggtac gtgcattacc    900
cgcgtcgtcg acggtgagcc tgatcaccgc gatttcttcc tgacggacgc cgaaaaggca    960
aaaaatgatc aatttacgcc gtgctgttcg cgggcgaaga gcgcctgcct cgtgctggac    1020
ttgtaaagtc aaaagcctcc gaccggaggc tttttactgc ggccgcccgt cttacgacga    1080
gggcaggatg actttcatgc ccg                                            1103
```

CONVERSION OF S-LIGNIN COMPOUNDS TO USEFUL INTERMEDIATES

CROSS-REFERENCE TO RELATED APPLICATIONS

This application claims priority from U.S. Provisional Patent Application No. 63/093,636 filed on Oct. 19, 2020, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

BACKGROUND

Lignin is the most abundant phenolic polymers on Earth found in plant tissue and formed through the polymerization of p-coumaryl, coniferyl and sinapyl alcohols compounds (H-, G-, and S-lignin types, respectively) by combinatorial oxidative radical coupling. *Pseudomonas putida* KT2440, a robust soil bacterium, can utilize aromatics from lignin biomass as carbon and energy sources and has been extensively engineered to convert various lignin-derived aromatics into added-value fuels and chemicals. The S-lignin degradation pathway has been well described and characterized in the Gram-negative bacterium, *Sphingobium* sp. SYK-6, however this is not the case for Pseudomonads. Thus, there remains a need for the development of other microbial strains that are capable of converting H-, G-, and S-lignin derived compounds into useful intermediates capable of being converted to fuels and/or chemicals.

SUMMARY

An aspect of the present disclosure is a genetically modified microbial cell that includes a first genetic modification resulting in the expression of an exogenous vanillate demethylase, such that the microbial cell is capable of metabolizing an S-lignin decomposition product and producing 2-pyrone-4,6-dicarboxylate (PDC). In some embodiments of the present disclosure, the exogenous vanillate demethylase may be derived from a bacterium. In some embodiments of the present disclosure, the bacterium may include at least one of *P. putida, P. fluorescens*, and/or *P. stutzeri*.

In some embodiments of the present disclosure, the exogenous vanillate demethylase may include a VanAB. In some embodiments of the present disclosure, the exogenous vanillate demethylase may include VanAB$^{HR199}$. In some embodiments of the present disclosure, a gene encoding the exogenous vanillate demethylase may be at least 80% identical to at least one of SEQ ID NO: 11 and/or SEQ ID NO: 13. In some embodiments of the present disclosure, the exogenous vanillate demethylase may be at least 60% identical to at least one of SEQ ID NO: 12 and/or SEQ ID NO: 14.

In some embodiments of the present disclosure, the genetically modified microbial cell may further include a second genetic modification resulting in the expression of an exogenous dioxygenase. In some embodiments of the present disclosure, the exogenous dioxygenase may be derived from a bacterium. In some embodiments of the present disclosure, the bacterium may include *Sphingobium* sp. In some embodiments of the present disclosure, the exogenous dioxygenase may include a LigAB. In some embodiments of the present disclosure, the exogenous dioxygenase may include LigAB$^{SYK6}$. In some embodiments of the present disclosure, a gene encoding the exogenous dioxygenase may be at least 80% identical to at least one of SEQ ID NO: 5 and/or SEQ ID NO: 7. In some embodiments of the present disclosure, the exogenous dioxygenase may be at least 60% identical to at least one of SEQ ID NO: 6 and/or SEQ ID NO: 8.

In some embodiments of the present disclosure, the microbial cell may be further capable of metabolizing at least one of a G-lignin decomposition product and/or an H-lignin decomposition product. In some embodiments of the present disclosure, the exogenous vanillate demethylase may be capable of demethylating vanillate. In some embodiments of the present disclosure, the exogenous vanillate demethylase may not be capable of demethylating 3-O-methylgallate. In some embodiments of the present disclosure, the S-ligin decomposition molecule may include at least one of syringaldehyde, syringate, and/or 3-O methylgallate. In some embodiments of the present disclosure, the G-ligin decomposition molecule may include ferulate.

An aspect of the present disclosure is a method for lignin valorization, where the method includes converting an S-lignin decomposition molecule to 2-pyrone-4,6-dicarboxylate (PDC) utilizing a genetically modified microbial cell that includes a first genetic modification resulting in the expression of an exogenous vanillate demethylase.

SEQUENCE LISTING

The instant application contains a Sequence Listing which has been submitted via EFS-web and is hereby incorporated by reference in its entirety. The ASCII copy as filed herewith was created on Oct. 19, 2021. The ASCII copy as filed herewith is named NREL 20-131_ST25.txt, is 45 kilobytes in size and is submitted with the instant application.

BRIEF DESCRIPTION OF THE DRAWINGS

Some embodiments are illustrated in referenced figures of the drawings. It is intended that the embodiments and figures disclosed herein are to be considered illustrative rather than limiting.

FIGS. 2A-2F illustrate catabolism of syringate by wild-type P. putida KT2440 requires an auxiliary energy source, according to some embodiments of the present disclosure. Wild-type P. putida KT2440 cultivations in M9 minimal media supplemented with: FIG. 2A SA, FIG. 2B VA, FIG. 2C SA and VA, FIG. 2D SA and VA with VA feeding every 24 hours ($VA_{(F)}$), FIG. 2E SA and GLU, or FIG. 2F SA and GLU with GLU feeding every 24 hours ($GLU_{(F)}$). Cultivations were sampled at the time points indicated to evaluate growth by $OD_{600}$ (using a cell-free blank) and metabolite concentration in the media were measured by HPLC-$UV_{VIS}$. Error bars represent the standard deviation of three biological replicates. Abbreviations: SA: syringate; VA: vanillate; 3MGA: 3-O-methylgallate; GLU: glucose; $OD_{600}$: optical density, measured as absorbance at 600 nm.

DETAILED DESCRIPTION

The present disclosure may address one or more of the problems and deficiencies of the prior art discussed above. However, it is contemplated that some embodiments as disclosed herein may prove useful in addressing other problems and deficiencies in a number of technical areas. Therefore, the embodiments described herein should not necessarily be construed as limited to addressing any of the particular problems or deficiencies discussed herein.

The present disclosure relates to genetically modified microorganisms including Pseudomonads (including *Pseudomonas putida*), *Acinetobacter* sp., various *Rhodococci* (e.g., *Rhodococcus erythryopolis*), *Sphingobium* sp., *Saccharomyces cerevisiae*, *Zygosaccharomyces bailii*, *Pichia kudriavzevii*, and *Candida glabrata* that have been metabolically engineered to direct various S-lignin-derived molecules to useful intermediates capable of being converted into useful products; e.g. chemicals, fuels, and/or polymers. Examples of S-lignin-derived molecules include syringaldehyde, syringic acid (syringate when deprotonated), 3-O-methyl gallate (3-MGA), and gallic acid (gallate when deprotonated). Another example of an S-lignin derived molecule is 1,3-butadiene-1,2,4-tricarboxylic acid, 4-hydroxy-, 1-methyl ester. Examples of useful intermediates include 2-hydroxy-2H-pyran-4,6-dicarboxylic acid (PDC), 2-oxo-2H-pyran-4,6-dicarboxylic acid, (1E,3E)-4-hydroxybuta-1,3-diene-1,2,4-tricarboxylic acid, (1E)-4-oxobut-1-ene-1,2,4-tricarboxylic acid, and 2-hydroxy-4-oxobutane-1,2,4-tricarboxylic acid.

Figure 1:
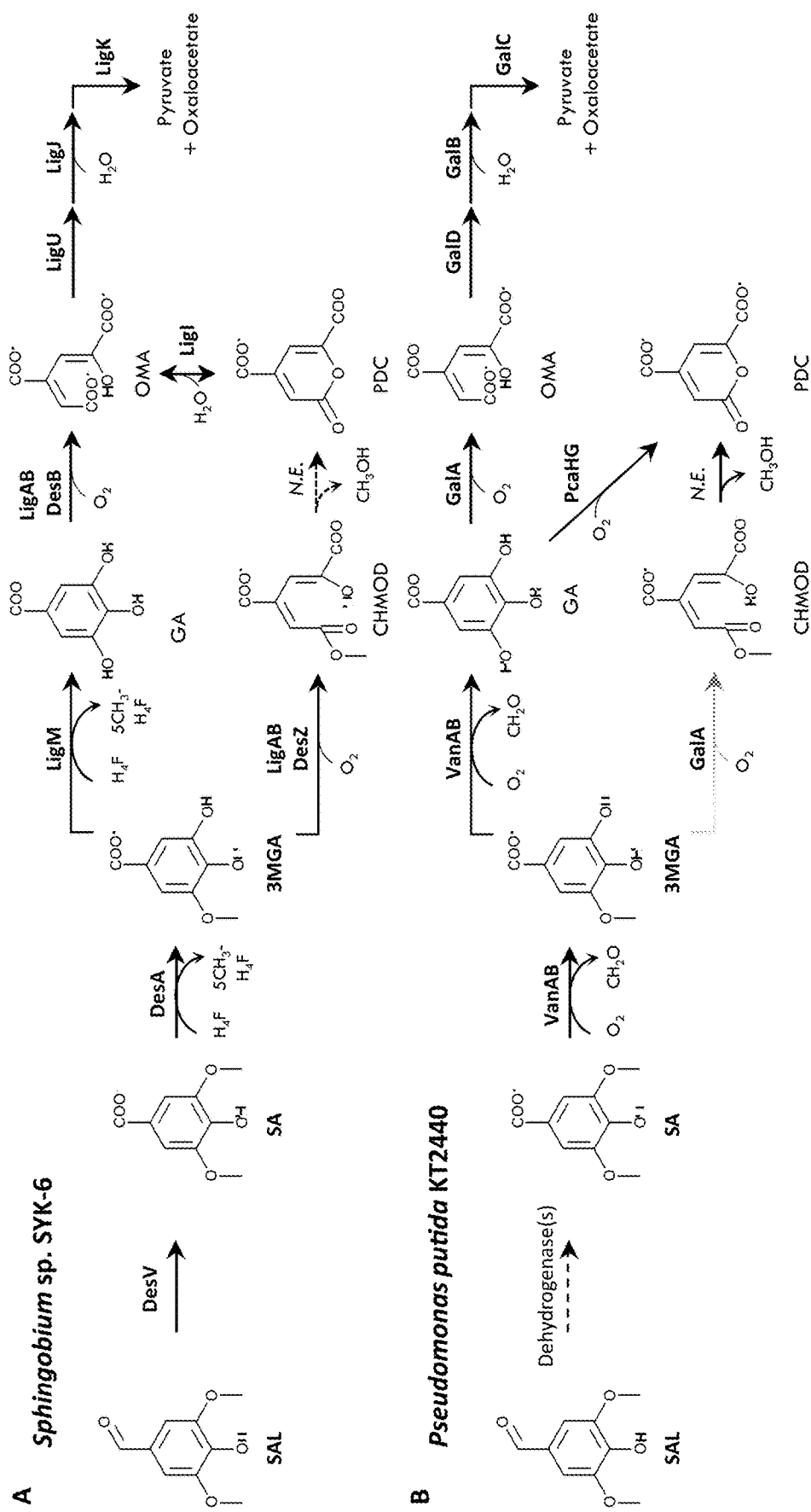
FIG. 1 illustrates metabolic pathways for syringate (SA) catabolism, according to some embodiments of the present disclosure. Panel (A) illustrates a pathway in *Sphingobium* sp. SYK-6 and Panel (B) illustrates a pathway in *Pseudomonas putida* KT2440. Cofactors and byproducts of key reactions are shown. Dashed lines represent reactions catalyzed by uncharacterized enzymes. The lighter dotted line represents a weak transformation catalyzed by GalA. Abbreviations: SA, syringate; H$_4$F, H$_4$folate ((6S)-5,6,7,8-tetrahydrofolate); 5CH$_3$—H$_4$F, (6S)-5-methyl-5,6,7,8-tetrahydrofolate; 3MGA, 3-O-methylgallate; GA, gallate; OMA, 4-oxalomesaconate, keto or enol form; CHA, 4-carboxy-4-hydroxy-2-oxoadipic acid; CHMOD, 4-carboxy-2-hydroxy-6-methyoxy-6-oxohexa-2,4-dienoate; PDC, 2-pyrone-4,6-dicarboxylic acid; VA, vanillate; 4-HIBA, 4-hydroxybenzoate; PCA, protocatechuate; VanAB, vanillate O-demethylase; GalA, gallate 3,4-dioxygenase; PcaHG, PCA 3,4-dioxygenase; GalD, 4-OMA tautomerase; GalB, 4-OMA hydratase; GalC, 4-hydroxy-4-methyl-2-oxoglutarate aldolase; DesA, SA O-demethylase; DesB, gallate dioxygenase; DesZ, 3MGA 3,4-dioxygenase; LigAB, PCA 4,5-dioxygenase; LigC, CHMS dehydrogenase; LigI, PDC hydrolase; LigM, vanillate/3MGA O-demethylase; N.E., non-enzymatic.

Panel A of FIG. 1 illustrates S-lignin catabolism by the Gram-negative soil bacterium *Sphingobium* sp. SYK-6. In *Sphingobium* sp. SYK-6, the aldehyde dehydrogenase DesV and, to a lesser extent LigV, converts syringaldehyde (SAL) to syringate (SA). Then, the tetrahydrofolate (THF)-dependent O-demethylases DesA and LigM demethylate SA and 3-O-methylgallate (3MGA), respectively. Ring-fission of gallate (GA) is then mediated by the dioxygenases DesB or LigAB to generate 4-oxalomesaconate (OMA). OMA can be further catabolized to pyruvate and carbon dioxide via LigU, LigJ, and LigK. Alternatively, 3MGA can be ring-opened to 4-carboxy-2-hydroxy-6-methyoxy-6-oxohexa-2,4-dienoate (CHMOD) by LigAB or the dioxygenase DesZ. Non-enzymatic dehydrogenation and methanol elimination from CHMOD to 2-pyrone-4,6-dicarboxylate (PDC) has been reported. Ring closure to PDC may be facilitated by the 3MGA ring-opening dioxygenase. Conversion between OMA and PDC may be mediated by a reversible hydrolase such as LigI.

P. putida KT2440 cannot grow on syringate (SA) alone, yet catabolizes SA in the presence of other lignin-derived aromatics. O-demethylation of SA can occur by the two-component monooxygenase VanAB in Pseudomonas sp. HR199. In the VanAB system, the VanB reductase contains a flavin and [2Fe-2S] redox center which transfers electrons from NAD(P)H to the oxygenase VanA, containing a Rieske-type [2Fe-2S] cluster, for oxidative demethylation.

The present disclosure relates to a pathway for SA catabolism in P. putida KT2440 wherein VanAB O-demethylates both SA to 3MGA and then GA, which is subsequently metabolized via GalA, GalD, GalB, and GalC (see Panel B of FIG. 1). Biochemical characterization of VanAB indicates a substrate preference for vannilate (VA) over SA, both of which are greatly preferred over 3MGA. In vivo, SA utilization only appears to occur in the presence of an additional energy source or chromosomal overexpression of a second copy of vanAB, the latter of which resulted in expression of the gallate degradation pathway (galADBC, Panel B of FIG. 1) as measured by transcriptomics and proteomics. The PCA 3,4-dioxygenase, PcaHG, ring-opened GA to form PDC, which enabled PDC production from SA via PcaHG-mediated GA cleavage. Additionally, GalA was found to have activity toward 3MGA, but was rapidly inactivated. Simultaneous conversion of SA, p-coumarate, and ferulate to PDC was obtained with heterologous expression of ligABC from Sphingobium sp. SYK-6 and vanAB from Pseudomonas sp. HR199. Together, the work described herein elucidates a S-lignin catabolic pathway in P. putida KT2440 and demonstrates the biocatalytic potential of this strain to convert monomers with S-, G-, and H-lignin functionality to PDC.

Figure 2A:
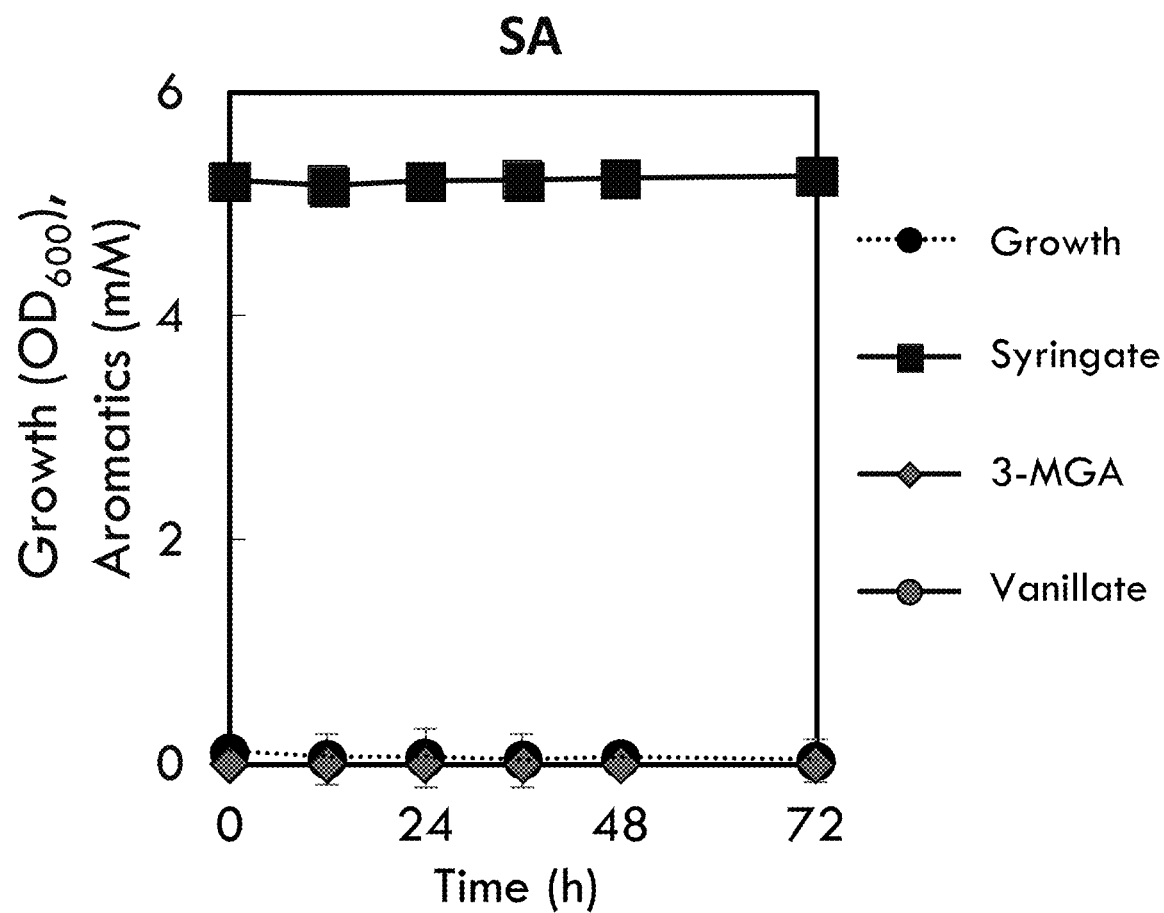
Figure 2B:
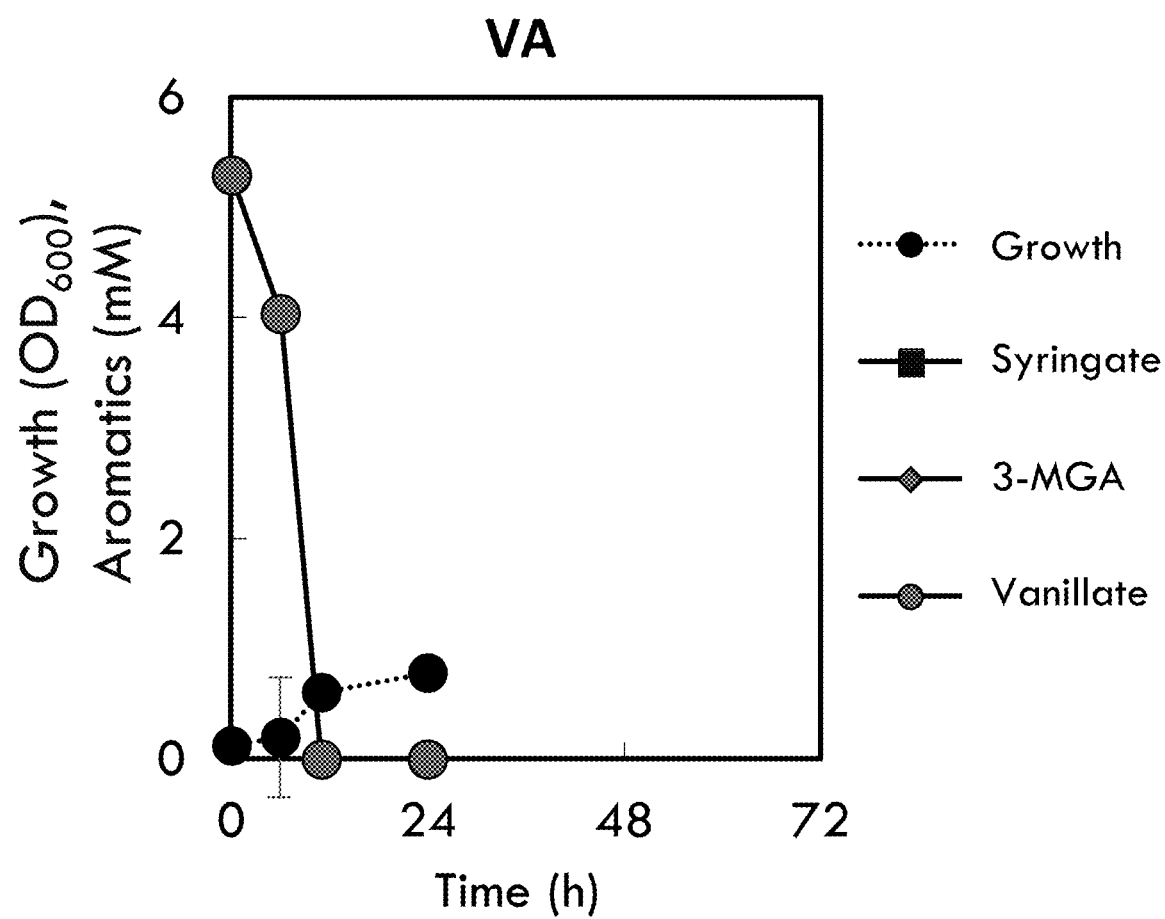
Figure 2C:
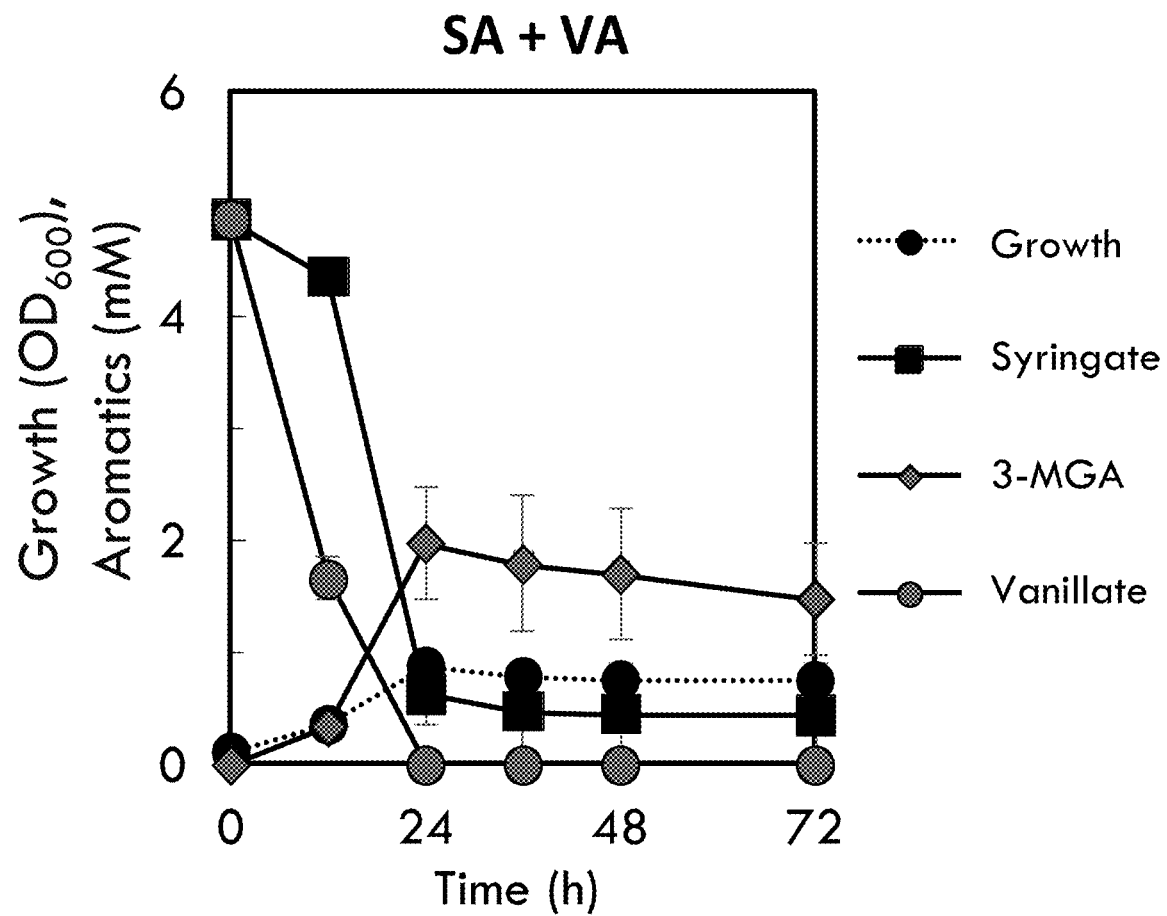
Figure 2D:
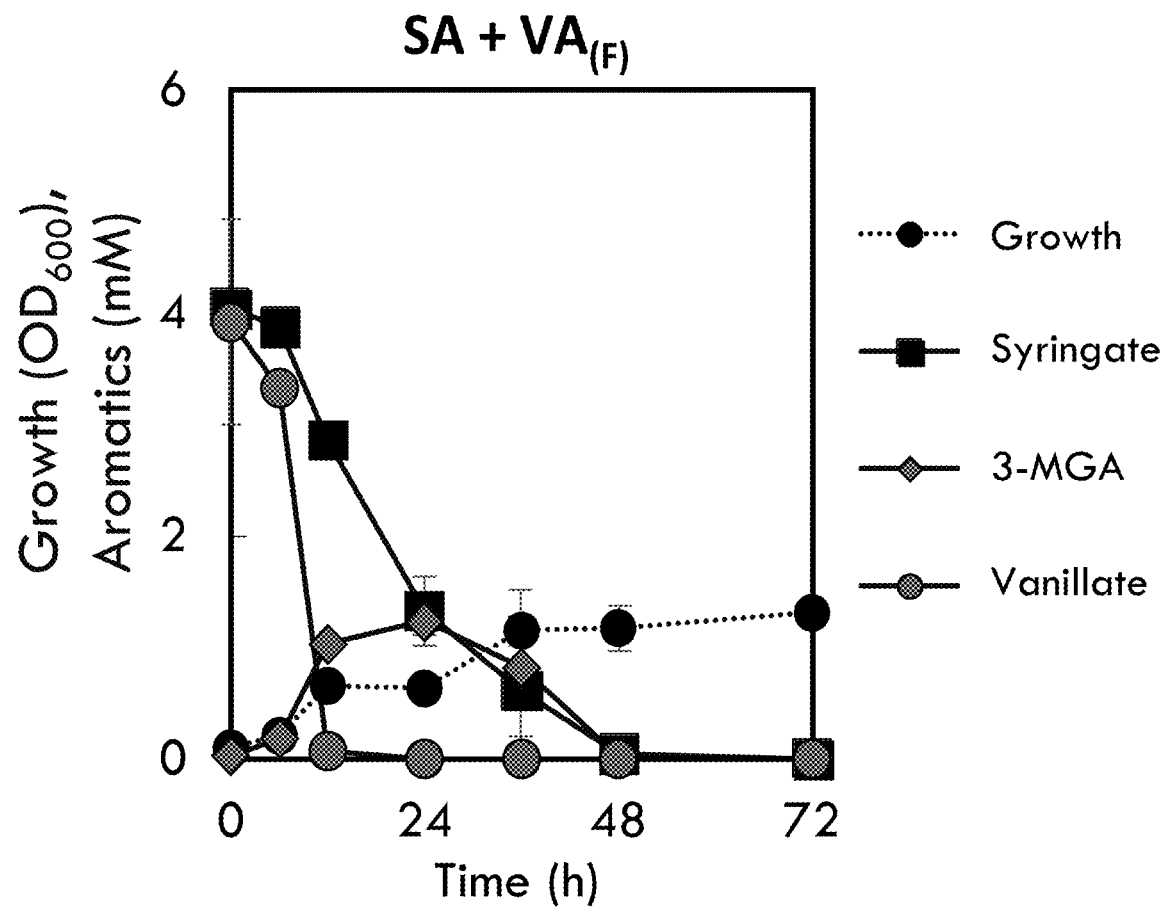
Figure 2E:
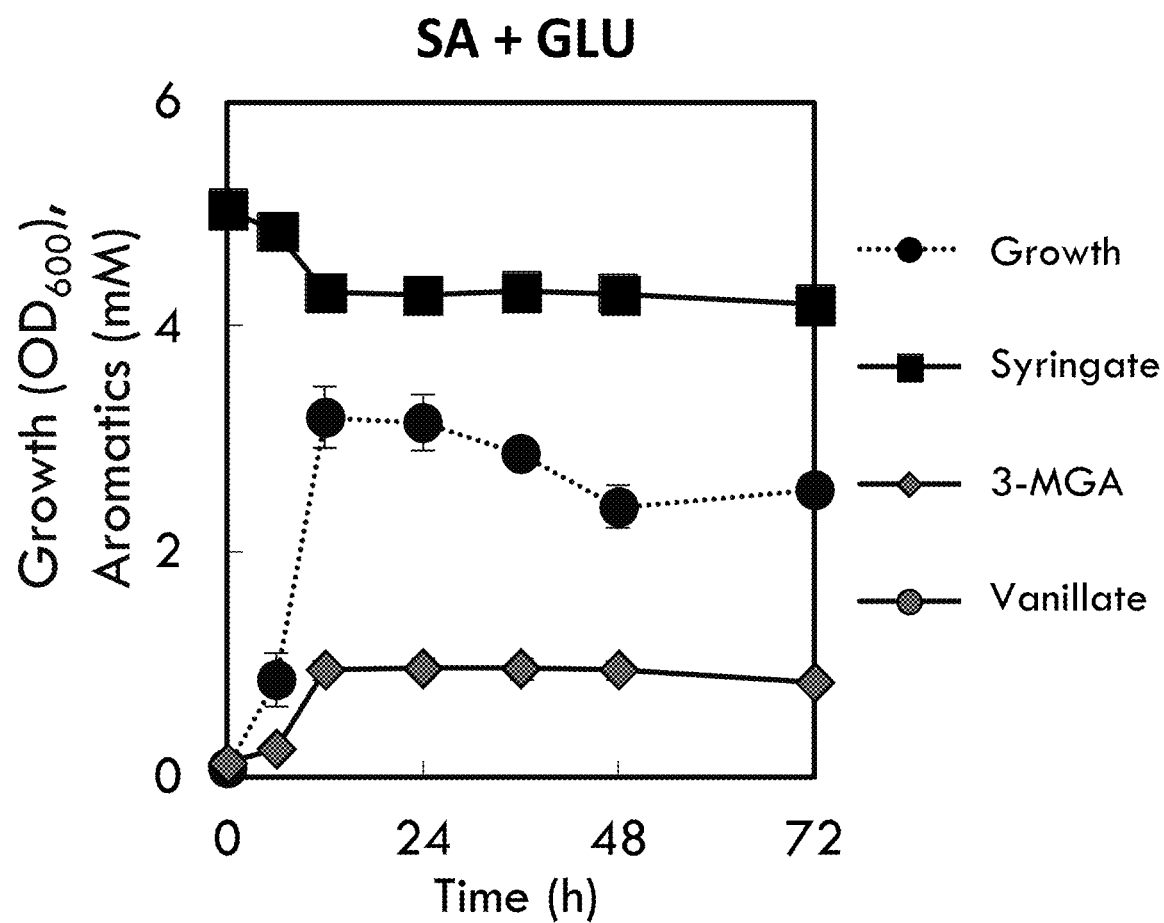
Figure 2F:
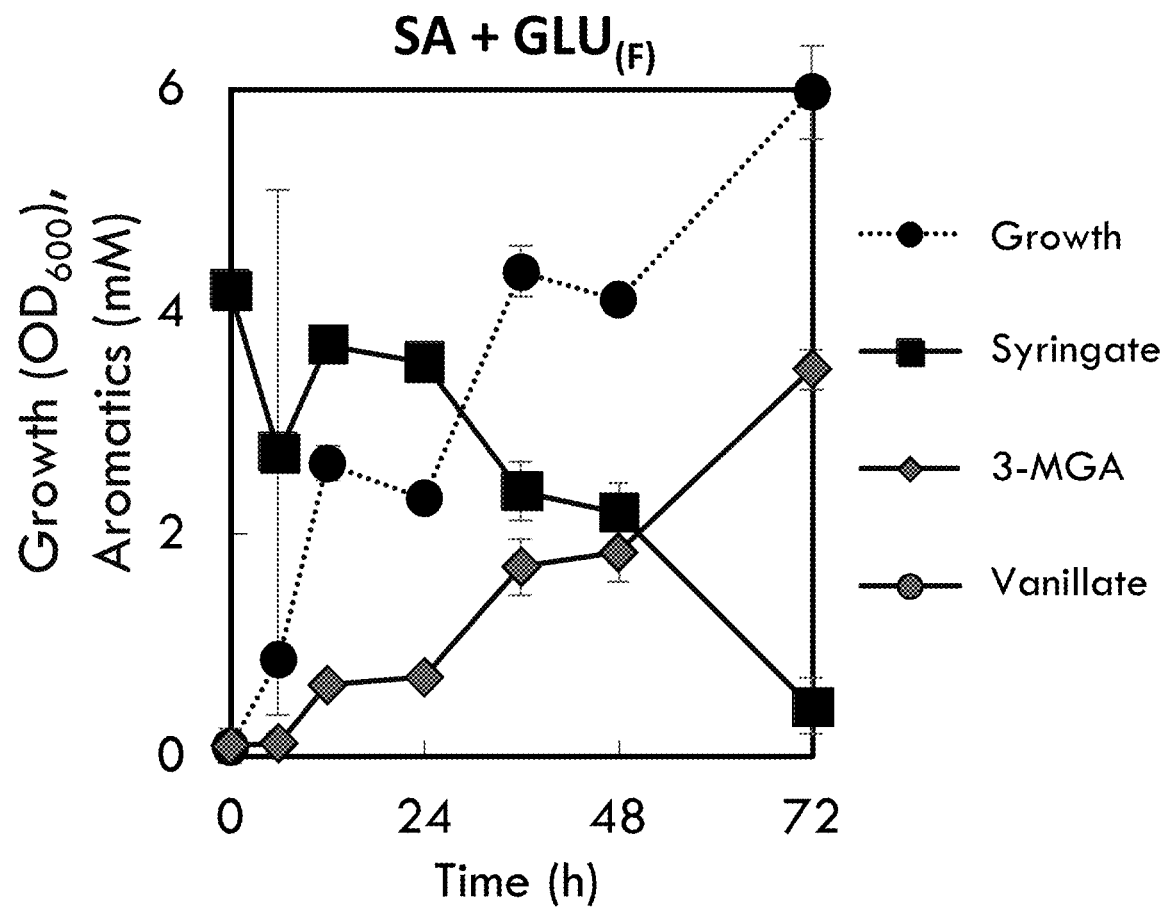
Figure 3A:
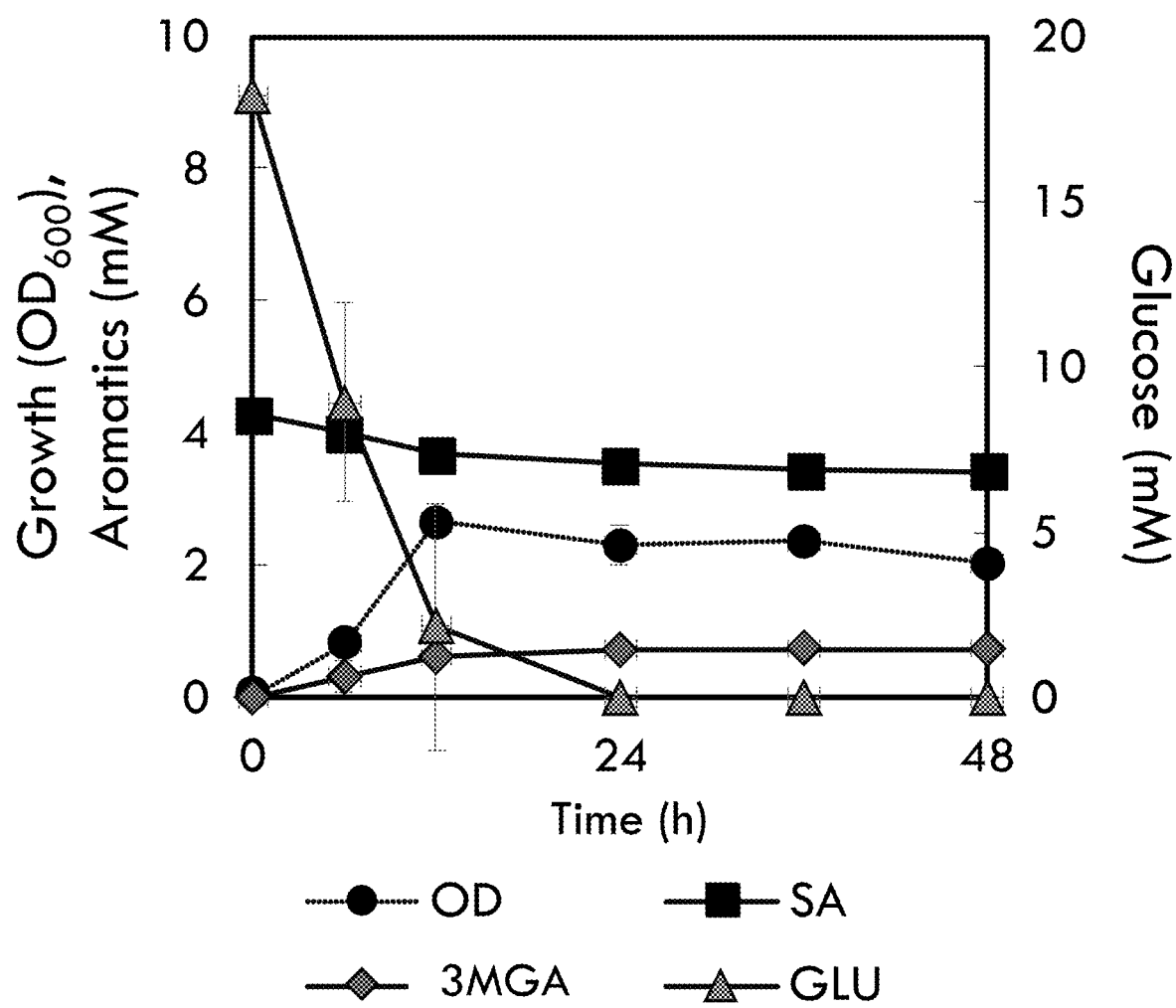
FIG. 3A illustrates P. putida wild-type cultivated in M9 minimal media supplemented with syringate and glucose and fed to 20 mM glucose every 24 hours, according to some embodiments of the present disclosure. Error bars represent the standard deviation of three biological replicates. Abbreviations: OD: optical density; 3-O-MGA: 3-O-methylgallate; SA: syringic acid; GLU: glucose.
Figure 3B:
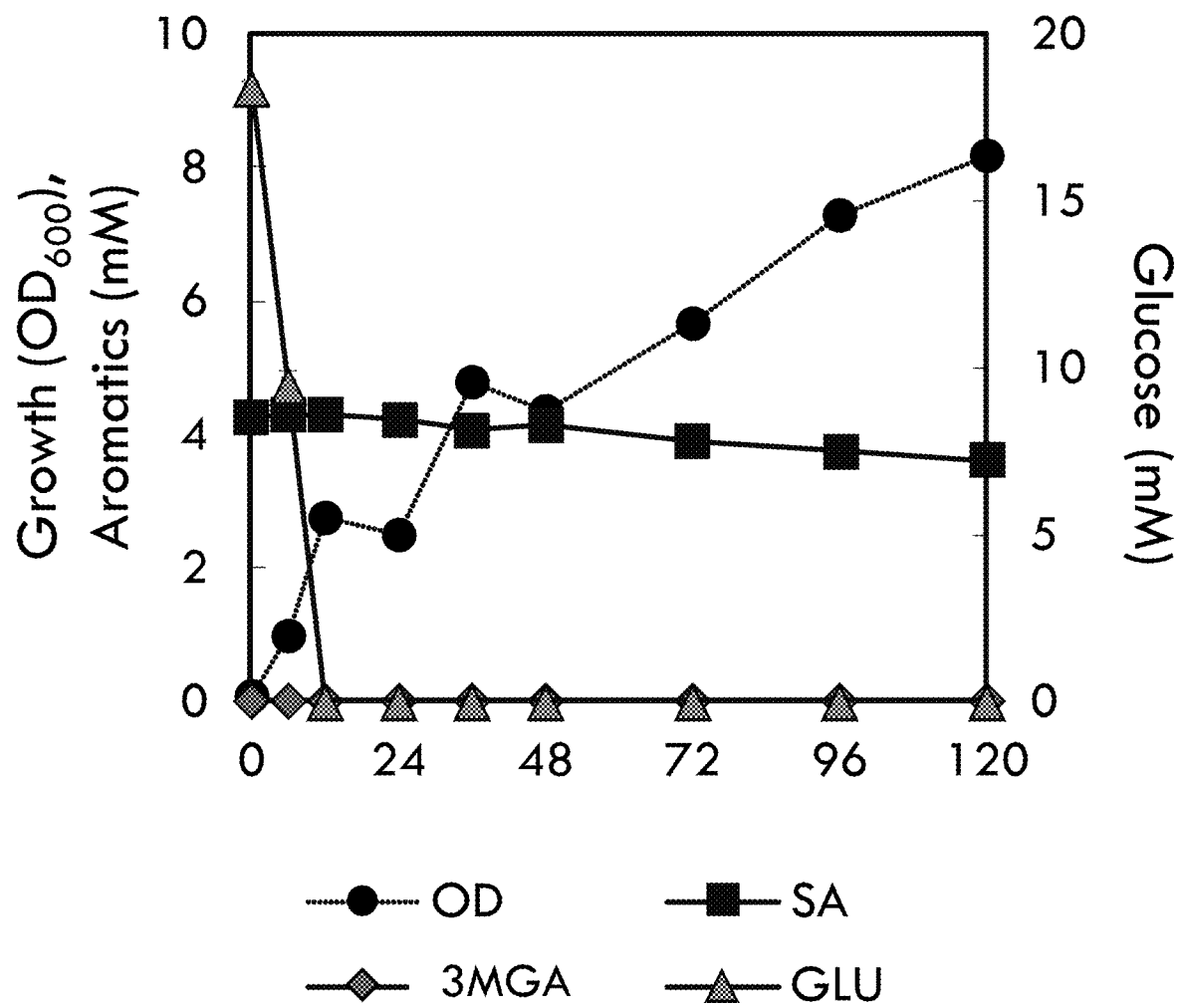
FIG. 3B illustrates P. putida ΔvanAB (SN166) cultivated in M9 minimal media supplemented with syringate and glucose and fed to 20 mM glucose every 24 hours, according to some embodiments of the present disclosure. Error bars represent the standard deviation of three biological replicates. Abbreviations: OD: optical density; 3-O-MGA: 3-O-methylgallate; SA: syringic acid; GLU: glucose.
Figure 4A:
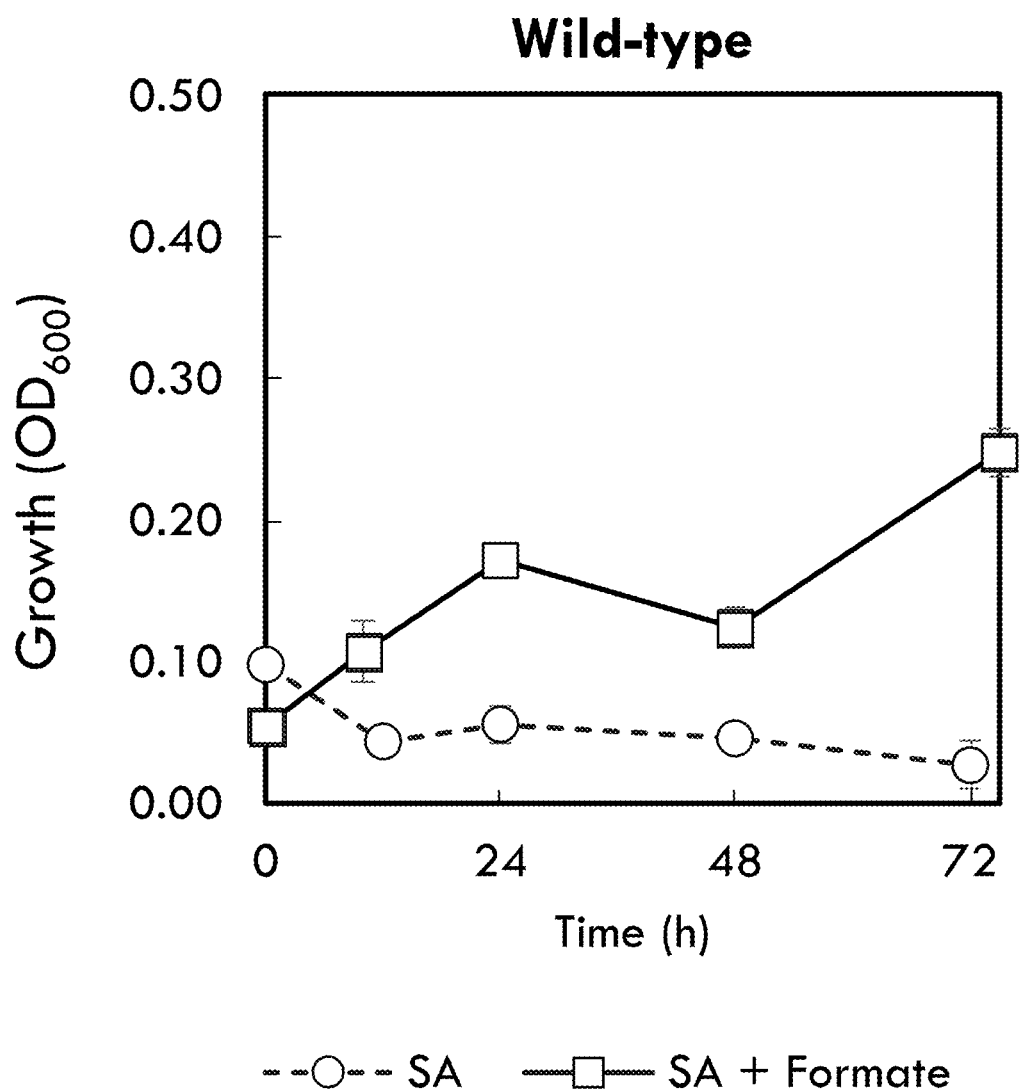
FIG. 4A illustrates wild-type P. putida growth in M9 minimal media supplemented with syringate (circles, dashed line) or syringate and formate (squares, solid line), according to some embodiments of the present disclosure. Formate was provided to 50 mM every 24 hours and cultures were subsequently pH adjusted to 7.1. Error bars represent the standard deviation of three biological replicates.
Figure 4B:
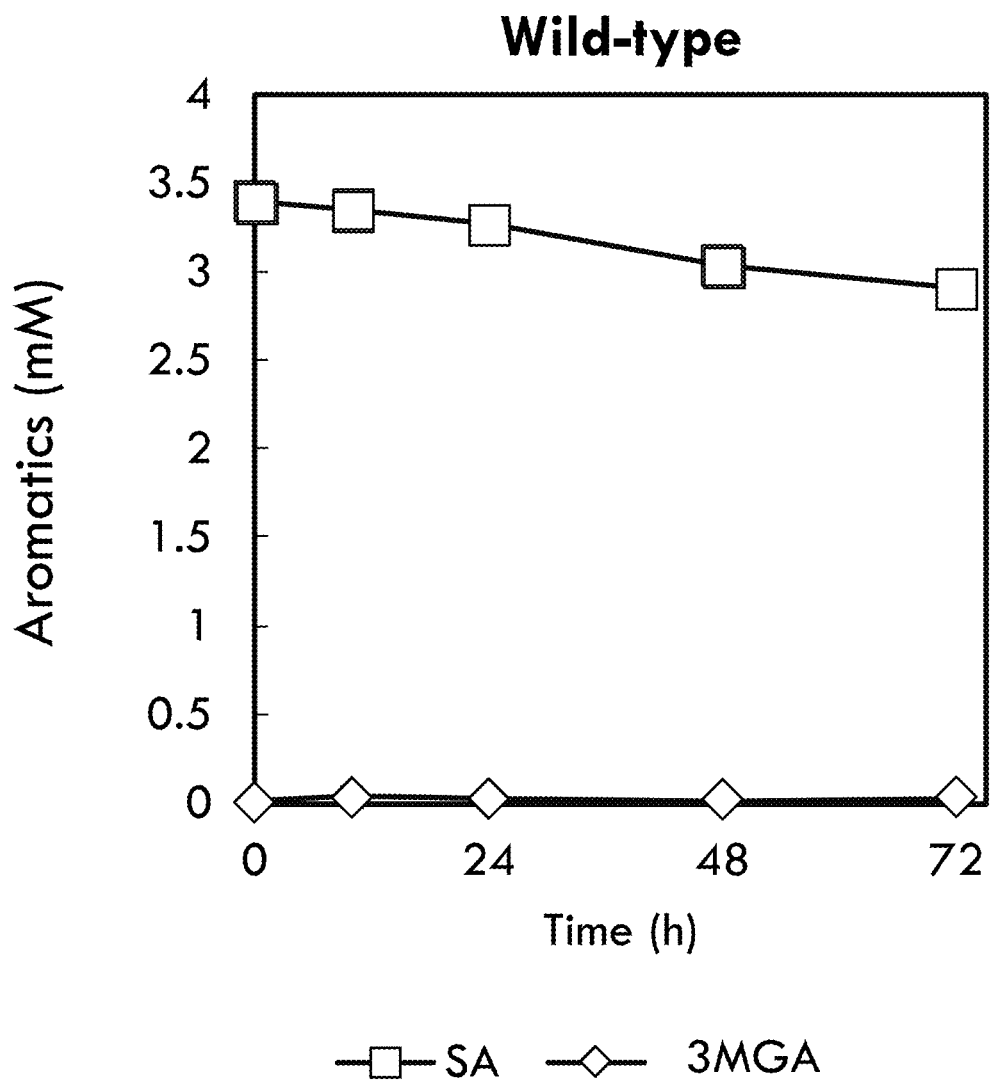
FIG. 4B illustrates metabolite quantification of wild-type P. putida during growth in M9 minimal media supplemented with syringate and formate, according to some embodiments of the present disclosure. Formate was provided to 50 mM every 24 hours and cultures were subsequently pH adjusted to 7.1. Error bars represent the standard deviation of three biological replicates.
Figure 4C:
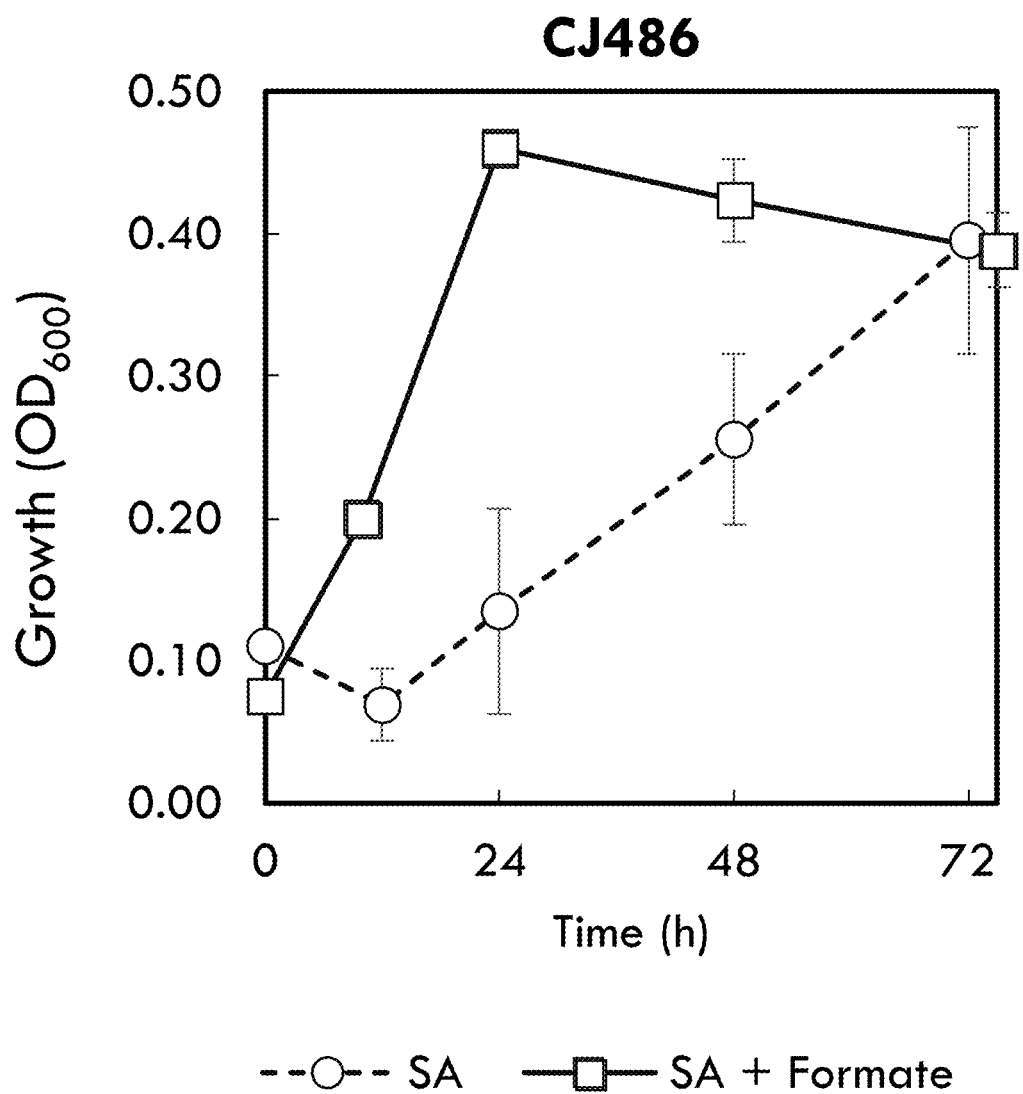
FIG. 4C illustrates CJ486 (2× vanAB) growth in M9 minimal media supplemented with syringate (circles, dashed line) or syringate and formate (squares, solid line), according to some embodiments of the present disclosure. Formate was provided to 50 mM every 24 hours and cultures were subsequently pH adjusted to 7.1. Error bars represent the standard deviation of three biological replicates.
Figure 4D:
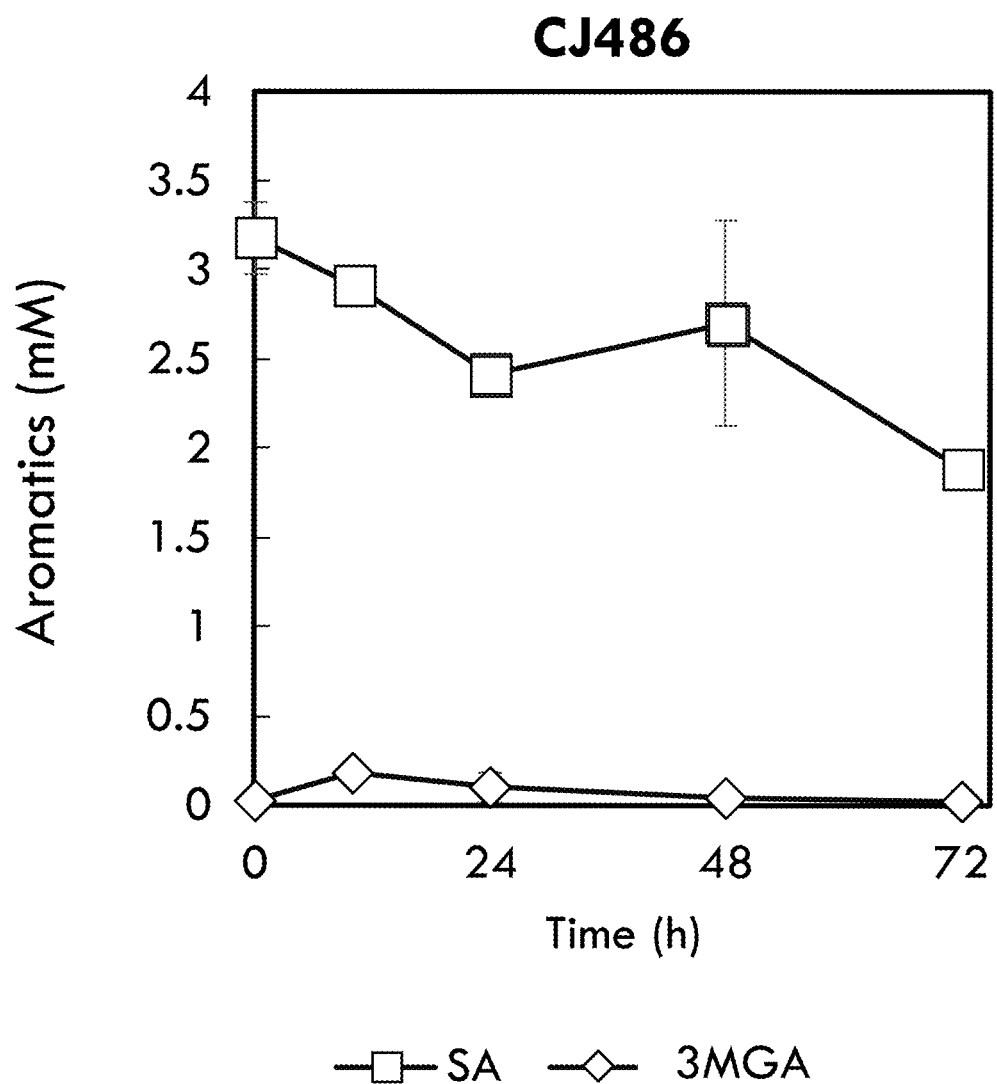
FIG. 4D illustrates metabolite quantification of CJ486 during growth in M9 minimal media supplemented with syringate and formate, according to some embodiments of the present disclosure. Formate was provided to 50 mM every 24 hours and cultures were subsequently pH adjusted to 7.1. Error bars represent the standard deviation of three biological replicates.

As shown herein, wild-type P. putida KT2440 did not utilize SA (see FIG. 2A) but did utilize VA (see FIG. 2B) as the sole carbon and energy source. However, SA was catabolized while VA was present (see FIG. 2C) and was completely catabolized when VA was fed periodically (see FIG. 2D). Therefore, endogenous VA O-demethylase VanAB can act on SA. Based on the abrupt termination of SA utilization upon VA depletion, it may be hypothesized that an additional carbon/energy source may be needed to support SA catabolism. In SA cultivations supplemented with 20 mM glucose as an auxiliary source of carbon and energy, SA was demethylated to produce 3MGA (see FIG. 2E), which ceased upon depletion of glucose (see FIG. 3A). With periodic glucose supplementation, SA was completely utilized albeit with intermittent accumulation of 3MGA (see FIG. 2F). SN166 (P. putida KT2440 ΔvanAB) did not utilize SA with glucose feeding (see FIG. 3B), further supporting VanAB as the enzyme that catalyzes SA O-demethylation.

To better understand this auxiliary carbon/energy requirement, the energetic demands of SA catabolism was studied. VanAB-mediated O-demethylation requires NAD(P)H and generates formaldehyde as a byproduct. Formaldehyde oxidation to formate and subsequent dehydrogenation to $CO_2$ in turn generates two molar equivalents of NADH, presenting the possibility of functional coupling of the two reactions to maintain the VanAB cofactor requirement. However, formaldehyde is highly toxic and P. putida KT2440 growing on VA generates formaldehyde more quickly than it is oxidized, ultimately secreting it into the media. O-demethylation of SAL and SA also generates twice the amount of formaldehyde than that of VA. Cellular demand for NAD(P)H increases in the presence of toxic compounds.

Therefore, it may be hypothesized that the reducing equivalents produced by demethylation might not be sufficient to generate the energy required for cell maintenance, growth, and tolerance to SA and/or metabolic intermediates, including formaldehyde, generated during its catabolism. To test this hypothesis, shake flask cultivations were performed similar to those above, but supplemented with formate rather than glucose or VA. P. putida KT2440 oxidizes formate to generate energy in the form of NADH reducing equivalents and $CO_2$, which cannot be used for growth, allowing the effect of proving an additional source of reducing equivalents without an additional source of carbon for growth to be examined. Indeed, it was found that the addition of formate increased utilization of SA (see FIGS. 4A-D). VanA and VanB protein abundances were not increased by the presence of formaldehyde (see Table 1), suggesting that the additional NADH generated by formate utilization, as opposed to changes in VanAB abundance underly the increased SA utilization. Together these data demonstrate that SA utilization is limited by energy availability in P. putida KT2440.

TABLE 1

VanAB pairwise comparisons. Fold-change protein abundance of VanA and VanB in P. putida CJ486 versus P. putida wild-type (WT) on glucose (GLU) or formaldehyde (FORM).

| Protein | Locus ID | WT_GLU vs. CJ486_GLU | WT_FORM vs. CAT86_FORM | WT_GLU vs. WT_FORM | CJ486_GLU vs. CJ486_FORM |
|---|---|---|---|---|---|
| VanA | PP_3736 | −11.4 | −11.0 | −0.5 | −0.2 |
| VanB | PP_3737 | −11.0 | −11.3 | 0.1 | −0.2 |

Figure 5A:
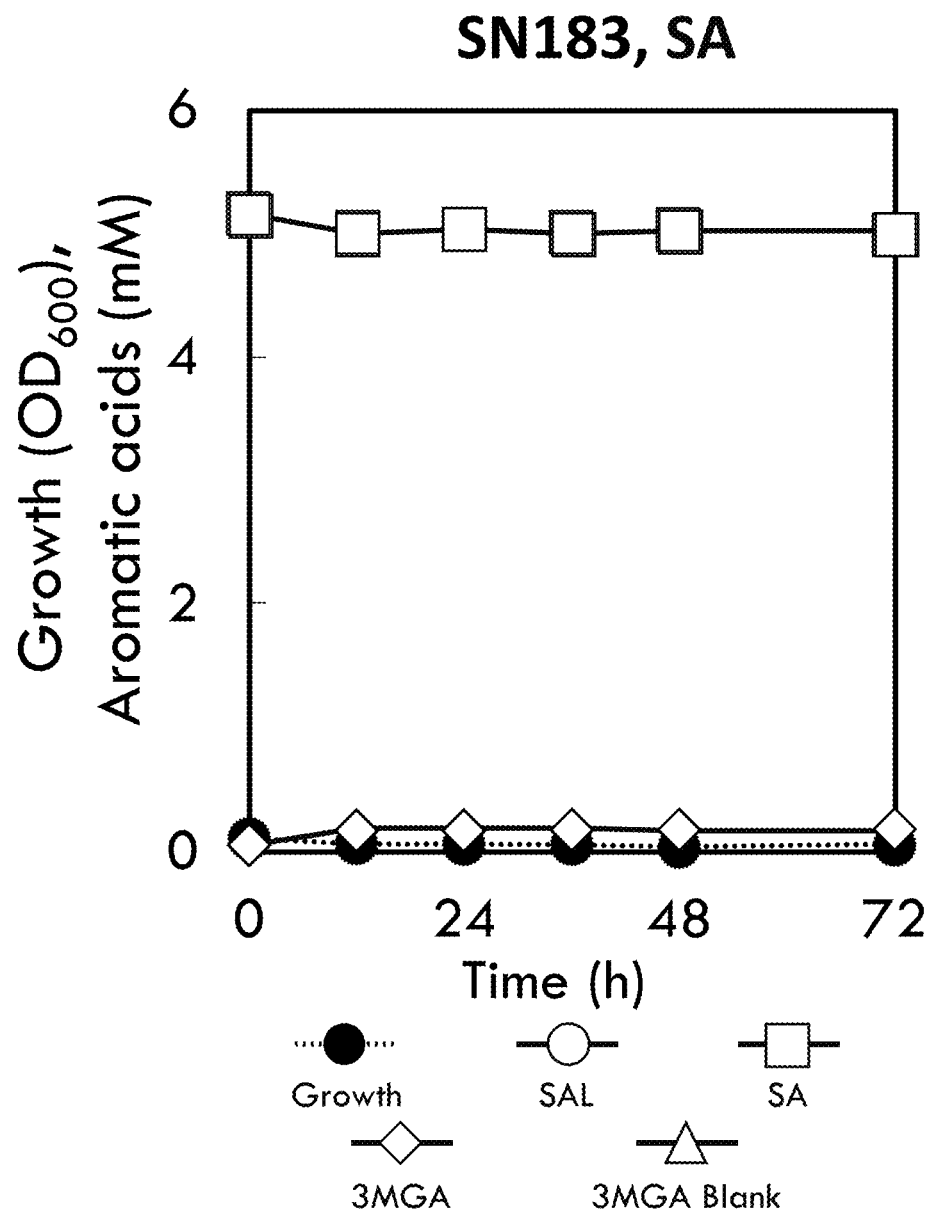
FIG. 5A illustrates growth of SN183 (P. putida KT2440 harboring pBTL-2: $P_{tac}$:vanAB) having chromosomal overexpression of vanAB for cultivations in M9 minimal media supplemented with SA, according to some embodiments of the present disclosure. In each of FIGS. 5A-5H, cultivations were sampled at the time points indicated to evaluate growth by $OD_{600}$ (using a cell-free blank) and metabolite concentration in the media were measured by HPLC-$UV_{VIS}$. Error bars represent the standard deviation of three biological replicates. Abbreviations: SA: syringate; SAL: syringaldehyde; 3MGA: 3-O-methylgallate; GLU: glucose; $OD_{600}$: optical density, measured as absorbance at 600 nm.
Figure 5B:
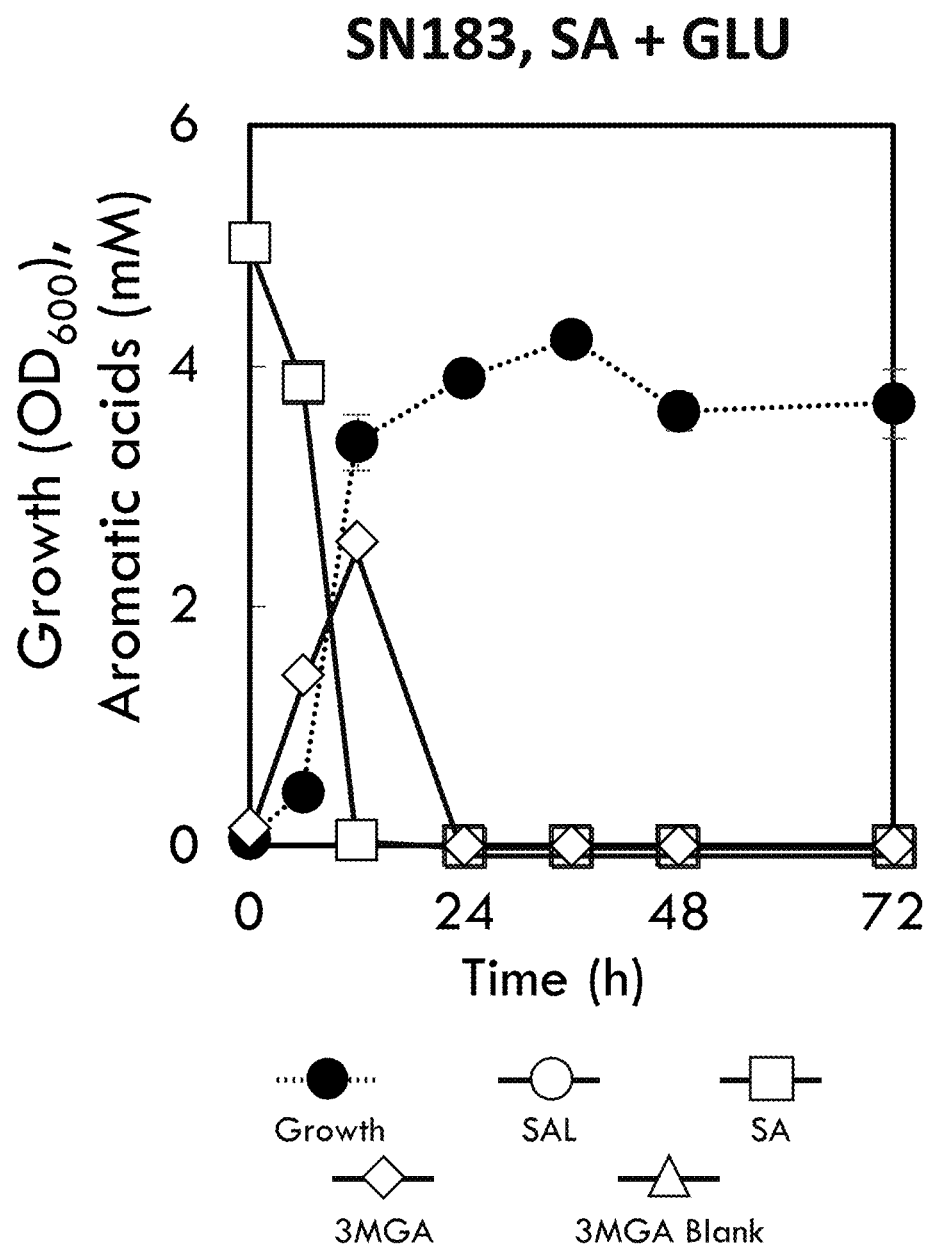
FIG. 5B illustrates growth of SN183 (P. putida KT2440 harboring pBTL-2: $P_{tac}$:vanAB) having chromosomal overexpression of vanAB for cultivations in M9 minimal media supplemented with SA and GLU, according to some embodiments of the present disclosure.
Figure 5C:
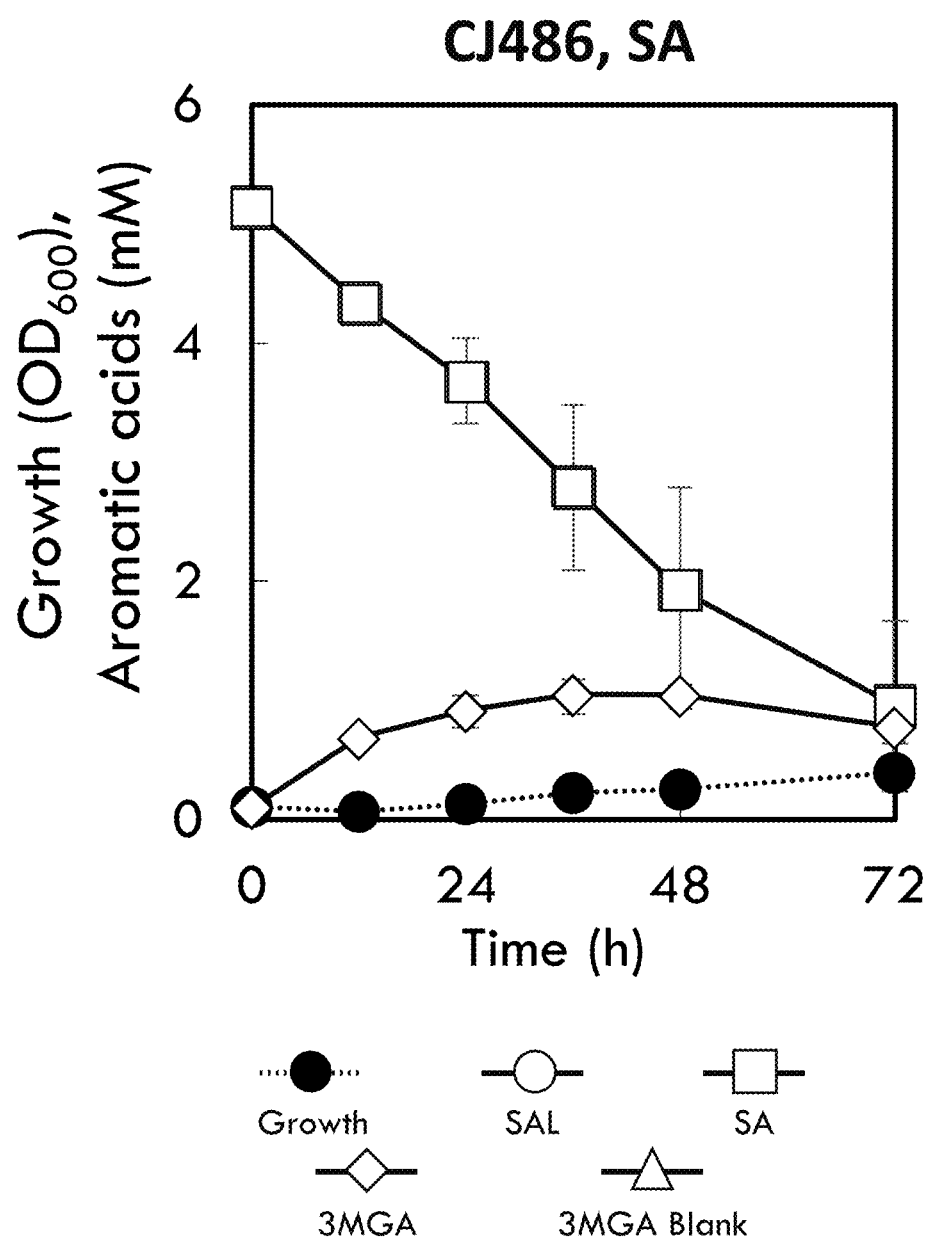
FIG. 5C illustrates growth of CJ486 (P. putida KT2440 fpvA:$P_{tac}$:vanAB) having chromosomal overexpression of vanAB for cultivations in M9 minimal media supplemented with SA, according to some embodiments of the present disclosure.
Figure 5D:
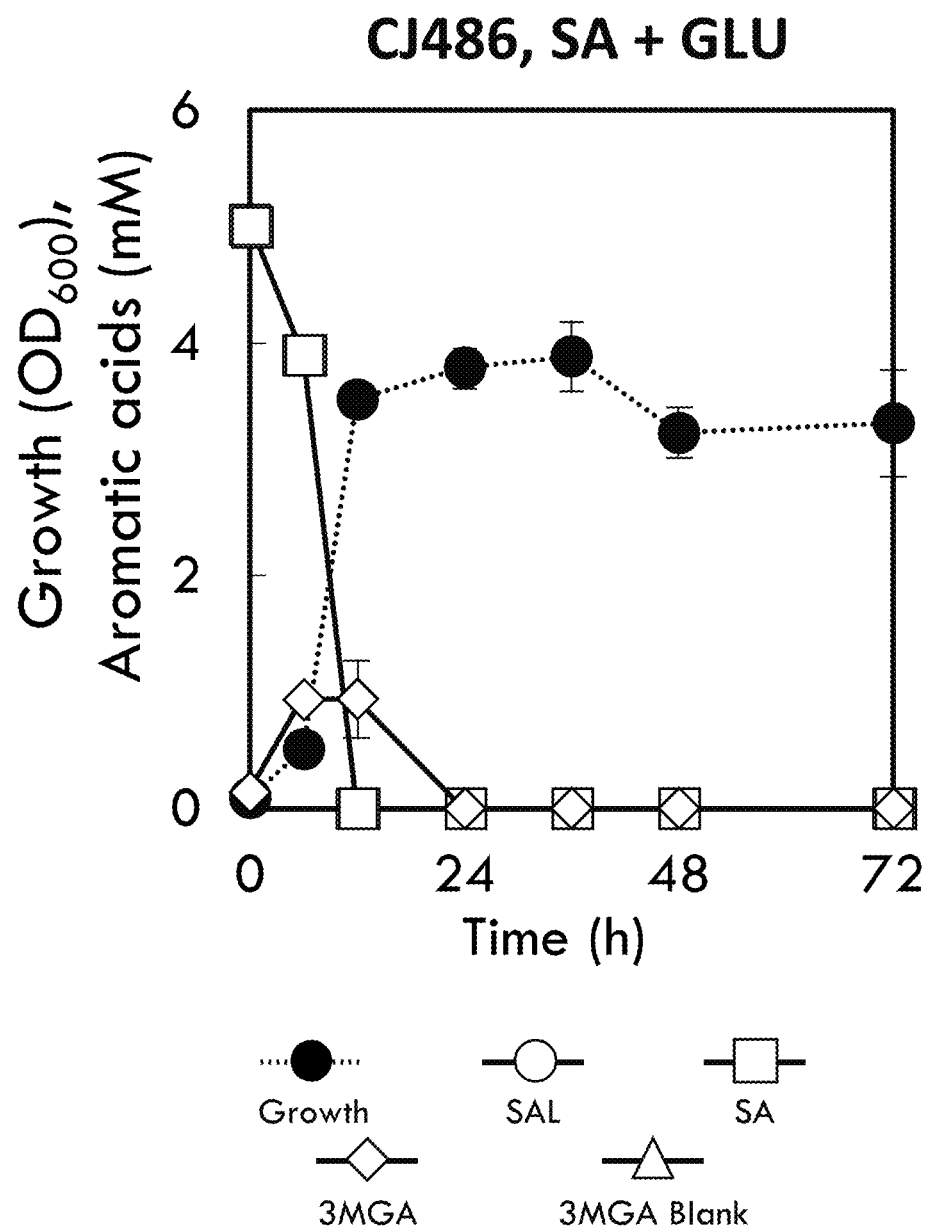
FIG. 5D illustrates growth of CJ486 (P. putida KT2440 fpvA:$P_{tac}$:vanAB) having chromosomal overexpression of vanAB for cultivations in M9 minimal media supplemented with SA and GLU, according to some embodiments of the present disclosure.
Figure 5E:
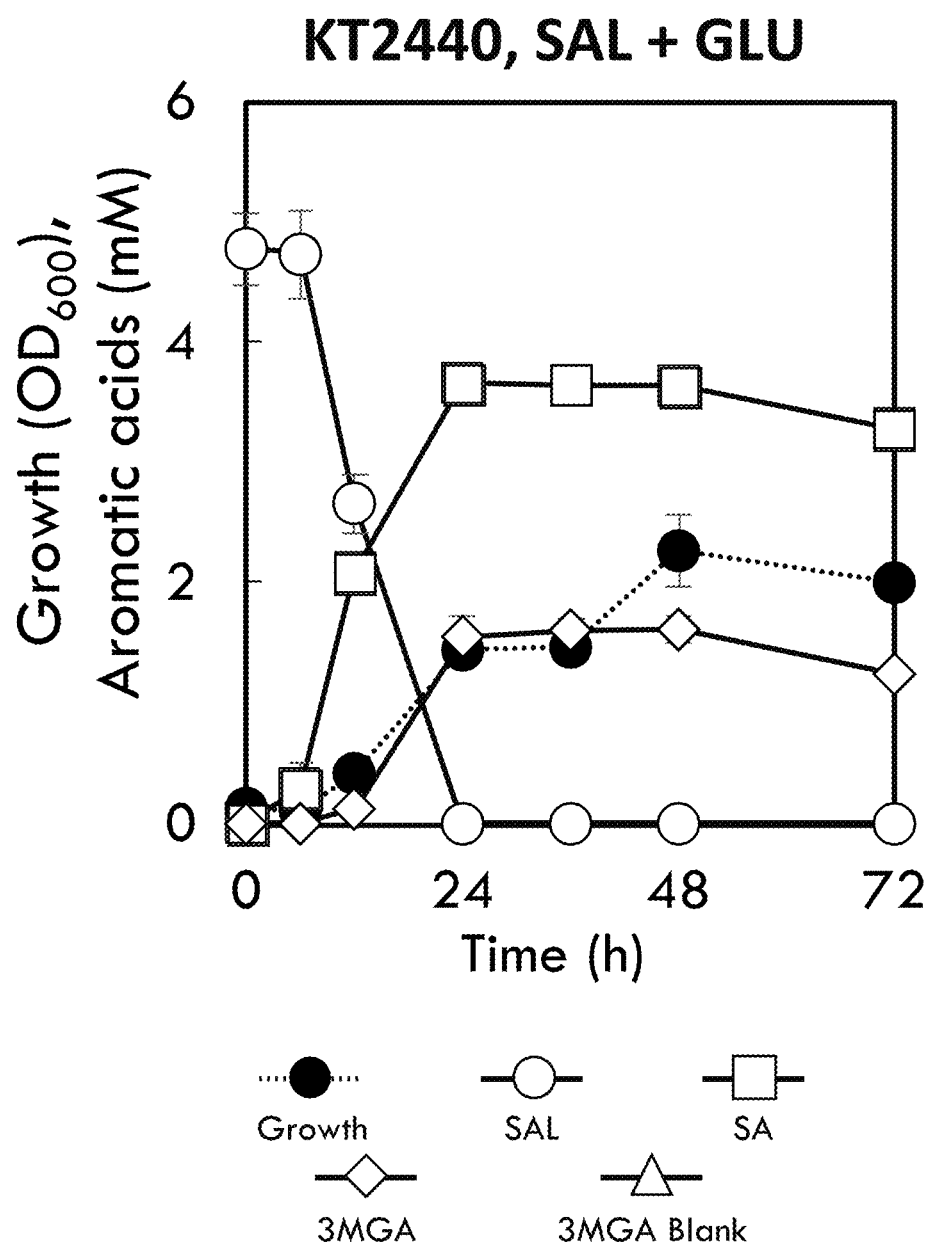
FIG. 5E illustrates growth of wild-type P. putida KT2440 for cultivations in M9 minimal media supplemented with SAL and GLU, according to some embodiments of the present disclosure.
Figure 5F:
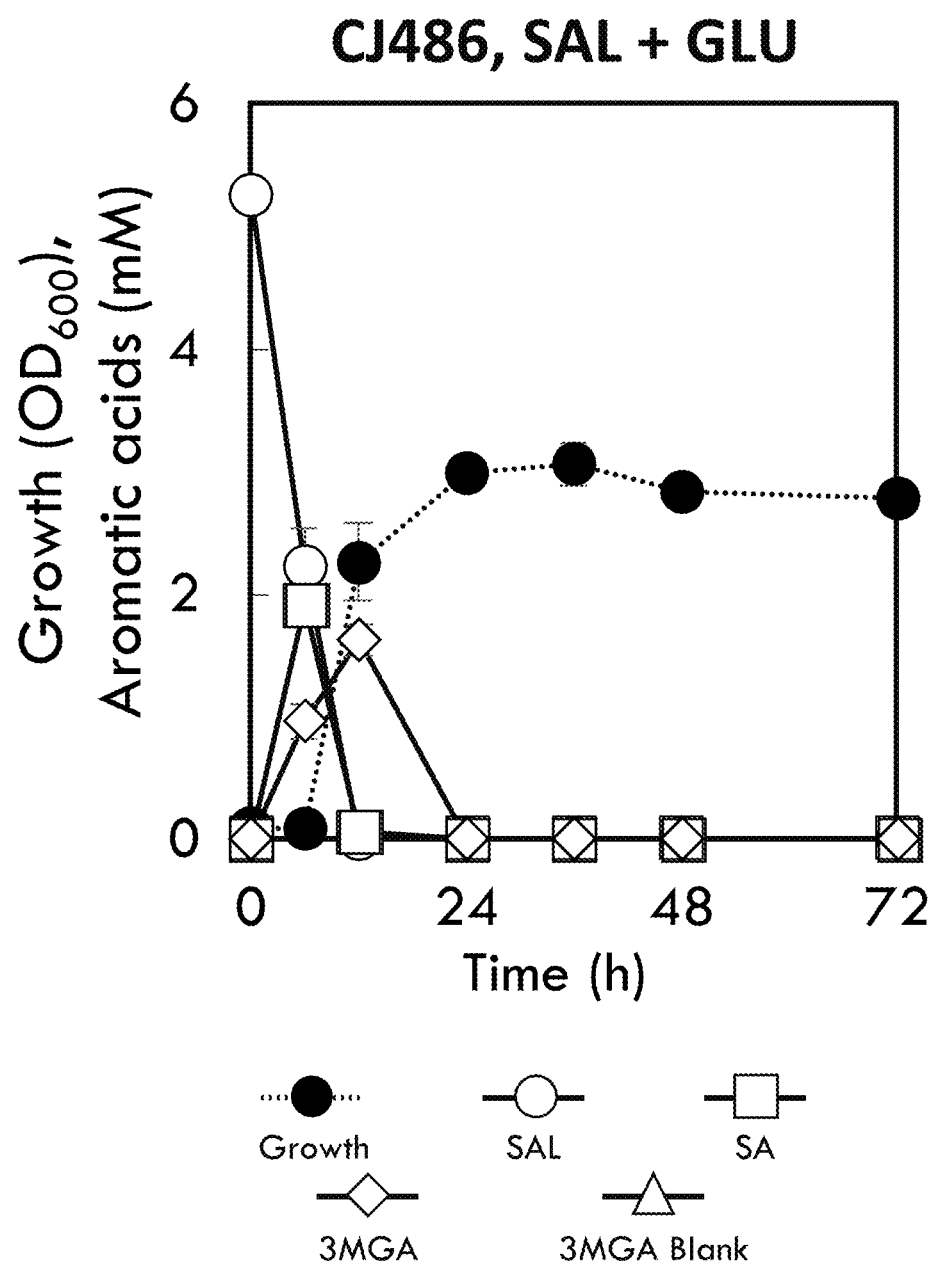
FIG. 5F illustrates growth of CJ486 (P. putida KT2440 fpvA:$P_{tac}$:vanAB) having chromosomal overexpression of vanAB for cultivations in M9 minimal media supplemented with SAL and GLU, according to some embodiments of the present disclosure.
Figure 5G:
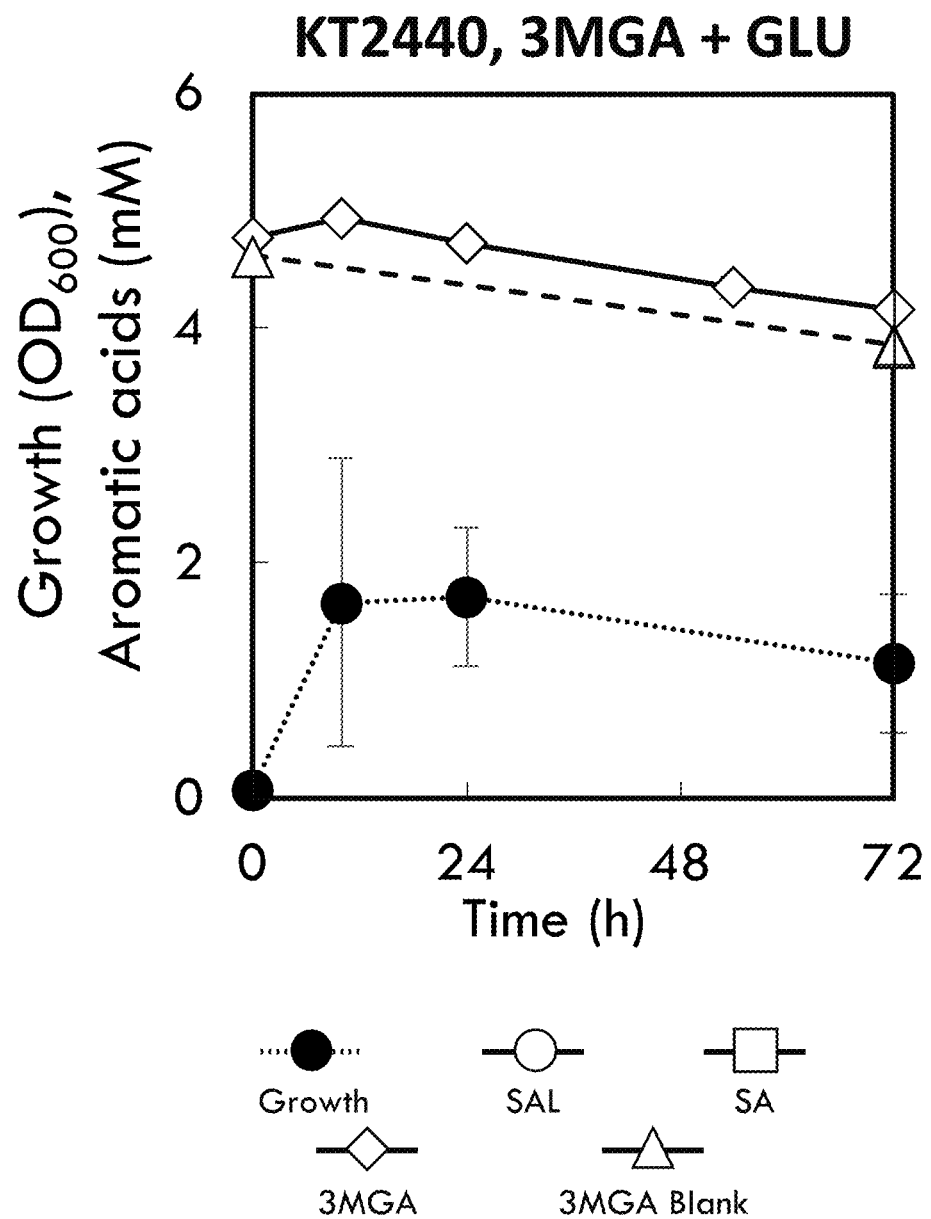
FIG. 5G illustrates growth of wild-type P. putida KT2440 for cultivations in M9 minimal media supplemented with 3MGA and GLU, according to some embodiments of the present disclosure.
Figure 5H:
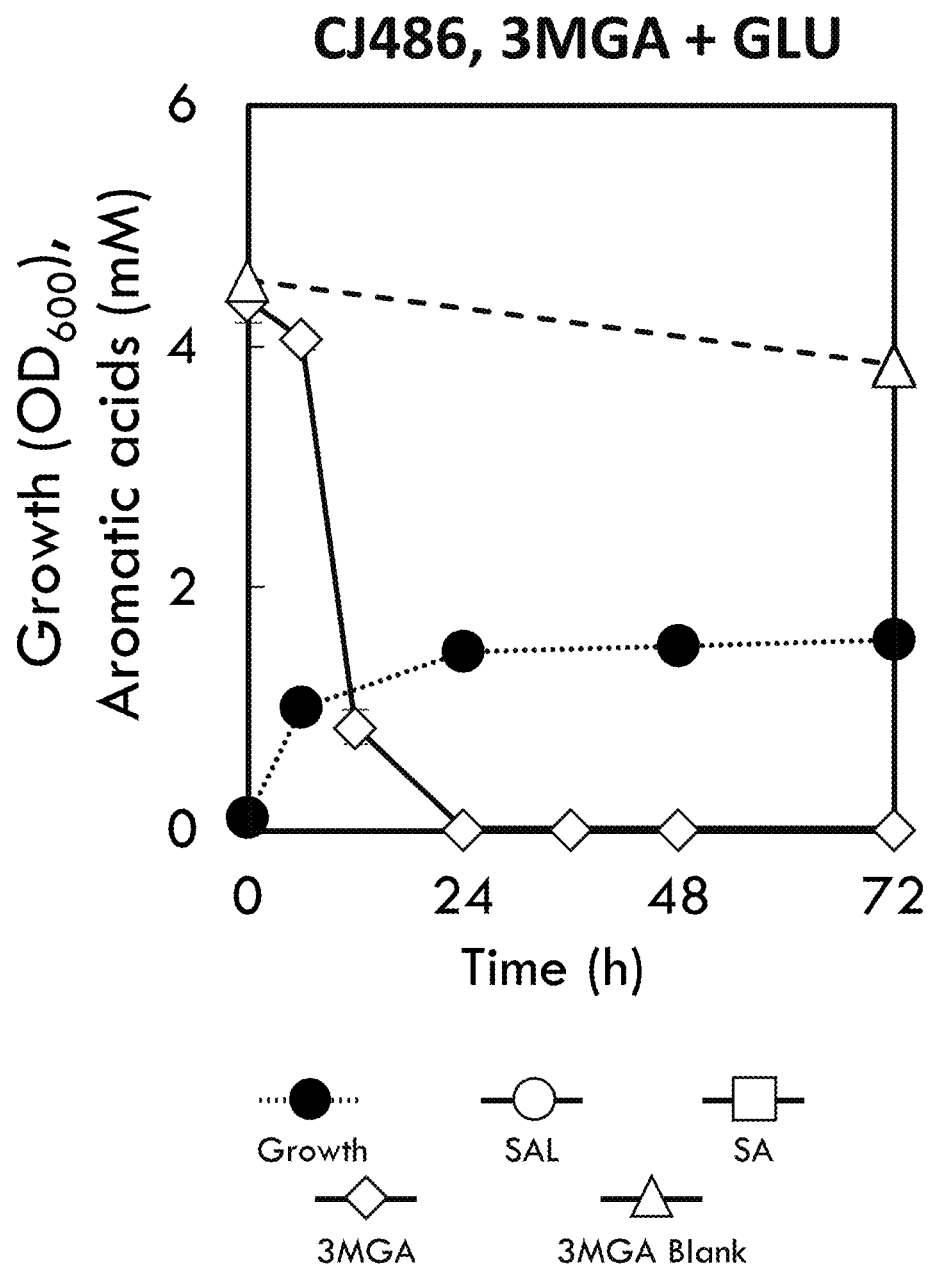
FIG. 5H illustrates growth of CJ486 (P. putida KT2440 fpvA:$P_{tac}$:vanAB) having chromosomal overexpression of vanAB for cultivations in M9 minimal media supplemented with 3MGA and GLU, according to some embodiments of the present disclosure.
Figure 6:
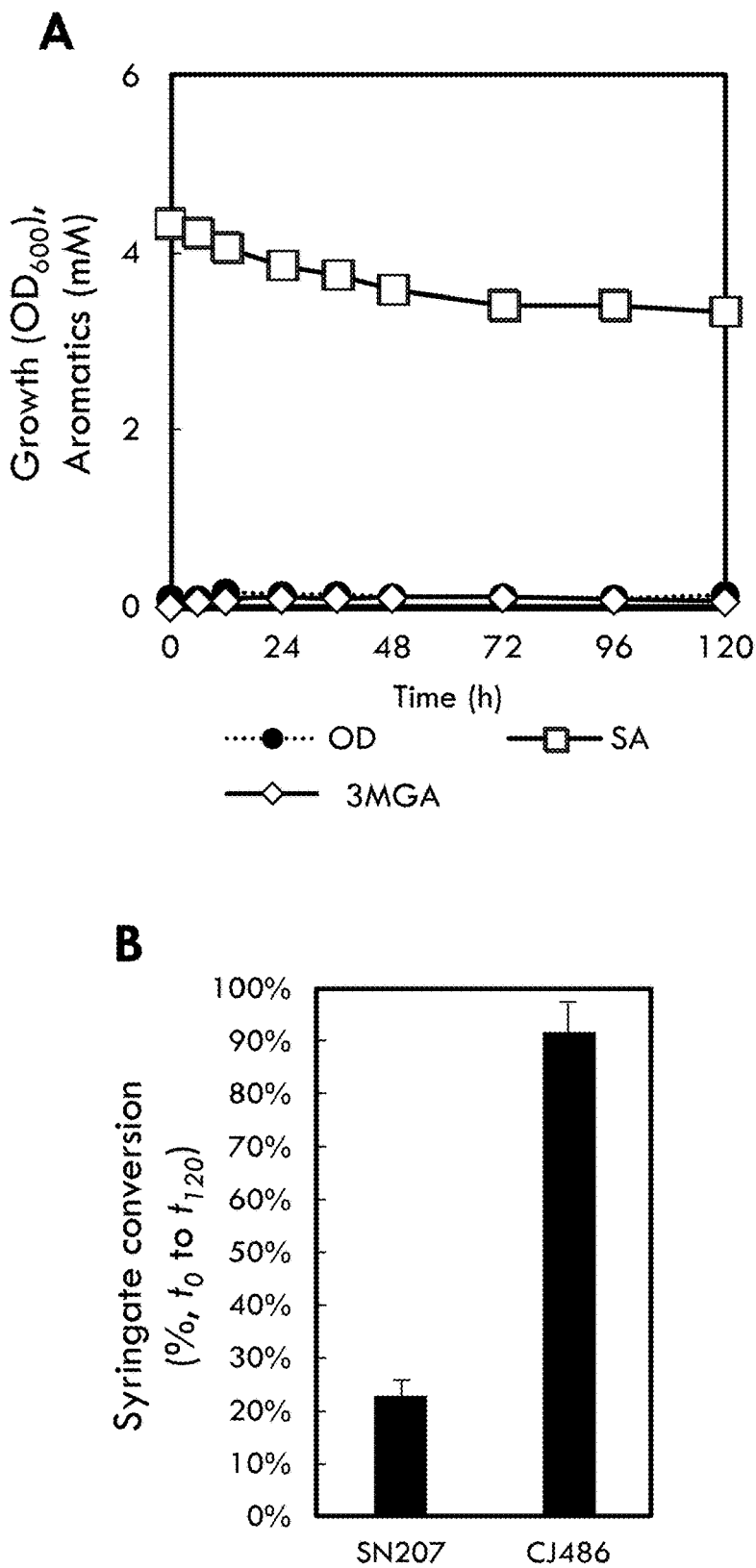
FIG. 6 illustrates in Panel (A) SN207 (CJ486+empty pBTL-2 vector) cultivation in M9 minimal media supplemented with syringate as the sole carbon source, according to some embodiments of the present disclosure. Panel (B) illustrates syringate conversion (%) after 120 hours of cultivation on M9 minimal media with supplemental syringate by SN207 (fpvA::$P_{tac}$:vanAB+empty pBTL-2 vector) and CJ486 (fpvA::$P_{tac}$:vanAB), according to some embodiments of the present disclosure. Cultures were sampled periodically to evaluate growth by $OD_{600}$ and metabolite concentrations in the media using HPLC. Error bars represent the standard deviation of biological triplicates. Abbreviations: OD: optical density; 3-O-MGA: 3-O-methylgallate; SA: syringate; GLU: glucose.

Next, the effect of increased expression of vanAB on SA utilization was examined. Expression of vanAB on a plasmid (strain SN183) did not enable SA utilization as the sole carbon source (see FIG. 5A). However, in the presence of glucose, SN183 rapidly catabolized SA (see FIG. 5B). Integration of a second copy of vanAB in the genome driven by the strong and constitutive tac promoter (62) (strain CJ486) resulted in catabolism of SA (see FIG. 5C) which was enhanced by the presence of glucose (see FIG. 5D). As with wild-type P. putida KT2440, the addition of formate improved CJ486 growth and SA catabolism (see FIGS. 4C-D). The phenotypic discrepancy between SN183 and CJ486 suggests that the burden of maintaining the vanAB overexpression plasmid precludes SA catabolism, consistent with the energy limitation described above. In support of this, SA utilization by CJ486 was significantly decreased when the strain harbored an empty pBTL-2 vector (see FIG. 6 and FIG. 5C). Despite the apparent energetic limitation, strains which catabolize SA generated more biomass (see FIGS. 2A-F and FIGS. 5A-5H). Together, these results demonstrate that chromosomal over-expression of vanAB is sufficient for catabolism of SA as the sole carbon source and that this activity is enhanced by supplementation with an auxiliary source of energy, such as glucose or formate.

Figure 7A:
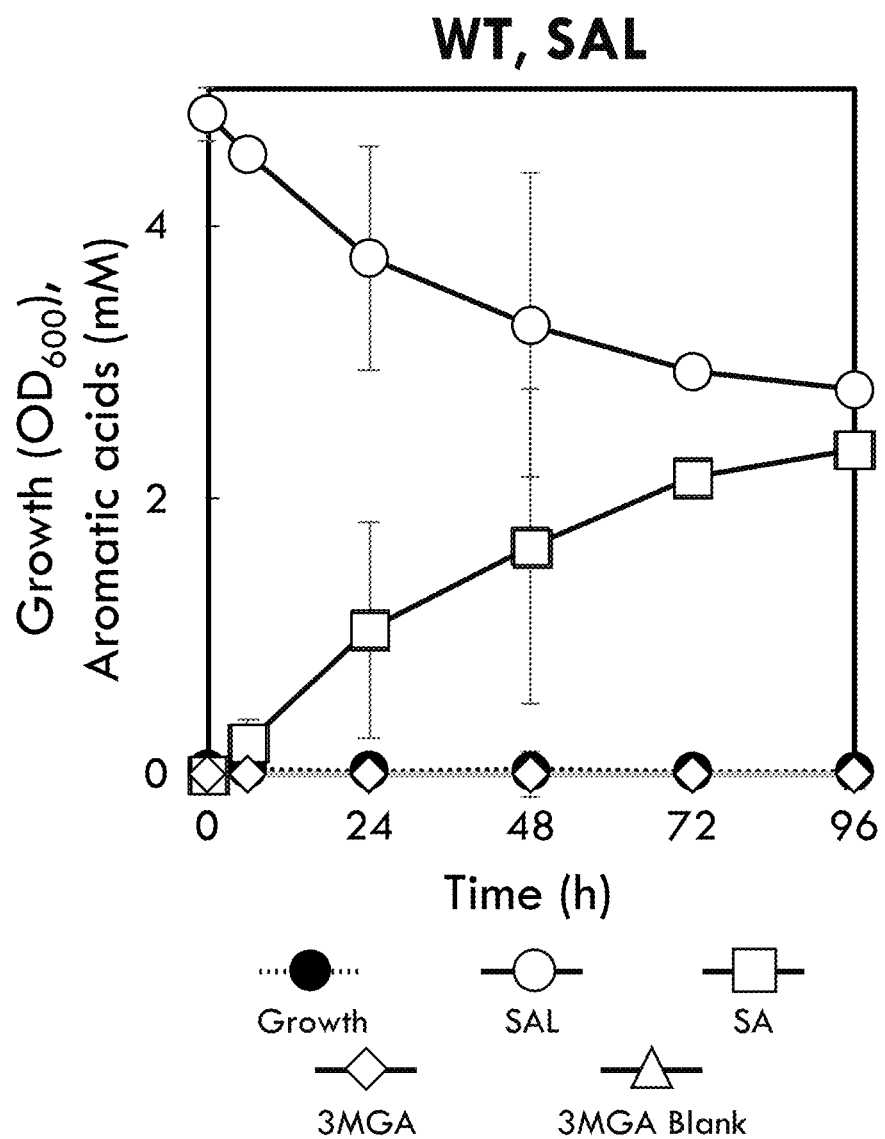
FIG. 7A illustrates wild-type P. putida KT2440 cultivated in M9 minimal medium containing 5 mM syringaldehyde (SAL) as the sole carbon source, according to some embodiments of the present disclosure. Cultures were sampled periodically to evaluate growth by $OD_{600}$ and metabolite concentrations in the media using HPLC. Error bars represent the standard deviation across biological triplicates.
Figure 7B:
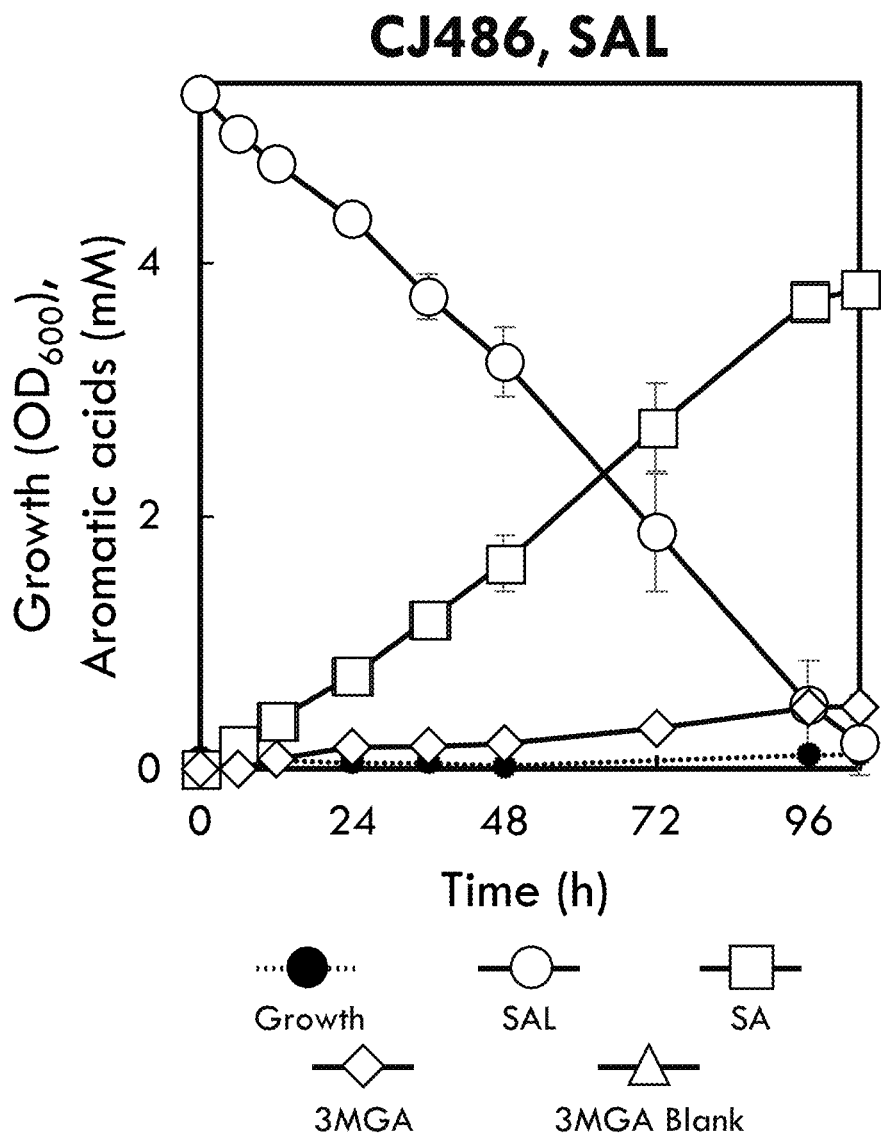
FIG. 7B illustrates P. putida CJ486 (P. putida fpvA::$P_{tac}$: vanAB) cultivated in M9 minimal medium containing 5 mM syringaldehyde (SAL) as the sole carbon source, according to some embodiments of the present disclosure. Cultures were sampled periodically to evaluate growth by $OD_{600}$ and metabolite concentrations in the media using HPLC. Error bars represent the standard deviation across biological triplicates.

To further characterize the S-lignin pathway in *P. putida* KT2440 catabolism of syringaldehyde (SAL) was examined, which was suspected to be converted to SA, and 3MGA, which is the product of SA O-demethylation and subsequently O-demethylated to generate GA. While *P. putida* KT2440 employs several redundant dehydrogenases, including Vdh, to catabolize the phenolic aldehydes vanillin and 4-hydroxybenzaldehyde, aldehyde dehydrogenases active toward SAL are not presently known. In minimal medium supplemented with SAL and glucose, wild-type *P. putida* KT2440 converted SAL to SA, which was then demethylated to 3MGA, but 3MGA was not catabolized further (see FIG. 5E) likely due to the depletion of glucose. In the absence of glucose, SAL was converted to SA which accumulated in the medium (see FIG. 7A). CJ486 completely catabolized SAL, SA, and 3MGA within 24 h in the presence of glucose (see FIG. 5F) with slower utilization observed in the absence of glucose (see FIG. 7B). Notably, both wild-type and CJ486 display negligible growth during cultivations in M9 minimal medium plus SAL, which was converted to SA and 3MGA that accumulated in the media rather than being metabolized further (see FIGS. 7A-B).

Figure 7C:
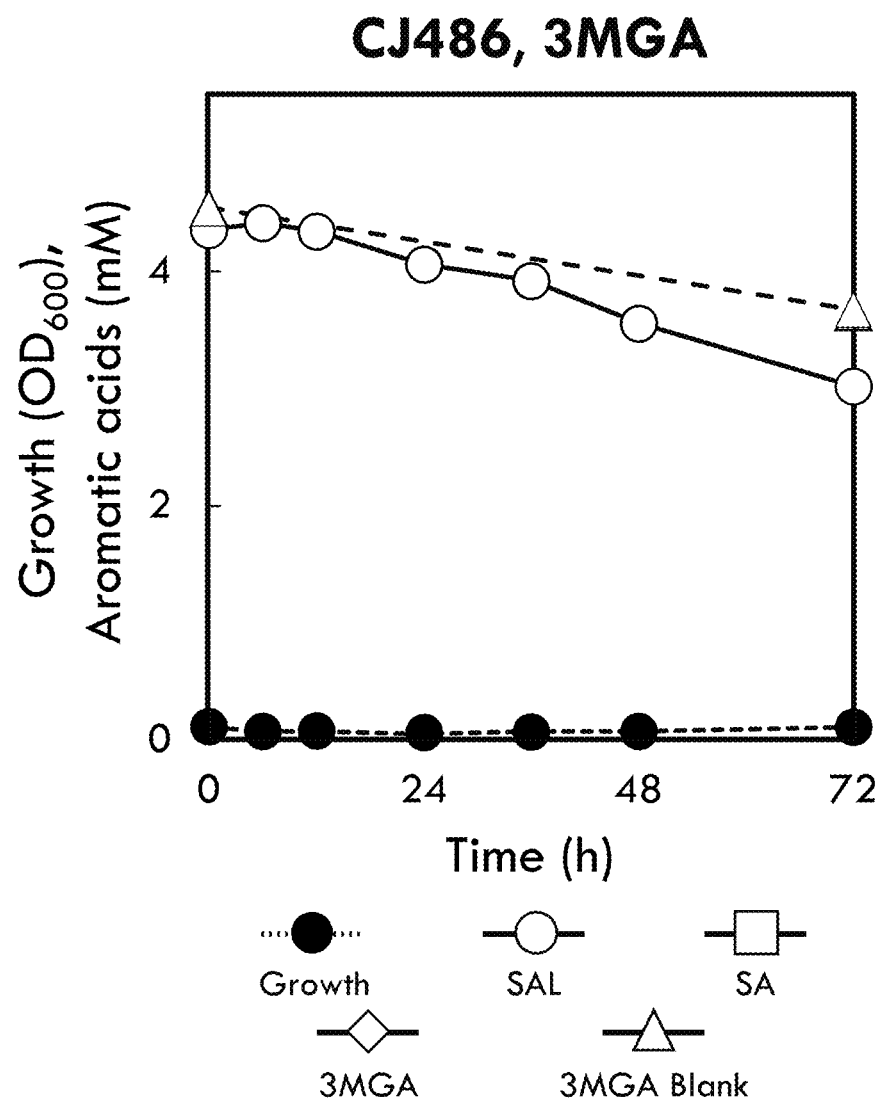
FIG. 7C illustrates CJ486 cultivated in M9 minimal medium containing 5 mM 3-O-methylgallate (3-MGA) as sole carbon source, according to some embodiments of the present disclosure. Cultures were sampled periodically to evaluate growth by $OD_{600}$ and metabolite concentrations in the media using HPLC. Error bars represent the standard deviation across biological duplicates.

O-Demethylation of 3MGA could occur by the action of VanAB, as in *Streptomyces* sp. NL15-2K, or a separate enzyme, as in *Sphingobium* sp. SYK-6. Wild-type *P. putida* KT2440 did not display 3MGA conversion greater than the abiotic degradation observed in the non-inoculated control, which is presumed to result from oxidation (see FIG. 5G). CJ486 completely converted 3MGA within 48 h in the presence of glucose (see FIG. 5H) but with markedly less 3MGA conversion observed in the absence of glucose (see FIG. 7C). Thus, these data suggest that, as with SA, VanAB is capable of mediating 3MGA O-demethylation in vivo, which may mediate a SAL catabolic pathway (see FIG. 1), but vanAB expression is not sufficiently induced by 3MGA.

Figure 8A:
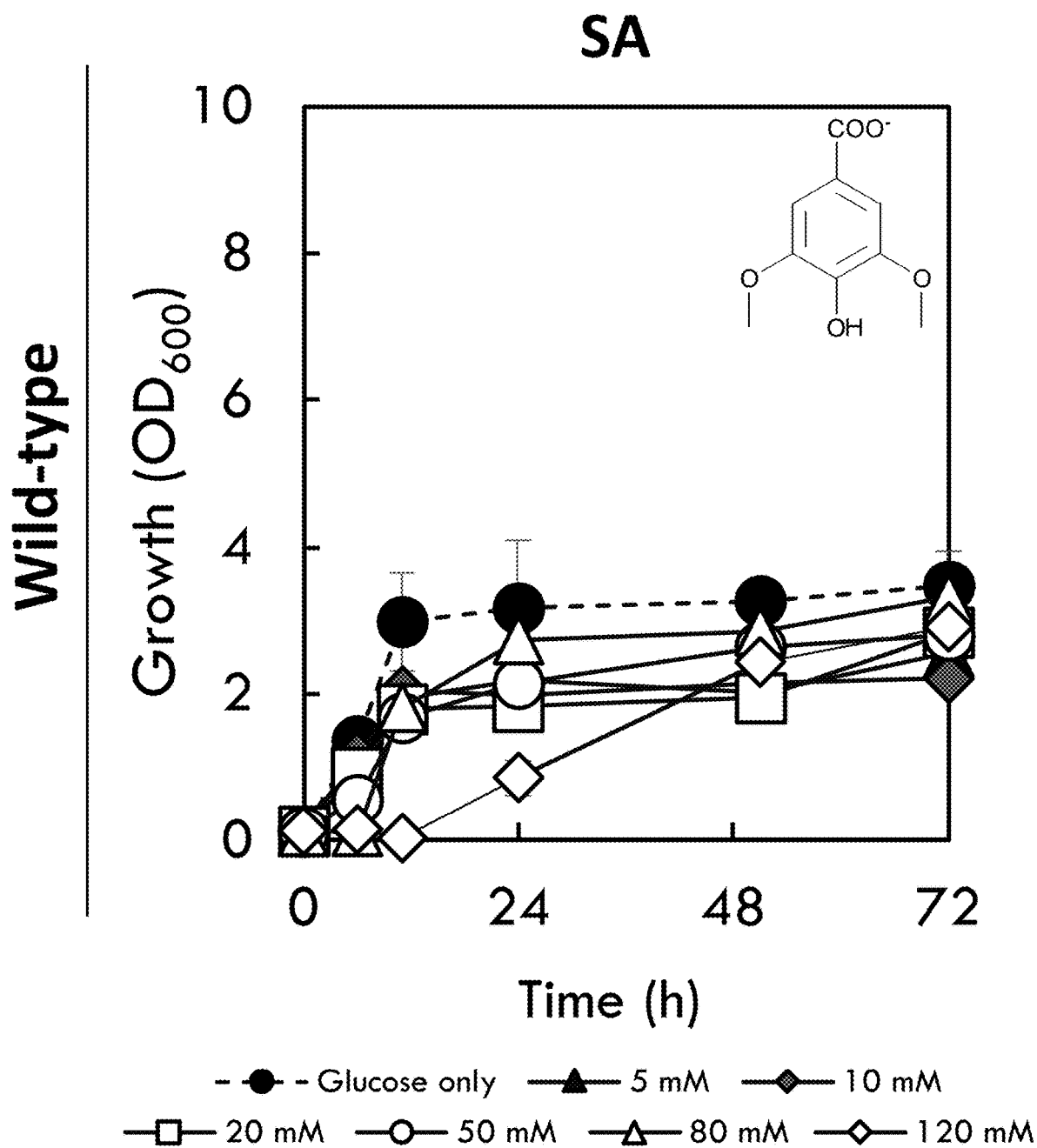
FIGS. 8A-8D illustrate the toxicity effects of SA, VA, GA, and SAL, on the growth of wild-type *P. putida* KT2440 in M9 minimal media supplemented with 20 mM glucose and 5, 10, 20, 50, 80, or 120 mM for each of FIG. 8A SA, FIG. 8B VA, FIG. 8C GA, or FIG. 8D SAL, according to some embodiments of the present disclosure. Error bars represent the absolute value of two biological replicates. Abbreviations: SA: syringate; VA: vanillate; GA: gallate; SAL: syringaldehyde; $OD_{600}$: optical density, measured as absorbance at 600 nm.
Figure 8B:
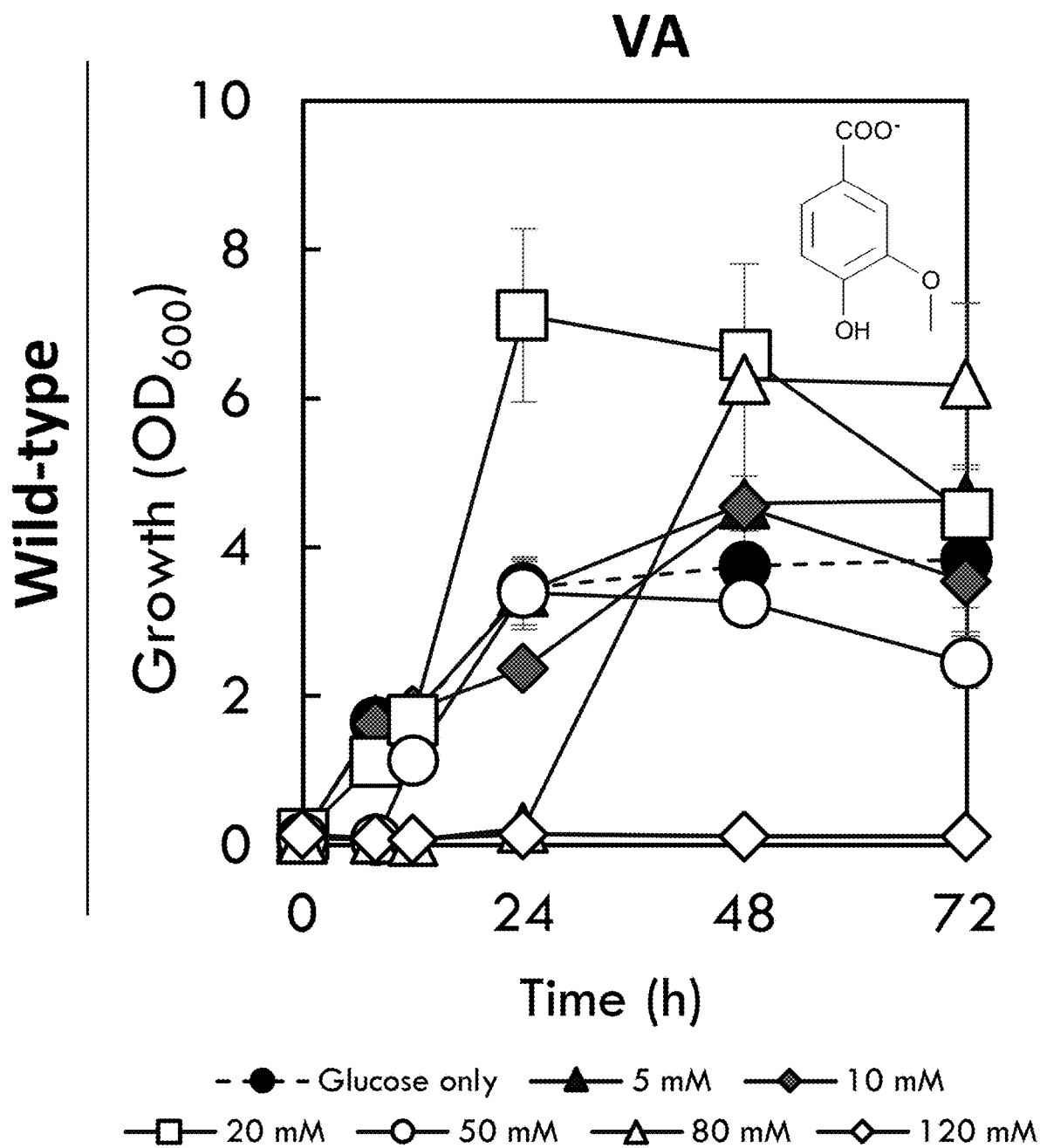
Figure 8C:
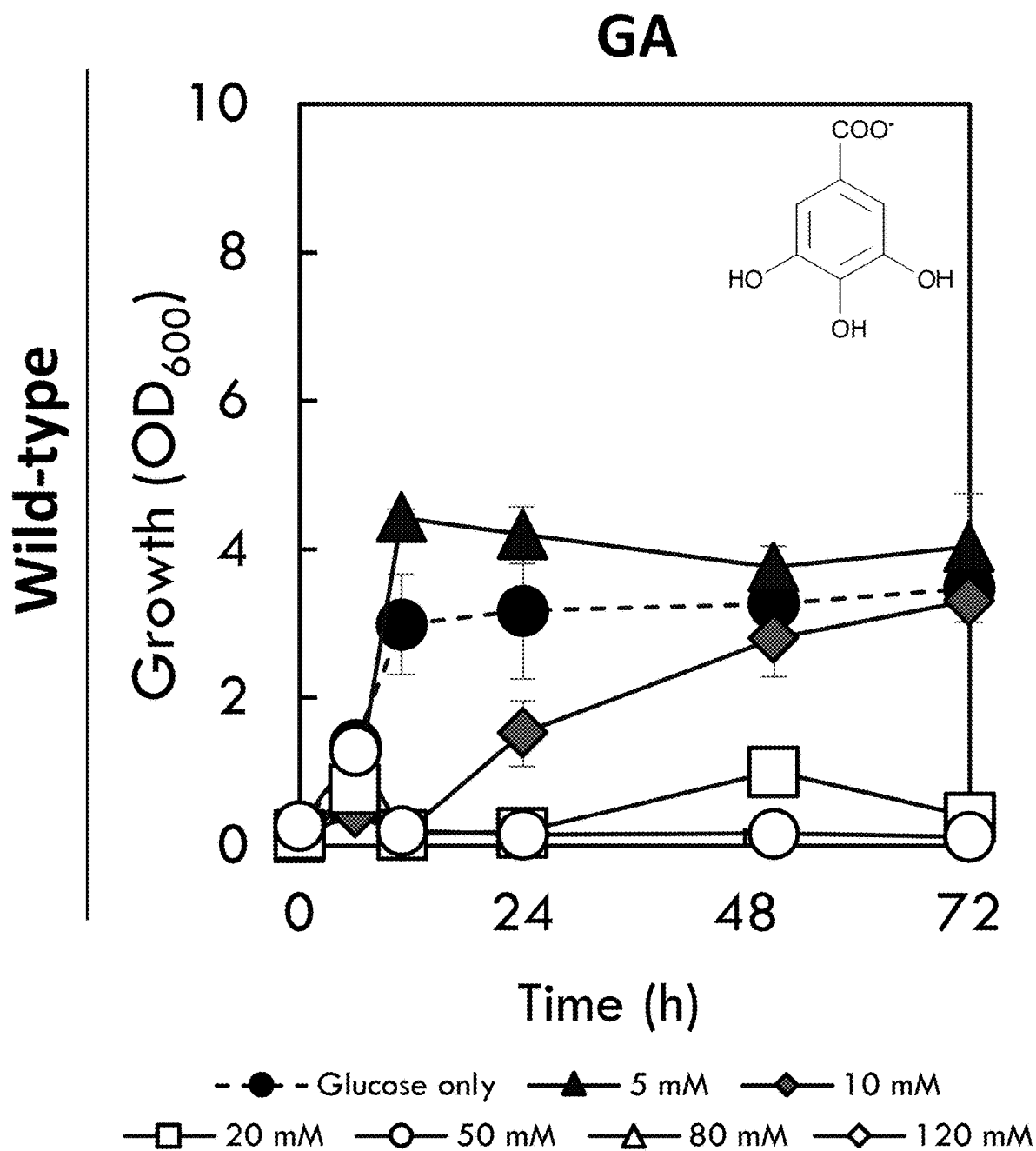
Figure 8D:
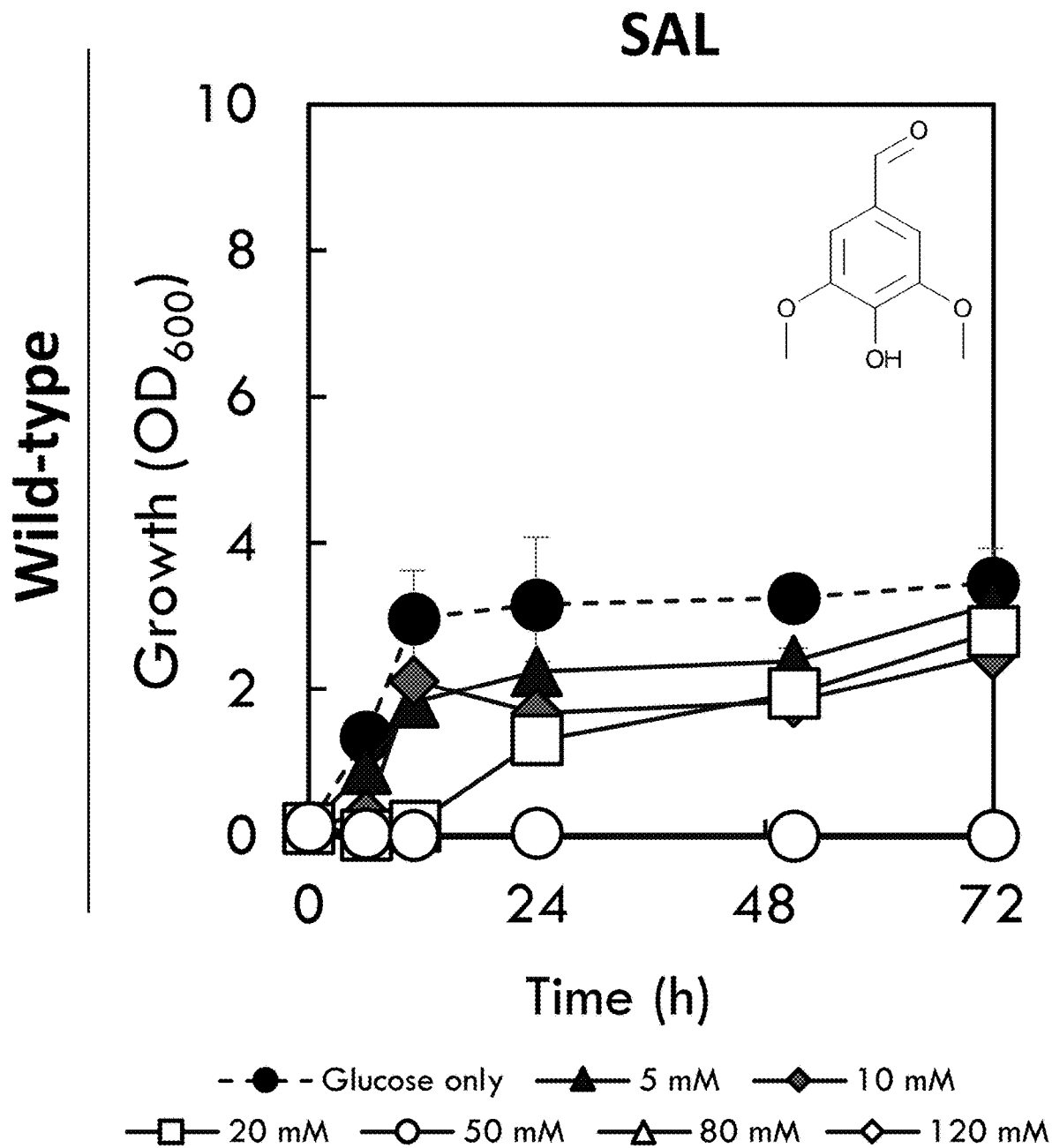
Figure 8E:
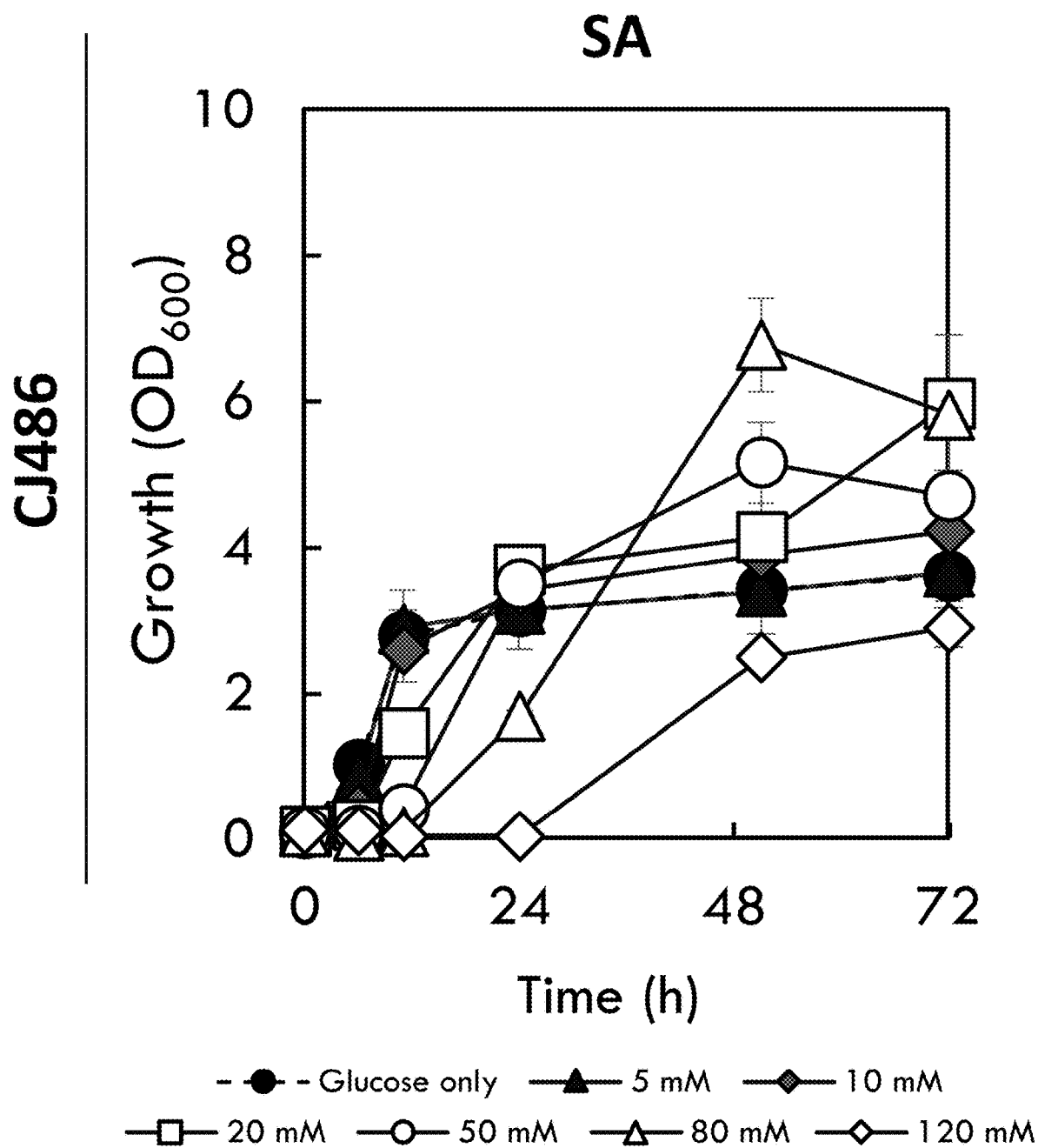
FIGS. 8E-8H illustrate the toxicity effects of SA, VA, GA, and SAL, on the growth of strain CJ486 (vanAB overexpression strain) in M9 minimal media supplemented with 20 mM glucose and 5, 10, 20, 50, 80, or 120 mM for each of SA (FIG. 8A), VA (FIG. 8B), GA (FIG. 8C), or SAL (FIG. 8D), according to some embodiments of the present disclosure. Error bars represent the absolute value of two biological replicates. Abbreviations: SA: syringate; VA: vanillate; GA: gallate; SAL: syringaldehyde; $OD_{600}$: optical density, measured as absorbance at 600 nm.
Figure 8F:
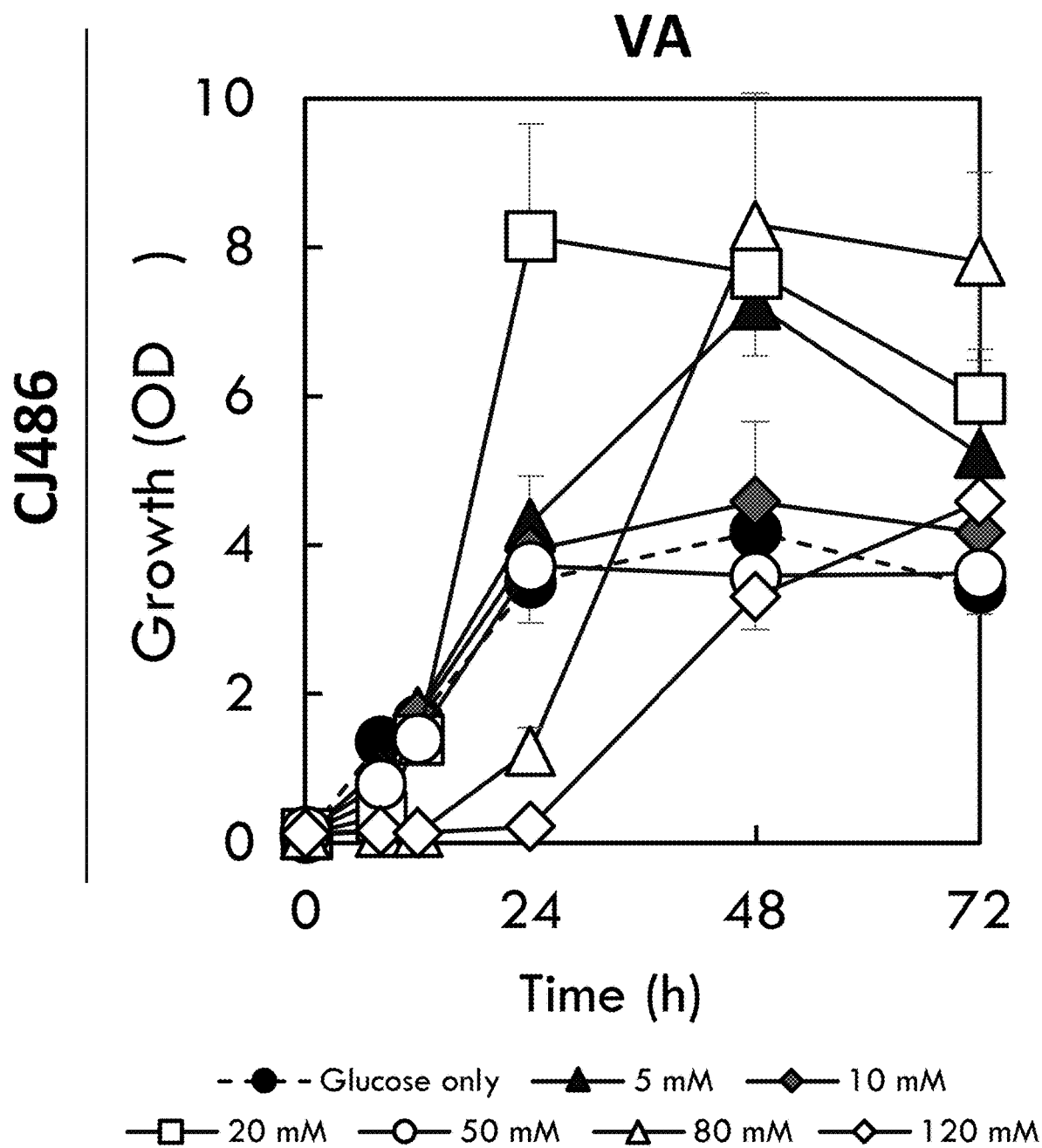
Figure 8G:
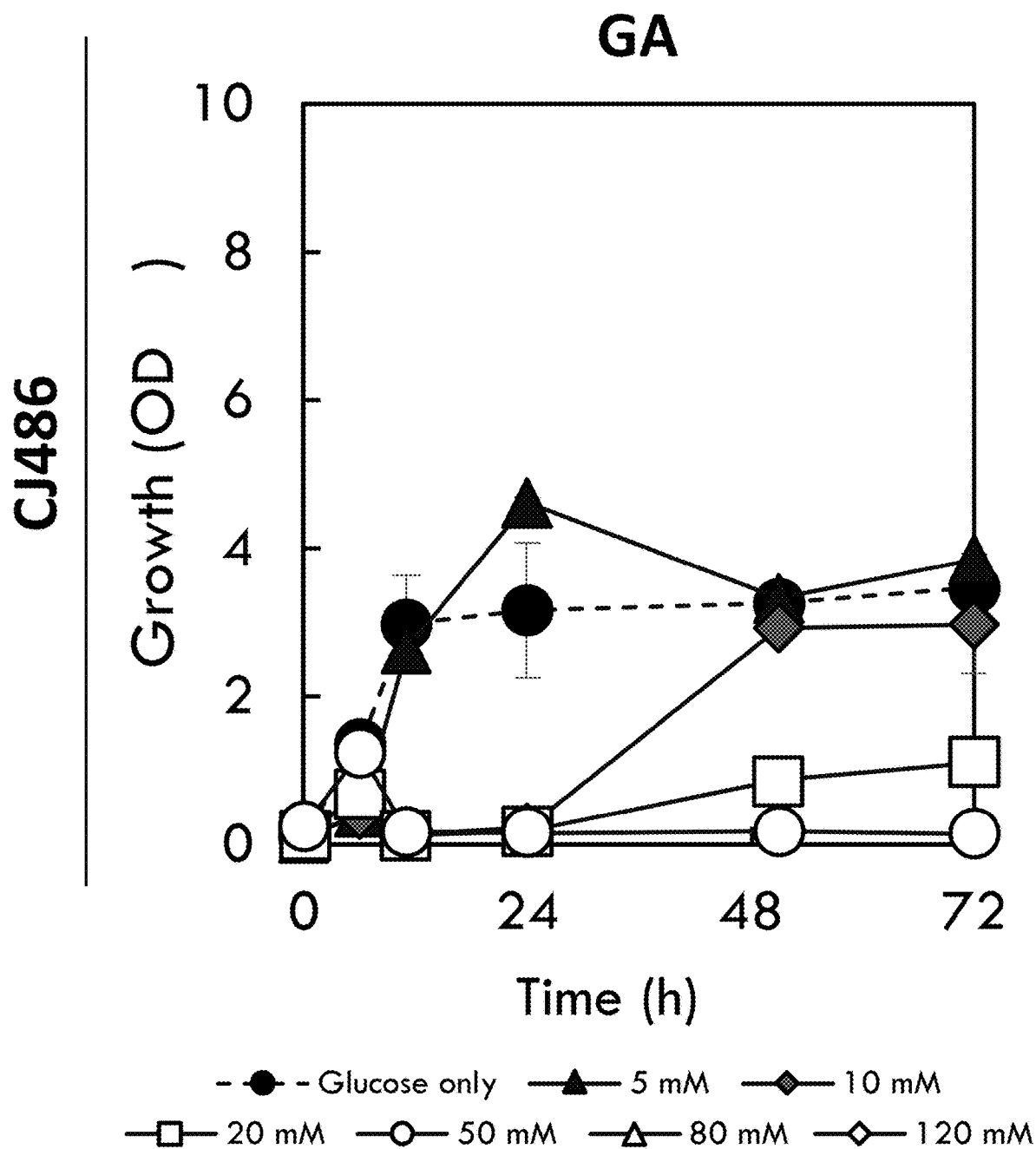
Figure 8H:
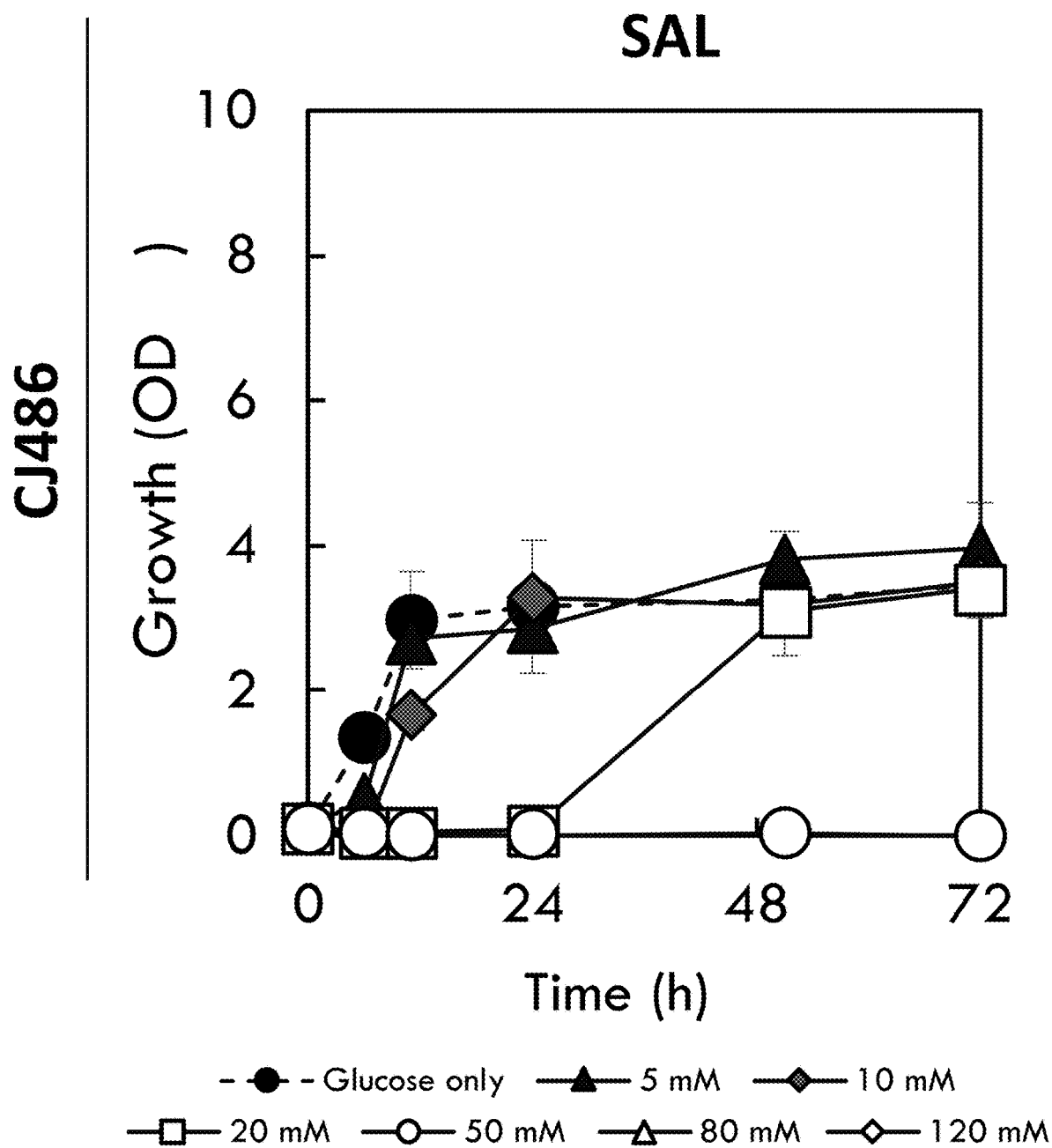

These data led to the hypothesis that the toxicity of S-lignin derived monomers, both intrinsic to the aromatic compounds as well as due to generated byproducts such as formaldehyde, may present an energetic barrier to catabolism as a sole carbon source. To examine the toxicity of compounds relevant to this study, the growth of wild-type *P. putida* KT2440 and CJ486 was studied in M9 minimal media containing 20 mM glucose and increasing concentrations of SA, VA, GA, and SAL. Surprisingly, wild-type *P. putida* KT2440 was able to grow on 120 mM SA but not VA; yet, at lower substrate concentrations, growth was enhanced by VA but not SA (see FIGS. 8A-B). CJ486 demonstrated improved growth in media containing SA, SAL, and VA—but not GA—as compared to wild-type, presumably due to rapid utilization of the substrates (see FIGS. 8E-H). GA and SAL were the most toxic substrates with growth only permitted below 50 mM (see FIGS. 8C-D and FIGS. 8G-H). Together these data indicate that SAL, SA, and GA are more toxic to *P. putida* KT2440 than VA, which is a robust growth substrate. Relative to wild-type, CJ486 also exhibited greater tolerance to SA, SAL, and VA presumably due to more rapid metabolism of these substrates resulting from overexpression of vanAB (see FIGS. 5A-5H).

Figure 9:
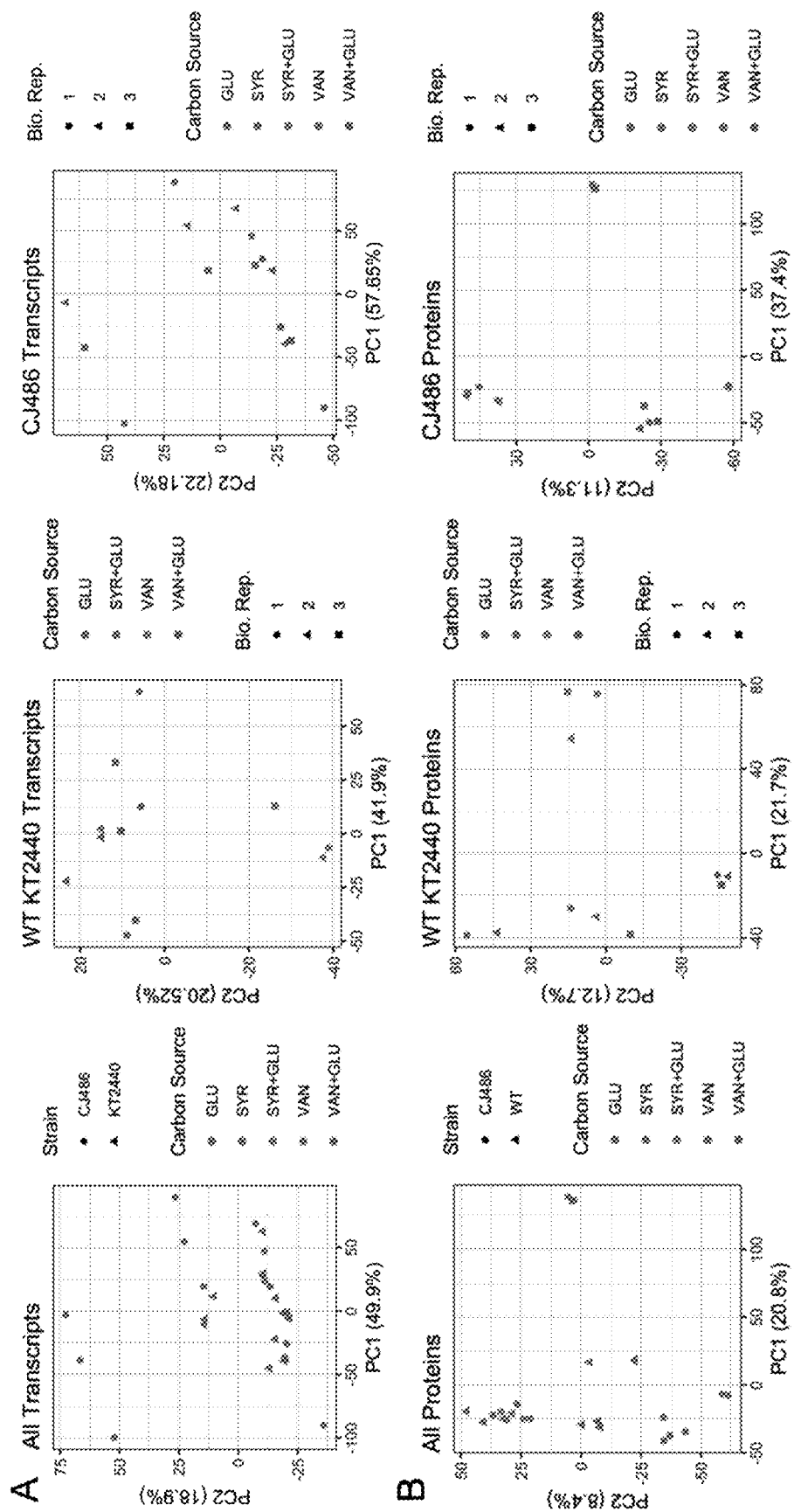
FIG. 9 illustrates principal component analysis of Panel (A) transcriptomics and Panel (B) proteomics data, according to some embodiments of the present disclosure. Analysis is shown for the entire data set and each strain individually. Log 2 transformed data was utilized for both datasets on glucose (GLU), syringate (SYR), syringate and glucose (SYR+GLU), vanillate (VAN), and vanillate and glucose (VAN+GLU). Biological replicates #3 on glucose were removed as outliers from the proteomics data set
Figure 10A:
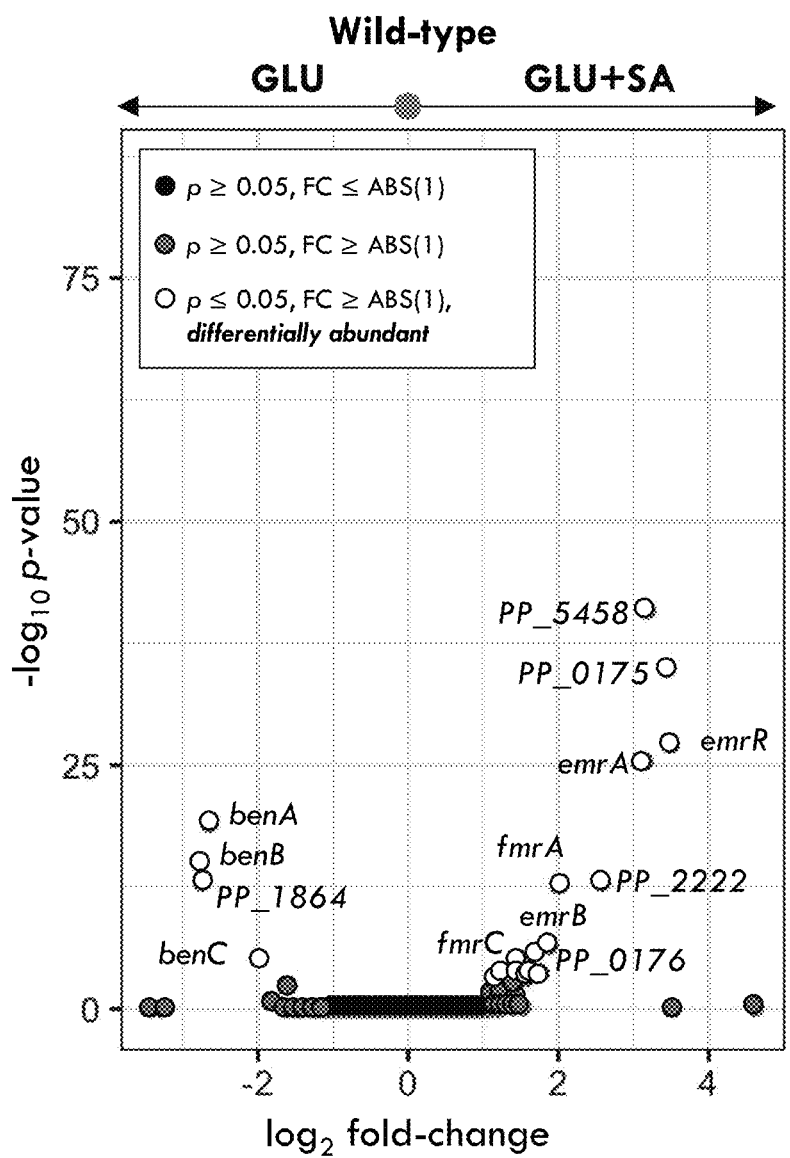
FIG. 10A illustrates a volanco plot of differentially regulated genes (shown in purple) between *P. putida* wild-type cultivated in M9 minimal medium supplemented with 20 mM glucose alone (GLU) or 20 mM glucose plus 5 mM syringate (GLU+SA), according to some embodiments of the present disclosure.
Figure 10B:
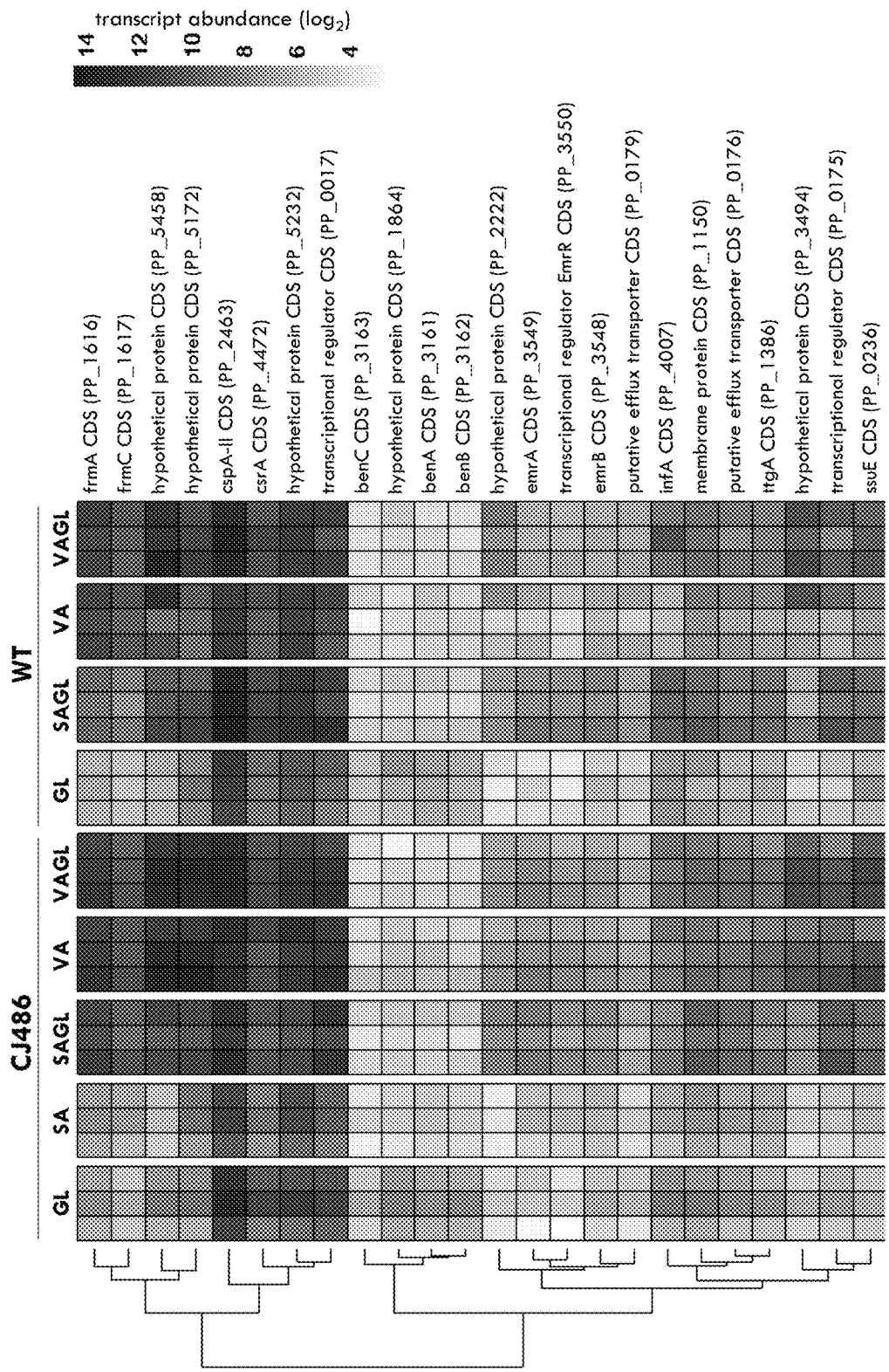
FIG. 10B illustrates a clustered heat map of log 2 transcript abundance for differentially abundant transcripts identified in for both CJ486 and wild-type (WT) in M9 minimal media supplemented with glucose alone (GL), syringate (SA), syringate and glucose (SAGL), vanillate (VA), or vanillate and glucose (VAGL), according to some embodiments of the present disclosure. No SA condition is provided for WT because no growth is observed under those conditions. Log 2 transcript abundance is provide for each of biological triplicates. Gene names and locus identifiers are provided.

The data presented thus far suggested that the native VanAB sequentially O-demethylates SA and 3MGA to GA which can be further catabolized by the GA pathway, yet wild-type *P. putida* KT2440 cannot grow on SA alone. Observation of the latent SA catabolic capacity suggests that SA may be insufficient to induce expression of the required genes. To examine this at the systems level, RNA-Seq transcriptomics and shotgun proteomics was utilized to examine wild-type *P. putida* KT2440 and CJ486 during cultivation in M9 minimal media supplemented with glucose, VA, SA, or a combination thereof. Principal component analysis revealed that global variations in transcript and protein abundances were driven by both media and genotype (see FIG. 9). Using stringent cut-offs (BH-corrected p<0.05, log 2 fold-change>|1|), we found only 24 differentially expressed transcripts (0.48% of total) between wild-type cultivations in glucose versus glucose and SA (see FIGS. 10A and 10B). Of these, frmA and frmC both putatively involved in formaldehyde detoxification-were significantly upregulated in all wild-type *P. putida* KT2440 cultivations in aromatics and CJ486 cultivations in aromatics except SA alone (see FIGS. 10A and 10B). Strong induction of frmA and frmC emphasizes the importance of formaldehyde detoxification during catabolism of SA and VA. More transcripts were differentially expressed in wild-type *P. putida* KT2440 cultivations in response to VA (121 transcripts, 2% of total), suggesting a higher amount of transcriptional response to VA than to SA. Still, putative transcriptional regulators and transporters upregulated in both wild-type and CJ486 cultivations on SA (see FIGS. 10A and 10B) are interesting targets for future study.

Figure 11:
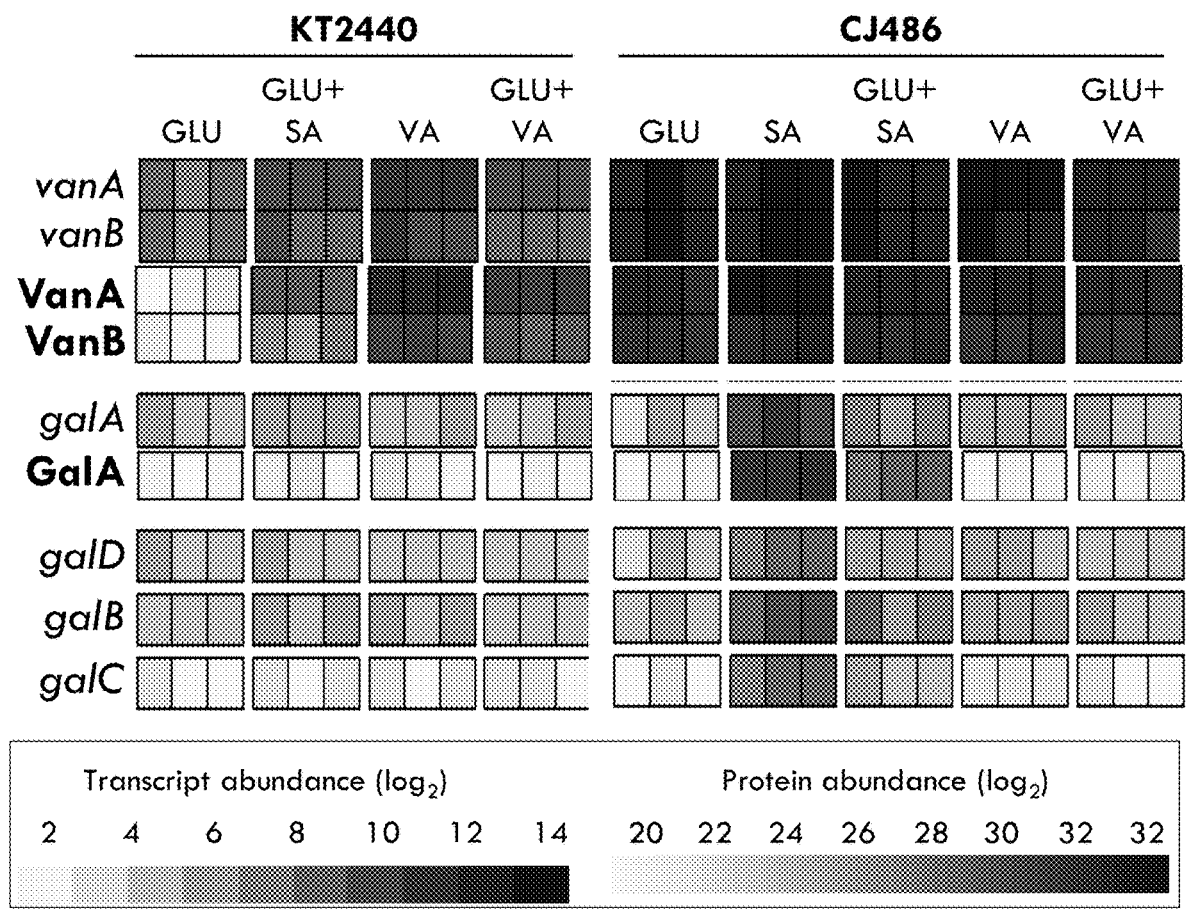
FIG. 11 illustrates transcriptomic and proteomic analysis of wild-type *P. putida* KT2440 and CJ486 in SA- and VA-containing medium, according to some embodiments of the present disclosure. Heatmap of transcript and protein levels for select genes/proteins involved in catabolism. For each biological triplicate, log 2 transcript abundance is displayed in italics and log 2 protein abundance is displayed in bold for both wild-type *P. putida* KT2440 and CJ486 (*P. putida* KT2440 fpvA:$P_{tac}$:vanAB). Cells were cultivated in M9 minimal media supplemented with a combination of the following, as indicated: SA: 5 mM syringic acid; VA: 5 mM vanillic acid; GLU: 20 mM glucose.
Figure 12:
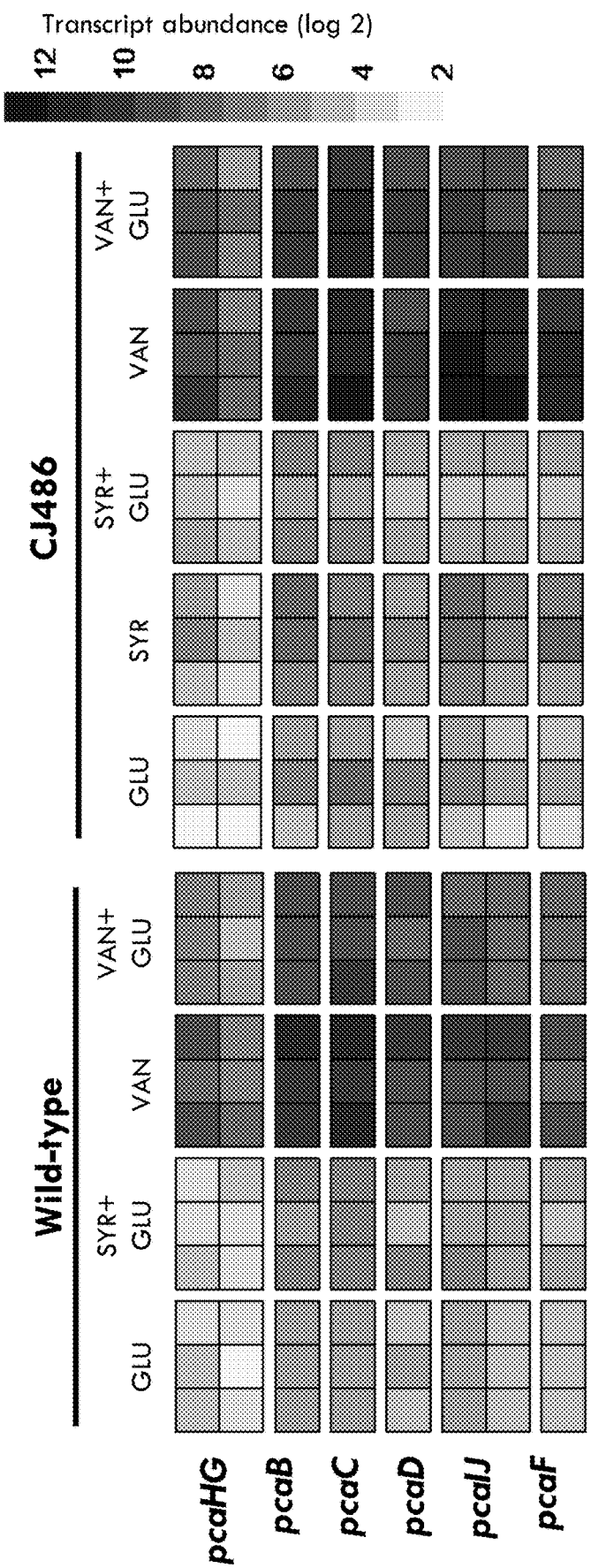
FIG. 12 illustrates transcript (log 2) abundance of genes involved in the ß-ketoadipate pathway for aromatic catabolism, according to some embodiments of the present disclosure. Values are displayed for each of biological triplicates for *P. putida* wild-type and CJ486 cultivations on glucose (GLU), GLU and syringate (SYR), vanillate (VAN), and VAN and GLU.

As expected, VanAB was significantly more abundant in CJ486 as compared to wild-type *P. putida* KT2440 at both the transcript and protein level (BH-adjusted p<0.05, FIG. 11, Table 2). In wild-type *P. putida* KT2440 cultivations in glucose versus glucose and SA, an insignificant change in vanAB transcripts was observed yet a 1.7- and 1.6-fold increase in VanA and VanB proteins were detected. However, the GA catabolic cluster required for SA catabolism was only significantly upregulated in CJ486 cultivations in SA or SA plus glucose as compared to glucose alone (see FIG. 11, Table 2). As expected, the β-ketoadipate pathway was upregulated in both wild-type *P. putida* KT2440 and CJ486 growing in VA-containing media (see Table 2, FIG. 12). Together, these data show that over-expression of a second copy of vanAB in CJ486 was sufficient for induction of the GA catabolic cluster during cultivation in minimal medium supplemented with SA, likely due to the generation of GA itself.

TABLE 2

Pairwise comparisons of select transciprt abundances. Wild-type *P. putida* (WT) and CJ486 (*P. putida* fpvA::P$_{tac}$:vanAB) cultivated in 20 mM glucose (GLU), 20 mM glucose plus 5 mM syringate (SAGLU), or 20 mM glucose plus 5 mm vanillate (VAGLU) were compared. The log$_2$ fold-change and Benjamini-Hochberg (BH)-adjusted p-value are displayed for each gene in a given comparison; BH-adjusted p-values which fall below the 0.05 threshold are shown in bold.

| Pathway/ Protein | Pairwise comparison | Locus tag | Gene name | Fold-change (Log2) | BH-adjusted p-value |
|---|---|---|---|---|---|
| Gallate catabolism | WT GLU vs. WT SAGLU | PP_2513 | gIID CDS | −0.58 | 1.00 |
| | | PP_2514 | gIIC CDS | −0.65 | NA |
| | | PP_2515 | gIIB CDS | 0.20 | 1.00 |
| | | PP_2518 | gIIIA CDS | 0.09 | 1.00 |

TABLE 2-continued

Pairwise comparisons of select transciprt abundances. Wild-type *P. putida* (WT) and CJ486 (*P. putida* fpvA::P$_{tac}$:vanAB) cultivated in 20 mM glucose (GLU), 20 mM glucose plus 5 mM syringate (SAGLU), or 20 mM glucose plus 5 mm vanillate (VAGLU) were compared. The log$_2$ fold-change and Benjamini-Hochberg (BH)-adjusted p-value are displayed for each gene in a given comparison; BH-adjusted p-values which fall below the 0.05 threshold are shown in bold.

| Pathway/ Protein | Pairwise comparison | Locus tag | Gene name | Fold-change (Log2) | BH-adjusted p-value |
|---|---|---|---|---|---|
| | CJ486 GLU vs. CJ486 SAGLU | PP_2513 | gIID CDS | 1.03 | 7.12E-03 |
| | | PP_2514 | gIIC CDS | 2.27 | 3.82E-06 |
| | | PP_2515 | gIIB CDS | 2.36 | 1.76E-11 |
| | | PP_2518 | gIIIA CDS | 1.75 | 0.000 |
| | WT GLU vs. VAGLU | PP_2513 | gIID CDS | 0.92 | 0.24 |
| | | PP_2514 | gIIC CDS | 0.39 | NA |
| | | PP_2515 | gIIB CDS | 0.23 | 0.82 |
| | | PP_2518 | gIIIA CDS | 0.65 | 0.47 |
| | CJ486 GLU vs. CJ486 VAGLU | PP_2513 | gIID CDS | -0.15 | 0.80 |
| | | PP_2514 | gIIC CDS | -0.58 | 0.59 |
| | | PP_2515 | gIIB CDS | -0.30 | 0.58 |
| | | PP_2518 | gIIIA CDS | -0.20 | 0.70 |
| VanAB | WT GLU vs. CJ486 GLU | PP_3736 | vanA CDS | -3.95 | -3.95E+00 |
| | | PP_3737 | vanB CDS | -4.47 | -4.47E+00 |
| | WT SAGLU vs. CJ486 SAGLU | PP_3736 | vanA CDS | -3.56 | 6.13E-99 |
| | | PP_3737 | vanB CDS | -4.36 | 2.83E-148 |
| | WT GLU vs. WT SAGLU | PP_3736 | vanA CDS | 0.14 | 1.00 |
| | | PP_3737 | vanB CDS | 0.01 | 1.00 |
| | CJ486 GLU vs. CJ486 SAGLU | PP_3736 | vanA CDS | -0.25 | 0.52 |
| | | PP_3737 | vanB CDS | -0.09 | 0.89 |
| Protocatechuate catabolism (lower β-ketoadipate pathway) | WT GLU vs. WT SAGLU | PP_4656 | pcaH CDS | -0.66 | 1.00 |
| | | PP_4655 | pcaG CDS | 0.29 | NA |
| | | PP_1379 | pcaB CDS | -0.05 | 1.00 |
| | | PP_1381 | pcaC CDS | 0.16 | 1.00 |
| | | PP_1380 | pcaD CDS | -0.45 | 1.00 |
| | | PP_1382 | pcaP CDS | -0.41 | 1.00 |
| | | PP_3952 | pcaJ CDS | 0.15 | 1.00 |
| | | PP_3951 | pcaI CDS | -0.63 | 1.00 |
| | | PP_2137 | pcaF-II CDS | 0.42 | 1.00 |
| | | PP_1377 | pcaF-I CDS | -0.05 | 1.00 |
| | | PP_1376 | pcaK CDS | 0.17 | 1.00 |
| | CJ486 GLU vs. CJ486 SAGLU | PP_4656 | pcaH CDS | 1.04 | 0.07 |
| | | PP_4655 | pcaG CDS | 0.69 | 0.52 |
| | | PP_1379 | pcaB CDS | 0.27 | 0.71 |
| | | PP_1381 | pcaC CDS | 0.00 | 0.95 |
| | | PP_1380 | pcaD CDS | -0.68 | 0.25 |
| | | PP_3951 | pcaI CDS | -0.55 | 0.30 |
| | | PP_3952 | pcaJ CDS | 0.07 | 0.93 |
| | | PP_1377 | pcaF-I CDS | 0.33 | 0.74 |
| | | PP_2137 | pcaF-II CDS | 0.14 | 0.85 |
| | | PP_1376 | pcaK CDS | 0.01 | 0.93 |
| | WT GLU vs. VAGLU | PP_4656 | pcaH CDS | 2.48 | 9.78E-09 |
| | | PP_4655 | pcaG CDS | 1.97 | 9.86E-04 |
| | | PP_1379 | pcaB CDS | 2.81 | 3.52E-17 |
| | | PP_1381 | pcaC CDS | 3.47 | 1.05E-34 |
| | | PP_1380 | pcaD CDS | 3.14 | 4.76E-21 |
| | | PP_3952 | pcaJ CDS | 2.85 | 5.06E-17 |
| | | PP_3951 | pcaI CDS | 2.52 | 2.13E-15 |
| | | PP_2137 | pcaF-II CDS | 0.29 | 6.98E-01 |
| | | PP_1377 | pcaF-I CDS | 2.80 | 1.32E-16 |
| | | PP_1376 | pcaK CDS | 1.29 | 6.78E-03 |
| | CJ486 GLU vs. VAGLU | PP_4656 | pcaH CDS | 4.88 | 1.33E-59 |
| | | PP_4655 | pcaG CDS | 3.42 | 1.11E-21 |
| | | PP_1379 | pcaB CDS | 3.68 | 4.45E-59 |
| | | PP_1381 | pcaC CDS | 3.89 | 9.76E-77 |
| | | PP_1380 | pcaD CDS | 3.58 | 1.33E-38 |
| | | PP_3952 | pcaJ CDS | 4.25 | 3.01E-63 |
| | | PP_3951 | pcaI CDS | 3.93 | 4.97E-60 |
| | | PP_2137 | pcaF-II CDS | 0.27 | 3.76E-01 |
| | | PP_1377 | pcaF-I CDS | 4.07 | 6.18E-56 |
| | | PP_1376 | pcaK CDS | 2.11 | 4.06E-13 |

Figure 13:
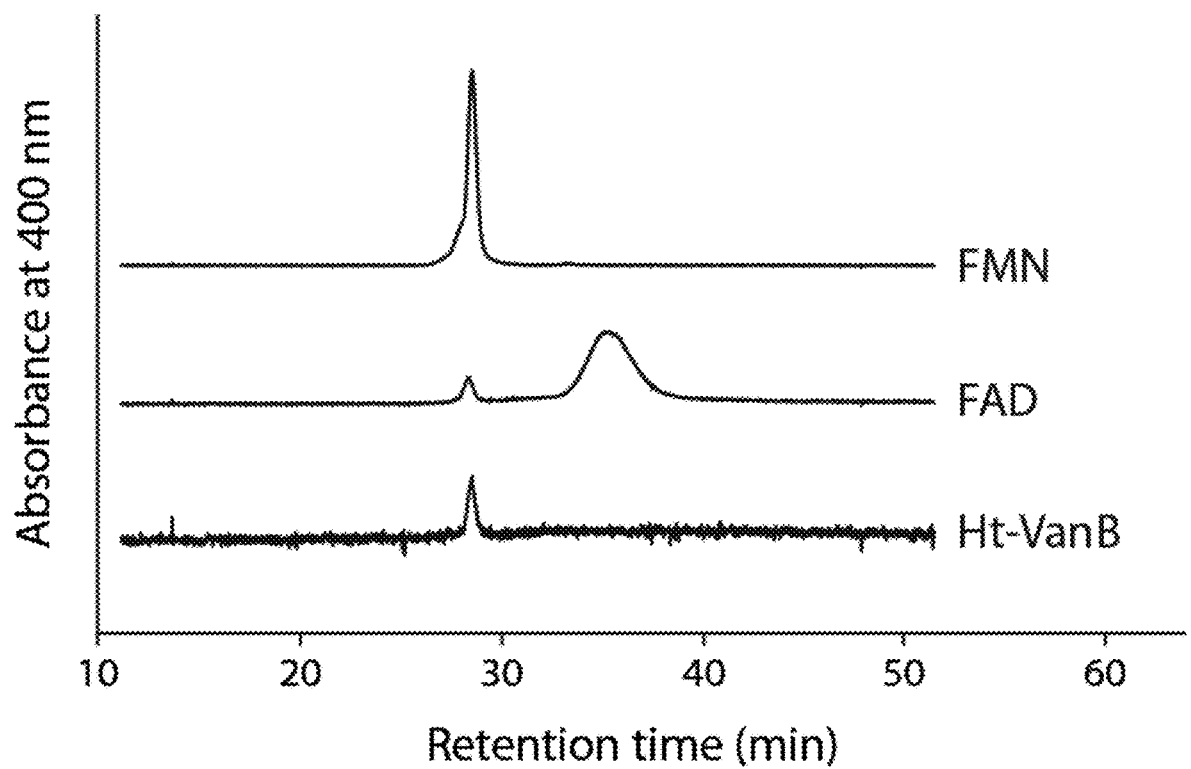
FIG. 13 illustrates HPLC analysis of Ht-VanB flavin. FMN and FAD were run as standards.

To further verify the proposed VanAB-mediated demethylation reactions, the apparent substrate specificity ($k_{cat}^{app}/K_M^{app}$) of VanAB was determined using steady-state kinetics. VanA was produced in *E. coli* and purified without an affinity tag to maximize the specific activity of the preparations, which contained 2.5±0.3 and 4±1 equivalents of Fe and S per mol of VanA, respectively. His-tagged (Ht)-VanB was produced and purified anaerobically to maximize specific activity as Ht-VanB is O2-labile, losing its activity and brown coloration in air-saturated buffer ($t_{1/2}$~24 h). VanB preparations contained 1.7±0.3 and 2.7±0.2 equivalents of Fe and S per mol of Ht-VanB, respectively, and contained FMN (see FIG. 13).

Figure 14:
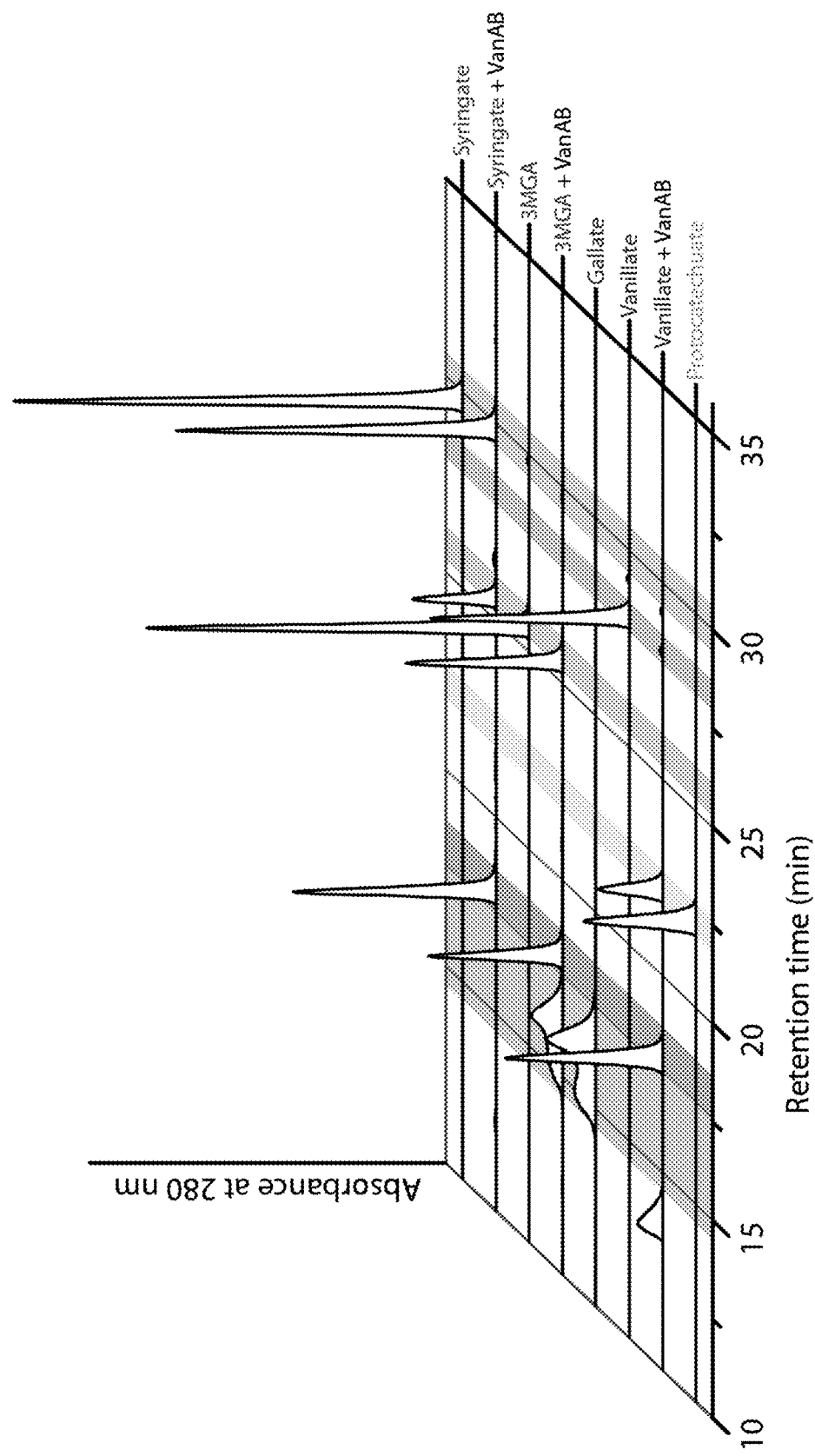
FIG. 14 illustrates HPLC analyses of VanAB-catalyzed reactions, according to some embodiments of the present disclosure. Reactions were performed with each of syringate, 3MGA, and vanillate. In addition, syringate, 3MGA, gallate, vanillate, and protocatechuate were run as standards.

The ability of VanAB to catalyze the O-demethylation of VA, SA, and 3MGA was evaluated first. Using an HPLC-based assay, the enzyme transformed VA, SA, and 3MGA to PCA, 3MGA, and GA, respectively (see FIG. 14). When reactions were quenched after ~100 µM of $O_2$ was consumed, the amounts of substrate consumed, and product detected, were equal to the amount of $O_2$ consumed within error (see Table 3). Moreover, the addition of catalase to these reactions after ~3 minutes did not result in a burst of 02 (data not shown), indicating that $H_2O_2$ is not produced during these reactions. Overall, these results establish that the VanAB-catalyzed O-demethylation of VA, 3MGA and SA are well-coupled to $O_2$-consumption. However, in the absence of VanA, VanB consumed NADH and $O_2$ to produce $H_2O_2$ in the presence of SA. This adventitious consumption of NADH and $O_2$ was not observed in the presence of VA or 3MGA. Further, in reactions containing 2 µM VanB, 1 µM VanA completely outcompeted the reaction of SA with VanB.

Figure 15:
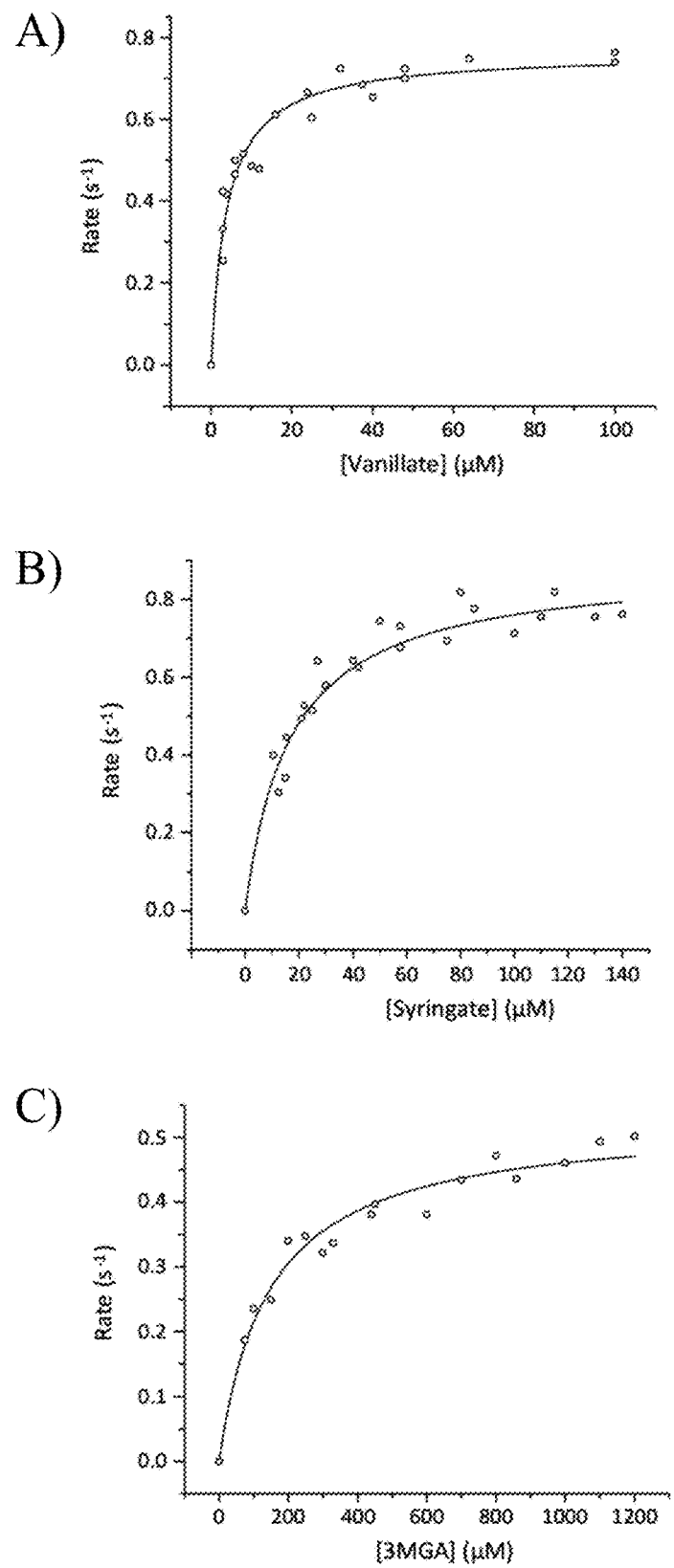
FIG. 15 illustrates steady-state kinetic analyses of the VanAB-catalyzed reactions, according to some embodiments of the present disclosure, according to some embodiments of the present disclosure. Dependence of initial velocity on VA (Panel A), SA (Panel B), and 3MGA (Panel C) concentrations in air-saturated HEPES (I=0.1 M, pH 7.5), 25° C. Lines represent fits of the Michaelis-Menten equation to the data.

In oxygraph assays, the dependence of the initial velocity of 02 consumption on aromatic acid concentration followed Michaelis-Menten behavior for each of VA, SA, and 3MGA (see FIG. 15). The apparent specificity of VanAB for VA (~$2\times10^5$ $s^{-1} \cdot M^{-1}$, Table 3) was comparable to that reported for other Rieske-type oxygenases for their cognate substrates. In evaluating the parameters for VA, 0.4 µM VanA was used to ensure steady-state conditions at low concentrations of VA. However, parameters of similar magnitude were measured using 1 µM VanA. VanAB catalyzed the O-demethylation of SA and 3MGA with approximately 10% and 1% the apparent specificity for VA, respectively (see Table 3). Overall, these assays demonstrate that VanAB catalyzes the O-demethylation of SA and 3MGA, albeit with decreased specificity as compared to VA.

Figure 16:
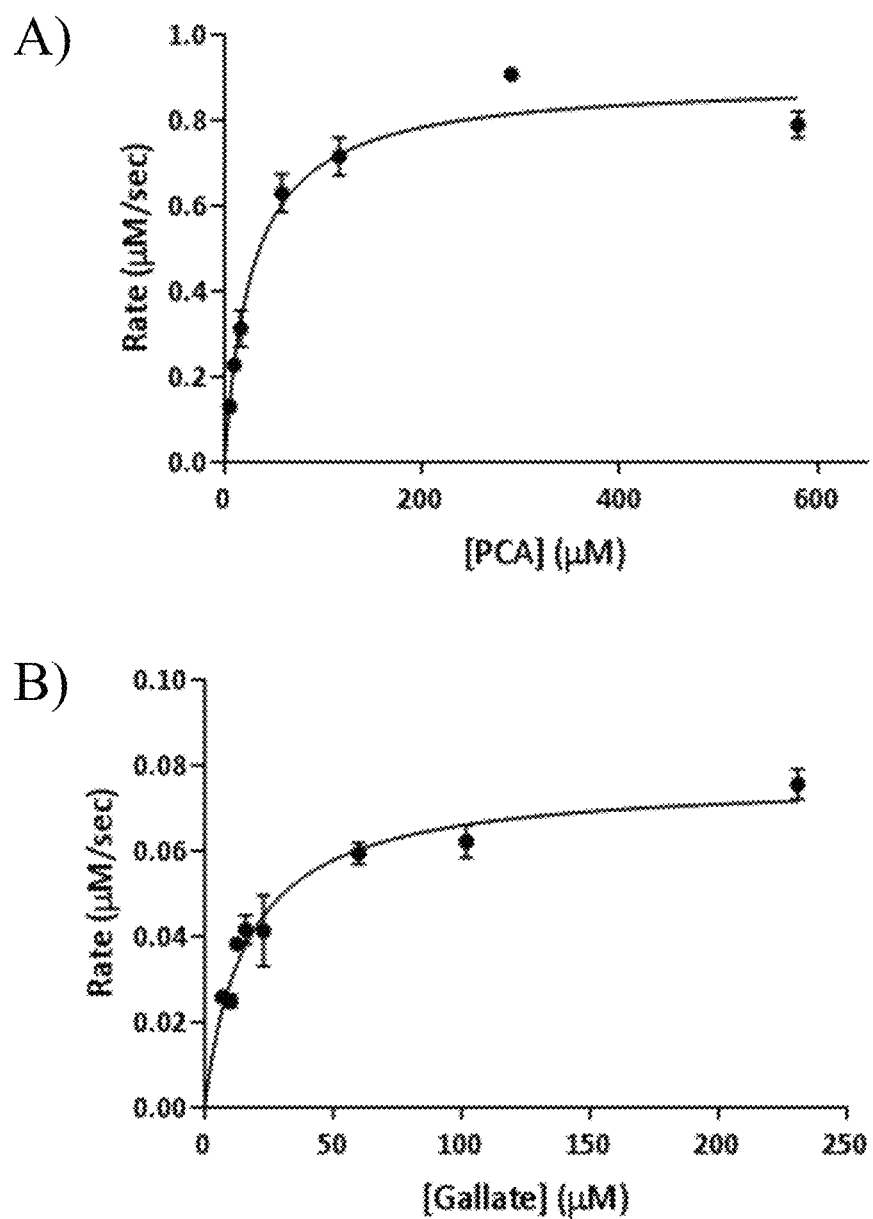
FIG. 16 illustrates steady-state kinetic analyses of PcaHG catalyzed reactions, according to some embodiments of the present disclosure. Dependence of initial velocity on PCA (Panel A) and GA (Panel B) concentrations in air-saturated HEPES (I=0.1 M, pH 7.5), 25° C. Error bars indicate the standard deviation of triplicate measurements. Lines represent fits of the Michaelis-Menten equation to the data.
Figure 17:
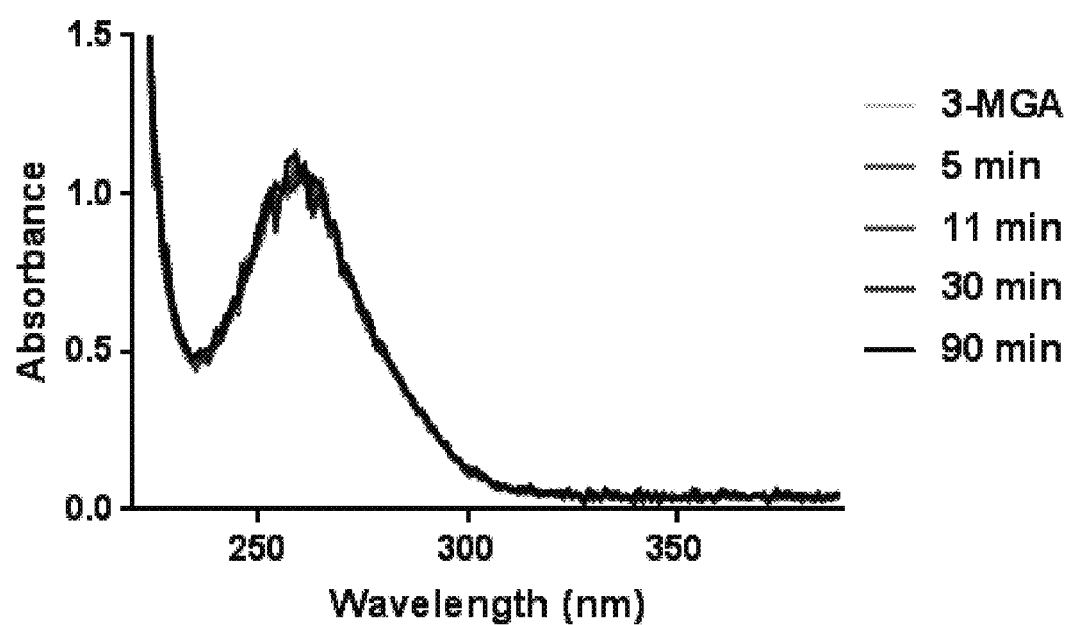
FIG. 17 illustrates UV-vis spectrum of 3MGA incubated with PcaHG for 90 minutes, according to some embodiments of the present disclosure.
Figure 18:
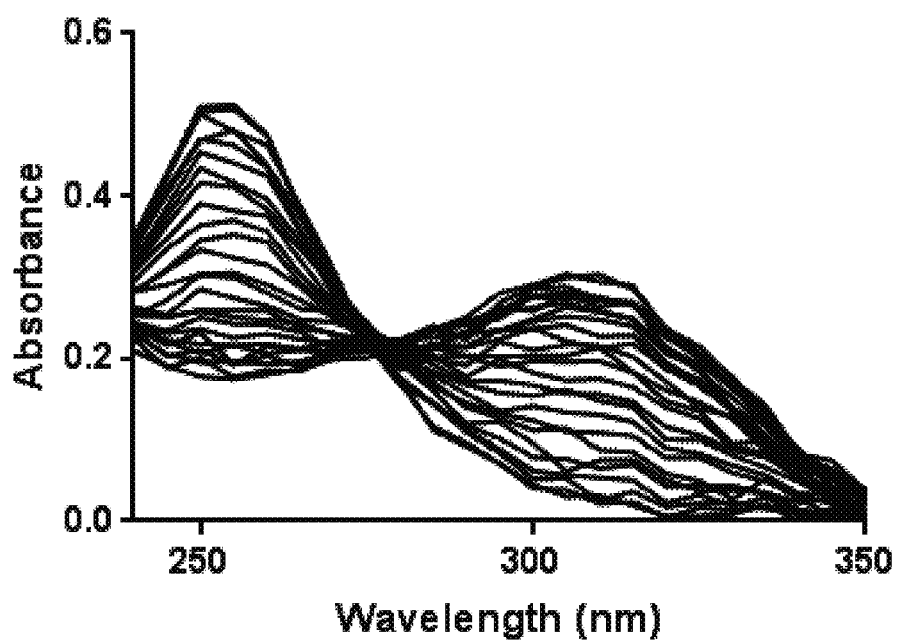
FIG. 18 illustrates spectrophotometric analysis of the PcaHG-catalyzed cleavage of gallate, according to some embodiments of the present disclosure. Spectra were recorded over 30 minutes.
Figure 19:
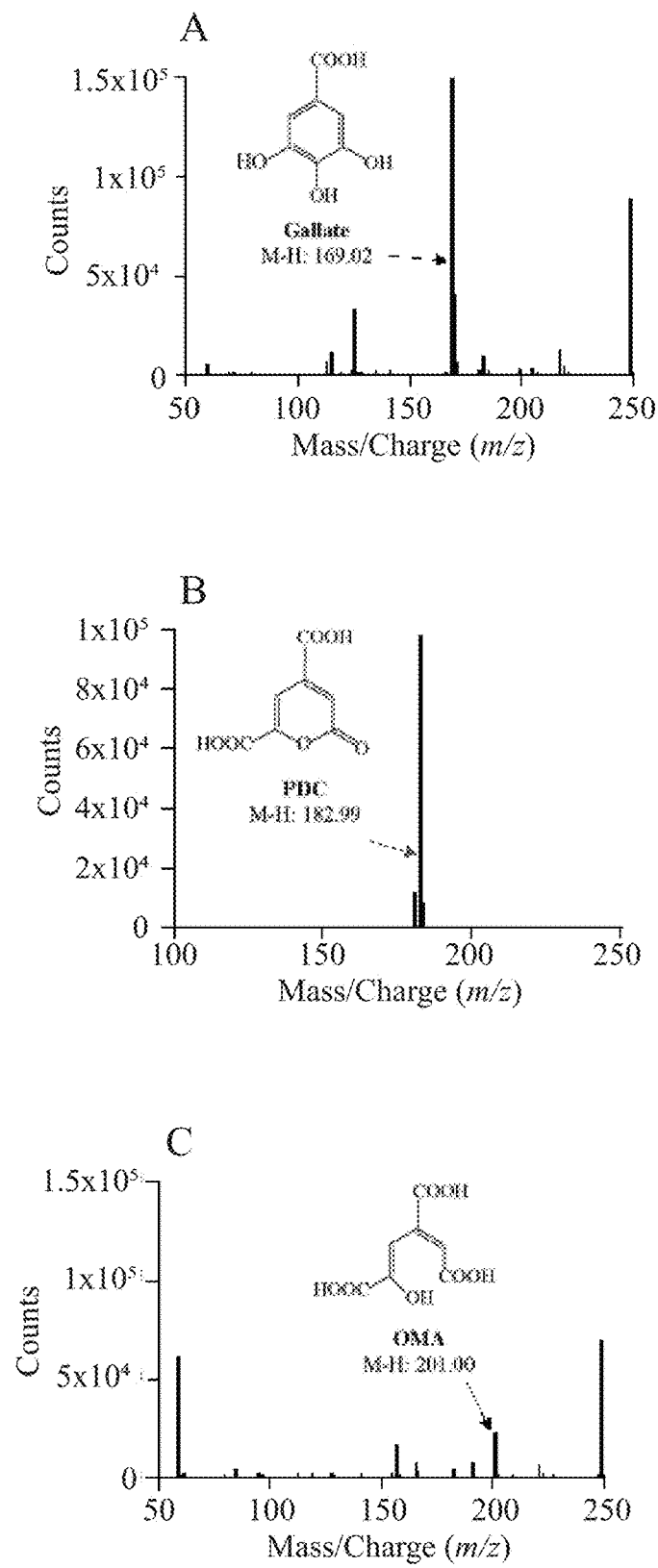
FIG. 19 illustrates mass spectra of gallate and its PcaHG-catalyzed cleavage products, according to some embodiments of the present disclosure. Reactions contained gallate, the standard reaction buffer and *E. coli* lysate containing Ht-PcaHG. (Panel A) Peak 1 ($t_R$=3.6 minutes), observed after incubation with lysate not containing PcaHG. (Panel B) Peak 2 ($t_R$=5.0 minutes) observed after incubation with lysate containing Ht-PcaHG. (Panel C) Peak 3 ($t_R$=8.4 minutes) observed after incubation with lysate containing Ht-PcaHG.

Next, whether or not *P. putida* KT2440 harbors dioxygenases with promiscuous activity toward the demethylation products 3MGA and GA was investigated, as has been reported for the PCA dioxygenase LigAB in *Sphingobium* sp. SYK-6 (see FIG. 1). We first characterized the activity of the PCA dioxygenase PcaHG toward 3MGA or GA in vitro. Purified PcaHG contained 0.3 equivalents of Fe per mol of PcaHG. and had a specific activity of 3.8 U/mg for PCA. The steady-state kinetic parameters of PcaHG for PCA were similar to previously values (67) (see Table 3, FIG. 16). In oxygraph and spectrophotometric assays, PcaHG did not detectably cleave 3MGA (see FIG. 17). Intriguingly, PcaHG catalyzed the cleavage of GA, but with 20% the apparent specificity of PCA. To investigate the PcaHG-cleavage product of GA, reactions containing 0.5 µM PcaHG and 90 µM GA were monitored spectrophotometrically. GA (?max at 258 nm) was converted to a product with a $\lambda_{max}$ of 312 nm, consistent with PDC (47) (see FIG. 18). The production of PDC was further validated using LC-MS (see FIG. 19). Overall, these data show that PcaHG cleaves GA relatively efficiently but does not detectably cleave 3MGA.

Figure 20:
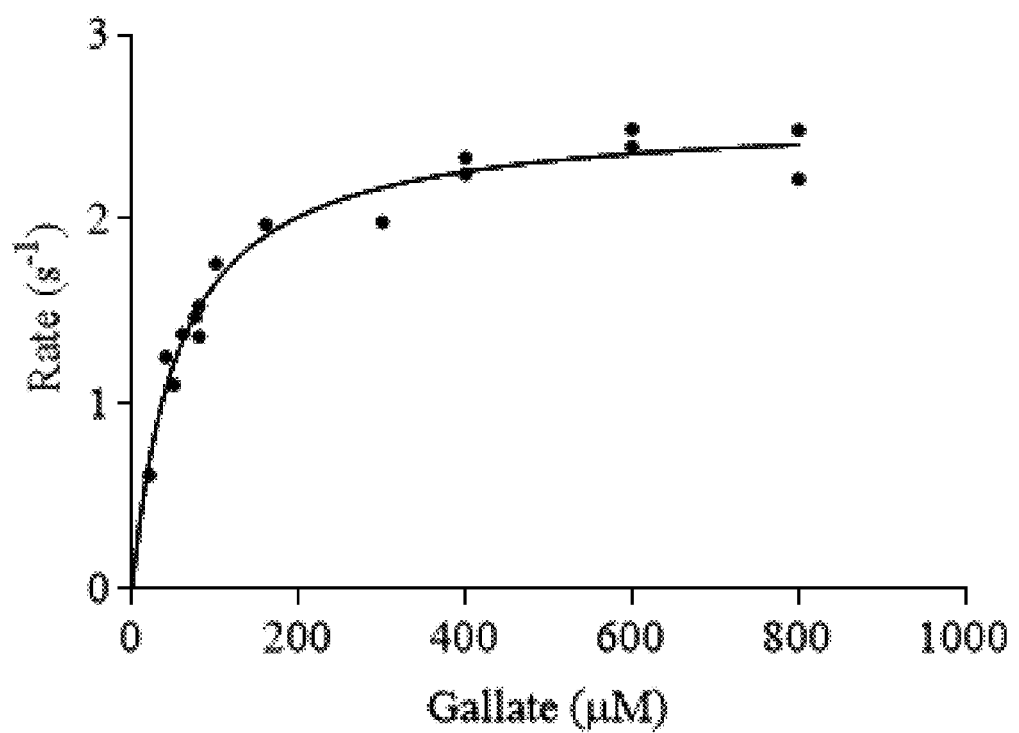
FIG. 20 illustrates steady-state kinetic analysis of gallate cleavage by GalA dependence of initial velocity on GA concentration in air-saturated MOPS (I=0.1 M), pH 7.5, 30° C., according to some embodiments of the present disclosure. The black line represents a fit of the Michaelis-Menten equation to the data.

Since PcaHG did not display activity toward 3MGA, the ability of GalA to cleave 3MGA was investigated. GalA preparations had 0.5 equivalents of Fe per mol GalA. GalA cleaved GA with 3-fold higher specificity (~$9\times10^5$ $s^{-1}$ $M^{-1}$, see Table 3, FIG. 20) than previously reported. The partition ratio for GA was ~1900 based on 02 consumption for given amount of GalA (see Table 3, Equation 1). Interestingly, GalA also catalyzed the cleavage of 3MGA but was inactivated too potently to evaluate steady-state kinetic param-

TABLE 3

Apparent steady-state kinetic parameters for VanAB, PcaHG, and GalA on select substrates.

| Enzyme | Substrate | $k_{cat}^{app}$ ($s^{-1}$) | $K_M^{app}$ (µM) | $k_{cat}^{app}/K_M^{app}$ ($\times 10^4$ $s^{-1} \cdot M^{-1}$) | Coupling[e] Substrate/O$_2$ | Product/O$_2$ | $j_3^{app}$ ($\times 10^{-2}$ $s^{-1}$) | Partition Ratio[f] |
|---|---|---|---|---|---|---|---|---|
| VanAB[a] | VA | 0.77 ± 0.02 | 4 ± 1 | 20 ± 2 | 1.3 ± 0.2 | 1.1 ± 0.1 | ND | ND |
| | SA | 0.89 ± 0.03 | 16 ± 2 | 5.5 ± 0.6 | 1.1 ± 0.1 | 0.9 ± 0.2 | ND | ND |
| | 3MGA | 0.53 ± 0.02 | 150 ± 20 | 0.36 ± 0.04 | 1.0 ± 0.1 | 1.1 ± 0.2 | ND | ND |
| PcaHG[b] | PCA | 0.95 ± 0.03 | 33 ± 2 | 2.92 ± 0.09 | ND | ND | ND | ND |
| | GA | 0.0675 ± 0.0003 | 15 ± 2 | 0.51 ± 0.06 | ND | ND | ND | ND |
| GalA[c] | GA | 52 ± 4 | 59 ± 5 | 90 ± 10 | ND | ND | 2.7 ± 0.2 | 1860 ± 200 |
| | 3MGA | 0.012 ± 0.002[d] | ND | ND | ND | ND | 3.8 ± 0.3 | 3.3 ± 0.6 |

Figure 21:
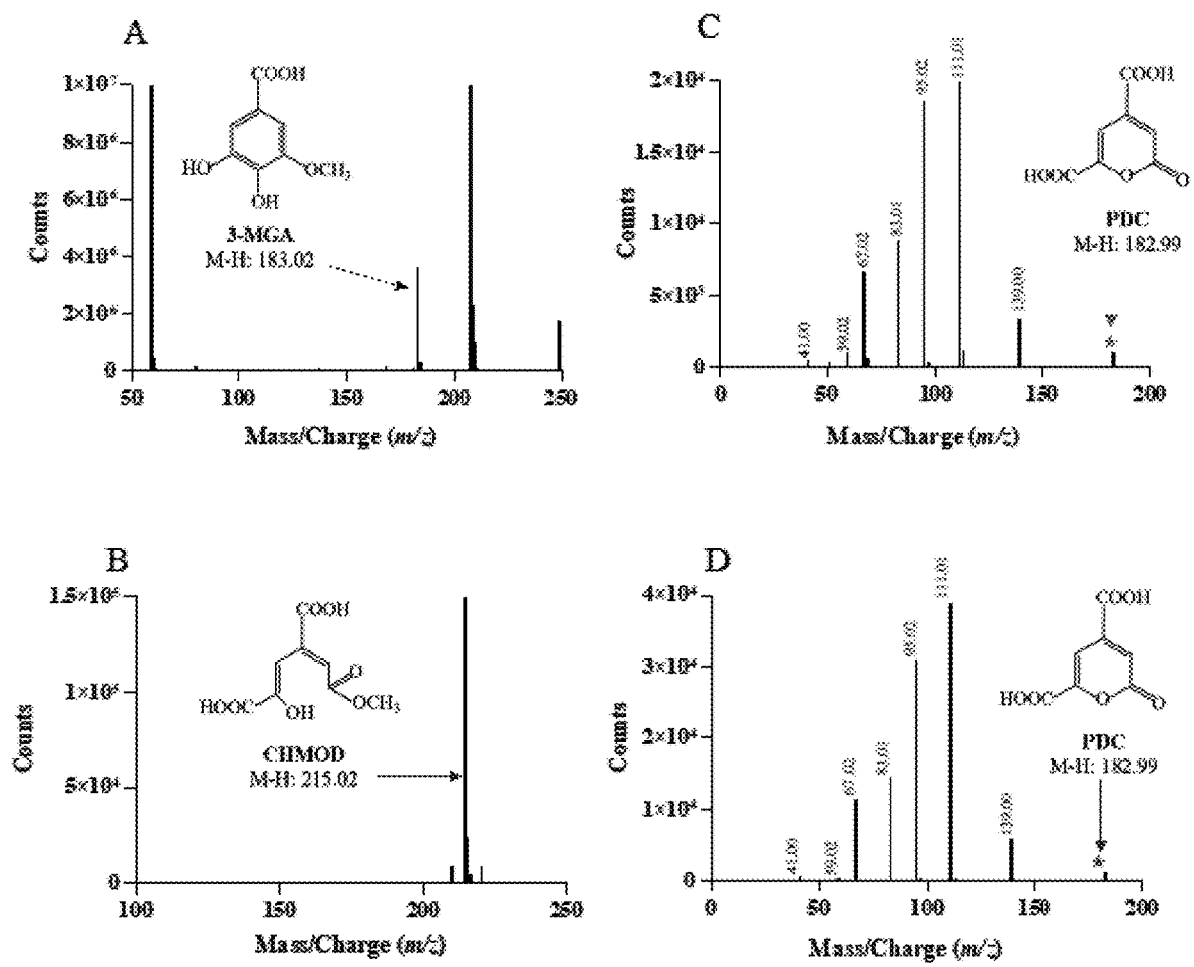
FIG. 21 illustrates mass spectra of 3MGA and its GalA-catalyzed cleavage products, according to some embodiments of the present disclosure. Reactions contained 3MGA, in the GalA standard reaction buffer, GalA and ferrous ammonium sulfate. (Panel A) Peak 1 ($t_R$=2.3 min), observed after incubating 3MGA with ferrous ammonium sulfate without GalA. (Panel B), Peak 2 ($t_R$=3.9 min) observed when 3MGA was incubated with GalA and ferrous ammonium sulfate (Panel C), Peak 3 ($t_R$=4.9 min, MS/MS spectrum (10 V collision energy)) from the incubation of 3MGA with GalA and ferrous ammonium sulfate, parent ion indicated by green star; and (Panel D), PDC ($t_R$=5.0 min, MS/MS spectrum (10 V collision energy)) observed from the incubation of gallate with lysate containing Ht-PcaHG, parent ion indicated by burgundy star. For (Panel C) and (Panel D), the fragmentation ion m z values are displayed above the peaks.

[a]Experiments were performed using 2 µM Ht-VanB, 400 µM NADH, and air-saturated HEPES (I = 0.1M), pH 7.5, at 25° C. The amount of VanA used was 0.4 µM for vanillate and 1 µM for syringate and 3MGA.
[b]Experiments were performed using air-saturated HEPES (1 = 0.1M), pH 7.5, at 25° C. Parameters were calculated using a minimum of 20 data points at various substrate concentrations.
[c]Experiments were performed using air-saturated 40 mM MOPS, 80 mM NaCl, (I = 0.1M, pH 7.0), 30° C. Steady-state parameters were calculated using a minimum of 16 data points at various substrate concentrations.
[d]Calculated from $j_3^{app}$ and partition ratio.
[e]Measured as ratio of aromatic substrate consumed (or product produced):O$_2$ consumed (mol:mol).
[f]Calculated from the O$_2$ consumption for a given amount of GalA.
ND: not determined.

eters. Because high concentrations of GalA were needed to detect 3MGA-cleavage activity, cell lysates were used to investigate the inactivation of GalA by 3MGA. Importantly, the inactivation of GalA by GA was similar for the purified enzyme in *E. coli* lysate ($j_3^{app}$~$3\times10^{-2}$ $s^{-1}$, Table 3, FIG. 21). The apparent rate constant of inactivation of GalA by 3MGA was less than 50% higher than for GA (see Table 3). However, the partition ratio for 3MGA was 0.2% that for GA, indicating that the $k_{cat}^{app}$ for 3MGA is ~0.025% that for GA. Despite the poor turnover of 3MGA, LC-MS analysis of the reaction products demonstrated that GalA transformed 3MGA to PDC (see FIG. 21).

$$\text{Partition Ratio} = \frac{\mu\text{mol of subtrate consumed}}{\mu\text{mol of GalA inactivated}} \qquad \text{Equation 1}$$

Figure 22A:
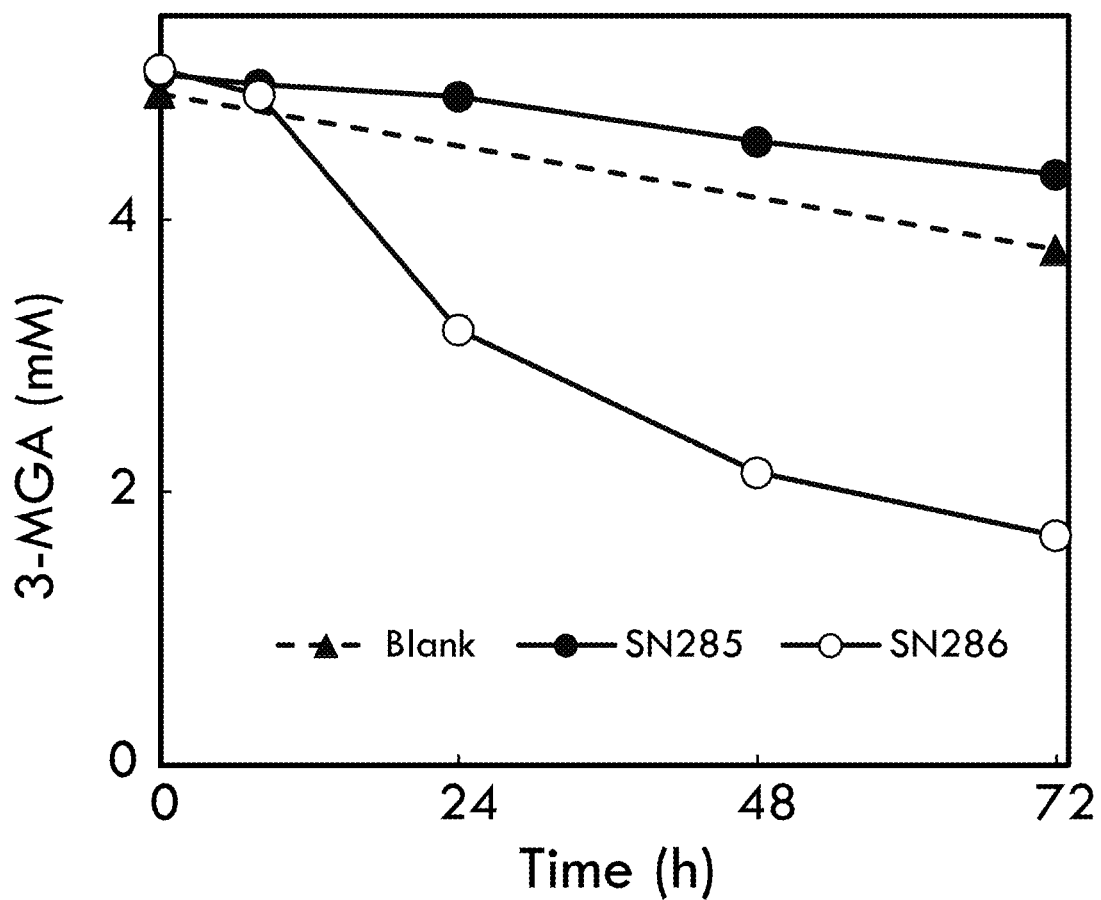
FIG. 22A illustrates 3MGA concentrations in cultivations in M9 minimal medium containing 5 mM 3-MGA and 20 mM glucose with SN285 (*P. putida* KT2440 ΔvanAB carrying pBTL-2-empty vector), SN286 (*P. putida* KT2440 ΔvanAB carrying pSN82 which constitutively overexpresses galA), or a 3MGA blank, according to some embodiments of the present disclosure. Culture was sampled periodically to evaluate 3-MGA consumption in the media using HPLC.
Figure 22B:
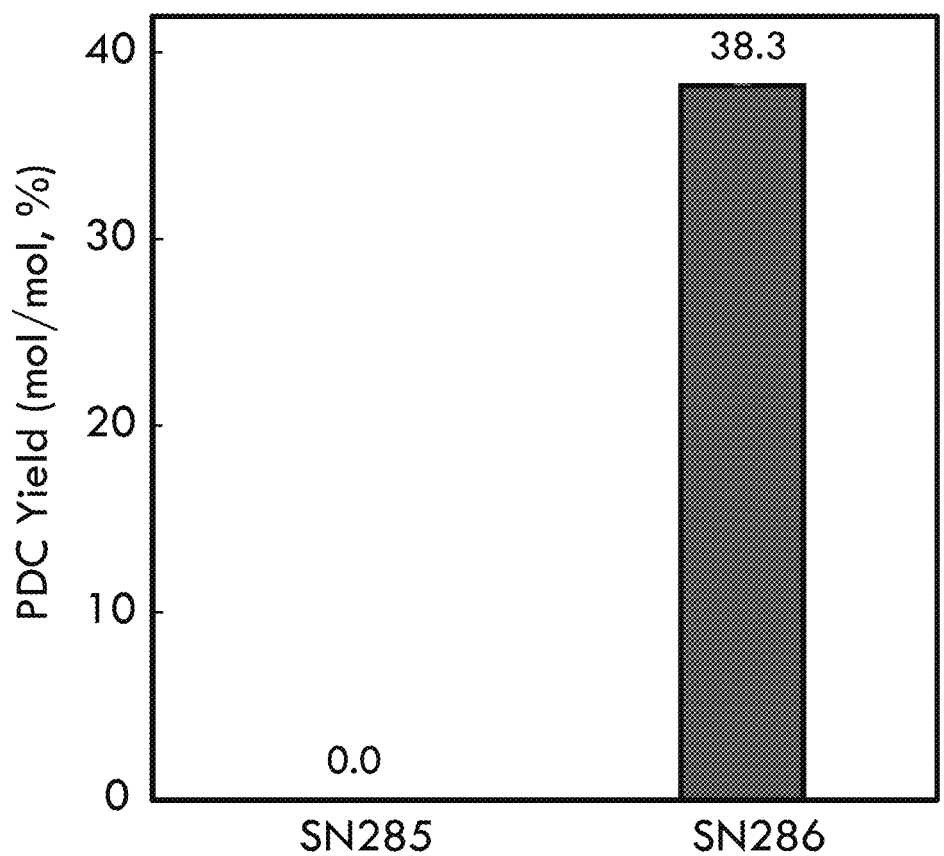
FIG. 22B illustrates PDC yield (mol/mol), as measured NMR, according to some embodiments of the present disclosure. Each experiment was in a 25 mL flask with 10 mL of culture. Each point represents the average of two measurements with error bars representing their range. Error bars represent absolute value difference.

To understand if GalA acts on 3MGA in vivo, vanAB was deleted to prevent 3MGA O-demethylation, and overexpressed galA on the pBTL-2 plasmid. The resulting strain utilized 3MGA and produced PDC, albeit slowly (67% utilization after 72 hours, see FIG. 22A), while the empty vector control did not, demonstrating that GalA does act on MGA in vivo. Presumably, the inactivation of GalA by 3MGA involves the oxidation of the enzyme's active site ferrous iron and that the enzyme is reactivated in vivo.

Figure 23A:
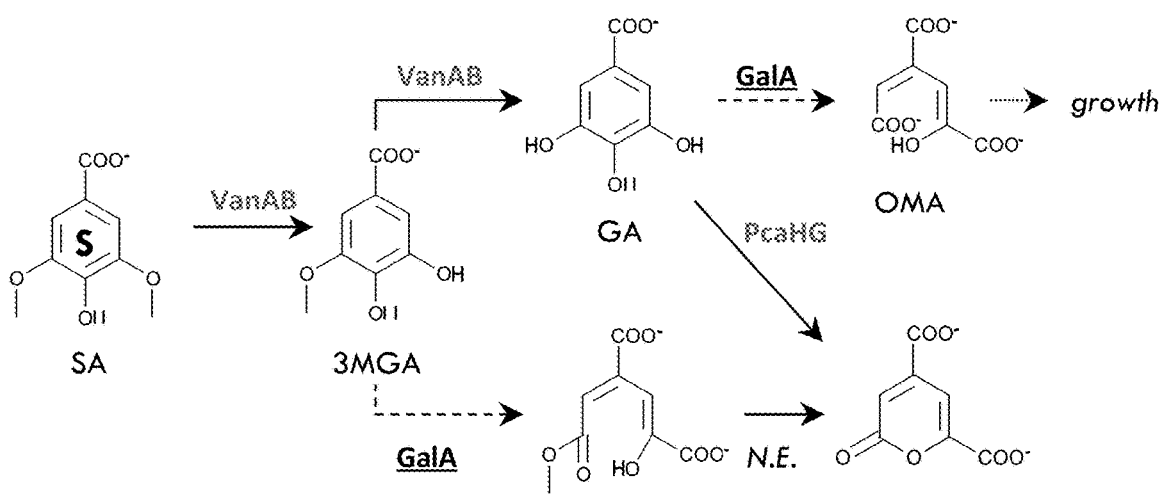
FIG. 23A illustrates a metabolic pathway to PDC production in engineered strain SN266 (*P. putida* KT2440 fpvA: $P_{tac}$:vanAB $P_{tac}$:pcaHG ΔgalA)
Figure 23B:
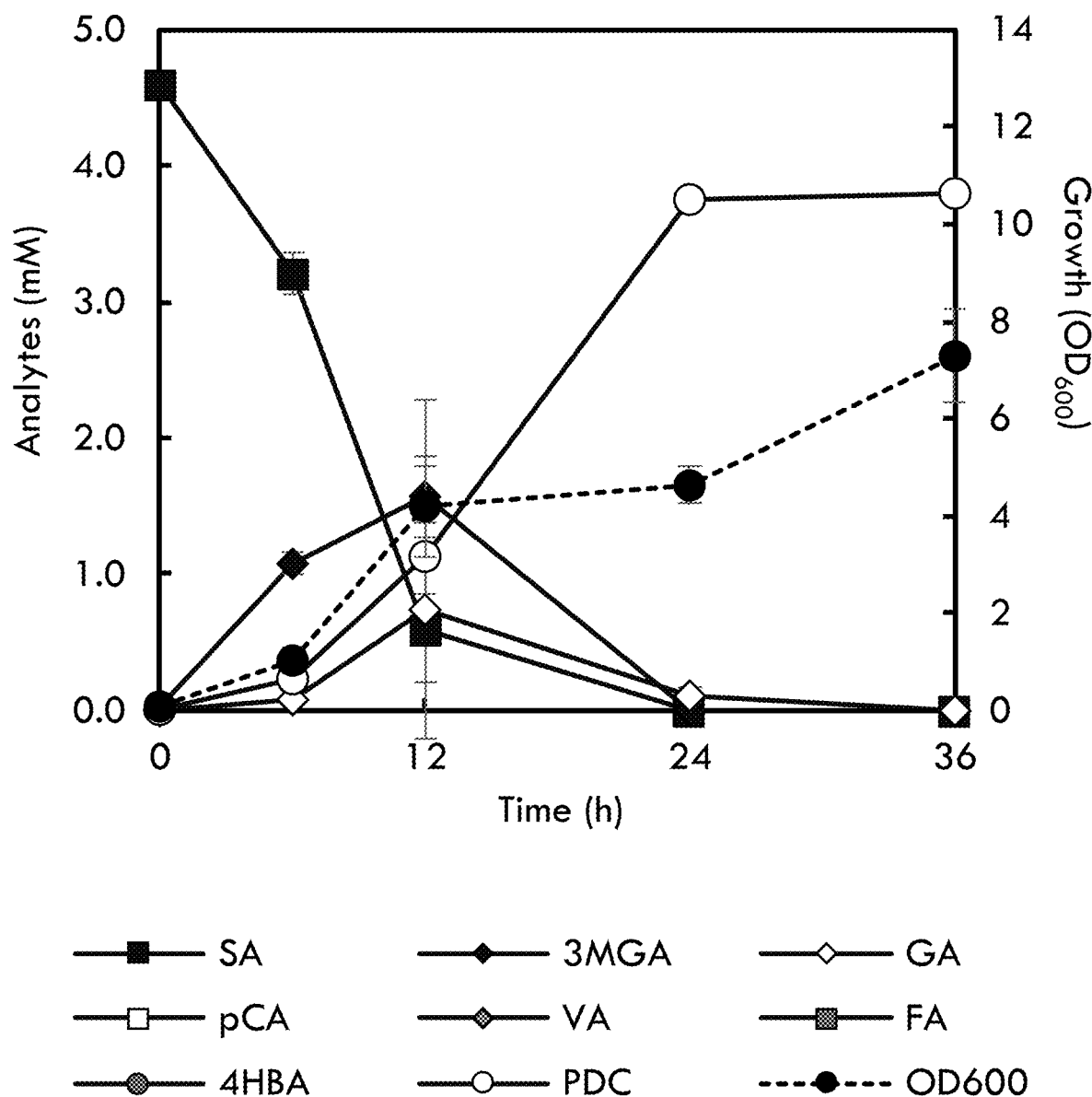
FIG. 23B illustrates the corresponding PDC production by SN266, according to some embodiments of the present disclosure. Strains were cultivated in M9 minimal medium supplemented 40 mM glucose plus aromatic substrate, as indicated, and fed to 20 mM glucose every 24 h. All analytes, including PDC, were quantified by C18(2). Average PDC concentration and molar PDC yield (mol PDC/mol substrate(s)) at 48 hours of cultivation is displayed where error bars represent the standard deviation across biological triplicates. Abbreviations: SA, syringate; 3MGA, 3-O-methylgallate; GA, gallate; OMA, 4-oxalomesaconate, keto or enol form; CHMS, 4-carboxy-2-hydroxy-cis,cis-muconate 6-semialdehyde; CHMOD, 4-carboxy-2-hydroxy-6-methyoxy-6-oxohexa-2,4-dienoate; PDC, 2-pyrone-4,6-dicarboxylic acid; VA, vanillate; 4-HBA, 4-hydroxybenzoate; PCA, protocatechuate; VanAB, vanillate O-demethylase; GalA, gallate 3,4-dioxygenase; PcaHG, PCA 3,4-dioxygenase; LigAB, PCA 4,5-dioxygenase; LigC, CHMS dehydrogenase; N.E., non-enzymatic. The same applies for FIGS. 23C and 23D.
Figure 24:
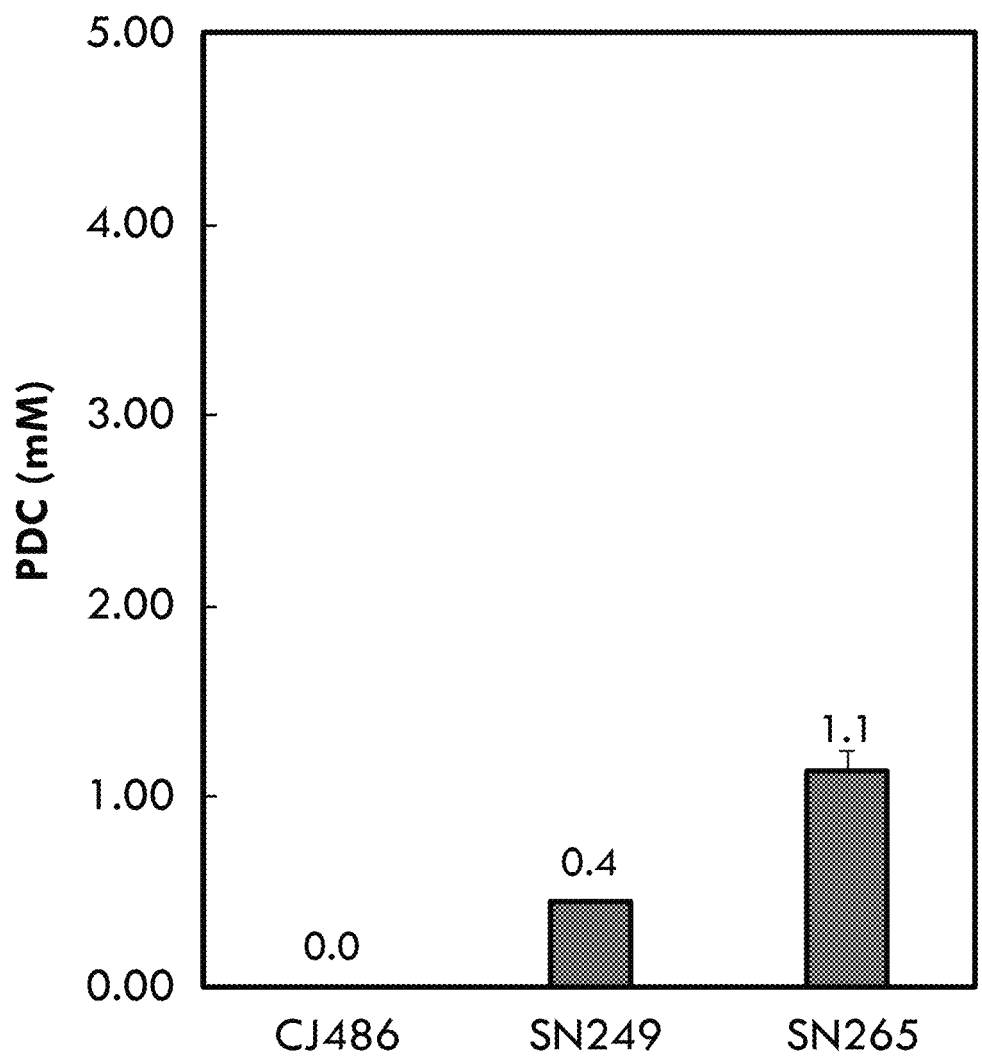
FIG. 24 illustrates PDC produced after 72 hours of cultivation in M9 minimal media supplemented with 20 mM glucose and 5 mM syringate by CJ486 (*P. putida* KT2440 fpvA:$P_{tac}$:vanAB), SN249 (*P. putida* KT2440 fpvA:$P_{tac}$:vanAB ΔgalA), or SN265 (*P. putida* KT2440 fpvA:$P_{tac}$:vanAB $P_{tac}$:pcaHG), according to some embodiments of the present disclosure. PDC was quantified by NMR. Error bars represent the standard deviation across biological triplicates.
Figure 25A:
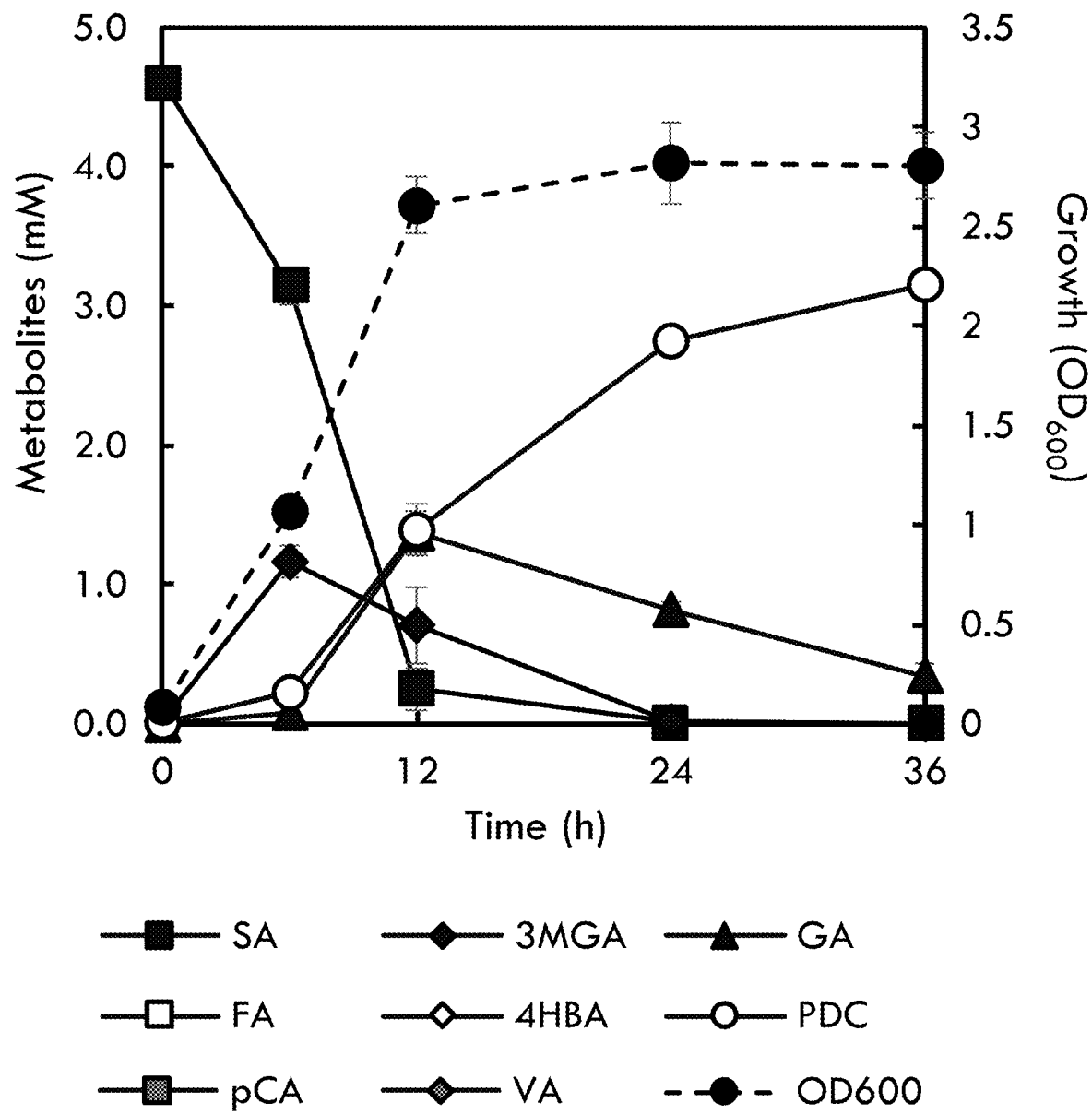
FIG. 25A illustrates cultivation results for SN266 (*P. putida* KT2440 fpvA:$P_{tac}$:vanAB $P_{tac}$:pcaHG ΔgalA) in M9 minimal medium supplemented with 20 mM glucose and 5 mM SA (without any additional feeding), according to some embodiments of the present disclosure.
Figure 25B:
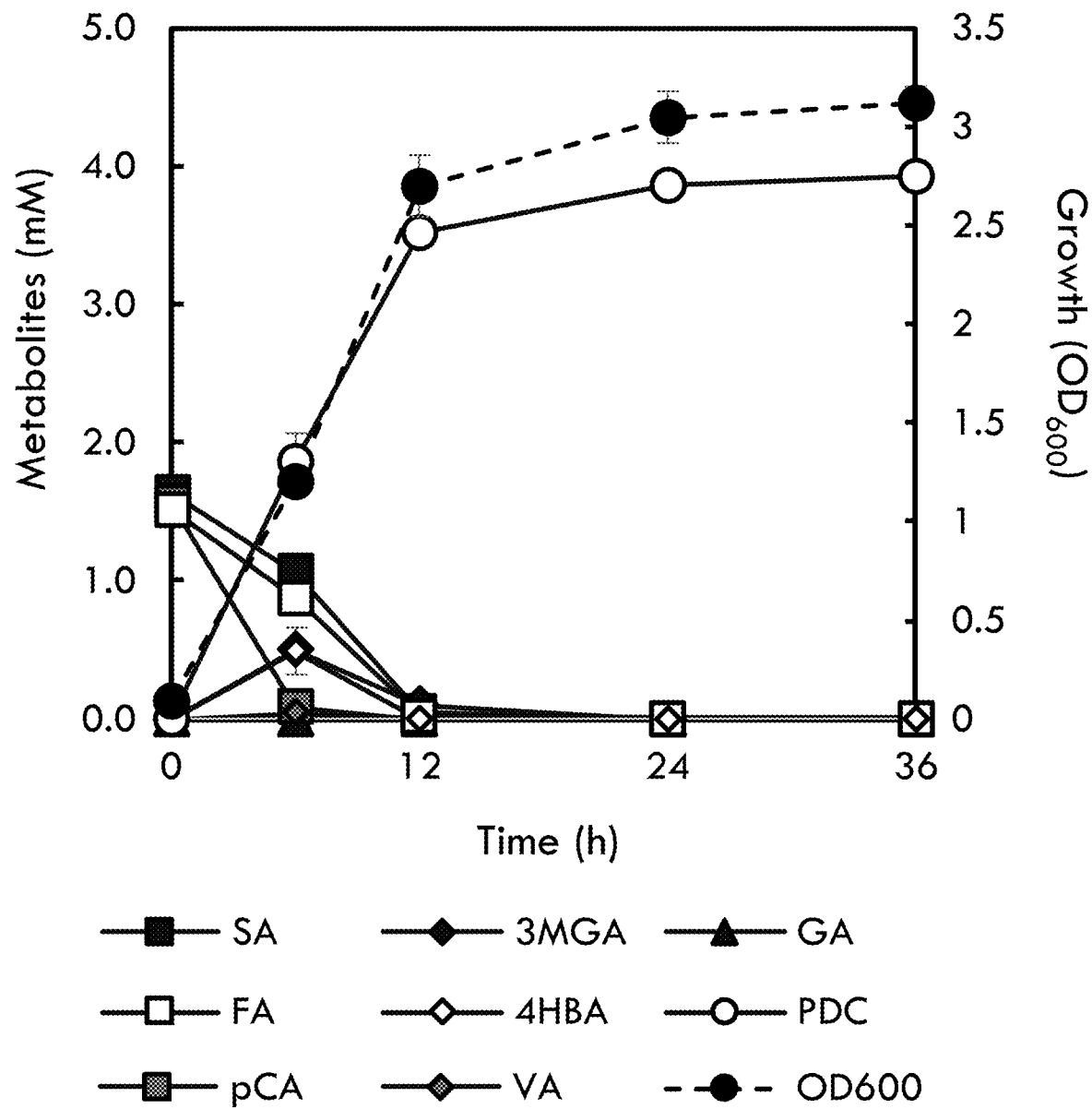
FIG. 25B illustrates cultivation results for AW045 (*P. putida* KT2440 ΔvanAB$^{KT2440}$::$P_{tac}$:vanAB$^{HR199}$ ΔpcaHG::$P_{tac}$:ligABC$_{SYK6}$) in M9 minimal medium supplemented with 20 mM glucose and a ~5 mM equimolar mix of pCA, FA, and SA, according to some embodiments of the present disclosure.
Figure 25C:
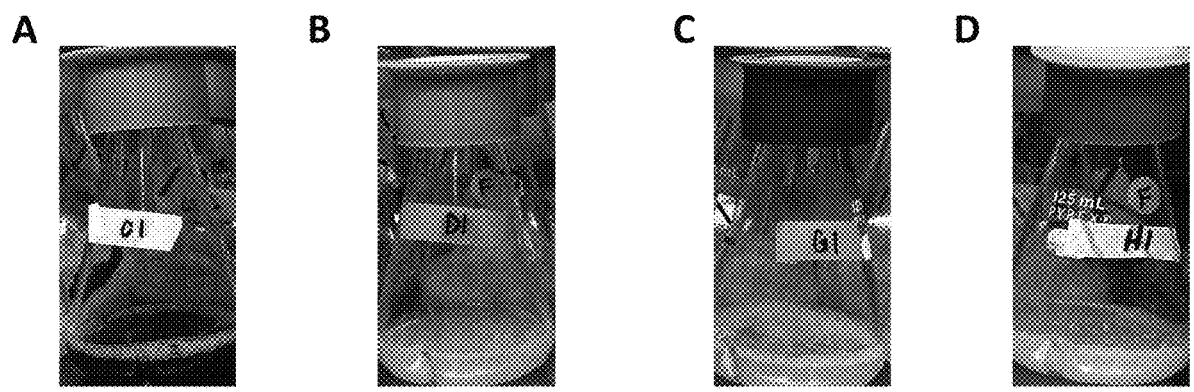
FIG. 25C illustrates photos after 24 hours of cultivations (Panel A) with SN266 in 5 mM SA and 20 mM glucose and no feeding, (Panel B) SN266 in 5 mM SA and 40 mM glucose with feeding to 20 mM glucose every 24 h, (Panel C) AW045 in a ~5 mM equimolar mix of pCA, FA, and SA (~1.55 mM each) and 20 mM glucose, and (Panel D) AW045 in a ~5 mM equimolar mix of pCA, FA, and SA (~1.55 mM each) and 40 mM glucose with feeding to 20 mM glucose every 24 h. Metabolite profiles corresponding to (Panel B) and (Panel D) are presented in the main text. SA: syringate; 3MGA, 3-O-methylgallate; GA, gallate; pCA, p-coumarate; VA, vanillate; FA, ferulate; 4HBA, 4-hydroxybenzoate; PDC, 2-pyrone-4,6-dicarboxylic acid; OD, optical density, all according to some embodiments of the present disclosure. Error bars represent the standard deviation across three biological replicates. All analytes were quantified by C18.
Figure 26:
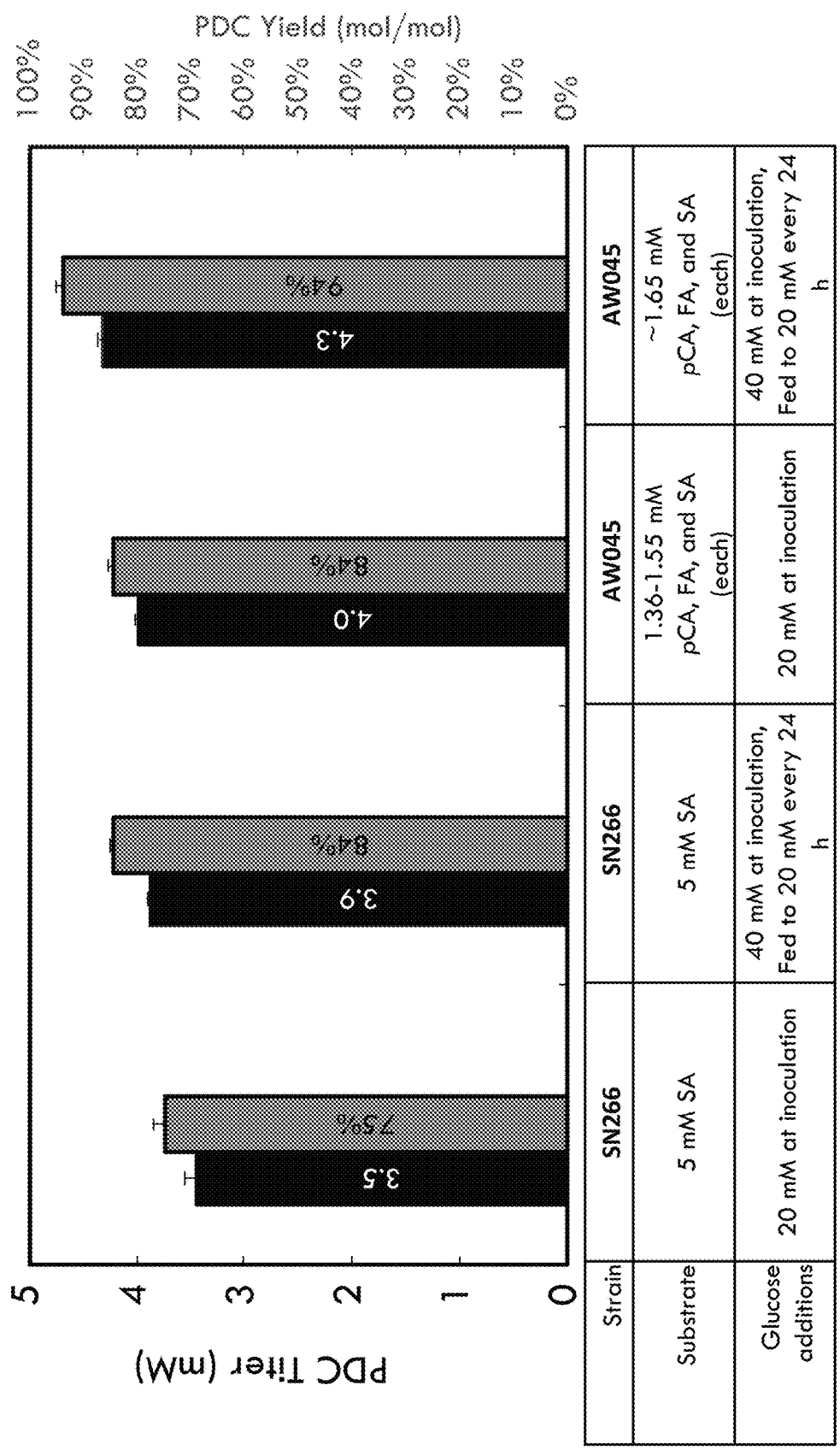
FIG. 26 illustrates PDC titer (mM) and yield (mol/mol) from SN266 (*P. putida* KT2440 fpvA:$P_{tac}$:vanAB $P_{tac}$:pcaHG ΔgalA) and AW045 (*P. putida* KT2440 ΔvanAB$^{KT}$::$P_{tac}$:vanAB$^{HR}$ ΔpcaHG::$P_{tac}$:ligABC$^{SYK6}$) after 48 hours of cultivation in M9 minimal media supplemented with aromatic compound and glucose, according to some embodiments of the present disclosure, as indicated. SA, syringate; pCA, p-coumarate, FA; ferulate.

PcaHG-mediated GA cleavage to PDC in vitro presented the intriguing possibility of in vivo SA conversion to PDC (69, 70) (see FIG. 23A). vanAB overexpression alone, with galA deleted, or with pcaHG overexpressed resulted in low PDC production (0, 0.44, and 1.14 mM PDC from 5 mM SA, respectively, FIG. 24). However, stacking all modifications together (strain SN266, $P.$ putida KT2440 fpvA:$P_{tac}$:vanAB $P_{tac}$:pcaHG ΔgalA) resulted in the production of 3.36 mM PDC, a 70% (mol/mol) yield (see FIG. 23B). Notably, these experiments were performed with 5 mM SA and 40 mM glucose at inoculation and fed 20 mM glucose every 24 h. With 5 mM SA and 20 mM glucose at inoculation and no feeding, the PDC yield achieved by SN266 cultivations dropped by 10% and the media turned dark brown (see FIGS. 25A-C and 26), suggesting that GA was secreted and subsequently oxidized in the absence of sufficient energy. This demonstrates a viable pathway from SA to PDC in $P.$ putida KT2440 via the native enzymes VanAB and PcaHG. However, the use of PcaHG is inconsistent with the goal of producing of PDC from S, G, and H-type compounds, since PcaHG would cause ortho-cleavage of PCA (from G and H-type compounds) rather than the 4,5 meta-cleavage required for conversion to PDC (see FIGS. 1 and 23A).

Figure 23C:
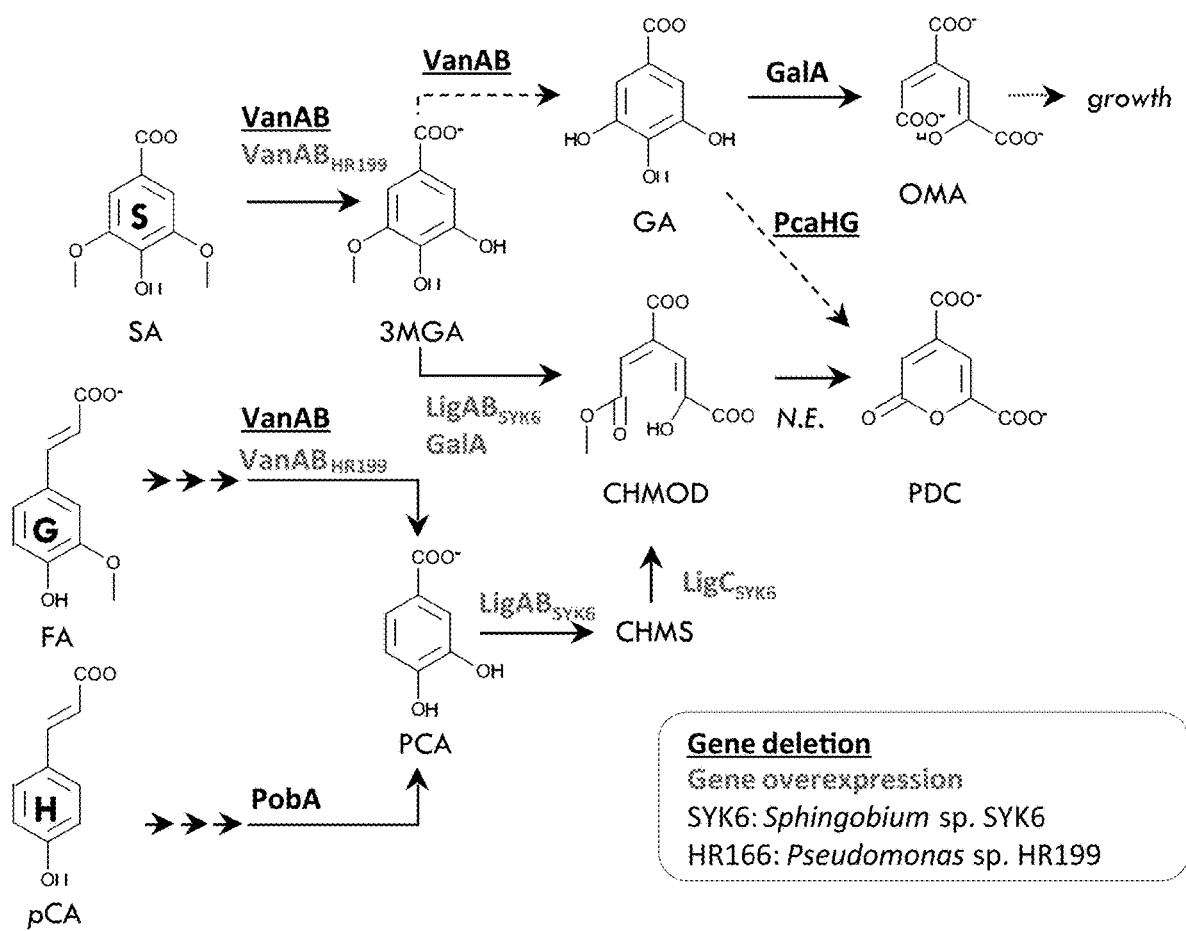
FIG. 23C illustrates a metabolic pathway to PDC production in engineered strain AW045 (*P. putida* KT2440 ΔpcaHG::$P_{tac}$:ligABC$_{SYK6}$ ΔvanAB$_{KT2440}$::$P_{tac}$:vanAB$_{HR199}$)
Figure 23D:
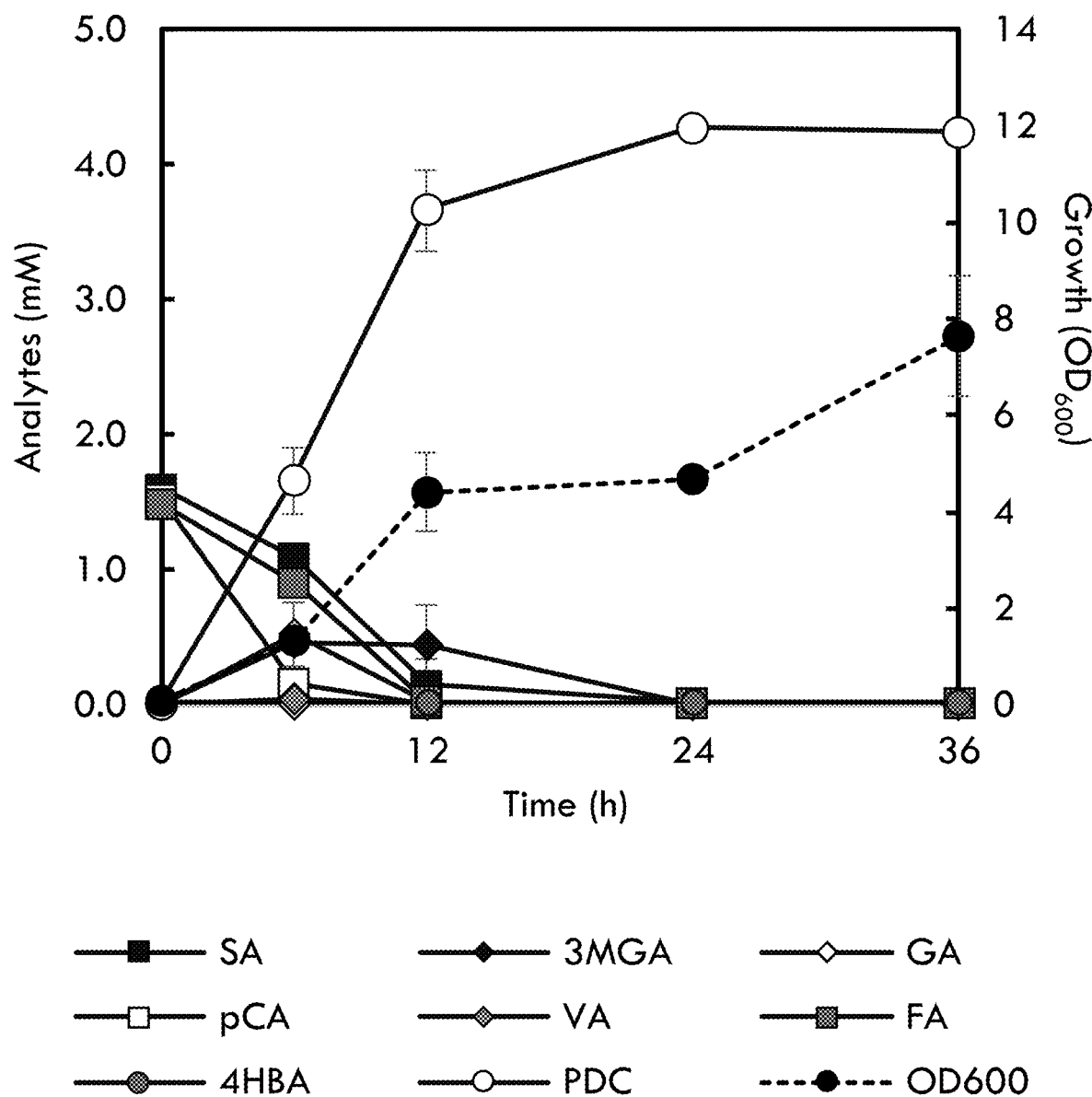
FIG. 23D illustrates the corresponding PDC production by SN266, according to some embodiments of the present disclosure.

A second pathway was then examined which would enable simultaneous conversion of S, G, and H lignin derived compounds to PDC (see FIG. 23C). First, pcaHG was replaced with ligABC from Sphingobium sp. SYK-6 to accomplish three reactions: LigAB-mediated ring-opening of 3MGA to CHMOD, LigAB-mediated ring-opening of PCA to 4-carboxy-2-hydroxy-cis,cis-muconate 6-semialdehyde (CHMS), and LigC-mediated conversion of CHMS to PDC (71). Next, the native vanAB (vanAB$_{KT2440}$) was replaced with vanAB from Pseudomonas sp. HR199 (vanAB$_{HR199}$) to prevent 3MGA O-methylation. These modifications generated strain AW045 ($P.$ putida KT2440 ΔpcaHG::$P_{tac}$:ligABC ΔvanAB$_{KT2440}$::$P_{tac}$:vanAB$_{HR199}$). Cultivations were performed in equimolar mixture (~1.55 mM each) of SA, p-coumarate (pCA), and ferulate (FA) with 40 mM glucose supplementation at inoculation and feeding to 20 mM glucose every 24 hours. AW045 completely consumed SA, pCA, and FA and all catabolic intermediates within 24 hours and produced 3.65 mM PDC at a 82% (mol/mol) yield (see FIG. 23D), which again was higher than with 20 mM glucose supplementation (see FIGS. 25A-C and 26). This demonstrated simultaneous conversion of S-, G-, and H-lignin monomers.

Experimental $P.$ putida Growth Experiments and Analysis $P.$ putida strain construction: Plasmids were constructed using the NEBuilder HiFi DNA Assembly in $E.$ coli DH5-alpha F'I$^q$ (NEB, USA) as described in Tables 5-7 and sequenced to confirm integrity. Gene deletion, insertion, or replacements in $P.$ putida KT2440 were performed using the antibiotic/sacB counter-selection method as previously described (28) and confirmed as described in Tables 5-7.

$P.$ putida Cultivation $P.$ putida growth experiments: Pseudomonas putida KT2440 (ATCC® 47054) strains were revived from glycerol stock, washed in M9 salts, inoculated at an OD$_{600}$ of ~0.1 in 25-30 mL of M9 minimal media supplemented with aromatic acids and/or glucose in the concentrations specified in 125 mL baffled flasks and cultivated at 30° C. shaking at 225 rpm. Cell growth was measured as OD$_{600}$ using the cell-free supernatant of each sample as a blank.

Quantification of metabolites: Cell culture was removed, centrifuged, the supernatant was 0.2 um filtered, and stored in glass vials at −20 C until analysis. For aromatic acid utilization studies, samples were analyzed by high performance liquid chromatography (HPLC)-diode array detector (DAD) or refractive index detector (RID). For glucose utilization, HPLC-RID for glucose was used. For preliminary PDC production analysis, nuclear magnetic resonance (NMR) was used. For aromatic acid conversion to PDC and calculation of PDC yields, HPLC-C18(2)-DAD was used.

Systems Analysis of Proteins and RNAs

Bacterial cultivation: Seed cultures of $P.$ putida strains were prepared as described above and inoculated into 1 L of M9 minimal media supplemented with 20 mM glucose, grown to log phase, washed, and reinoculated at an OD$_{600}$ of 0.1 in 100 mL of M9 minimal media supplemented with 20 mM glucose+/−5 mM vanillate or syringate, as specified, and cultivated as described above. When cultures reached an OD$_{600}$ of 0.1, cells were centrifuged, the cell pellet was quenched in liquid nitrogen, and stored at −80° C. until analysis.

Proteomics analysis: Cell pellets were resuspended in sodium dodecyl sulfate (SDS) lysis buffer, disrobed by bead beating, boiled, cysteines were blocked, proteins were precipitated, resuspended in SDS, protein amounts were estimated using a BCA assay, proteins were digested with trypsin, and SDS was removed. Samples were dried, desalted, and analyzed on a nanospray ionization Q Exative Plus mass spectrometer (MS) coupled to an EASY-nLC 1200.

RNA-Seq analysis: Cell pellets were resuspended in TRIzol, chloroform was added and the samples were centrifuged, the aqueous layer was removed and mixed with ethanol, RNA was purified, RNA concentration and purity was assessed. rRNA was depleted, and RNA was concentrated on, quantified and visualized, and used as input material to synthesize cDNA libraries. cDNA was purified, barcodes were added, the library was purified, quantified, library quality was assessed, and samples were pooled and diluted prior to sequencing on an Illumina NextSeq500 and by synthesis chemistry.

Plasmid construction for $P.$ putida engineering: Plasmids for the transformation of $P.$ putida KT2440 and heterologous expression in Escherichia coli BL-21 λ(DE3) were constructed via NEBuilder® HiFi DNA Assembly Master Mix, KLD Mix, or T4 ligase system (New England Biolabs, USA) and transformed into $E.$ coli DH5-alpha F'I$^q$ (NEB, USA, Table 5) or equivalent strains. Codon optimization for expression in the host and utilization of synthetic ribosome binding sites with the Salis RBS Calculator were performed as described in Table 5. Oligos and DNA fragments were synthesized by Integrated DNA Technologies (IDT, USA) or amplified from genomic DNA with Q5® Hot Start Fidelity 2× Master Mix or Phusion PCR systems (NEB, USA, Tables 6 and 7). Transformants were selected on LB Lennox medium plates (10 g/L tryptone, 5 g/L yeast extract, 5 g/L NaCl, and 15 g/L agar) supplemented with 100 μg/mL ampicillin or 50 μg/mL kanamycin and grown at 37° C. Sanger sequencing (GENEWIZ Inc., USA) was used to confirm the correct sequence of all plasmid inserts.

Bacterial strains, media, and cultivations: Pseudomonas putida KT2440 (ATCC® 47054) was utilized as the wild-type and base strain for all further engineering. Gene deletion, insertion, or replacements in $P.$ putida KT2440 were performed using the antibiotic/sacB counter-selection method as previously described. Diagnostic colony PCR was performed with MyTaq® HS Red Mix (Bioline, USA) to confirm gene deletion, insertion, or replacement (see Table 3 and Table 8). M9 minimal medium was prepared as 6.78 g/L Na$_2$HPO$_4$, 3 g/L KH$_2$PO$_4$, 0.5 g/L NaCl, 1 g/L NH$_4$Cl, 2 mM MgSO$_4$, 100 μM CaCl$_2$), and 18 μM FeSO$_4$, pH 7.0. Stocks of VA (Acros, Belgium), SA (AK Sci., USA), 3MGA, GA, p-CA (Acros, Belgium), and FA (Sigma, USA) were made by adding the compounds to water and gradually pH adjusting to 7.0 with NaOH until fully solubilized. Sodium formate (Sigma, USA) was used to prepare formate stocks in water. Stocks of syringaldehyde were made in 2% (v/v) DMSO. Glucose at 1 M concentration (Sigma, USA) was prepared in water. All carbon sources were 0.2 μm filtered prior to media addition. KT2440 strains were revived from glycerol stocks in LB medium overnight at 30° C. prior to washing in M9 minimal medium. Washed cells were inoculated to an OD$_{600}$ of 0.1 in 25 mL of M9 minimal media supplemented with the specified carbon/energy source in 125 mL baffled flasks and incubated at 30° C., 225 rpm in biological duplicate or triplicate, as indicated. In the case of 3MGA, the culture volume was reduced to 10 mL in 50 mL baffled flasks due to the cost of this substrate. When and as specified, stock compounds were provided as feed to cultivations every 24 h in a volume that did not exceed 5% of the total cultivation volume. In the case of formate feeding, cultivations were subsequently pH adjusted to pH 7.1-7.3 with formic acid, which provided an additional 0.13-1.75 mmol of formate. To measure cell growth and quantify metabolites, cultures were sampled by removing 1 mL, measuring OD$_{600}$ of a 1:10 or 1:100 dilution, centrifuging to pellet the cells, and blanking with the OD$_{600}$ of the supernatant to account for darkening of some cultures due to oxidation of intermediates.

In vivo reactions: Wild-type *P. putida* KT2440 and engineered strains were cultivated overnight in LB medium and centrifuged. The cell pellets were washed 1-3× with 1×M9 medium (6.78 g/L disodium phosphate, 3 g/L monopotassium phosphate, 0.5 g/L NaCl, 1 g/L NH$_4$Cl, 2 mM MgSO$_4$, 100 μM CaCl$_2$), and 18 μM FeSO$_4$, pH 7.0) and used to inoculate 125 mL baffled flasks containing 25 mL 1×M9 medium supplemented with various concentrations of aromatic compounds (vanillate, syringate, 3-MGA, gallate, or syringaldehyde, the latter dissolved in 2% DMSO (v/v)) in the presence or absence of 20 mM glucose. Flasks were inoculated to an OD$_{600}$ of 0.1 and incubated at 30° C., 225 rpm. Cultures were sampled periodically by removing 1 mL that was used to measure the OD$_{600}$ as well as metabolite analysis (see below). Shake flask experiments were performed in triplicate. In the case of 3-MGA, the culture was downscaled to 10 mL in 50 mL baffled flasks and performed in duplicate.

Quantification of metabolites: Samples were centrifuged, the supernatants were 0.2 μm syringe filtered, and stored in glass vials at −20° C. prior to analysis. Analysis of aromatic acid utilization was performed using an Agilent 1100 series HPLC equipped with a Phenomenex Rezex™ RFQ-Fast Acid H$^+$ (8%) column with a cation H+ guard cartridge (Bio-Rad Laboratories, Hercules, CA), a diode array detector (DAD), and refractive index detector (RID). Isocratic chromatographic separation was carried out using 0.01N H$_2$SO$_4$ mobile phase at a flow rate of 1.0 mL/min with the column temperature set to 85° C. and the RID held at 55° C. Standard curves were used for each compound and a calibration verification standard was run every 6-10 samples to verify calibration consistency and assess instrument drift.

Analysis of glucose was performed on an Agilent 1200 series HPLC equipped with an Aminex HPX-87H column (Bio-Rad Laboratories, Hercules, CA) and a RID. Isocratic chromatographic separation was carried out using 0.01N H$_2$SO$_4$ mobile phase at a flow rate of 0.6 mL/min with the column and RID temperatures set to 55° C.

Preliminary PDC quantification was performed using nuclear magnetic resonance (NMR) as follows: 200 μL of sample was added to 400 μL of deuterium oxide (Cambridge Isotope Laboratories Inc, USA) and 50 μL of deuterium oxide containing a known mass succinic acid and analyzed by $^1$H 2D NMR spectrum run with the Nuclear Overhauser and Exchange Spectroscopy (NOESY) water suppression program (Callihan et al., 1996) (delay of 30 s, 16 scans).

Quantification of PDC and aromatic acids for the calculation of yield was analyzed on an Agilent 1260 series HPLC (Agilent Technologies, Santa Clara, CA) coupled with a DAD and a Phenomenex Luna C18(2) 5 μm, 4.6×150 mm column. The column was held at a constant temperature of 40° C., and compounds were monitored at wavelengths 310 nm, 280 nm, and 210 nm. An injection volume of 6 μL was utilized for all samples and standards and a standard was analyzed every 10-20 samples to verify calibration stability. A gradient of 10 mM phosphoric acid (A) and acetonitrile (B) was used at a flow rate of 0.80 mL/min. The following program was used to attain analyte separation: initial (t0) to t=5 min: A-90% and B-10%; ramp to A-70% and B-30% from t=5 to 20 min; return to A-90% and B-10% from t=20 to 20.10 min and maintain for a total run time of 27 min.

A PDC standard for quantification was purified from biological culture broth. Briefly, broth was filtered through a dual 0.8 and 0.2 μm PES membrane followed by 10 g/L activated carbon 100 mesh, precipitated at pH ~2 (using H$_2$SO$_4$) and ~5° C. for 24 h, vacuum filtered, dried in a vacuum oven at 40° C. for 24 h, and dissolved in 200 proof ethanol to separate the precipitated fermentation salts from soluble PDC. The ethanol solution was filtered, concentrated by rotary evaporation, and further purified through flash chromatography using a gradient of 0-100% of 5% acetone: dichloromethane. Purified PDC was reduced by rotary evaporation to a white solid and purity was evaluated using differential scanning calorimetry to yield 95.2%. PDC yield from biological cultivations was calculated as mM PDC/mM aromatic substrates at to.

Proteomics and RNA-seq samples preparation: Seed cultures of wild-type *P. putida* KT2440 and the engineered strain, CJ486, were grown overnight in LB and used to inoculate 1 L precultures of 1×M9 minimal medium supplemented with 20 mM glucose in 2 L flask. The cells were grown to log phase (OD$_{600}$ 0.5-0.7), washed one time with 1×M9 minimal medium (to remove any trace of glucose), concentrated, and used to inoculate at an OD$_{600}$ of 0.1 in 500 mL flask containing 100 mL of 1×M9 minimal medium supplemented with the different substrates (5 mM vanillate or syringate in the presence or absence of 20 mM glucose and 20 mM glucose alone). The cells were grown to OD$_{600}$ 0.3, split evenly into 50 mL falcon tubes, centrifuged at 4° C., 4100 rpm, for 5 min and fixed in liquid nitrogen before being stored at −80° C. until further analysis for proteomics or RNA-seq. These experiments were performed in triplicate. The growth curves of these strains are shown in the results section.

RNA isolation and ribosomal RNA removal: Cells pelleted from 50 mL of each culture were resuspended in TRIzol (ThermoFisher-Invitrogen, Waltham, MA USA) and mixed by vortex and pipetting. Chloroform was then added to the samples and after centrifugation the aqueous layer was removed and the samples were mixed with 80% ethanol. RNeasy columns (Qiagen Hilden, Germany) were used for RNA purification. RNA was eluted off the column in 35 μL RNAse free H$_2$O (Qiagen, Hilden, Germany). RNA concentration was determined using a Nanodrop 1000 (Thermo-Scientific, Waltham, MA) and RNA quality was verified by obtaining RNA Integrity Numbers (RIN) using an RNA 6000 Nanochip on an Agilent 2100 Bioanalyzer (Agilent Technologies, Santa Clara, CA). Ribosomal RNA was depleted from total RNA samples using a RiboZero rRNA Removal Kit for bacteria (Illumina-Epicentre, San Diego, CA). The depleted sample was purified on an RNA Clean & Concentrator-5 (Zymo Research, Irvine, CA), quantified using a Nanodrop 1000, and visualized on an Agilent 2100 Bioanalyzer instrument with an RNA 6000 Nanochip (Agilent Technologies, Santa Clara, CA). RNA depleted of ribosomal RNA was used as input material to synthesize cDNA libraries using a ScriptSeq v2 RNA-Seq Library Preparation Kit (Illumina-Epicentre, San Diego, CA). Agencount AMPure beads (Beckman Coulter, Indianapolis, USA) were used to purify the cDNA, and unique, TruSeq-compatible barcodes were added during 13 cycles of library amplification. The final RNA-Seq libraries were purified with Agencount AMPure beads (Beckman Coulter, Indianapolis) and quantified with a Qubit fluorometer (Life Technologies, Carlsbad, CA, USA). The library quality was assessed on a Bioanalyzer DNA 7500 DNA Chip (Agilent, Santa Clara, CA, USA), and samples were pooled and diluted. Pooled barcoded libraries were sequenced in one direction for 75 bases (SE75) on an Illumina NextSeq500 (high output) and by sequencing by synthesis chemistry (Illumina Inc. San Diego, CA), and de-multiplexed by Vanderbilt University Medical Center (VUMC VANTAGE Vanderbilt Technologies for Advanced Genomics (Nashville, TN)).

Preparation of proteins and proteomics: Cell pellets were suspended in SDS lysis buffer (4% in 100 mM of NH$_4$HCO$_3$, 10 mM DTT). Samples were boiled for 5 min at 90° C., physically disrupted by bead beating (0.15 mm Zirconium oxide beads) at 8 k rpm for 10 min, and boiled again for 5 min at 90° C. Cysteines were blocked by adjusting each sample to 30 mM IAA and incubated in the dark for 15 min at room temperature. Proteins were precipitated using a chloroform/methanol/water extraction. Dried protein pellets were resuspended in 2% SDC (100 mM NH$_4$HCO$_3$) and protein amounts were estimated by performing a BCA assay. For each sample, an aliquot of ~500 ug of protein was digested via two aliquots of sequencing-grade trypsin (Promega, 1:75 (w/w)) twice, overnight followed by a 3 h at 37° C. The peptide mixture was adjusted to 1% FA to precipitate SDC. Hydrated ethyl acetate was added to each sample at a 1:1 (v/v) ratio three times to effectively remove SDC. Samples were then placed in a SpeedVac Concentrator (Thermo Fischer Scientific) to remove ethyl acetate and further concentrate the sample. The peptide-enriched flow through was quantified by BCA assay, desalted on RP-C18 stage tips (Pierce Biotechnology) and then stored at −80° C.

A 2 μg aliquot of each sample was analyzed via nanospray ionization on a Q Exactive Plus mass spectrometer coupled to an EASY-nLC 1200 (Thermo Fischer Sci., USA). Data-dependent LC-MS/MS data were acquired with Thermo Xcalibur (version 4.27.19).

MS raw data files were searched against the *P. putida* KT2440 genome (Assembly Acc. GCF_000007565.2) to which common contaminate proteins had been added. A decoy database, consisting of the reversed sequences of the target database, was appended in order to discern the false-discovery rate (FDR) at the spectral level. MS/MS data were analyzed by the Crux pipeline v3.0 (4), searched using the Tide algorithm (5), processed by Percolator (6), and peptide spectrum matches (PSMs) identified at q<0.01. Resulting proteins were required to have at least two distinct peptide sequences and two spectra per protein. For label-free quantification, MS1-level precursor intensities were derived by moFF (7). Protein intensity-based values, which were calculated by summing together quantified peptides, were log 2-transformed and normalized by LOESS and median central tendency in InfernoRDN (8). All proteomics raw data is available at the ProteomeXchange Consortium via the MassIVE repository (ftp://massive.ucsd.edu/MSV000085948/).

Cell pellets were suspended in SDS lysis buffer (4% in 100 mM of NH$_4$HCO$_3$, 10 mM DTT). Samples were boiled for 5 min at 90° C., physically disrupted by bead beating (0.15 mm Zirconium oxide beads) at 8 k rpm for 10 min, and boiled again for 5 min at 90° C. Cysteines were blocked by adjusting each sample to 30 mM IAA and incubated in the dark for 15 min at room temperature. Proteins were precipitated using a chloroform/methanol/water extraction. Dried protein pellets were resuspended in 2% SDC (100 mM NH$_4$HCO$_3$) and protein amounts were estimated by performing a BCA assay. For each sample, an aliquot of ~500 ug of protein was digested via two aliquots of sequencing-grade trypsin (Promega, 1:75 (w/w)) twice, overnight followed by a 3 h at 37° C. The peptide mixture was adjusted to 1% FA to precipitate SDC. Hydrated ethyl acetate was added to each sample at a 1:1 (v/v) ratio three times to effectively remove SDC. Samples were then placed in a SpeedVac Concentrator (Thermo Fischer Scientific) to remove ethyl acetate and further concentrate the sample. The peptide-enriched flow through was quantified by BCA assay, desalted on RP-C18 stage tips (Pierce Biotechnology) and then stored at −80° C.

Protein identification and quantification: All samples were analyzed by nanospray ionization on a Q Exactive Plus mass spectrometer (Thermo Fischer Scientific) coupled an EASY-nLC 1200 liquid chromatography (LC) pump (Thermo Fisher Scientific). Peptides were separated on a 75 μm inner diameter microcapillary column packed with 25 cm of Kinetex C18 resin (1.7 m, 100 Å, Phenomenex). For each sample, a 2 μg aliquot was loaded in buffer A (0.1% formic acid, 2% acetonitrile) and eluted with a linear 150 min gradient of 2-20% of buffer B (0.1% formic acid, 80% acetonitrile), followed by an increase in buffer B to 50% buffer for 10 min and concluding with a 10 min wash at 98% buffer A. The flow rate was kept at 200 nL/min. MS data was acquired with the Thermo Xcalibur software version 4.27.19, a topN method where N could be up to 15. Target values for the full scan MS spectra were 1×10$^6$ charges in the 300-1,500 m/z range with a maximum injection time of 25 ms. Transient times corresponding to a resolution of 70,000 at m/z 200 were chosen. A 1.6 m/z isolation window and fragmentation of precursor ions was performed by higher-energy C-trap dissociation (HCD) with a normalized collision energy (NCE) of 27. MS/MS sans were performed at a resolution of 17,500 at m/z 200 with an ion target value of 1×10$^6$ and a maximum injection time of 50 ms. Dynamic exclusion was set to 45 s to avoid repeated sequencing of peptides.

MS raw data files were searched against the *P. putida* KT2440 NCBI reference proteome database to which common contaminate proteins had been added. A decoy database, consisting of the reversed sequences of the target database, was appended in order to discern the false-discovery rate (FDR) at the spectral level. Peptide fragmentation spectra (MS/MS) were analyzed by the Crux pipeline v3.0. The MS/MS were searched using the Tide algorithm and was configured to derive fully-tryptic peptides using default settings except for the following parameters: allowed clip n-term methionine, a precursor mass tolerance of 10 parts per million (ppm), a static modification on cysteines (iodoacetamide; +57.0214 Da), and dynamic modifications on methionine (oxidation; +15.9949). The results were processed by Percolator to estimate q values. Peptide spectrum matches (PSMs) and peptides were considered identified at a q value <0.01. Across the entire experimental dataset, proteins were required to have at least 2 distinct peptide sequences and 2 minimum spectra per protein. For label-free quantification, MS1-level precursor intensities were derived from moFF using the following parameters: 10 ppm mass tolerance, retention time window for extracted ion chromatogram was 3 min, time window to get the apex for MS/MS precursor was 30 s. Protein intensity-based values, which were calculated by summing together quantified peptides, were log 2-transformed and normalized by LOESS and median central tendency in InfernoRDN.

Plasmid constructions for protein production: For protein expression and kinetics characterization, DNA was purified, manipulated, and propagated using standard procedures as follows. The vanA and vanB genes of KT2440 were synthesized by back translating the proteins' amino acid sequences using codons optimized for expression in *Escherichia coli* (ATUM, Inc.) and cloned into pSN95 and pSN96 to yield pD444-CH-VanA and pD444-CH-VanB. The genes were amplified from these constructs and cloned into pET41b and pET28a (Novagen), respectively, to yield pET41VanA, carrying a gene encoding untagged VanA, and pET28VanB. The latter carries a gene encoding VanB with an N-terminal, TEV$^{pro}$-cleavable poly-histidine tag (Ht-VanB). The pcaHG genes are contained in a pVP91 backbone, described previously, which encodes an enzyme with a poly-histidine tag at the N-terminus of PcaH. 5' Phosphorylated oligonucleotides were used to insert a TEV$^{pro}$ cleavage site between the tag and PcaH, creating pVP91-Ht-PcaHG. The galA gene was amplified from pBTL2-galA (pSN82) and cloned into pET41b to yield pET41GalA, carrying a gene encoding GalA. The nucleotide sequence of all constructs was confirmed. The oligonucleotides used in this study are listed in Table 7.

Protein production and purification: VanA was produced heterologously using *E. coli* BL-21 λ(DE3) containing pET41VanA. Freshly transformed cells were grown at 37° C. in LB broth supplemented with 50 mg/L kanamycin to an optical density ($OD_{600}$) of ~0.7. Expression of vanA was induced with 0.5 mM isopropyl β-D-thiogalactopyranoside (IPTG), at which time the medium was further supplemented with 0.1 mM $FeCl_3$ and the cells were incubated at 30° C. for an additional 16 hours. Cells were harvested by centrifugation and stored at −80° C. until further processing. Cells collected from 4 L of culture were suspended in ~40 ml 20 mM HEPPS, pH 8.0 and lysed at 4° C. using an EmulsiFlex-C5 homogenizer (Avestin). Cellular debris was removed by centrifugation. Ammonium sulfate was added to the cleared lysate to a final concentration of 1.0 M and the precipitate was removed by centrifugation. Ammonium sulfate was added to the supernatant to a final concentration of 1.6 M and the pellet was collected by centrifugation. The protein pellet was solubilized to ~20 mL using 20 mM HEPPS, 1 M ammonium sulfate, pH 8.0, passed through a 0.45 μm filter, and loaded onto a Source 15 Phenyl column (1×10 cm) equilibrated with 20 mM HEPPS, 1 M ammonium sulfate, pH 8.0. VanA was eluted using a 100 mL linear gradient from 1 to 0 M ammonium sulfate in 20 mM HEPPS, pH 8.0 (ÄKTA Purifier, GE Healthcare). Fractions containing VanA, as determined using SDS-PAGE, were pooled, dialyzed into 20 mM HEPPS, pH 8.0 and loaded onto a Source 15 Q column (GE Healthcare; 1×10 cm) equilibrated with 20 mM HEPPS, pH 8.0. The protein was eluted with a linear gradient from 0 to 0.5 M NaCl in 100 mL 20 mM HEPPS, pH 8.0. Fractions containing VanA were pooled, dialyzed into 20 mM HEPPS, pH 8.0, concentrated to ~20 mg/ml, flash frozen as beads in liquid $N_2$, and stored at −80° C. until needed.

Ht-VanB was produced heterologously using *E. coli* BL-21 λ(DE3) containing pET41VanB essentially as described for VanA except that the cells were incubated at 20° C. Cells were processed and the lysate was cleared as for VanA. Subsequent steps were performed in a glovebox (Labmaster Model 100, Mbraun) to minimize the reductase's exposure to $O_2$. Purification buffers were sparged with $N_2$ then placed in the glovebox for equilibration overnight. The filtered lysate was briefly sparged with argon then applied to Ni-NTA resin (GE Healthcare) which was pre-equilibrated with 20 mM HEPPS, 100 mM NaCl, pH 8.0. The resin was washed and eluted with 20 mM HEPPS, 100 mM NaCl, pH 8.0, containing 20 mM and 400 mM imidazole, respectively. Eluted Ht-VanB was dialyzed into 20 mM HEPPS, 100 mM NaCl, pH 8.0, concentrated to ~20 mg/ml, then frozen and stored as described for VanA.

PcaHG was heterologously produced using *E. coli* BL-21 λ(DE3) containing pVP91-Ht-PcaHG. Freshly transformed cells were used to inoculate 4 L LB broth supplemented with 100 μg/mL ampicillin at 37° C. and grown to an optical density of ~0.7. Gene expression was induced with 1 mM IPTG, at which time the medium was further supplemented with 0.4 mM $FeCl_3$ and the cells were incubated for an additional 18 hours at 17° C. Cells were harvested by centrifugation and stored at −80° C. until further processing. Cells collected from 4 L of culture were suspended in ~40 mL 50 mM Tris-HCl, pH 7.5, 200 mM NaCl, 10% (v/v) glycerol (TSG buffer) and 15 mM imidazole and cOmplete, EDTA-free Protease Inhibitor (Roche) and lysed and clarified as for VanA. The cleared lysate was incubated with Ni-NTA resin (equilibrated with TSG buffer) for 45 minutes with gentle shaking at 4° C. The resin was washed twice: first with TSG buffer containing 25 mM imidazole and then with TSG buffer containing 55 mM imidazole. Ht-PcaHG was eluted with TSG buffer containing 250 mM imidazole and was exchanged into 20 mM Tris-HCl, pH 8.0 containing 1 mM DTT. Fractions containing Ht-PcaHG were identified with SDS-PAGE, pooled and buffer-exchanged into 20 mM Tris-HCl, pH 8.0, 1 mM DTT. The His-tag was removed by digestion with TEV$^{pro}$ (10:1 ratio) for 1 hour at 30° C. The digestion mixture was diluted three-fold with 20 mM MOPs, pH 6.8 and then loaded onto a Source 15 Q column (GE Healthcare; 1×10 cm) equilibrated with 20 mM MOPS, pH 7.5. PcaHG was eluted with a 60 mL linear gradient from 0 to 350 mM NaCl in 20 mM MOPS, pH 7.5 (ÄKTA Purifier, GE Healthcare). Fractions containing PcaHG were pooled, dialyzed into 20 mM HEPES, pH 7.5, concentrated to ~15 mg/mL, then frozen and stored as described for VanA.

GalA was heterologously produced using *E. coli* BL-21 λ(DE3) containing pET41GalA essentially as described for VanA except that the cells were incubated for 5 hours at 37° C. after induction of expression with 0.1 mM IPTG and the medium further supplemented with 0.4 mM $FeCl_3$. Cells collected from 2 L of culture were suspended in ~25 mL 50 mM HEPPS, pH 8.0, 200 mM NaCl, 1 mM DTT and lysed and clarified as for VanA. The clarified lysate was brought to a concentration of 1.5 M ammonium sulfate using a 3 M ammonium sulfate stock solution in 50 mM HEPPS, pH 8.0, 1 mM DTT buffer to precipitate GalA. The precipitate was removed by centrifugation and the protein pellet solubilized with ~10 mL 50 mM HEPPS, pH 8.0, 1 mM DTT and 3 M ammonium sulfate stock added to a final concentration of 0.5 M. A final centrifugation and clarification step as for VanA were conducted prior to the 0.5 M ammonium sulfate GalA solution being loaded onto a Source 15 Phenyl column (1×10 cm), equilibrated with 50 mM HEPPS, pH 8.0, 0.5 M ammonium sulfate. GalA was eluted with a 60 mL linear gradient from 0.5 to 0 M ammonium sulfate in 50 mM HEPPS, pH 8.0. The fractions containing GalA were identified using SDS-PAGE, pooled and dialyzed into 20 mM HEPPS, pH 8.0 and then loaded onto a Source 15 Q column (GE Healthcare; 1×10 cm). GalA was eluted using a 80 mL linear gradient from 0 to 0.6 M NaCl in 20 mM HEPPS, pH 8.0 (GE Healthcare; ÄKTA purifier). Immediately prior to kinetic assays, GalA was reconstituted anaerobically inside a glovebox by incubating the enzyme with a 10-fold molar excess of ferrous ammonium sulfate for 45 minutes. Excess iron was removed with a 1.2 mL G25 (fine) Sephadex resin packed into glass pipette equilibrated with 20 mM HEPPS, pH 8.0. Eluate containing GalA were identified using $A_{280}$, pooled and diluted 5 fold into 20 mM HEPPS, pH 8.0, 10% (v/v) glycerol, 1 mM DTT in a screw-top HPLC vial prior to removal from the glovebox.

Protein analytical methods: Protein purity was evaluated using SDS-polyacrylamide gel stained with Coomassie Blue according to established procedures. Protein concentrations were determined using micro BCA™ Protein Assay Kit (Pierce) using bovine serum albumin as a standard. Acid-labile sulfur content and iron content of samples was determined using colorimetric assays adapted for 96-well plate. PcaHG concentrations were determined with $\varepsilon_{280}$=61.2 mM$^{-1}$cm$^{-1}$ (per αβ dimer) and $\varepsilon_{450}$=2.86 mM$^{-1}$cm$^{-1}$. GalA concentrations were determined with ε280=52.6 mM$^{-1}$ cm$^{-1}$.

Steady-state kinetic analyses: Kinetic assays were performed by monitoring the consumption of $O_2$ using a Clark-type polarographic $O_2$ electrode OXYG1 (Hansatech) connected to a circulating water bath. Assays with the exception of GalA were performed in 1 mL of air-saturated 40 mM HEPES, 80 mM NaCl (I=0.1 M, pH 7.5) at 25° C. GalA assays were performed in 40 mM MOPS, 80 mM NaCl (I=0.1 M, pH 7.0) at 30° C. The electrode was calibrated daily according to the manufacturer's instructions using air-saturated buffer and water depleted of 02 via addition of sodium hydrosulfite. Stock solutions were prepared fresh daily. The background rate of $O_2$-consumption was recorded prior to initiating the reaction and was subtracted from the measured reaction rate. Steady-state kinetic parameters were evaluated by fitting the Michaelis-Menten equation to the data using the least-squares fitting of LEONORA.

For VanAB, the standard reaction contained 1 μM VanA, 2 μM Ht-VanB, and 400 μM NADH. This mixture was allowed to equilibrate for 1-2 min before initiating the reaction by addition of 200 μM vanillate. Stock solutions of the substrates were made in dimethylsulfoxide (DMSO). The final concentration of DMSO in the assay solutions was <1% (v/v). For PcaHG, the standard reaction contained 250 μM PCA. The reaction was initiated by adding 0.1 μM PcaHG. For GalA, the standard reaction contained 500 μM gallate. The reaction was initiated by adding 0.05 μM GalA.

Inactivation kinetic analyses: GalA inactivation assays were performed by monitoring consumption of 02 using OXYG1 as described in Steady-state kinetic analyses. The GalA rate of inactivation during turnover ($j_3^{app}$) and the partition ratio for gallate and 3MGA were determined by using either reconstituted GalA or an E. coli lysate containing GalA. To obtain soluble E. coli lysate containing GalA, 50 mL of culture was suspended in ~900 μL of 50 mM HEPPS, pH 8.0, 100 mM NaCl. The resuspension was pipetted into a 1.5 mL screw cap tube containing ~100 μL of 0.1 mm silica sand. Cell were lysed using a Bead Beater rotor (MP Biomedical). Cellular debris and sand were removed by centrifugation. The clarified was removed to a micro centrifuge tube and kept on ice until use.

The amount of GalA added to the assay was such that the enzyme was completely inactivated before 10% of either the catecholic substrate or 02 was consumed in the reaction mixture. The partition ratio was calculated using Equation 1 shown above.

The apparent apparent rate constant of inactivation during catalytic turnover in air-saturated buffer, $j_3^{app}$, was determined by fitting Equation 2 to reaction progress curves where $S_t$ is the substrate concentration at time t.

$$s_t=(s_0-s_\infty)e^{-j_3^{app}t}+s_\infty \qquad \text{Equation 2}$$

HPLC characterization of transformation products and flavin content: Oxygenase turnover and VanB flavin content were evaluated using a Waters 2695 Separation HPLC module (Milford, MA) equipped with a Waters 2996 photodiode array detector. VanAB reactions contained ~1 μM VanA, ~1 μM VanB and 200 μM substrate in air-saturated HEPES (I=0.1 M, pH 7.5). Reactions were incubated for 30 min at 25° C., quenched with glacial acetic acid (final concentration 10% (v/v)), then centrifuged and filtered (0.2 μm) to remove protein. Substrates and products were resolved using a 250×4.6 mm Luna 5 m C18(2) column (Phenomenex, Torrance, CA) and a linear gradient of 0.1% formic acid and methanol. Compound amounts were assessed using integrated peak areas at 260 nm and standard curves for each compound.

Flavins were characterized using the method of Faeder and Siegel. Briefly, flavins were resolved using a 250×4.60-mm C18 Prodigy 10u ODS-Prep column (Phenomenex, Torrance, CA) and a linear gradient of 0.5% phosphoric acid and methanol. Solutions of FMN and FAD were run as standards.

LC-MS-Q-TOF analyses of PcaHG and GalA reaction products: LC-Q-TOF-MS analysis was performed using an Agilent 6546 Q-TOF equipped with a dual AJS ESI source and interfaced to an Agilent 1290 Infinity II UHPLC. The UHPLC was equipped with an InfinityLab Poroshell 120 HILIC-Z column (100 mm×2.1 mm×2.7 um). Solvent A was 10 mM ammonium acetate, pH 9.0 and Solvent B was 90% acetonitrile and 10% 10 mM ammonium acetate, pH 9.0 (v/v). The flow rate was 0.25 mL/min and 2 uL of sample was injected. The column was equilibrated in 90% B and held for 2 minutes following injection, followed by a linear gradient from 90% to 60% B over 10 minutes and held at 60% B for another 3 minutes before returning to starting conditions over a 1 minute gradient and re-equilibrated for 8 minutes before the next injection. The MS was operated in negative mode using the following parameters: capillary voltage, 3500 V; nozzle voltage, 1000 V; drying gas temp, 250° C.; drying gas flow rate, 10 L/min; sheath gas temperature, 300° C.; sheath gas flow rate 12 L/min, nebulizer pressure, 45 psi; nebulizer gas temperature, 350° C.; fragmentor voltage, 100 V. The expected mass/charge (m/z)

values of substrates and predicted products were calculated using MassHunter Qualitative Analysis Software Version 10 (Agilent).

For PcaHG, reactions for LC/MS analysis were prepared by incubating gallate with cellular lysates. Lysates were obtained as for GalA in Inactivation Kinetic Analyses but here the cells were suspended in 50 mM Tris-HCl, pH 7.5, 200 mM NaCl. Reactions were performed in 450 uL of standard reaction buffer containing 40 µL of the cleared supernatant and 400 µM gallate. Reactions for GalA were performed in 180 µL 40 mM MOPS, pH 7.0 containing 800 µM 3-MGA. Reactions were initiated by adding 50 µM reconstituted GalA as described in protein minus the final buffer exchange. Both PcaHG and GalA reactions were frequently and gently inverted at room temperature over the course of 10 and 20 min respectively after which the mixture was stopped by adding 10% (v/v) hydrochloric acid. Precipitated proteins were removed by centrifugation. The supernatants were removed and diluted 2-fold using LC-MS grade water and acetonitrile.

TABLE 4

DNA and Amino acid Sequences

| Name (SEQ ID Number) | Sequence |
|---|---|
| pcaH$^{KT2440}$ (SEQ ID NO: 1) | ATGCCCGCCCAGGACAACAGCCGCTTCGTGATCCGTGATCGCAACTG GCACCCTAAAGCCCTTACGCCTGACTACAAGACCTCCGTTGCCCGCTC GCCGCGCCAGGCACTGGTCAGCATTCCGCAGTCGATCAGCGAAACCA CTGGTCCGGACTTTTCCCATCTGGGCTTCGGCGCCCACGACCATGACC TGCTGCTGAACTTCAATAACGGTGGCCTGCCCATTGGCGAGCGCATCA TCGTCGCCGGCCGTGTCGTCGACCAGTACGGCAAGCCTGTGCCGAAC ACTTTGGTGGAGATGTGGCAAGCCAACGCCGGCGGCCGCTATCGCCA CAAGAACGATCGCTACCTGGCGCCCCTGGACCCGAACTTCGGTGGTG TTGGGCGGTGTCTGACCGACCGTGACGGCTATTACAGCTTCCGCACCA TCAAGCCGGGCCCGTACCCATGGCGCAACGGCCCGAACGACTGGCGC CCGGCGCATATCCACTTCGCCATCAGCGGCCCATCGATCGCCACCAAG CTGATCACCCAGTTGTACTTCGAAGGTGACCCGCTGATCCCGATGTGC CCGATCGTCAAGTCGATCGCCAACCCGCAAGCCGTGCAGCAGTTGATC GCCAAGCTCGACATGAGCAACGCCAACCCGATGGACTGCCTGGCCTA CCGCTTTGACATCGTGCTGCGCGGCCAGCGCAAGACCCACTTCGAAAA CTGCTGA |
| PcaH$^{KT2440}$ (SEQ ID NO: 2) | MPAQDNSRFVIRDRNWHPKALTPDYKTSVARSPRQALVSIPQSISETTGP DFSHLGFGAHDHDLLLNFNNGGLPIGERIIVAGRVVDQYGKPVPNTLVEM WQANAGGRYRHKNDRYLAPLDPNFGGVGRCLTDRDGYYSFRTIKPGPY PWRNGPNDWRPAHIHFAISGPSIATKLITQLYFEGDPLIPMCPIVKSIANPQ AVQQLIAKLDMSNANPMDCLAYRFDIVLRGQRKTHFENC* |
| pcaG$^{KT2440}$ (SEQ ID NO: 3) | ATGCCAATCGAACTGCTGCCGGAAACCCCTTCGCAGACTGCCGGCCC CTACGTGCACATCGGCCTGGCCCTGGAAGCCGCCGGCAACCCGACC CGCGACCAGGAAATCTGGAACTGCCTGGCCAAGCCAGACGCCCCGG GCGAGCACATTCTGCTGATCGGCCACGTATATGACGGAAACGGCCAC CTGGTGCGCGACTCGTTCCTGGAAGTGTGGCAGGCCGACGCCAACG GTGAGTACCAGGATGCCTACAACCTGGAAAACGCCTTCAACAGCTTT GGCCGCACGGCTACCACCTTCGATGCCGGTGAGTGGACGCTGCAAA CGGTCAAGCCGGGTGTGGTGAACAACGCTGCTGGCGTGCCGATGGC GCCGCACATCAACATCAGCCTGTTTGCCCGTGGCATCAACATCCACC TGCACACGCGCCTGTATTTCGATGATGAGGCCCAGGCCAATGCCAAG TGCCCGGTGCTCAACCTGATCGAGCAGCCGCAGCGGCCGTGAAACCT TGATTGCCAAGCGTTGCGAAGTGGATGGGAAGACGGCGTACCGCTTT GATATCCGCATTCAGGGGGAAGGGGAGACCGTCTTCTTCGACTTCTG A |
| PcaG$^{KT2440}$ (SEQ ID NO: 4) | MPIELLPETPSQTAGPYVHIGLALEAAGNPTRDQEIWNCLAKPDAPGEHIL LIGHVYDGNGHLVRDSFLEVWQADANGEYQDAYNLENAFNSFGRTATTF DAGEWTLQTVKPGVVNNAAGVPMAPHINISLFARGINIHLHTRLYFDDEA QANAKCPVLNLIEQPQRRETLIAKRCEVDGKTAYRFDIRIQGEGETVFFDF* |
| ligA$^{SYK-6}$ (SEQ ID NO: 5) | ATGACCGAGAAGAAAGAACGCATCGACGTGCACGCCTACCTGGCCGA GTTCGACGACATCCCAGGCACCCGTGTGTTCACCGCCCAGCGTGCC CGTAAGGGCTACAACCTGAACCAGTTCGCCATGAGCCTGATGAAGGC CGAGAACCGCGAGCGCTTCAAGGCCGACGAGAGCGCCTACCTGGAC GAATGGAACCTGACCCCAGCCGCCAAAGCCGCCGTGCTGGCCCGTG ACTACAACGCCATGATCGACGAGGGTGGCAACGTGTACTTCCTGAGC AAGCTGTTCAGCACCGACGGCAAGAGCTTCCAGTTCGCCGCCGGTAG CATGACCGGCATGACCCAAGAGGAATACGCCCAGATGATGATCGATG GCGGTCGCAGCCCAGCCGGTGTGCGCAGCATCAAGGGTGGCTACTG A |
| LigA$^{SYK-6}$ (SEQ ID NO: 6) | MTEKKERIDVHAYLAEFDDIPGTRVFTAQRARKGYNLNQFAMSLMKAEN RERFKADESAYLDEWNLTPAAKAAVLARDYNAMIDEGGNVYFLSKLFST DGKSFQFAAGSMTGMTQEEYAQMMIDGGRSPAGVRSIKGGY* |
| ligB$^{SYK-6}$ (SEQ ID NO: 7) | ATGGCCCGTGTGACCACCGGCATCACCAGCAGCCACATCCCAGCCCT GGGTGCCGCCATCCAAACCGGCACCAGCGACAACGACTACTGGGGT CCGGTGTTCAAGGGCTACCAGCCGATCCGCGACTGGATCAAGCAGC CAGGCAACATGCCGGACGTGGTGATCCTGGTGTACAACGACCACGC CAGCGCCCTTCGACATGAACATCATCCCGACCTTCGCCATCGGCTGCG |

TABLE 4-continued

DNA and Amino acid Sequences

| Name (SEQ ID Number) | Sequence |
|---|---|
| | CCGAAACCTTCAAGCCAGCCGACGAGGGCTGGGGTCCGCGTCCAGT<br>GCCGGATGTGAAGGGCCATCCGGACCTGGCCTGGCATATCGCCCAG<br>AGCCTGATCCTGGACGAATTCGATATGACCATCATGAACCAGATGGA<br>CGTGGACCACGGCTGCACCGTGCCGCTGAGCATGATCTTCGGCGAG<br>CCGGAAGAGTGGCCGTGCAAGGTGATCCCGTTCCCGGTGAACGTGG<br>TGACCTATCCGCCACCGAGCGGCAAGCGCTGCTTCGCCCTGGGCGA<br>CAGCATCCGTGCCGCCGTGGAAAGCTTCCCCGAGGACCTGAACGTG<br>CACGTGTGGGGCACCGGTGGCATGTCGCACCAGCTGCAAGGTCCGC<br>GTGCCGGTCTGATCAACAAAGAGTTCGACCTGAACTTCATCGACAAG<br>CTGATCAGCGACCCGGAAGAACTGAGCAAGATGCCGCACATCCAGTA<br>CCTGCGCGAGAGCGGCAGCGAGGGCGTGGAACTGGTGATGTGGCTG<br>ATCATGCGTGGTGCCCTGCCGGAAAAGGTGCGCGACCTGTACACCTT<br>CTACCATATCCCAGCCAGCAACACCGCTGGGTGCCATGATCCTGC<br>AGCCGGAAGAAACCGCCGGCACCCCACTGGAACCGCGTAAGGTGAT<br>GAGCGGTCACAGCCTGGCCCAGGCCTGA |
| LigB$^{SYK-6}$ (SEQ ID NO: 8) | MARVTTGITSSHIPALGAAIQTGTSDNDYWGPVFKGYQPIRDWIKQPGNM<br>PDVVILVYNDHASAFDMNIIPTFAIGCAETFKPADEGWGPRPVPDVKGHP<br>DLAWHIAQSLILDEFDMTIMNQMDVDHGCTVPLSMIFGEPEEWPCKVIPF<br>PVNVVTYPPPSGKRCFALGDSIRAAVESFPEDLNVHVWGTGGMSHQLQ<br>GPRAGLINKEFDLNFIDKLISDPEELSKMPHIQYLRESGSEGVELVMWLIM<br>RGALPEKVRDLYTFYHIPASNTALGAMILQPEETAGTPLEPRKVMSGHSL<br>AQA* |
| ligC$^{SYK-6}$ (SEQ ID NO: 9) | ATGCGTATCGCCCTGGCCGGTGCCGGTGCCTTCGGCGAAAAGCATCT<br>GGACGGGCCTGAAGAACATCGACGGCGTGGAAATCGTGAGCATCATCA<br>GCCGCAAGGCCGAGCAAGCCGCCGAGGTGGCCGCCAAGTACGGTG<br>CCAAACACAGCGGCACCGACCTGAGCGAAGCCCTGGCCCGTGATGA<br>CGTGGACGCCGTGATCCTGTGCACCCCGACCCAGATGCACGCCGAG<br>CAAGCGATCGCCTGCATGAACGCCGGTAAGCACGTGCAGGTCGAGA<br>TCCCGCTGGCCGACAGCTGGGCCGACGCCGAGGCCGTGATGAAGAA<br>GTCGCAAGAAACCGGTCTGGTGTGCATGGTGGGCCACACCCGTCGC<br>TTCAACCCCGAGCCACCAGTACATCCACAACAAGATCGTGGCCGGTGA<br>GCTGGCCATCCAGCAGATGGACGTCCAGACCTACTTCTTCCGTCGCA<br>AGAACATGAACGCCAAGGGCGAACCGCGTAGCTGGACCGACCATCT<br>GCTGTGGCACCATGCCGCCCACACCGTGGACCTGTTCGCCTACCAAG<br>CCGGTAAGATCGTCCAGGCCAACGCCGTGCAGGGTCCGATCCACCC<br>GGAACTGGGTATCGCCATGGACATGAGCATCCAGCTGAAGTCGGAAA<br>CCGGTGCCATCTGCACCCTGAGCCTGAGCTTCAACAACGACGGTCCG<br>CTGGGCACCTTCTTCCGCTACATCTGCGACAACGGCACCTGGATCGC<br>CCGTTACGACGACCTGGTGACCGGCAAAGAGGAACCGGTCGACGTC<br>AGCAAGGTGGACGTGAGCATGAACGGCATCGAGCTGCAGGACCGCG<br>AGTTCATCGCCGCCATCCGCGAAGGCCGTGAGCCGAACAGCAGCGT<br>GGCCCGTGTGCTGGACTGCTACCGCGTGCTGGGCGAGCTGGAAGTG<br>CAGCTGGAAAAGCAGGGCTGA |
| LigC$^{SYK-6}$ (SEQ ID NO: 10) | MRIALAGAGAFGEKHLDGLKNIDGVEIVSIISRKAEQAAEVAAKYGAKHSG<br>TDLSEALARDDVDAVILCTPTQMHAEQAIACMNAGKHVQVEIPLADSWAD<br>AEAVMKKSQETGLVCMVGHTRRFNPSHQYIHNKIVAGELAIQQMDVQTY<br>FFRRKNMNAKGEPRSWTDHLLWHHAAHTVDLFAYQAGKIVQANAVQGP<br>IHPELGIAMDMSIQLKSETGAICTLSLSFNNDGPLGTFFRYICDNGTWIARY<br>DDLVTGKEEPVDVSKVDVSMNGIELQDREFIAAIREGREPNSSVARVLDC<br>YRVLGELEVQLEKQG* |
| vanA$^{HR199}$ (SEQ ID NO: 11) | ATGTTTCCGAAAAACGCATGGTATGTGGCGTGTACGCCGGATGAAAT<br>CGCAGATAAACCGCTGGGCCGCCAAATCTGCAACGAAAAATCGTGT<br>TTTATCGCGGGCCCGAGGGTCGTGTGGCCGCTGTCGAGGACTTTTGT<br>CCACACCGTGGGGCCCCACTCTCGCTGGGTTTCGTCCGGGATGGCA<br>AGCTCATCTGCGGTTATCACGGTTTGGAGATGGGGTGCGAGGGTAAA<br>ACCCTCGCTATGCCGGGCCAGCGCGTGCAGGGTTTTCCTTGTATTAA<br>GTCGTACGCTGTCGAGGAGCGGTATGGGTTTATCGGGTCTGGCCTG<br>GTGATCGTGAACTGGCCGACCCTGCTTTGATTCACCATTTGGAGTGG<br>GCAGACAACCCGGAGTGGGCTTACGGCGGGGGCTTGTATCATATTGC<br>ATGCGACTACCGGCTGATGATTGACAACCTGATGGACTTGACCCACG<br>AGACCTATGTGCACGCATCCTCCATCGGTCAGAAAGAGATTGATGAG<br>GCCCCGGTGAGCACCCGCGTCGAAGGGACACGGTGATTACCTCCC<br>GGTACATGGACAACGTCATGGCCCCGCCGTTCTGGCGCGCTGCCTT<br>GCGTGGCAATGGGCTCGCCGATGATGTCCCAGTGGATCGCTGGCAA<br>ATCTGTCGTTTCGCGCCACCATCGCATGTCCTCATCGAAGTGGGCGT<br>GGCACATGCTGGCAAAGGGGGTTATGATGCCCCTGCCGAATACAAAG<br>CCGGCTCGATCGTCGTCGATTTTATTACGCCAGAGTCGGACACGAGC<br>ATTTGGTACTTTTGGGGCATGGCTCGCAATTTCGTCCCAAGGTACG<br>GAGTTGACGGAGACCATTCGTGTCGGGCAAGGCAAGATCTTTGCGGA |

TABLE 4-continued

DNA and Amino acid Sequences

| Name (SEQ ID Number) | Sequence |
|---|---|
| | AGACCTGGACATGCTGGAGCAGCAGCAGCGGAACTTGCTGGCCTATC<br>CTGAGCGGCAACTCCTGAAACTCAATATCGATGCTGGGGGCGTGCAA<br>TCGCGTCGGGTGATCGATCGCATTCTGGCGGCTGAACAAGAAGCTGC<br>GGATGCGGCCCTGATCGCTCGTTCGGCGAGCTGA |
| VanA$^{HR199}$ (SEQ ID NO: 12) | MFPKNAWYVACTPDEIADKPLGRQICNEKIVFYRGPEGRVAAVEDFCPH<br>RGAPLSLGFVRDGKLICGYHGLEMGCEGKTLAMPGQRVQGFPCIKSYAV<br>EERYGFIWVWPGDRELADPALIHHLEWADNPEWAYGGGLYHIACDYRL<br>MIDNLMDLTHETYVHASSIGQKEIDEAPVSTRVEGDTVITSRYMDNVMAP<br>PFWRAALRGNGLADDVPVDRWQICRFAPPSHVLIEVGVAHAGKGGYDA<br>PAEYKAGSIVVDFITPESDTSIWYFWGMARNFRPQGTELTETIRVGQKIF<br>AEDLDMLEQQQRNLLAYPERQLLKLNIDAGGVQSRRVIDRILAAEQEAAD<br>AALIARSAS* |
| VanB$^{HR199}$ (SEQ ID NO: 13) | ATGATTGAGGTGATTATTTCGGCGATGCGCCTGGTCGCCCAAGATATT<br>ATCTCGCTCGAATTCGTCCGCGCTGATGGCGGTTTGCTCCCCCCCGT<br>GGAAGCTGGCGCTCATGTCGATGTGCATTTGCCTGGCGGTCTCATCC<br>GCCAATACTCGCTGTGGAATCAACCTGGGGCCCAATCCCACTACTGT<br>ATTGGTGTGCTGAAGGATCCTGCCTCGCGGGGTGGGTCGAAAGCTGT<br>GCATGAAAACCTCCGTGTCGGTATGCGGGTGCAGATCTCGGAGCCTC<br>GCAATCTCTTTCCATTGGAGGAAGGCGTCGAGCGCAGCTTGCTGTTC<br>GCCGGGGGATTGGGATTACCCCTATCCTGTGTATGGCTCAAGAATT<br>GGCAGCCCGTGAACAAGATTTCGAATTGCATTACTGTGCGCGGTCGA<br>CGGATCGCGCCGCCTTTGTGGAGTGGCTCAAAGTCTGCGATTTTGCC<br>GATCACGTCCGTTTCCATTTCGATAACGGGCCCGACCAACAAAGTTG<br>AACGCTGCTGCTCTTGGCAGCAGAGGCTGAGGGCACGCACCTCTA<br>TGTCTGTGGTCCTGGGGGTTTCATGGGTCATGTGCTGGACACCGCGA<br>AAGAACAGGGTTGGGCTGATAACCGCTTGCATCGTGAGTACTTTGCT<br>GCTGCCCCAAATGTCTCCGCGGATGATGGTTCCTTCGAGGTGCGTAT<br>CCATTCGACGGGTCAGGTCCTGCAAGTCCCAGCGGACCAAACCGTGT<br>CCCAAGTCCTGGACGCTGCAGGTATTATCGTCCCAGTGAGCTGTGAG<br>CAAGGCATTTGCGGTACGTGCATTACCCGCGTCGTCGACGGTGAGCC<br>TGATCACCGCGATTTCTTCCTGACGGACGCCGAAAAGGCAAAAAATG<br>ATCAATTTACGCCGTGCTGTTCGCGGGCGAAGAGCGCCTGCCTCGTG<br>CTGGACTTGTAA |
| VanB$^{HR199}$ (SEQ ID NO: 14) | MIEVIISAMRLVAQDIISLEFVRADGGLLPPVEAGAHVDVHLPGGLIRQYSL<br>WNQPGAQSHYCIGVLKDPASRGGSKAVHENLRVGMRVQISEPRNLFPL<br>EEGVERSLLFAGGIGITPILCMAQELAAREQDFELHYCARSTDRAAFVEW<br>LKVCDFADHVRFHFDNGPDQQKLNAAALLAAEAEGTHLYVCGPGGFMG<br>HVLDTAKEQGWADNRLHREYFAAAPNVSADDGSFEVRIHSTGQVLQVP<br>ADQTVSQVLDAAGIIVPVSCEQGICGTCITRVVDGEPDHRDFFLTDAEKA<br>KNDQFTPCCSRAKSACLVLDL* |

TABLE 5

Plasmids used in this study.

| Plasmid | Utility | Construction details |
|---|---|---|
| pBTL-2 | Plasmid maintained in *P. putida* KT2440 | Addgene plasmid # 22806. Previously described in Lynch, M. D., Gill, R. T., 2006. Broad host range vectors for stable genomic library construction. Biotechnol. Bioeng. 94, 151-158. doi:10.1002/bit.20836 |
| pCJ020 | For integration of Ptac promoter upstream pcaHG | Previously described in Johnson, C.W., Beckham, G. T., 2015. Aromatic catabolic pathway selection for optimal production of pyruvate and lactate from lignin. Metab. Eng. 28, 240-247. doi:10.1016/j.ymben.2015.01.005. |
| pCJ051 | To insert P$_{tac}$:ligAB (where ligAB is from *Sphingobium* sp. SYK-6) into the genome with simultaneous deletion of pcaHG | Previously described Johnson, C. W., Salvachúa, D., Rorrer, N. A., Black, B. A., Vardon, DR., John, P. C. S., Cleveland, N. S., Dominick, G., Elmore, J. R., Grundl, N., Khanna, P., Martinez, C. R., Michener, WE., Peterson, D. J., Ramirez, K. J., Singh, P., VanderWall, T. A., Wilson, A. N., Yi, X., Biddy, M. J., Bomble, Y. J., Guss, A. M., Beckham, G. T., 2019. Innovative Chemicals and Materials from Bacterial Aromatic Catabolic Pathways. Joule 3, 1523-1537. doi:10.1016/j.joule.2019.05.011. |
| pCJ107 | To insert a second copy of vanAB constitutively expressed into the genome in the intergenic region donstream of fpvA | Previously described in Salvachtla, D., Johnson, C. W., Singer, C. A., Rohrer, H., Peterson, D. J., Black, B. A., Knapp, A., Beckham, G. T., 2018. Bioprocess development for muconic acid production from aromatic compounds and lignin. Green Chem. 167, 75-13. doi:10.1039/C8GCO2519C |

TABLE 5-continued

Plasmids used in this study.

| Plasmid | Utility | Construction details |
| --- | --- | --- |
| pSN66 | To delete vanAB | The 5' and 3' targeting region were amplified from *P. putida* KT2440 with the primer pairs oSN099/oSN223 and oSN224/oSN225 and assembled into pK18mobsacB (ATCC ® 87097 ™) vector, digested with BamHI and EcoRI. The plasmid was sequenced with the primers oCJ290, oCJ291, oSN103 and, oSN226. |
| pSN73 | To delete galA | The 5' and 3' targeting region were amplified from *P. putida* KT2440 with the primer pairs oSN234/oSN235 and oSN236/oSN237 and assembled into pK18mobsacB (ATCC ® 87097 ™), digested with BamHI and EcoRI. The plasmid was sequenced with the primers oCJ290 and oCJ291. |
| pSN82 | To overexpress galA gene on a plasmid | The galA gene was amplified from the genomic DNA of *P. putida* KT2440 with the primer pair oSN267/oSN268 and was assembled into pBTL-2 vector (Addagene plasmid # 22806), digested with EcoRV and XbaI. The plasmid was sequenced with the primers oCJ534, oCJ163 and, oSN269. |
| pSN95 | To synthesize the vanA gene codon optimized for *E. coli* | The vanA gene was codon optimized for *E. coli* expression (named vanA_EC, Table 7), synthesized, and cloned into the plasmid pD444-CH by ATUM Bio, Inc. (Accession # pD444-CH). |
| pSN96 | To synthesize the vanB gene codon optimized for *E. coli* | The vanB gene was codon optimized for *E. coli* expression (named vanB_EC, Table 7), synthesized, and cloned into the plasmid pD444-CH by ATUM Bio, Inc. (Accession # pD444-CH). |
| pET41VanA | To inducibly express a codon optimized vanA gene in *E. coli* | The vanA gene was amplified from pSN95 using the primers vanA-F (contains a NdeI cut-site) and vanA-R (contains a HindIII cut-site, Table 6) using Phusion Polymerase (NEB) where the PCR product is named vanA_EC_UBC and notably does not contain a His-tag (Table 7). The PCR product was ligated into pET41b digested with NdeI and HindIII using the T4 Ligase (NEB). The resulting plasmid was transformed into *E. coli* BL-21 λ(DE3) and sequence confirmed with T7_fw and T7_rv to generate LDE001 (Table 8). |
| pET28VanB | To inducibly express a codon optimized vanB gene in *E. coli* | The vanB gene was amplified from pSN96 by vanB-F (contains a NdeI cut-site) and vanB-R (contains a Hind III cut-site, Table 6) using Phusion Polymerase (NEB) where the PCR product is named vanB_EC_UBC and notably contains an N-terminal, $TEV^{pro}$-cleavable poly-histidine tag (Ht-VanB, Table 7). The PCR product was ligated into pET28a digested with NdeI and HindIII using the T4 Ligase (NEB). The resulting plasmid was transformed into *E. coli* BL-21 λ(DE3) and sequence confirmed with T7_fw and T7_rv to generate LDE002 (Table 8). |
| pVP91-Ht-PcaHG | To express pcaHG in *E. coli* | The plasmid encoding an N-terminal poly-histidine tagged PcaHG (pVP91-PcaHG) was previously described in Senavirathne, G., Lopez, M. A., Jr., Messer, R., Fishel, R., Yoder, K. E., 2018. Expression and purification of nuclease-free protocatechuate 3,4-dioxygenase for prolonged single-molecule fluorescence imaging. Anal Biochem. 556, 78-84. doi: 10.1016/j.ab.2018.06.016. The pcaHG genes were amplified from pVP91-PcaHG with whole plasmid PCR using the 5' phosphorylated primers pcaH-F and pcaH-R (introducing the sequence for a $TEV^{pro}$ cleavage site before the start codon of pcaHG, Table 6) and Q5 High fidelity polymerase (NEB) to create pcaHG_UBC (Table 7) that notably contains a $TEV^{pro}$ cleavage site between the poly-histidine tag and PcaH (Ht-PcaHG). The resulting plasmid was transformed into *E. coli* BL-21 λ(DE3) and sequence confirmed with Ht-pcaH_fw, pcaH-i_fw and pcaG-i_rv (Table 6) to generate LDE003 (Table 8). |
| pET41GalA | To express pcaHG in *E. coli* | The galA gene was amplified from pSN82 using primers galA-F (contains a NdeI cut-site) and galA-R (contains a XhoI cut-site) and Q5 High-Fidelity polymerase (NEB) where the PCR product is named galA_UBC (Table 7). The PCR product was inserted into pET41b digested with NdeI and XhoI using the T4 Ligase (NEB). The resulting plasmid was transformed into *E. coli* BL-21 λ(DE3) and sequence confirmed with T7_fw and T7_rv to generate LDE004 (Table 8). |
| pAW07 | To integrate vanAB from *Pseudomonas* sp. HR199 codon optimized for expression in *P. putida* KT2440 ($vanAB^{HR99}$) into the chromosome with simultaneous deletion of the native vanAB ($vanAB^{KT2440}$) | The vanA and vanB genes from *Pseudomonas* sp. HR1999 were codon optimized for expression in *P. putida* via IDT and synthesized as gBlocks by IDT with a Salis-designed RBS upstream of each gene (gAW007 and gAW008 in Table 7). gAW007 and gAW008 were integrated into pSN66 digested with NotI using the NEB HiFi Assembly Kit and transformed into *E. coli* DH5A F'Iq competent cells (NEB). Construction was confirmed via cPCR using oAW093 and oAW094 (Tm = 60 C., 2,915 bp product). Isolate 5 was sequence confirmed to be correct via oAW093, oAW100, oAW101, and oAW102. |

TABLE 6

DNA Sequences of oligos used in this study. Integrated DNA Technologies was used for synthesis unless otherwise noted.

| Primer | Sequence (5'→3') |
|---|---|
| oAM204 (SEQ ID NO: 15) | AACGAGAAGGTCAACGTGC |
| oAM205 (SEQ ID NO: 16) | TTGAGCAACACCTGCTTGC |
| oCJ054 (SEQ ID NO: 17) | ATCGGCTCGTATAATGTGTGG |
| oCJ135 (SEQ ID NO: 18) | AGGCTGATGTTGATGTGC |
| oCJ163 (SEQ ID NO: 19) | TTGTCCAGCAGGGTTGTC |
| oCJ290 (SEQ ID NO: 20) | AATACGCAAACCGCCTCTC |
| oCJ291 (SEQ ID NO: 21) | GTAGCTGACATTCATCCG |
| oCJ534 (SEQ ID NO: 22) | CCTCGGTGAGTTTTCTCC |
| oSN099 (SEQ ID NO: 23) | agtgagcgcaacgcaattaatgtgagttag GAATTCATGGCGCCGCCAGTG |
| oSN103 (SEQ ID NO: 24) | CCACTGCGCCAGCGACGC |
| oSN223 (SEQ ID NO: 25) | GAAAGTCATCCTGCCCTCGTCGTAAGACGG GGCGGCCGCGGGAGGCTCTCCGGG |
| oSN224 (SEQ ID NO: 26) | TAAATAAAAACAAAACCCGGAGAGCCTCCC GCGGCCGCCCCGTCTTACGACGAGGGC |
| oSN225 (SEQ ID NO: 27) | cctgagtgcttgcggcagcgtgaagctag GGATCCGAGGTGAACTACACCTTCCAGAGC |
| oSN226 (SEQ ID NO: 28) | GCTTCAGGCGAGTTGGCG |
| oSN238 (SEQ ID NO: 29) | tgacctacttcatgggcctg |
| oSN239 (SEQ ID NO: 30) | GAAGTTGAAACGGTCCGAGG |
| oSN234 (SEQ ID NO: 31) | agtgagcgcaacgcaattaatgtgagttag GAATTCatcggcggcgcagt |
| oSN235 (SEQ ID NO: 32) | CCGTCACACGATCAAGCGGGTTGCATCGGG CGGCCGCgccatattgctcgtctacgccc |

TABLE 6-continued

DNA Sequences of oligos used in this study. Integrated DNA Technologies was used for synthesis unless otherwise noted.

| Primer | Sequence (5'→3') |
|---|---|
| oSN236 (SEQ ID NO: 33) | ttcaccctgggcgtagacgagcaatatggc GCGGCCGCCCGATGCAACCCGCTTGATC |
| oSN237 (SEQ ID NO: 34) | ccctgagtgcttgcggcagcgtgaagctag GGATCCAGGCTCATGTCCTGCATGCTG |
| oSN267 (SEQ ID NO: 35) | ggaattgtgagcggataacaatttcacac TCTAGAgAACAGAGGACTTTCGCATGGCTC |
| oSN268 (SEQ ID NO: 36) | ttacgctggagtctgaggctcgtcctgaat GATATCTCAGTTGGGCGCTTTGCC |
| oSN269 (SEQ ID NO: 37) | CCGCGACAAGCCGCTGGAC |
| vanA-F (SEQ ID NO: 38) | ACCCCATATGTATCCAAAGAATACCTGGTATG (underlined NdeI restriction site introduced) |
| vanA-R (SEQ ID NO: 39) | TGGGAAGCTTTCACGCCGGATTCGC (underlined HindIII restriction site introduced) |
| vanB-F (SEQ ID NO: 40) | ACCCCATATGATTGACGCAGTGGTCGT (underlined NdeI restriction site introduced) |
| vanB-R (SEQ ID NO: 41) | TGGGAAGCTTTCAGATATCCAGCACGAGCA (underlined HindIII restriction site introduced) |
| galA-F (SEQ ID NO: 42) | TCTAGATCATATGGCTCGTATCATTGGTGGC CTG (underlined NdeI restriction site introduced) |
| galA-R (SEQ ID NO: 43) | TGTCTCGAGATTGGATTGGAAGTACAGGT TCTCGTTGGGCGCTTTGCCAGCC (underlined XhoI restriction site introduced) |
| pcaH-F (SEQ ID NO: 44) | TTCCAATCCAATATGCCCGCCCAG (encoded TEVpro site underlined) |
| pcaH-R (SEQ ID NO: 45) | CACCATGCGATCGCAGAGAACCTGTAC (encoded TEVpro site underlined) |
| Ht-pcaH_fw (SEQ ID NO: 46) | AGGCGTATCACGAGGCCCTTTC |
| pcaH-i_fw (SEQ ID NO: 47) | GCACAAGAACGACCGTTACC |
| PcaG-i_rv (SEQ ID NO: 48) | TGGGCTTCATCATCGAAGTA |
| oAW093 (SEQ ID NO: 49) | GCATTGACCTACCACGCCGAC |
| oAW094 (SEQ ID NO: 50) | CCCAACCGCTGAACTGTTCGG |

TABLE 6-continued

DNA Sequences of oligos used in this study. Integrated DNA Technologies was used for synthesis unless otherwise noted.

| Primer | Sequence (5'→3') |
|---|---|
| oAW099 (SEQ ID NO: 51) | GCACATAGGTCTCGTGGGTCAAG |
| oAW100 (SEQ ID NO: 52) | GACCAACAAAAGTTGAACGCTGCTGC |
| oAW101 (SEQ ID NO: 53) | GGATCGCTGGCAAATCTGTCG |
| oAW102 (SEQ ID NO: 54) | TGTATGGCTCAAGAATTGGCAGCC |
| T7_fw (SEQ ID NO: 55) | TAATACGACTCACTATAGGG |
| T7_rv (SEQ ID NO: 56) | GCTAGTTATTGCTCAGCGG |

TABLE 7

Synthesized genes used in this study. Integrated DNA Technologies was used for synthesis unless otherwise noted.

| Name | Sequence (5'→3') | Desc. |
|---|---|---|
| vanA_EC (SEQ ID NO: 57) | ATGTATCCAAAGAATACCTGGTATGTTGCGTGTACGCCAGATG AAATTGCTACTAAGCCGCTGGGCCGTCAAATCTGTGGCGAGAA AATCGTTTTCTACCGTGCACGTGAGAATCAAGTCGCGGCCGTT GAAGATTTCTGCCCGCATCGCGGTGCGCCGCTGAGCCTGGGT TACGTGGAACATGGCAACCTGGTTTGCGGTTACCACGGCCTG GTCATGGGCTGCGATGGTAAGACCGTGAGCATGCCGGGTCAA CGTGTCCGCGGTTTTCCGTGCAATAAAACCTTCGCAGCCGTGG AACGTTACGGTTTTATCTGGGTCTGGCCGGGTGACCAAGCGCA GGCAGACCCGGCTCTGATCCCGCACCTGGAGTGGGCAGTGTC CGATGAGTGGGCGTACGGTGGCGGCCTGTTCCATATTGGTTG CGACTACCGCTTGATGATCGACAACCTGATGGACTTGACCCAC GAAACGTATGTTCACGCCAGCAGCATTGGTCAGAAAGAAATCG ACGAAGCGCCGCCGGTTACGACGGTCACCGGCGACGAAGTTG TGACTGCCCGTCACATGGAAAACATTATGGCGCCTCCGTTCTG GCGTATGGCACTGCGCGGTAATGGTCTGGCGGACGACGTGCC GGTGGACCGTTGGCAGATTTGTCGCTTTACCCCTCCGTCGCAC GTTTTGATTGAGGTCGGCGTCGCCCATGCTGGTAAGGGTGGCT ATCACGCTGAGGCACAACATAAAGCGAGCTCCATCGTTGTGGA TTTCATCACCCCGGAGAGCGACACCTCTATTTGGTACTTTTGG GGCATGGCGCGCAACTTTGCAGCACACGATCAGACCCTGACG GATAATATTCGCGAGGGTCAGGGTAAGATCTTCAGCGAAGATC TGGAAATGCTGGAGCGTCAGCAACAAAACCTGTTAGCGCATCC GGAGCGTAACCTCCTGAAACTGAACATTGATGCCGGTGGCGTG CAGAGCCGTAAGGTACTGGAGCGCATCATTGCCCAAGAGCGT GCGCCGCAGCCGCAGCTGATTGCGACGAGCGCGAATCCGGC GGGTcatcaccaccaccaccattga | The vanA DNA sequence from *P. putida* KT2440 codon optimized for expression in *E. coli* (dotted underline) with a His tag (underlined). The sequence was synthesized in the commercial vector pD444-CH (www.ATUM.bio, Accession #PD444-CH) between the BsaI sites, which contains the T5 promoter and a strong ribosome binding site upstream of the ORF. The resulting plasmid is named pSN95. |

TABLE 7-continued

Synthesized genes used in this study. Integrated DNA Technologies was used for synthesis unless otherwise noted.

| Name | Sequence (5'→3') | Desc. |
|---|---|---|
| vanB_EC (SEQ ID NO: 58) | ATGATTGACGCAGTGGTCGTGTCCCGCAATGATGAAGCACAAG GAATCTGTTCGTTCGAGCTCGCGGCGGCCGACGGCAGCCTGC TGCCCGCGTTCAGCGCCGGGGCCCATATCGACGTGCATCTGC CCGATGGCTTGGTCCGACAGTATAGCCTCTGCAACCACCCTGA GGAACGCCACAGATACCTGATCGGTGTCCTCAACGACCCTGC GAGCCGGGGCGGATCCCGGTCACTGCATGAACAAGTGCAGGC CGGTGCCAGGCTCCGGATCTCCGCCCCGCGGAACTTGTTTCC TCTGGCCGAGGGCGCCCAGAGGTCCCTGCTGTTCGCGGGCG GAATCGGCATCACTCCAATCCTGTGCATGGCCGAACAGCTGTC CGACTCCGGACAGGCCTTTGAGCTCCACTACTGTGCCCGCTCA TCCGAGAGAGCAGCCTTCGTGGAACGGATTAGATCCGCTCCTT TCGCGGACCGCCTGTTTGTGCACTTCGACGAGCAGCCCGAGA CTGCCCTGGATATTGCGCAAGTGCTGGGAAACCCGCAGGACG ATGTGCACCTCTACGTGTGCGGCCCCGGGGGCTTCATGCAAC ACGTGCTGGATTCCGCCAAGGGACTGGGGTGGCAGGAAGCCA ACCTTCACCGGGAATACTTCGCCGCCGCACCGGTGGACGCCT CCAATGATGGATCGTTCGCTGTGCAAGTCGGGTCAACCGGACA AGTGTTCGAAGTGCCGGCCGACCGCACCGTGGTCCAAGTGCT TGAAGAGAACGGAATCGAAATCGCTATGTCGTGCGAACAGGGA ATTTGCGGTACCTGTCTGACTCGGGTGCTGCAGGGTACCCCC GACCACCGGGACCTTTTCCTGACCGAAGAGGAACAGGCTCTG AACGACCAGTTCACCCCATGCTGCTCGAGGTCTAAGACCCCGC TGCTCGTGCTGGATATCGGTcatcaccaccaccaccattga | The vanB DNA sequence from *P. putida* KT2440 codon codon optimized for expression in *E. coli* (dotted underline) with a His tag (underlined). The sequence was synthesized in the commercial vector pD444-CH (www.ATUM.bio, Accession #PD444-CH) between the BsaI sites, which contains the T5 promoter and a strong ribosome binding site upstream of the ORF. The resulting plasmid is named pSN96. |
| vanA_EC-UBC (SEQ ID NO: 59) | ACCCCATATGTATCCAAAGAATACCTGGTATGTTGCGTGTACG CCAGATGAAATTGCTACTAAGCCGCTGGGCCGTCAAATCTGTG GCGAGAAAATCGTTTTCTACCGTGCACGTGAGAATCAAGTCGC GGCCGTTGAAGATTTCTGCCCGCATCGCGGTGCGCCGCTGAG CCTGGGTTACGTGGAAGATGGCAACCTGGTTTGCGGTTACCAC GGCCTGGTCATGGGCTGCGATGGTAAGACCGTGAGCATGCCG GGTCAACGTGTCCGCGGTTTTCCGTGCAATAAAAACCTTCGCAG CCGTGGAACGTTACGGTTTTATCTGGGTCTGGCCGGGTGACCA AGCGCAGGCAGACCCGGCTCTGATCCCGCACCTGGAGTGGGC AGTGTCCGATGAGTGGGCGTACGGTGGCGGCCTGTTCCATATT GGTTGCGACTACCGCTTGATGATCGACAACCTGATGGACTTGA CCCACGAAACGTATGTTCACGCCAGCAGCATTGGTCAGAAAGA AATCGACGAAGCGCCGCCGGTTACGACGGTCACCGGCGACGA AGTTGTGACTGCCCGTCACATGGAAAACATTATGGCGCCTCCG TTCTGGCGTATGGCACTGCGCGGTAATGGTCTGGCGGACGAC GTGCCGGTGGACCGTTGGCAGATTTGTCGCTTTACCCCTCCGT CGCACGTTTTGATTGAGGTCGGCGTCGCCCATGCTGGTAAGG | The vanA DNA sequence from *P. putida* KT2440 codon optimized for expression in *E. coli* (dotted underline) The introduced NdeI and Hind III sites are in bold. |

TABLE 7-continued

Synthesized genes used in this study. Integrated DNA Technologies was used for synthesis unless otherwise noted.

| Name | Sequence (5'→3') | Desc. |
|---|---|---|
| | GTGGCTATCACGCTGAGGCACAACATAAAGCGAGCTCCATCGT | |
| | TGTGGATTTCATCACCCCGGAGAGCGACACCTCTATTTGGTAC | |
| | TTTTGGGGCATGGCGCGCAACTTTGCAGCACACGATCAGACCC | |
| | TGACGGATAATATTCGCGAGGGTCAGGGTAAGATCTTCAGCGA | |
| | AGATCTGGAAATGCTGGAGCGTCAGCAACAAAACCTGTTAGCG | |
| | CATCCGGAGCGTAACCTCCTGAAACTGAACATTGATGCCGGTG | |
| | GCGTGCAGAGCCGTAAGGTACTGGAGCGCATCATTGCCCAAG | |
| | AGCGTGCGCCGCAGCCGCAGCTGATTGCGACGAGCGCGAATC | |
| | CGGCGGGTAAGCTTCCCA | |
| vanB_EC-UBC (SEQ ID NO: 60) | ACCCCATATGATTGACGCAGTGGTCGTGTCCCGCAATGATGAA GCACAAGGAATCTGTTCGTTCGAGCTCGCGGCGGCCGACGGC AGCCTGCTGCCCGCGTTCAGCGCCGGGGCCCATATCGACGTG CATCTGCCCGATGGCTTGGTCCGACAGTATAGCCTCTGCAACC ACCCTGAGGAACGCCACAGATACCTGATCGGTGTCCTCAACGA CCCTGCGAGCCGGGGCGGATCCCGGTCACTGCATGAACAAGT GCAGGCCGGTGCCAGGCTCCGGATCTCCGCCCCGCGGAACTT GTTTCCTCTGGCCGAGGGCGCCCAGAGGTCCCTGCTGTTCGC GGGCGGAATCGGCATCACTCCAATCCTGTGCATGGCCGAACA GCTGTCCGACTCCGGACAGGCCTTTGAGCTCCACTACTGTGCC CGCTCATCCGAGAGAGCAGCCTTCGTGGAACGGATTAGATCC GCTCCTTTCGCGGACCGCCTGTTTGTGCACTTCGACGAGCAGC CCGAGACTGCCCTGGATATTGCGCAAGTGCTGGGAAACCCGC AGGACGATGTGCACCTCTACGTGTGCGGCCCCGGGGGCTTCA TGCAACACGTGCTGGATTCCGCCAAGGGACTGGGGTGGCAGG AAGCCAACCTTCACCGGGAATACTTCGCCGCCGCACCGGTGG ACGCCTCCAATGATGGATCGTTCGCTGTGCAAGTCGGGTCAAC CGGACAAGTGTTCGAAGTGCCGGCCGACCGCACCGTGGTCCA AGTGCTTGAAGAGAACGGAATCGAAATCGCTATGTCGTGCGAA CAGGGAATTTGCGGTACCTGTCTGACTCGGGTGCTGCAGGGT ACCCCCGACCACCGGGACCTTTTCCTGACCGAAGAGGAACAG GCTCTGAACGACCAGTTCACCCCATGCTGCTCGAGGTCTAAGA CCCCGCTGCTCGTGCTGGATATCGGTcatcaccaccaccaccattgaAA GCTTCCCA | The vanB DNA sequence from *P. putida* KT2440 codon optimized for expression in *E. coli* (dotted underline) with a His tag (underlined). The introduced NdeI and HindIII sites are in bold. |
| pcaHG_UBC (SEQ ID NO: 61) | atgcatcaccatcatcaccatcaccatGCGATCGCAGAGAACCTGTACTTCC AATCCAATATGCCCGCCCAGGACAACAGCCGCTTCGTGATCCG TGATCGCAACTGGCACCCCAAAGCCCTTACGCCTGACTACAAA ACGTCCATTGCCCGCTCGCCGCGCCAGGCACTGGTCAGCATT CCACAGTCGATCAGCGAAACCACTGGTCCGAACTTTTCCCACC TGGGCTTCGGCGCCCACGACCATGACCTGCTGCTGAACTTCAA CAACGGTGGCCTGCCAATCGGCGAGCGCATCATCGTGGCCGG CCGCGTCGTCGACCAGTACGGCAAGCCTGTGCCGAACACCCT GGTGGAGATGTGGCAAGCCAACGCCGGTGGCCGCTACCGGCA CAAGAACGACCGTTACCTGGCACCGCTGGACCCGAACTTTGGT GGTGTCGGCCGTTGCCTGACCGACAGCGACGGCTACTACAGC TTCCGCACCATCAAGCCGGGCCCGTACCCCTGGCGCAACGGC CCGAACGACTGGCGCCCGGCGCACATCCACTTCGGCATCAGC | The pcaHG DNA sequence from KT2440, amplified from pVP91-PcaHG (dotted underline) with a His tag (underlined) and an encoded TEV<sup>pro</sup> cleavage site (underlined) |

TABLE 7-continued

Synthesized genes used in this study. Integrated DNA Technologies was used for synthesis unless otherwise noted.

| Name | Sequence (5'→3') | Desc. |
|---|---|---|
| | GGCCCGTCGATTGCGACCAAGCTGATCACCCAGTTGTATTTCG AGGGTGACCCGCTGATCCCGATGTGCCCGATCGTCAAGTCGA TCGCCAACCCTGAAGCTGTACAGCAGTTGATCGCCAAGCTCGA CATGAACAACGCCAACCCGATGGACTGCCTGGCCTACCGCTTT GACATCGTGCTGCGCGGCCAGCGCAAGACCCACTTCGAAAAC TGCTGAGGAACCCGCCATGCCAATCGAACTGCTGCCGGAAAC CCCTTCGCAGACCGCCGGCCCCTACGTGCACATCGGCCTGGC CCTGGAAGCGGCCGGCAACCCGACCCGCGATCAGGAAATCTG GAACCGCCTGGCCAAGCCGGACGCGCCAGGCGAGCACATTCT GCTACTCGGCCAGGTGTATGACGGTAACGGCCACCTGGTGCG CGACTCGTTCCTGGAAGTGTGGCAGGCCGACGCCAATGGCGA GTATCAGGATGCCTACAACCTGGAGAACGCCTTCAACAGCTTC GGCCGCACCGCCACCACCTTCGATGCTGGCGAGTGGACGCTG CACACGGTCAAGCCGGGTGTGGTGAACAATGCTGCTGGCGTG CCGATGGCGCCGCACATCAACATCAGCCTGTTTGCCCGTGGC ATCAACATCCACCTGCACACGCGCCTGTACTTCGATGATGAAG CCCAAGCCAACGCCAAGTGCCCGGTGCTCAACCTGATTGAGC AGCCGCAGCGGCGTGAAACCTTGATTGCCAAGCGTTGCGAAG TGGATGGGAAAACGGCGTATCGTTTCGATATCCGTATTCAGGG GGAAGGCGAGACCGTCTTCTTCGACTTCTGA | |
| galA_UBC (SEQ ID NO: 62) | CATATGGCTCGTATCATTGGTGGCCTGGCCGTCTCCCACACCC CAACCATCGGCTTCGCAGTCGACCACGACAAACAGGAAGAAG CCGCCTGGGCGCCGATCTTCGAAAGCTTCGAGCCGATCCGCA CGTGGCTGCAGCAGCGCCAGCCGGACGTACTCTTCTATATCTT CAACGACCACATCACCTCGTTCTTCTTTGACCATTACAGCGCCT TCACCCTGGGCGTAGACGAGCAATATGGCGTGGCCGATGAAG GGGGCAACCCGCGGGACCTGCCGCCAGTGGGCGGCCACGCA GCGCTGTCGCGACACATCGGCCAGAGCCTGATGGCCGATGAG TTCGACATGAGCTTTTTCCGCGACAAGCCGCTGGACCACGGCT TCTTCTCGCCCATGTCGGCGCTGCTGCCCTGCGATGAAAGCTG GCCCGTACAGATCGTGCCGCTGCAGGTCGGCGTACTGCAGCT GCCGATACCCACGGCGCGGCGCTGCTACAAACTGGGCCAGGC ATTGCGCCGCGCCATCGAGAGCTACCCCGAAGACCTCAAGGT GGCGATCGTCGCCACCGGCGGGGTGTCACACCAGGTGCACG GCGAGCGTTGCGGCTTCAACAACCCAGAGTGGGACGCGCAGT TCCTTGACCTGCTGGTGAACGACCCGCAGCGCCTTACCGAGAT GACACTGGCCGAGTACGCCACGCTCGGCGGCATGGAAGGTGC CGAGGTGATTACCTGGCTGATCATGCGTGGCACGTTGTCTGCC AACGTTGAGCGCAAGCACCAAAGCTACTACCTGCCGTCGATGA CCGGCATCGCCACCCTGCTGCTGGAAAACCGTGACCAGGCAC TGCCGGCGCCGGTCAACGAACGTCACCGCCAGCACATGCAGC ATCAGCTGGCAGGGGCTGAGCAGCTTGAAGGCACCTACCCCT ACACCCTGGAGCGCAGTGCCAAGGGCTACCGCCTGAACAAGT TCTTGCATCGCATGATTGAGCCGCAGTGGCGCCAGCGTTTCCT GAGCGAACCCGAAGCGCTGTACCGCGAGGCGGGCCTGAGCG AAGAGGAAAGCGACCTGCTGCGCCGCCGCGACTGGCGTGGG CTGATCCACTATGGGGTGATCTTCTTTGTACTGGAGAAGCTAG GCGCCGTACTGGGTGTGTCCAACCTGGACATTTACGCCGCCAT GCGCGGGCAGAGCATCGAGGACTTCATGAAGACCCGTAACCA | The galA DNA sequence from *P. putida* KT2440 codon optimized for expression in *E. coli*, amplified from pSN82 (dotted underline) The introduced NdeI and XhoI sites are in bold. |

TABLE 7-continued

Synthesized genes used in this study. Integrated DNA Technologies was used for synthesis unless otherwise noted.

| Name | Sequence (5'→3') | Desc. |
|---|---|---|
| | GCAGGTTCGCTACTCGGTGGCTGGCAAAGCGCCCAACTGACT CGAG | |
| gAW007 (SEQ ID NO: 63) | CGCAGCCTTAATGGATCCATTAAATAAAAACAAAACCCGGAGA GCCTCCCGCGGCCGCgagctgttgacaattaatcatcggctcgtataatgtgtgga attgtgagcggataacaatttcacacTCTGGCTGAGAGGCATCAAAATAAG GTAGGTCGTTTATGTTTCCGAAAAACGCATGGTATGTGGCGTG TACGCCGGATGAAATCGCAGATAAACCGCTGGGCCGCCAAATC TGCAACGAAAAAATCGTGTTTTATCGCGGGCCCGAGGGTCGTG TGGCCGCTGTCGAGGACTTTTGTCCACACCGTGGGGCCCCAC TCTCGCTGGGTTTCGTCCGGGATGGCAAGCTCATCTGCGGTTA TCACGGTTTGGAGATGGGGTGCGAGGGTAAAACCCTCGCTAT GCCGGGCCAGCGCGTGCAGGGTTTTCCTTGTATTAAGTCGTAC GCTGTCGAGGAGCGGTATGGGTTTATCTGGGTCTGGCCTGGT GATCGTGAACTGGCCGACCCTGCTTTGATTCACCATTTGGAGT GGGCAGACAACCCGGAGTGGGCTTACGGCGGGGGCTTGTATC ATATTGCATGCGACTACCGGCTGATGATTGACAACCTGATGGA CTTGACCCACGAGACCTATGTGCACGCATCCTCCATCGGTCAG AAAGAGATTGATGAGGCCCCGGTGAGCACCCGCGTCGAAGGG GACACGGTGATTACCTCCCGGTACATGGACAACGTCATGGCCC CGCCGTTCTGGCGCGCTGCCTTGCGTGGCAATGGGCTCGCCG ATGATGTCCCAGTGGATCGCTGGCAAATCTGTCGTTTCGCGCC ACCATCGCATGTCCTCATCGAAGTGGGCGTGGCACATGCTGG CAAAGGGGGTTATGATGCCCCTGCCGAATACAAAGCCGGCTC GATCGTCGTCGATTTTATTACGCCAGAGTCGGACACGAGCATT TGGTACTTTTGGGGCATGGCTCGCAATTTTCGTCCCCAAGGTA CGGAGTTGACGGACACCATTCGTGTCGGGCAAGGCAAGATCT TTGCGGAAGACCTGGACATGCTGGAGCAGCAGCAGCGGAACT TGCTGGCCTATCCTGAGCGGCAACTCCTGAAACTCAATATCGA TGCTGGGGGCGTGCAATCGCGTCGGGTGATCGATCGCATTCT GGCGGCTGAACAAGAAGCTGCGGATGCGGCCCTGATCGCTCG TTCGGCGAGCTGATCTAGACTACAAAGCGACACGGCAACGTAT AAGGAGGTTTTTTATGATTGAGGTGATTATTTCG | The vanA DNA sequence from *Pseudomonas* sp. HR199 codon optimized for expression in *P. putida* KT2440 (dotted underline). The operon is expressed by the P*tac* promoter (double underline) and each gene is preceded by a synthetic RBS (underline). Flanking sequences serve as overhangs for Gibson assembly. |
| gAW008 (SEQ ID NO: 64) | CGGCCCTGATCGCTCGTTCGGCGAGCTGATCTAGACTACAAAG CGACACGGCAACGTATAAGGAGGTTTTTTATGATTGAGGTGATT ATTTCGGCGATGCGCCTGGTCGCCCAAGATATTATCTCGCTCG AATTCGTCCGCGCTGATGGCGGTTTGCTCCCCCCCGTGGAAG CTGGCGCTCATGTCGATGTGCATTTGCCTGGCGGTCTCATCCG CCAATACTCGCTGTGGAATCAACCTGGGGCCCAATCCCACTAC TGTATTGGTGTGCTGAAGGATCCTGCCTCGCGGGGTGGGTCG AAAGCTGTGCATGAAAACCTCCGTGTCGGTATGCGGGTGCAGA TCTCGGAGCCTCGCAATCTCTTTCCATTGGAGGAAGGCGTCGA | The vanB DNA sequence from *Pseudomonas* sp. HR199 codon optimized for expression in *P. putida* KT2440 (dotted underline) and is preceded by a |

TABLE 7-continued

Synthesized genes used in this study. Integrated DNA Technologies was used for synthesis unless otherwise noted.

| Name | Sequence (5'→3') | Desc. |
|---|---|---|
| | GCGCAGCTTGCTGTTCGCCGGGGGGATTGGGATTACCCCTAT | synthetic RBS (underline). The operon is terminated by TonB (squiggle underline). Flanking sequences serve as overhangs for Gibson assembly. |
| | CCTGTGTATGGCTCAAGAATTGGCAGCCCGTGAACAAGATTTC | |
| | GAATTGCATTACTGTGCGCGGTCGACGGATCGCGCCGCCTTTG | |
| | TGGAGTGGCTCAAAGTCTGCGATTTTGCCGATCACGTCCGTTT | |
| | CCATTTCGATAACGGGCCCGACCAACAAAAGTTGAACGCTGCT | |
| | GCTCTCTTGGCAGCAGAGGCTGAGGGCACGCACCTCTATGTCT | |
| | GTGGTCCTGGGGGTTTCATGGGTCATGTGCTGGACACCGCGA | |
| | AAGAACAGGGTTGGGCTGATAACCGCTTGCATCGTGAGTACTT | |
| | TGCTGCTGCCCCAAATGTCTCCGCGGATGATGGTTCCTTCGAG | |
| | GTGCGTATCCATTCGACGGGTCAGGTCCTGCAAGTCCCAGCG | |
| | GACCAAACCGTGTCCCAAGTCCTGGACGCTGCAGGTATTATCG | |
| | TCCCAGTGAGCTGTGAGCAAGGCATTTGCGGTACGTGCATTAC | |
| | CCGCGTCGTCGACGGTGAGCCTGATCACCGCGATTTCTTCCTG | |
| | ACGGACGCCGAAAAGGCAAAAAATGATCAATTTACGCCGTGCT | |
| | GTTCGCGGGCGAAGAGCGCCTGCCTCGTGCTGGACTTGTAAA | |
| | GTCAAAAGCCTCCGACCGGAGGCTTTTTACTGCGGCCGCCCG | |
| | TCTTACGACGAGGGCAGGATGACTTTCATGCCCG | |

TABLE 8

Strains and construction details for bacterial strains used in this study.

| Strain | Genotype | Construction details |
|---|---|---|
| Wild-type | Pseudomonas putida KT2440 (P. putida KT2440) | ATCC ® 47054 |
| CJ251 | P. putida KT2440 ΔpcaHG::P$_{tac}$:ligABC ΔvanAB | P$_{tac}$:ligAB (where ligAB is from Sphingobium sp. SYK-6) was integrated into the genome with simultaneous deletion of pcaHG in P. putida KT2440 using pCJ051 as described Johnson, C. W., Salvachúa, D., Rorrer, N. A., Black, B. A., Vardon, D.R., John, P. C. S., Cleveland, N. S., Dominick, G., Elmore, J. R., Grundl, N., Khanna, P., Martinez, C. R., Michener, W. E., Peterson, D. J., Ramirez, K. J., Singh, P., VanderWall, T. A., Wilson, A. N., Yi, X., Biddy, M. J., Bomble, Y. J., Guss, A. M., Beckham, G. T., 2019. Innovative Chemicals and Materials from Bacterial Aromatic Catabolic Pathways. Joule 3, 1523-1537. doi:10.1016/j.joule.2019.05.011 |
| CJ486 | P. putida KT2440 fpvA:P$_{tac}$:vanAB | A second copy of vanAB, driven by the tac promoter, was integrated in the intergenic region downstream of fpvA in the genome of P. putida KT2440 using pCJ107 as described in Salvachúa, D., Johnson, C. W., Singer, C. A., Rohrer, H., Peterson, D. J., Black, B. A., Knapp, A., Beckham, G. T., 2018. Bioprocess development for muconic acid production from aromatic compounds and lignin. Green Chem. 167, 75-13. doi:10.1039/C8GC02519C. |
| SN207 | P. putida KT2440 fpvA:P$_{tac}$:vanAB carrying pBTL-2 (empty vector) | CJ486 transformed with pBTL-2 (empty vector). |
| SN166 | P. putida KT2440 ΔvanAB | vanAB was deleted from the genome of P. putida KT2440 using pSN66. This deletion was confirmed by amplification of a 1201 bp product rather than the 3224 bp wild-type product in a colony PCR reaction using primer pair oSN103/oSN226. |
| SN168 | P. putida KT2440 ΔpcaHG::P$_{tac}$:ligABC ΔvanAB | vanAB was deletion from the genome using pSN66. After diagnostic PCR with primers oSN103/oSN226, PCR product of 1201 bp in the deleted strain rather than 3224 bp in the WT. |
| SN249 | P. putida KT2440 fpvA:P$_{tac}$:vanAB ΔgalA | galA was deleted from the genome of CJ486 using pSN73. This deletion was confirmed by amplification of a 155 bp product rather than the 2579 bp wild-type product in a colony PCR reaction using primer pair oSN238/oSN239. |

TABLE 8-continued

Strains and construction details for bacterial strains used in this study.

| Strain | Genotype | Construction details |
|---|---|---|
| SN265 | P. putida KT2440 fpvA:$P_{tac}$:vanAB $P_{tac}$:pcaHG | The Ptac promoter was integrated upstream of pcaHG gene into the genome of CJ486 using pCJ020. This addition was confirmed by amplification of a 1182 bp product in a colony PCR reaction using primer pair oCJ054/oCJ135. |
| SN266 | P. putida KT2440 fpvA:$P_{tac}$:vanAB ΔgalA $P_{tac}$:pcaHG | The Ptac promoter was integrated upstream of pcaHG gene into the genome of SN249 using pCJ020. This addition was confirmed by amplification of a 1182 bp product in a colony PCR reaction using primer pair oCJ054/oCJ135. |
| SN285 | P. putida KT2440 ΔvanAB carrying pBTL-2 (empty vector) | SN166 was transformed with the empty vector pBTL-2. |
| SN286 | P. putida KT2440 ΔvanAB carrying pSN82 | SN166 was transformed with pSN82. |
| AW045 | P. putida KT2440 ΔvanAB$^{KT2440}$::$P_{tac}$:vanAB$^{HR199}$ ΔpcaHG::$P_{tac}$:ligABC | SN168 was transformed with pAW07 and confirmed by colony PCR with oSN103/oAW99 (1113 bp, Tm = 72C). |
| LDE001 | E. coli BL-21 A(DE3) | E. coli BL21(DE3) transformed with pET41VanA. |
| LDE002 | E. coli BL-21 A(DE3) | E. coli BL21(DE3) transformed with pET28VanB. |
| LDE003 | E. coli BL-21 A(DE3) | E. coli BL21(DE3) transformed with pVP91-Ht-PcaHG. |
| LDE004 | E. coli BL-21 A(DE3) | E. coli BL21(DE3) transformed with pET41GalA. |

EXAMPLES

Example 1. A genetically modified microbial cell comprising: a first genetic modification resulting in the expression of an exogenous vanillate demethylase, wherein: the microbial cell is capable of metabolizing an S-lignin decomposition product, and the microbial cell is capable of producing 2-pyrone-4,6-dicarboxylate (PDC).

Example 2. The genetically modified microbial cell of Example 1, wherein the exogenous vanillate demethylase is derived from a bacterium.

Example 3. The genetically modified microbial cell of either Example 1 or Example 2, wherein the bacterium comprises at least one of P. putida, P. fluorescens, or P. stutzeri.

Example 4. The genetically modified microbial cell of any one of Examples 1-3, wherein the exogenous vanillate demethylase comprises a VanAB.

Example 5. The genetically modified microbial cell of any one of Examples 1-4, wherein the exogenous vanillate demethylase comprises VanAB$^{HR199}$.

Example 6. The genetically modified microbial cell of any one of Examples 1-5, wherein a gene encoding the exogenous vanillate demethylase is at least 80% identical to at least one of SEQ ID NO: 11 or SEQ ID NO: 13.

Example 7. The genetically modified microbial cell of any one of Examples 1-6, wherein the exogenous vanillate demethylase is at least 60% identical to at least one of SEQ ID NO: 12 or SEQ ID NO: 14.

Example 8. The genetically modified microbial cell of any one of Examples 1-7, further comprising a first gene deletion of an endogenous vanillate demethylase.

Example 9. The genetically modified microbial cell of any one of Examples 1-8, wherein the endogenous vanillate demethylase is derived from a bacterium.

Example 10. The genetically modified microbial cell of any one of Examples 1-9, wherein the bacterium comprises at least one of P. putida, P. fluorescens, or P. stutzeri.

Example 11. The genetically modified microbial cell of any one of Examples 1-10, wherein the endogenous vanillate demethylase comprises a VanAB.

Example 12. The genetically modified microbial cell of any one of Examples 1-11, wherein the endogenous vanillate demethylase comprises VanAB$^{KT2440}$.

Example 13. The genetically modified microbial cell of any one of Examples 1-12, further comprising a second genetic modification resulting in the expression of an exogenous dioxygenase.

Example 14. The genetically modified microbial cell of any one of Examples 1-13, wherein the exogenous dioxygenase is derived from a bacterium.

Example 15. The genetically modified microbial cell of any one of Examples 1-14, wherein the bacterium comprises Sphingobium sp.

Example 16. The genetically modified microbial cell of any one of Examples 1-15, wherein the exogenous dioxygenase comprises a LigAB.

Example 17. The genetically modified microbial cell of any one of Examples 1-16, wherein the exogenous dioxygenase comprises LigAB$^{SYK6}$.

Example 18. The genetically modified microbial cell of any one of Examples 1-17, wherein a gene encoding the exogenous dioxygenase is at least 80% identical to at least one of SEQ ID NO: 5 or SEQ ID NO: 7.

Example 19. The genetically modified microbial cell of any one of Examples 1-18, wherein the exogenous dioxygenase is at least 60% identical to at least one of SEQ ID NO: 6 or SEQ ID NO: 8.

Example 20. The genetically modified microbial cell of any one of Examples 1-19, further comprising a second gene deletion of an endogenous dioxygenase.

Example 21. The genetically modified microbial cell of any one of Examples 1-20, wherein the endogenous dioxygenase is derived from a bacterium.

Example 22. The genetically modified microbial cell of any one of Examples 1-21, wherein the bacterium comprises at least one of P. putida, P. fluorescens, or P. stutzeri.

Example 23. The genetically modified microbial cell of any one of Examples 1-22, wherein the endogenous dioxygenase comprises a PcaHG.

Example 24. The genetically modified microbial cell of any one of Examples 1-23, wherein the endogenous dioxygenase comprises PcaHG$^{KT2440}$.

Example 25. The genetically modified microbial cell of any one of Examples 1-24, wherein a gene encoding the endogenous dioxygenase is at least 80% identical to at least one of SEQ ID NO: 1 or SEQ ID NO: 3.

Example 26. The genetically modified microbial cell of any one of Examples 1-25, wherein the endogenous dioxygenase is at least 80% identical to at least one of SEQ ID NO: 2 or SEQ ID NO: 4.

Example 27. The genetically modified microbial cell of any one of Examples 1-26, wherein the microbial cell is capable of metabolizing at least one of a G-lignin decomposition product or an H-lignin decomposition product.

Example 28. The genetically modified microbial cell of any one of Examples 1-27, wherein the exogenous vanillate demethylase is capable of demethylating vanillate.

Example 29. The genetically modified microbial cell of any one of Examples 1-28, wherein the exogenous vanillate demethylase is not capable of demethylating 3-O-methylgallate.

Example 30. The genetically modified microbial cell of any one of Examples 1-29, wherein the genetically modified microbial cell comprises a bacterium.

Example 31. The genetically modified microbial cell of any one of Examples 1-30, wherein the genetically modified microbial cell comprises at least one of a fungus, a bacterium, or a yeast.

Example 32. The genetically modified microbial cell of any one of Examples 1-31, wherein the bacterium is from the genus *Psuedomonas*.

Example 33. The genetically modified microbial cell of any one of Examples 1-32, wherein the bacterium comprises at least one of *P. putida, P. fluorescens*, or *P. stutzeri*.

Example 34. The genetically modified microbial cell of any one of Examples 1-33, wherein the bacterium is derived from at least one of *P. putida* KT2440 or *Pseudomonas* sp. HR199.

Example 35. The genetically modified microbial cell of any one of Examples 1-34, wherein the S-ligin decomposition product comprises at least one of syringaldehyde, syringate, or 3-O methylgallate.

Example 36. The genetically modified microbial cell of any one of Examples 1-35, wherein the G-ligin decomposition product comprises ferulate.

Example 37. The genetically modified microbial cell of any one of Examples 1-36, wherein the H-ligin decomposition product comprises p-coumarate.

Example 38. The genetically modified microbial cell of any one of Examples 1-37, wherein the microbial cell is capable of producing, in addition to PDC, at least one of 4-oxalomesaconic acid (enol form), 4-oxalomesaconic acid (keto form), or 4-carboxy-4-hydroxy-2-oxoadipic acid.

Example 39. The genetically modified microbial cell of any one of Examples 1-38, wherein the 4-oxalomesaconic acid comprises at least one of the enol form of 4-oxalomesaconic acid or the keto form of 4-oxalomesaconic acid.

Example 40. A method for lignin valorization, the method comprising: converting an S-lignin decomposition product to 2-pyrone-4,6-dicarboxylate (PDC) utilizing a genetically modified microbial cell comprising a first genetic modification resulting in the expression of an exogenous vanillate demethylase.

Definitions

A "vector" or "recombinant vector" is a nucleic acid molecule that is used as a tool for manipulating a nucleic acid sequence of choice or for introducing such a nucleic acid sequence into a host cell. A vector may be suitable for use in cloning, sequencing, or otherwise manipulating one or more nucleic acid sequences of choice, such as by expressing or delivering the nucleic acid sequence(s) of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

A vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the nucleic acid molecule of choice. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector can contain at least one selectable marker.

The term "expression vector" refers to a recombinant vector that is capable of directing the expression of a nucleic acid sequence that has been cloned into it after insertion into a host cell or other (e.g., cell-free) expression system. A nucleic acid sequence is "expressed" when it is transcribed to yield an mRNA sequence. In most cases, this transcript will be translated to yield an amino acid sequence. The cloned gene is usually placed under the control of (i.e., operably linked to) an expression control sequence. The phrase "operatively linked" refers to linking a nucleic acid molecule to an expression control sequence in a manner such that the molecule can be expressed when introduced (i.e., transformed, transduced, transfected, conjugated or conduced) into a host cell.

Vectors and expression vectors may contain one or more regulatory sequences or expression control sequences. Regulatory sequences broadly encompass expression control sequences (e.g., transcription control sequences or translation control sequences), as well as sequences that allow for vector replication in a host cell. Transcription control sequences are sequences that control the initiation, elongation, or termination of transcription. Suitable regulatory sequences include any sequence that can function in a host cell or organism into which the recombinant nucleic acid molecule is to be introduced, including those that control transcription initiation, such as promoter, enhancer, terminator, operator and repressor sequences. Additional regulatory sequences include translation regulatory sequences, origins of replication, and other regulatory sequences that are compatible with the recombinant cell. The expression vectors may contain elements that allow for constitutive expression or inducible expression of the protein or proteins of interest. Numerous inducible and constitutive expression systems are known in the art.

Typically, an expression vector includes at least one nucleic acid molecule of interest operatively linked to one or more expression control sequences (e.g., transcription control sequences or translation control sequences). In one aspect, an expression vector may comprise a nucleic acid encoding a recombinant polypeptide, as described herein, operably linked to at least one regulatory sequence. It should be understood that the design of the expression vector may depend on such factors as the choice of the host cell to be transformed and/or the type of polypeptide to be expressed.

Expression and recombinant vectors may contain a selectable marker, a gene encoding a protein necessary for survival or growth of a host cell transformed with the vector. The presence of this gene allows growth of only those host cells that express the vector when grown in the appropriate selective media. Typical selection genes encode proteins that confer resistance to antibiotics or other toxic substances, complement auxotrophic deficiencies, or supply critical nutrients not available from a particular media. Markers may be an inducible or non-inducible gene and will generally allow for positive selection. Non-limiting examples of selectable markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable expression vectors may include (or may be derived from) plasmid vectors that are well known in the art, such as those commonly available from commercial sources. Vectors can contain one or more replication and inheritance systems for cloning or expression, one or more markers for selection in the host, and one or more expression cassettes. The inserted coding sequences can be synthesized by standard methods, isolated from natural sources, or prepared as hybrids. Ligation of the coding sequences to transcriptional regulatory elements or to other amino acid encoding sequences can be carried out using established methods. A large number of vectors, including bacterial, yeast, and mammalian vectors, have been described for replication and/or expression in various host cells or cell-free systems, and may be used with the sequences described herein for simple cloning or protein expression.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

A nucleic acid molecule or polynucleotide can include a naturally occurring nucleic acid molecule that has been isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional enzyme. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequences represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm. As a result of the degeneracy of the genetic code, many nucleic acid sequences can encode a given polypeptide with a particular enzymatic activity. Such functionally equivalent variants are contemplated herein.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Bacillus* (e.g., *B. subtilis, B. megaterium* or *B. brevis*), *Caulobacter* (e.g., *C. crescentus*), *Lactoccocus* (e.g., *L. lactis*), *Streptomyces* (e.g., *S. coelicolor*), *Streptococcus* (e.g., *S. lividans*), and *Corynybacterium* (e.g., *C. glutamicum*); fungi from the genera *Trichoderma* (e.g., *T. reesei, T. viride, T. koningii*, or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori*, or *A. aculeatus*), *Fusarium, Neurospora, Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC. Exemplary culture/fermentation conditions and reagents are known. Media may be supplemented with aromatic substrates like guaiacol, guaethol or anisole for dealkylation reactions.

The nucleic acid molecules described herein encode the enzymes with amino acid sequences such as those represented by the SEQ ID NOs presented herein. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented herein, or may include up to a certain integer number of amino acid alterations. Such protein or polypeptide variants retain functionality as enzymes, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences presented herein and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

While the present disclosure relates to engineered strains that utilize enzymes from *P. putida* KT2440, similar strains could be constructed in different hosts using different endogenous or exogenous enzymes that catalyze the same reactions described herein. Thus, variations to these pathways present in other organisms that may enable the production of the compounds targeted here, or related molecules not described herein, are considered within the scope of the present disclosure.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A genetically modified *Pseudomonas* sp. comprising:
   a first genetic modification of a first gene encoding an exogenous vanillate demethylase, wherein the first gene has a sequence that is at least 80% identical to at least one of SEQ ID NO: 11 or SEQ ID NO: 13, and wherein the expressed exogenous vanillate demethylase has a sequence that is at least 80% identical to at least one of SEQ ID NO: 12 or SEQ ID NO: 14; and
   a second genetic modification of a second gene encoding an exogenous protocatechuate dioxygenase, wherein the second gene has a sequence that is at least 80% identical to at least one of SEQ ID NO: 5 or SEQ ID NO: 7, and wherein the exogenous protocatechuate dioxygenase has a sequence that is at least 80% identical to at least one of SEQ ID NO: 6 or SEQ ID NO: 8; wherein:
   the *Pseudomonas* sp. metabolizes a S-lignin decomposition product, and
   the *Pseudomonas* sp. produces 2-pyrone-4,6-dicarboxylate (PDC).

2. The genetically modified *Pseudomonas* sp. of claim 1, wherein the *Pseudomonas* sp. is selected from the group consisting of *P. putida*, *P. fluorescens*, or *P. stutzeri*.

3. The genetically modified *Pseudomonas* sp. of claim 1, wherein the exogenous dioxygenase is derived from a bacterium.

4. The genetically modified *Pseudomonas* sp. of claim 1, wherein the exogenous dioxygenase comprises a LigAB.

5. The genetically modified *Pseudomonas* sp. of claim 1, wherein the *Pseudomonas* sp. metabolizes at least one of a G-lignin decomposition product or an H-lignin decomposition product.

6. The genetically modified *Pseudomonas* sp. of claim 1, wherein the exogenous vanillate demethylase demethylates vanillate.

7. The genetically modified *Pseudomonas* sp. of claim 1, wherein the exogenous vanillate demethylase cannot demethylate 3-O-methylgallate.

8. The genetically modified *Pseudomonas* sp. of claim 1, wherein the S-lignin decomposition molecule comprises at least one of syringaldehyde, syringate, or 3-0 methylgallate.

9. The genetically modified *Pseudomonas* sp. of claim 5, wherein the G-lignin decomposition molecule comprises ferulate.

10. A method for lignin valorization, the method comprising:
    converting an S-lignin decomposition product to 2-pyrone-4,6-dicarboxylate (PDC) utilizing a genetically modified *Pseudomonas* sp., wherein:
    the genetically modified *Pseudomonas* sp. comprises:
    a first genetic modification of a first gene encoding an exogenous vanillate demethylase, wherein the first gene has a sequence that is at least 80% identical to at least one of SEQ ID NO: 11 or SEQ ID NO: 13 and wherein the expressed exogenous vanillate demethylase has a sequence that is at least 80% identical to at least one of SEQ ID NO: 12 or SEQ ID NO: 14; and
    a second genetic modification of a second gene encoding an exogenous protocatechuate dioxygenase, wherein the second gene has a sequence that is at least 80% identical to at least one of SEQ ID NO: 5 or SEQ ID NO: 7 and wherein the exogenous protocatechuate dioxygenase has a sequence that is at least 80% identical to at least one of SEQ ID NO: 6 or SEQ ID NO: 8.

11. The genetically modified *Pseudomonas* sp. of claim 1 wherein the first genetic modification consists of replacing a native vanAB gene with the first genetic modification.

12. The genetically modified *Pseudomonas* sp. of claim 11 wherein the first genetic modification consists of replacing a native chromosomal vanAB gene with the first genetic modification.

13. The genetically modified *Pseudomonas* sp. of claim 1 wherein the second genetic modification consists of replacing a native pcaHG gene with the second genetic modification.

14. The genetically modified *Pseudomonas* sp. of claim 1 wherein the second genetic modification consists of replacing a native chromosomal pcaHG gene with the second genetic modification.

15. The genetically modified *Pseudomonas* sp. of claim 1 wherein the first genetic modification consists of replacing a native chromosomal vanAB gene with the first genetic modification and wherein the second genetic modification consists of replacing a native chromosomal pcaHG gene with the second genetic modification.

16. The genetically modified *Pseudomonas* sp. of claim 15 wherein 2-pyrone-4,6-dicarboxylate (PDC) is produced by the cell at a concentration of up to 3.65 mM.

* * * * *